(12) United States Patent
Cheung et al.

(10) Patent No.: US 11,555,177 B2
(45) Date of Patent: Jan. 17, 2023

(54) ANTIGEN-PRESENTING CELL-MIMETIC SCAFFOLDS AND METHODS FOR MAKING AND USING THE SAME

(71) Applicant: President and Fellows of Harvard College, Cambridge, MA (US)

(72) Inventors: Alexander Sing Cheung, Cambridge, MA (US); David J. Mooney, Sudbury, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 537 days.

(21) Appl. No.: 16/316,778

(22) PCT Filed: Jul. 13, 2017

(86) PCT No.: PCT/US2017/041912
§ 371 (c)(1),
(2) Date: Jan. 10, 2019

(87) PCT Pub. No.: WO2018/013797
PCT Pub. Date: Jan. 18, 2018

(65) Prior Publication Data
US 2019/0292517 A1  Sep. 26, 2019

Related U.S. Application Data

(60) Provisional application No. 62/361,891, filed on Jul. 13, 2016.

(51) Int. Cl.
| | |
|---|---|
| C12N 5/00 | (2006.01) |
| A61P 35/00 | (2006.01) |
| A61K 9/00 | (2006.01) |
| A61K 35/17 | (2015.01) |
| A61K 38/18 | (2006.01) |
| A61K 38/19 | (2006.01) |
| A61K 38/20 | (2006.01) |
| A61K 39/00 | (2006.01) |
| A61K 39/395 | (2006.01) |
| A61L 27/02 | (2006.01) |
| A61L 27/28 | (2006.01) |
| A61L 27/38 | (2006.01) |
| A61L 27/54 | (2006.01) |
| A61L 27/56 | (2006.01) |
| C12N 5/0783 | (2010.01) |

(52) U.S. Cl.
CPC .......... *C12N 5/0075* (2013.01); *A61K 9/0019* (2013.01); *A61K 35/17* (2013.01); *A61K 38/1841* (2013.01); *A61K 38/193* (2013.01); *A61K 38/2013* (2013.01); *A61K 39/0011* (2013.01); *A61K 39/395* (2013.01); *A61L 27/025* (2013.01); *A61L 27/28* (2013.01); *A61L 27/3804* (2013.01); *A61L 27/54* (2013.01); *A61L 27/56* (2013.01); *A61P 35/00* (2018.01); *C12N 5/0638* (2013.01); *A61L 2300/426* (2013.01); *A61L 2300/45* (2013.01); *C12N 2501/15* (2013.01); *C12N 2501/22* (2013.01); *C12N 2501/2302* (2013.01); *C12N 2501/998* (2013.01); *C12N 2533/00* (2013.01); *C12N 2533/20* (2013.01)

(58) Field of Classification Search
CPC .................................................... C12N 5/0075
See application file for complete search history.

(56) References Cited

U.S. PATENT DOCUMENTS

| | | |
|---|---|---|
| 3,773,919 A | 11/1973 | Boswell et al. |
| 4,522,811 A | 6/1985 | Eppstein et al. |
| 4,946,778 A | 8/1990 | Ladner et al. |
| 5,091,513 A | 2/1992 | Huston et al. |
| 5,132,405 A | 7/1992 | Huston et al. |
| 5,885,829 A | 3/1999 | Mooney et al. |
| 5,888,987 A | 3/1999 | Haynes et al. |
| 5,906,826 A | 5/1999 | Emery et al. |

(Continued)

FOREIGN PATENT DOCUMENTS

| | | |
|---|---|---|
| AU | 2014200405 A1 | 2/2014 |
| AU | 2018201930 A1 | 4/2018 |

(Continued)

OTHER PUBLICATIONS

U.S. Appl. No. 15/434,781, filed Feb. 16, 2017, 2017-0246281, Published.
U.S. Appl. No. 16/121,988, filed Sep. 5, 2018, 2019-0183992, Published.
U.S. Appl. No. 15/564,905, filed Oct. 6, 2017, 2018-0164298, Published.
U.S. Appl. No. 16/170,313, filed Oct. 25, 2018, 2019-0125849, Published.

(Continued)

*Primary Examiner* — Scott Long
(74) *Attorney, Agent, or Firm* — McCarter & English, LLP; Maria Laccotripe Zacharakis; Maneesh Gulati

(57) ABSTRACT

Embodiments herein described provide antigen-presenting cell-mimetic scaffolds (APC-MS) and use of such scaffolds to manipulating T-cells. More specifically, the scaffolds are useful for promoting growth, division, differentiation, expansion, proliferation, activity, viability, exhaustion, anergy, quiescence, apoptosis, or death of T-cells in various settings, e.g., in vitro, ex vivo, or in vivo. Embodiments described herein further relate to pharmaceutical compositions, kits, and packages containing such scaffolds. Additional embodiments relate to methods for making the scaffolds, compositions, and kits/packages. Also described herein are methods for using the scaffolds, compositions, and/or kits in the diagnosis or therapy of diseases such as cancers, immunodeficiency disorders, and/or autoimmune disorders.

30 Claims, 53 Drawing Sheets
Specification includes a Sequence Listing.

(56) References Cited

U.S. PATENT DOCUMENTS

| | | |
|---|---|---|
| 5,951,976 A | 9/1999 | Segal |
| 6,129,716 A | 10/2000 | Steer |
| 6,160,084 A | 12/2000 | Langer et al. |
| 6,193,970 B1 | 2/2001 | Pardoll et al. |
| 6,251,396 B1 | 6/2001 | Gaur et al. |
| 6,281,256 B1 | 8/2001 | Harris et al. |
| 6,334,968 B1 | 1/2002 | Shapiro et al. |
| 6,352,694 B1 | 3/2002 | June et al. |
| 6,403,374 B1 | 6/2002 | Tsien et al. |
| 6,429,199 B1 | 8/2002 | Krieg et al. |
| 6,511,511 B1 | 1/2003 | Slivka et al. |
| 6,511,650 B1 | 1/2003 | Eiselt et al. |
| 6,541,022 B1 | 4/2003 | Murphy et al. |
| 6,642,363 B1 | 11/2003 | Mooney et al. |
| 6,685,963 B1 | 2/2004 | Taupin et al. |
| 6,748,954 B2 | 6/2004 | Lee et al. |
| 6,767,928 B1 | 7/2004 | Murphy et al. |
| 6,783,712 B2 | 8/2004 | Slivka et al. |
| 6,790,840 B1 | 9/2004 | Lee et al. |
| 6,797,738 B2 | 9/2004 | Harris et al. |
| 6,800,733 B2 | 10/2004 | Tsien et al. |
| 6,858,222 B2 | 2/2005 | Nelson et al. |
| 6,974,698 B1 | 12/2005 | Miller et al. |
| 7,015,205 B1 | 3/2006 | Wallack et al. |
| 7,157,566 B2 | 1/2007 | Tsien et al. |
| 7,186,413 B2 | 3/2007 | Bouhadir et al. |
| 7,192,693 B2 | 3/2007 | Bryant et al. |
| 7,244,714 B1 | 7/2007 | Gonda et al. |
| 7,357,936 B1 | 4/2008 | Garcon |
| 7,410,953 B2 | 8/2008 | Kawasaki |
| 7,427,602 B1 | 9/2008 | Shea et al. |
| 7,569,850 B2 | 8/2009 | Noy et al. |
| 7,575,759 B2 | 8/2009 | Murphy et al. |
| 7,687,241 B2 | 3/2010 | Chen |
| 7,709,458 B2 | 5/2010 | Karaolis et al. |
| 7,790,699 B2 | 9/2010 | Melvik et al. |
| 8,067,237 B2 | 11/2011 | Mooney et al. |
| 8,188,058 B2 | 5/2012 | Hackam et al. |
| 8,273,373 B2 | 9/2012 | Alsberg et al. |
| 8,354,119 B2 | 1/2013 | Geistlich et al. |
| 8,367,628 B2 | 2/2013 | Goodwin et al. |
| 8,535,719 B2 | 9/2013 | Badylak et al. |
| 8,709,464 B2 | 4/2014 | Ma et al. |
| 8,728,456 B2 | 5/2014 | Sands et al. |
| 8,883,308 B2 | 11/2014 | Polshettiwar et al. |
| 8,932,583 B2 | 1/2015 | Mooney et al. |
| 9,012,399 B2 | 4/2015 | Cao et al. |
| 9,132,210 B2 | 9/2015 | Mooney et al. |
| 9,139,809 B2 | 9/2015 | Porcelli et al. |
| 9,150,631 B2 | 10/2015 | Super et al. |
| 9,370,558 B2 | 6/2016 | Ali et al. |
| 9,381,235 B2 | 7/2016 | Sands et al. |
| 9,446,107 B2 | 9/2016 | Mooney et al. |
| 9,486,512 B2 | 11/2016 | Kim et al. |
| 9,591,360 B2 | 3/2017 | Jennings et al. |
| 9,610,328 B2 | 4/2017 | Mooney |
| 9,675,561 B2 | 6/2017 | Bencherif et al. |
| 9,770,535 B2 | 9/2017 | Mooney et al. |
| 9,821,045 B2 | 11/2017 | Ali et al. |
| 9,937,249 B2 | 4/2018 | Kim et al. |
| 10,045,947 B2 | 8/2018 | Bencherif et al. |
| 10,080,789 B2 | 9/2018 | Sands et al. |
| 10,137,184 B2 | 11/2018 | Mooney et al. |
| 10,149,897 B2 | 12/2018 | Mooney et al. |
| 10,258,677 B2 | 4/2019 | Mooney et al. |
| 10,328,133 B2 | 6/2019 | Mooney et al. |
| 10,406,216 B2 | 9/2019 | Kim et al. |
| 11,059,050 B2 | 7/2021 | Kang et al. |
| 2002/0045672 A1 | 4/2002 | Harris et al. |
| 2002/0131853 A1 | 9/2002 | Nagasawa |
| 2002/0131953 A1 | 9/2002 | Takashima et al. |
| 2002/0150604 A1 | 10/2002 | Yi et al. |
| 2003/0075822 A1 | 4/2003 | Slivka et al. |
| 2003/0082806 A1 | 5/2003 | Berenson et al. |
| 2003/0095994 A1 | 5/2003 | Geistlich et al. |
| 2003/0100527 A1 | 5/2003 | Krieg et al. |
| 2003/0194397 A1 | 10/2003 | Mishra |
| 2003/0232895 A1 | 12/2003 | Omidian et al. |
| 2003/0235557 A1 | 12/2003 | Gaiger et al. |
| 2004/0028745 A1 | 2/2004 | Bouhadir et al. |
| 2004/0043034 A1 | 3/2004 | Jensenius et al. |
| 2004/0058883 A1 | 3/2004 | Phillips et al. |
| 2004/0063206 A1 | 4/2004 | Rowley et al. |
| 2004/0136968 A1 | 7/2004 | Zheng et al. |
| 2004/0151764 A1 | 8/2004 | Zamora |
| 2004/0213795 A1 | 10/2004 | Collins et al. |
| 2004/0220111 A1 | 11/2004 | Kleinman et al. |
| 2004/0228858 A1 | 11/2004 | Hanson et al. |
| 2004/0242469 A1 | 12/2004 | Lee et al. |
| 2004/0242482 A1 | 12/2004 | Gehring et al. |
| 2005/0002915 A1 | 1/2005 | Atala et al. |
| 2005/0037330 A1 | 2/2005 | Fischer et al. |
| 2005/0053667 A1 | 3/2005 | Irvine et al. |
| 2005/0079159 A1 | 4/2005 | Shastri et al. |
| 2005/0090008 A1 | 4/2005 | Segura et al. |
| 2005/0106211 A1 | 5/2005 | Nelson et al. |
| 2005/0154376 A1 | 7/2005 | Riviere et al. |
| 2005/0177249 A1 | 8/2005 | Kladakis et al. |
| 2005/0202394 A1 | 9/2005 | Dobson |
| 2006/0083712 A1 | 4/2006 | Anversa |
| 2006/0141018 A1 | 6/2006 | Cochrum et al. |
| 2006/0264380 A1 | 11/2006 | Hellstrom et al. |
| 2006/0292134 A1 | 12/2006 | Stohs |
| 2007/0003595 A1 | 1/2007 | Wang et al. |
| 2007/0020232 A1 | 1/2007 | Rossignol et al. |
| 2007/0026518 A1 | 2/2007 | Healy et al. |
| 2007/0081972 A1 | 4/2007 | Sandler et al. |
| 2007/0116680 A1 | 5/2007 | Stegemann et al. |
| 2007/0178159 A1 | 8/2007 | Chen et al. |
| 2007/0190646 A1 | 8/2007 | Engler et al. |
| 2008/0044900 A1 | 2/2008 | Mooney et al. |
| 2008/0044990 A1 | 2/2008 | Lee |
| 2008/0051490 A1 | 2/2008 | Williams et al. |
| 2008/0113929 A1 | 5/2008 | Lipford et al. |
| 2008/0138416 A1 | 6/2008 | Rauh et al. |
| 2008/0152624 A1 | 6/2008 | Paludan et al. |
| 2008/0159993 A1 | 7/2008 | Stauss et al. |
| 2008/0206308 A1 | 8/2008 | Jabbari et al. |
| 2008/0233181 A1 | 9/2008 | Nagy et al. |
| 2008/0268019 A1 | 10/2008 | Badylak et al. |
| 2008/0268052 A1 | 10/2008 | Voytik-Harbin et al. |
| 2009/0017096 A1 | 1/2009 | Lowman et al. |
| 2009/0041825 A1 | 2/2009 | Kotov et al. |
| 2009/0192079 A1 | 7/2009 | Santos et al. |
| 2009/0238853 A1 | 9/2009 | Liu et al. |
| 2009/0252752 A1 | 10/2009 | Tahara et al. |
| 2009/0297551 A1 | 12/2009 | Sattentau et al. |
| 2009/0297579 A1 | 12/2009 | Semino et al. |
| 2009/0305983 A1 | 12/2009 | Ying et al. |
| 2010/0015709 A1 | 1/2010 | Rehfeldt et al. |
| 2010/0055102 A1 | 3/2010 | Langermann |
| 2010/0055186 A1 | 3/2010 | Dadsetan et al. |
| 2010/0080816 A1 | 4/2010 | Hadeiba et al. |
| 2010/0129422 A1 | 5/2010 | Han et al. |
| 2010/0159008 A1 | 6/2010 | Barron et al. |
| 2010/0174346 A1 | 7/2010 | Boyden et al. |
| 2010/0189760 A1 | 7/2010 | Schaffer et al. |
| 2010/0190741 A1 | 7/2010 | Cohen et al. |
| 2010/0272771 A1 | 10/2010 | Harlow et al. |
| 2011/0008443 A1 | 1/2011 | Alsberg et al. |
| 2011/0020216 A1 | 1/2011 | Mooney et al. |
| 2011/0117170 A1 | 5/2011 | Cao et al. |
| 2011/0159023 A1 | 6/2011 | Langermann |
| 2011/0207166 A1 | 8/2011 | Vaiselbuh |
| 2011/0223255 A1 | 9/2011 | Thiesen et al. |
| 2011/0253643 A1 | 10/2011 | Polshettiwar et al. |
| 2011/0256119 A1 | 10/2011 | Lei et al. |
| 2011/0300186 A1 | 12/2011 | Hellstrom et al. |
| 2012/0040011 A9 | 2/2012 | Boons et al. |
| 2012/0121539 A1 | 5/2012 | Sands et al. |
| 2012/0122218 A1 | 5/2012 | Huebsch et al. |
| 2012/0134967 A1 | 5/2012 | Mooney et al. |
| 2012/0256336 A1 | 10/2012 | Yano et al. |
| 2012/0264599 A1 | 10/2012 | Komatsu et al. |

(56) References Cited

U.S. PATENT DOCUMENTS

| | | |
|---|---|---|
| 2012/0294888 A1 | 11/2012 | Kishimoto et al. |
| 2012/0329791 A1 | 12/2012 | Ashwell et al. |
| 2013/0029030 A1 | 1/2013 | Larsen |
| 2013/0035283 A1 | 2/2013 | Super et al. |
| 2013/0045246 A1 | 2/2013 | Edwards et al. |
| 2013/0052117 A1 | 2/2013 | Imai et al. |
| 2013/0072547 A1 | 3/2013 | Hackam et al. |
| 2013/0145488 A1 | 6/2013 | Wang et al. |
| 2013/0177536 A1 | 7/2013 | Mooney et al. |
| 2013/0202707 A1 | 8/2013 | Ali et al. |
| 2013/0251784 A1 | 9/2013 | Kim et al. |
| 2013/0302396 A1 | 11/2013 | Mooney et al. |
| 2013/0331343 A1 | 12/2013 | Cao et al. |
| 2014/0072510 A1 | 3/2014 | Shea et al. |
| 2014/0079752 A1 | 3/2014 | Huebsch et al. |
| 2014/0112990 A1 | 4/2014 | Bencherif et al. |
| 2014/0178964 A1 | 6/2014 | Mooney et al. |
| 2014/0193488 A1 | 7/2014 | Kim et al. |
| 2014/0227327 A1 | 8/2014 | Bencherif et al. |
| 2014/0227723 A1 | 8/2014 | Ingber et al. |
| 2014/0234423 A1 | 8/2014 | Sands et al. |
| 2015/0024026 A1 | 1/2015 | Mooney et al. |
| 2015/0030669 A1* | 1/2015 | Platscher .............. A61P 37/06 424/450 |
| 2015/0072009 A1* | 3/2015 | Kim .............. A61K 39/001162 424/489 |
| 2015/0080321 A1 | 3/2015 | Li et al. |
| 2015/0094518 A1 | 4/2015 | Wu et al. |
| 2015/0359928 A1 | 12/2015 | Gu et al. |
| 2015/0366956 A1 | 12/2015 | Mooney et al. |
| 2016/0033511 A1 | 2/2016 | Pannell et al. |
| 2016/0129053 A1 | 5/2016 | Brass et al. |
| 2016/0220668 A1 | 8/2016 | Mooney et al. |
| 2016/0228543 A1 | 8/2016 | Mooney et al. |
| 2016/0271298 A1 | 9/2016 | Mooney et al. |
| 2016/0279219 A1 | 9/2016 | Mooney et al. |
| 2016/0279220 A1 | 9/2016 | Mooney et al. |
| 2016/0296611 A1 | 10/2016 | Ali et al. |
| 2017/0042995 A1 | 2/2017 | Ali et al. |
| 2017/0246281 A1 | 8/2017 | Super et al. |
| 2017/0362307 A1 | 12/2017 | Ingber et al. |
| 2017/0368169 A1 | 12/2017 | Loew et al. |
| 2018/0021253 A1 | 1/2018 | Sandeep et al. |
| 2018/0117171 A1 | 5/2018 | Mooney et al. |
| 2018/0164298 A1 | 6/2018 | Ali et al. |
| 2018/0243231 A1 | 8/2018 | Bencherif et al. |
| 2018/0289789 A1 | 10/2018 | Ali et al. |
| 2018/0298047 A1 | 10/2018 | Cheng et al. |
| 2018/0320157 A1 | 11/2018 | Super et al. |
| 2018/0326073 A1 | 11/2018 | Mooney et al. |
| 2018/0344821 A1 | 12/2018 | Kim et al. |
| 2018/0371058 A1 | 12/2018 | Watters et al. |
| 2019/0060525 A1 | 2/2019 | Shah et al. |
| 2019/0076373 A1 | 3/2019 | Bencherif et al. |
| 2019/0125849 A1 | 5/2019 | Mooney et al. |
| 2019/0183992 A1 | 6/2019 | Sands et al. |
| 2019/0216910 A1 | 7/2019 | Mooney et al. |
| 2019/0290696 A1 | 9/2019 | De Miroschedji |
| 2019/0367550 A1 | 12/2019 | Cheng et al. |
| 2020/0024339 A1 | 1/2020 | Springer et al. |
| 2020/0206333 A1 | 7/2020 | Shah et al. |
| 2020/0276290 A1 | 9/2020 | Ali et al. |
| 2020/0297854 A1 | 9/2020 | Ingber et al. |
| 2021/0170007 A1 | 6/2021 | Super et al. |
| 2021/0205233 A1 | 7/2021 | Bencherif et al. |
| 2022/0047778 A1 | 2/2022 | Shah et al. |
| 2022/0107308 A1 | 4/2022 | Mi et al. |
| 2022/0192986 A1 | 6/2022 | Huebsch et al. |

FOREIGN PATENT DOCUMENTS

| | | |
|---|---|---|
| CN | 1487839 A | 4/2004 |
| CN | 1527697 A | 9/2004 |
| CN | 1757662 A | 4/2006 |
| CN | 101584612 A | 11/2009 |
| CN | 101655611 A | 2/2010 |
| CN | 101829361 A | 9/2010 |
| CN | 102000689 A | 4/2011 |
| CN | 102006891 A | 4/2011 |
| CN | 102170903 A | 8/2011 |
| CN | 102947341 A | 2/2013 |
| CN | 103237885 A | 8/2013 |
| CN | 104244929 A | 12/2014 |
| CN | 104411331 A | 3/2015 |
| EP | 0562862 A1 | 9/1993 |
| EP | 1452191 A2 | 9/2004 |
| EP | 1561481 A2 | 8/2005 |
| EP | 1712238 A1 | 10/2006 |
| EP | 1975230 A1 | 10/2008 |
| EP | 2254602 A2 | 12/2010 |
| JP | 2000-503884 A | 4/2000 |
| JP | 2001-049018 A | 2/2001 |
| JP | 2001-524136 A | 11/2001 |
| JP | 2003-506401 A | 2/2003 |
| JP | 2003-180815 A | 7/2003 |
| JP | 2004-159849 A | 6/2004 |
| JP | 2004-520043 A | 7/2004 |
| JP | 2005-160669 A | 6/2005 |
| JP | 2005-168760 A | 6/2005 |
| JP | 2005-170816 A | 6/2005 |
| JP | 2005-528401 A | 9/2005 |
| JP | 2007-500673 A | 1/2007 |
| JP | 2007-503881 A | 3/2007 |
| JP | 2007-505827 A | 3/2007 |
| JP | 2007-528848 A | 10/2007 |
| JP | 2008-515503 A | 5/2008 |
| JP | 2008-528114 A | 7/2008 |
| JP | 2009-519042 A | 5/2009 |
| JP | 2009-521406 A | 6/2009 |
| JP | 2009-540921 A | 11/2009 |
| JP | 2010-502824 A | 1/2010 |
| JP | 2010-508976 A | 3/2010 |
| JP | 2010-227012 A | 10/2010 |
| JP | 2011-511684 A | 4/2011 |
| JP | 2011-511834 A | 4/2011 |
| JP | 2013-531043 A | 8/2013 |
| JP | 2015-503626 A | 2/2015 |
| JP | 2015-516398 A | 6/2015 |
| JP | 2018-117680 A | 8/2018 |
| WO | WO-1996/02555 A1 | 2/1996 |
| WO | WO-1996/16086 A1 | 5/1996 |
| WO | WO-1998/12228 A1 | 3/1998 |
| WO | WO-1998/16266 A1 | 4/1998 |
| WO | WO-1999/44583 A2 | 9/1999 |
| WO | 1999/52356 A1 | 10/1999 |
| WO | WO-1999/51259 A2 | 10/1999 |
| WO | WO-2000/50006 A2 | 8/2000 |
| WO | WO-2001/10421 A1 | 2/2001 |
| WO | WO-2001/35932 A2 | 5/2001 |
| WO | WO-2001/37810 A2 | 5/2001 |
| WO | WO-2002/16557 A2 | 2/2002 |
| WO | WO-2002/40071 A1 | 5/2002 |
| WO | WO-2002/058723 A2 | 8/2002 |
| WO | WO-2002/092054 A2 | 11/2002 |
| WO | 2003/070291 A1 | 3/2003 |
| WO | WO-2003/020161 A2 | 3/2003 |
| WO | WO-2003/020884 A2 | 3/2003 |
| WO | WO-2003/088905 A2 | 10/2003 |
| WO | WO-2004/006990 A2 | 1/2004 |
| WO | WO-2004/029230 A2 | 4/2004 |
| WO | WO-2004/030706 A2 | 4/2004 |
| WO | WO-2004/031371 A2 | 4/2004 |
| WO | WO-2004/089413 A1 | 10/2004 |
| WO | WO-2005/013896 A2 | 2/2005 |
| WO | WO-2005/013933 A1 | 2/2005 |
| WO | WO-2005/020849 A2 | 3/2005 |
| WO | WO-2005/025614 A2 | 3/2005 |
| WO | WO-2005/026318 A2 | 3/2005 |
| WO | WO-2005/037190 A2 | 4/2005 |
| WO | WO-2005/037293 A1 | 4/2005 |
| WO | WO-2005/046748 A1 | 5/2005 |
| WO | WO-2005/072088 A2 | 8/2005 |
| WO | WO-2005/104755 A2 | 11/2005 |

(56) References Cited

FOREIGN PATENT DOCUMENTS

| | | |
|---|---|---|
| WO | WO-2006/039045 A2 | 4/2006 |
| WO | WO-2006/040128 A1 | 4/2006 |
| WO | WO-2006/078987 A2 | 7/2006 |
| WO | WO-2006/113407 A2 | 10/2006 |
| WO | WO-2006/119619 A1 | 11/2006 |
| WO | WO-2006/136905 A2 | 12/2006 |
| WO | 2007/001332 A2 | 1/2007 |
| WO | WO-2007/030901 A1 | 3/2007 |
| WO | WO-2007/039150 A2 | 4/2007 |
| WO | WO-2007/042554 A2 | 4/2007 |
| WO | 2007/051120 A2 | 5/2007 |
| WO | 2007/068489 A2 | 6/2007 |
| WO | WO-2007/063075 A1 | 6/2007 |
| WO | WO-2007/064152 A1 | 6/2007 |
| WO | WO-2007/070660 A2 | 6/2007 |
| WO | WO-2007/078196 A1 | 7/2007 |
| WO | WO-2007/087585 A1 | 8/2007 |
| WO | WO-2007/089870 A2 | 8/2007 |
| WO | WO-2007/107739 A1 | 9/2007 |
| WO | WO-2007/149161 A2 | 12/2007 |
| WO | WO-2007/150020 A1 | 12/2007 |
| WO | WO-2008/008266 A2 | 1/2008 |
| WO | WO-2008/018707 A1 | 2/2008 |
| WO | WO-2008/031525 A1 | 3/2008 |
| WO | WO-2008/043157 A1 | 4/2008 |
| WO | WO-2008/057600 A2 | 5/2008 |
| WO | WO-2008/109852 A2 | 9/2008 |
| WO | WO-2008/114149 A2 | 9/2008 |
| WO | WO-2008/148761 A1 | 12/2008 |
| WO | WO-2008/157394 A2 | 12/2008 |
| WO | WO-2009/002401 A2 | 12/2008 |
| WO | WO-2009/005769 A2 | 1/2009 |
| WO | WO-2009/018500 A1 | 2/2009 |
| WO | WO-2009/024775 A1 | 2/2009 |
| WO | WO-2009/072767 A2 | 6/2009 |
| WO | WO-2009/074341 A1 | 6/2009 |
| WO | WO-2009/100716 A2 | 8/2009 |
| WO | WO-2009/102465 A2 | 8/2009 |
| WO | WO-2009/146456 A1 | 12/2009 |
| WO | WO-2009/155583 A1 | 12/2009 |
| WO | WO-2010/078209 A2 | 7/2010 |
| WO | WO-2010/120749 A2 | 10/2010 |
| WO | WO-2011/014871 A1 | 2/2011 |
| WO | WO-2011/043834 A1 | 4/2011 |
| WO | WO-2011/043835 A1 | 4/2011 |
| WO | WO-2011/063336 A2 | 5/2011 |
| WO | WO-2011/109834 A2 | 9/2011 |
| WO | WO-2011/130753 A2 | 10/2011 |
| WO | WO-2011/150240 A1 | 12/2011 |
| WO | WO-2011/151431 A1 | 12/2011 |
| WO | WO-2011/163669 A2 | 12/2011 |
| WO | WO-2012/009611 A2 | 1/2012 |
| WO | WO-2012/019049 A1 | 2/2012 |
| WO | WO-2012/048165 A2 | 4/2012 |
| WO | WO-2012/064697 A2 | 5/2012 |
| WO | WO-2012/148684 A1 | 11/2012 |
| WO | WO-2012/149358 A1 | 11/2012 |
| WO | WO-2012/167230 A1 | 12/2012 |
| WO | WO-2013/012924 A2 | 1/2013 |
| WO | WO-2013/106852 A1 | 7/2013 |
| WO | WO-2013/158673 A1 | 10/2013 |
| WO | WO-2013/172967 A1 | 11/2013 |
| WO | WO-2013/190555 A1 | 12/2013 |
| WO | WO-2014/063128 A1 | 4/2014 |
| WO | 2014/190229 A1 | 11/2014 |
| WO | WO-2014/189805 A1 | 11/2014 |
| WO | WO-2015/066535 A1 | 5/2015 |
| WO | 2015/148775 A1 | 10/2015 |
| WO | WO-2015/154078 A1 | 10/2015 |
| WO | WO-2015/168379 A2 | 11/2015 |
| WO | WO-2016/004068 A1 | 1/2016 |
| WO | WO-2016/123573 A1 | 8/2016 |
| WO | WO-2016/161372 A1 | 10/2016 |
| WO | 2017/136837 A1 | 8/2017 |
| WO | WO-2017/143024 A2 | 8/2017 |
| WO | WO-2018/013797 A1 | 1/2018 |
| WO | WO-2018/026884 A1 | 2/2018 |
| WO | 2018/144966 A1 | 8/2018 |
| WO | 2018/170414 A1 | 9/2018 |
| WO | 2018/213631 A1 | 11/2018 |
| WO | 2018/227205 A1 | 12/2018 |
| WO | 2020/061129 A1 | 3/2020 |
| WO | 2021/155297 A1 | 8/2021 |

OTHER PUBLICATIONS

U.S. Appl. No. 13/877,572, filed Nov. 19, 2013, 2014-0079752, Published.
U.S. Appl. No. 15/617,837, filed Jun. 8, 2017, 2018-0243231, Published.
U.S. Appl. No. 15/935,392, filed Mar. 26, 2018, 2018-0344821, Issued.
U.S. Appl. No. 15/303,985, filed Oct. 13, 2016, 2017-0042995, Published.
U.S. Appl. No. 15/135,216, filed Apr. 21, 2016, U.S. Pat. No. 9,821,045, Issued.
U.S. Appl. No. 15/818,509, filed Nov. 20, 2017, 2018-0289789, Published.
U.S. Appl. No. 15/563,878, filed Oct. 2, 2017, 2018-0117171, Published.
Kim et al., Galectin-3 binding protein promotes cell motility in colon cancer by stimulating the shedding of protein tyrosine phosphatase kappa by proprotein convertase 5. Biochem Biophys Res Commun. Jan. 7, 2011;404(1):96-102.
Wegman et al., Combination of bone morphogenetic protein-2 plasmid DNA with chemokine CXCL12 creates an additive effect on bone formation onset and volume. Eur Cell Mater. Jul. 27, 2015;30:1-11.
Yu et al., Specific bone cells produce DLL4 to generate thymus-seeding progenitors from bone marrow. J Exp Med. May 4, 2015;212(5):759-74.
Abrahams et al., Expression and secretion of antiviral factors by trophoblast cells following stimulation by the TLR-3 agonist, Poly(I : C). Hum Reprod. Sep. 2006;21(9):2432-9.
Agache et al., Mechanical properties and Young's modulus of human skin in vivo. Arch Dermatol Res. 1980;269(3):221-32.
Agrawal et al., Cutting edge: different Toll-like receptor agonists instruct dendritic cells to induce distinct Th responses via differential modulation of extracellular signal-regulated kinase-mitogen-activated protein kinase and c-Fos. J Immunol. Nov. 15, 2003;171(10):4984-9.
Aguado et al., Improving viability of stem cells during syringe needle flow through the design of hydrogel cell carriers. Tissue Eng Part A. Apr. 2012;18(7-8):806-15.
Akira et al., Pathogen recognition and innate immunity. Cell. Feb. 24, 2006;124(4):783-801.
Akira et al., Toll-like receptors: critical proteins linking innate and acquired immunity. Nat Immunol. Aug. 2001;2(8):675-80.
Akpalo et al., Fibrin-polyethylene oxide interpenetrating polymer networks: new self-supported biomaterials combining the properties of both protein gel and synthetic polymer. Acta Biomater. Jun. 2011;7(6):2418-27.
Aldhous, Print Me a Heart and a Set of Arteries. New Scientist. 2006;2547:19.
Ali et al., Biomaterial-based vaccine induces regression of established intracranial glioma in rats. Pharm Res. May 2011;28(5):1074-80.
Ali et al., Controlled Local Delivery of GM-CSF From Polymer-Based Vaccines Enhances Anti-Tumor Immune Responses by Priming Host Dendritic Cells. 2007 AACR Annual Meeting. 2007;48:652, Abstract #2736.
Ali et al., Converging Cell Therapy with Biomaterials. Cell Transplantation from Laboratory to Clinic. 2006:591-609.
Ali et al., Identification of immune factors regulating antitumor immunity using polymeric vaccines with multiple adjuvants. Cancer Res. Mar. 15, 2014;74(6):1670-81.
Ali et al., In situ regulation of DC subsets and T cells mediates tumor regression in mice. Sci Transl Med. Nov. 25, 2009;1(8):8ra19, 1-10.

(56) References Cited

OTHER PUBLICATIONS

Ali et al., Infection-mimicking materials to program dendritic cells in situ. Nat Mater. Feb. 2009;8(2):151-8.
Ali et al., Inflammatory cytokines presented from polymer matrices differentially generate and activate DCs in situ.. Adv Funct Mater. Aug. 1, 2013;23(36):4621-4628.
Ali et al., Relationship of vaccine efficacy to the kinetics of DC and T-cell responses induced by PLG-based cancer vaccines. Biomater. 2011;1(1):66-75.
Ali et al., Sustained GM-CSF and PEI condensed pDNA presentation increases the level and duration of gene expression in dendritic cells. J Control Release. Dec. 18, 2008;132(3):273-8.
Ali et al., The efficacy of intracranial PLG-based vaccines is dependent on direct implantation into brain tissue. J Control Release. Sep. 25, 2011;154(3):249-57.
Allen et al., Regulation of satellite cells during skeletal muscle growth and development. Proc Soc Exp Biol Med. Jun. 1990;194(2):81-6.
Allen et al., Regulation of skeletal muscle satellite cell proliferation by bovine pituitary fibroblast growth factor. Exp Cell Res. May 1984;152(1):154-60.
Almarza et al., Evaluation of three growth factors in combinations of two for temporomandibular joint disc tissue engineering. Arch Oral Biol. Mar. 2006;51(3):215-21.
Alsberg et al., Cell-interactive alginate hydrogels for bone tissue engineering. J Dent Res. Nov. 2001;80(11):2025-9.
Alsberg et al., Engineering growing tissues. Proc Natl Acad Sci U S A. Sep. 17, 2002;99(19):12025-30.
Alsberg et al., Regulating bone formation via controlled scaffold degradation. J Dent Res. Nov. 2003;82(11):903-8.
Ambrosini et al., Astrocytes produce dendritic cell-attracting chemokines in vitro and in multiple sclerosis lesions. J Neuropathol Exp Neurol. Aug. 2005;64(8):706-15.
Anderson et al., Biomaterial microarrays: rapid, microscale screening of polymer-cell interaction. Biomaterials. Aug. 2005;26(23):4892-7.
Anderson et al., Crosslinking CD3 with CD2 using sepharose-immobilized antibodies enhances T lymphocyte proliferation. Cell Immunol. Sep. 1988;115(2):246-56.
Anderson et al., Nanoliter-scale synthesis of arrayed biomaterials and application to human embryonic stem cells. Nat Biotechnol. Jul. 2004;22(7):863-6.
Anderson, A role for nitric oxide in muscle repair: nitric oxide-mediated activation of muscle satellite cells. Mol Biol Cell. May 2000;11(5):1859-74.
Annabi et al., Controlling the porosity and microarchitecture of hydrogels for tissue engineering. Tissue Eng Part B Rev. Aug. 2010;16(4):371-83.
Annual Review. 2008:122-131.
Arany et al., At the edge of translation—materials to program cells for directed differentiation. Oral Dis. Apr. 2011;17(3):241-51.
Aschner et al., Metabolic memory for vascular disease in diabetes. Diabetes Technol Ther. Jun. 2012;14 Suppl 1:S68-74.
Atala et al., Endoscopic treatment of vesicoureteral reflux with a chondrocyte-alginate suspension. J Urol. Aug. 1994; 152(2 Pt 2):641-3.
Aubin et al., Directed 3D cell alignment and elongation in microengineered hydrogels. Biomaterials. Sep. 2010;31(27):6941-6951.
Augst et al., Alginate hydrogels as biomaterials. Macromol Biosci. Aug. 7, 2006;6(8):623-33.
Babensee et al., Host response to tissue engineered devices. Advanced Drug Delivery Reviews. Aug. 3, 1998;33(1-2):111-139.
Bachelder et al., Acid-degradable polyurethane particles for protein-based vaccines: biological evaluation and in vitro analysis of particle degradation products. Mol Pharm. Sep.-Oct. 2008;5(5):876-84.

Bachem et al., Superior antigen cross-presentation and XCR1 expression define human CD11c+CD141+ cells as homologues of mouse CD8+ dendritic cells. J Exp Med. Jun. 7, 2010;207(6):1273-81.
Badovinac et al., Regulation of CD8+ T cells undergoing primary and secondary responses to infection in the same host. J Immunol. May 15, 2003;170(10):4933-42.
Bakri et al., Pharmacokinetics of intravitreal bevacizumab (Avastin). Ophthalmology. May 2007;114(5):855-9.
Balakrishna et al., Structural correlates of antibacterial and membrane-permeabilizing activities in acylpolyamines. Antimicrob Agents Chemother. Mar. 2006;50(3):852-61.
Banchereau et al., Dendritic cells and the control of immunity. Nature. Mar. 19, 1998;392(6673):245-52.
Bar-Cohen et al., Electroactive Polymer Actuators and Sensors. MRS Bullet. 2008;33(3):173-181.
Bar-Or et al., Induction of antigen-specific tolerance in multiple sclerosis after immunization with DNA encoding myelin basic protein in a randomized, placebo-controlled phase 1/2 trial. Arch Neurol. Oct. 2007;64(10):1407-15.
Barbero et al., Growth factor supplemented matrigel improves ectopic skeletal muscle formation—a cell therapy approach. J Cell Physiol. Feb. 2001;186(2):183-92.
Barbucci et al., Hyaluronic acid hydrogel in the treatment of osteoarthritis. Biomaterials. Dec. 2002;23(23):4503-13.
Baroja et al., The anti-T cell monoclonal antibody 9.3 (anti-CD28) provides a helper signal and bypasses the need for accessory cells in T cell activation with immobilized anti-CD3 and mitogens. Cell Immunol. Apr. 15, 1989;120(1):205-17.
Barrio et al., A two-dimensional numerical study of spatial pattern formation in interacting Turing systems. Bull Math Biol. May 1999;61(3):483-505.
Baskin et al., Copper-free click chemistry for dynamic in vivo imaging. Proc Natl Acad Sci U S A. Oct. 23, 2007;104(43):16793-7.
Bates, Improved muscle regeneration by combining VEGF with IGF1. Regen Med. Nov. 2010;5(6):853-4.
Beaucage et al., The Functionalization of Oligonucleotides Via Phosphoramidite Derivatives. Tetrahedron. Mar. 5, 1993;49(10):1925-1963.
Beauchamp et al., Dynamics of myoblast transplantation reveal a discrete minority of precursors with stem cell-like properties as the myogenic source. J Cell Biol. Mar. 22, 1999;144(6):1113-22.
Becker et al., Cytological demonstration of the clonal nature of spleen colonies derived from transplanted mouse marrow cells. Nature. Feb. 2, 1963;197:452-4.
Beebe et al., Functional hydrogel structures for autonomous flow control inside microfluidic channels. Nature. Apr. 6, 2000;404(6778):588-90.
Bekiari et al., Study of poly(N,N-dimethylacrylamide)/CdS nanocomposite organic/inorganic gels. Langmuir. Sep. 14, 2004;20(19):7972-5.
Bell, Models for the specific adhesion of cells to cells. Science. May 12, 1978;200(4342):618-27.
Bencherif et al., End-group effects on the properties of PEG-co-PGA hydrogels. Acta Biomater. Jul. 2009;5(6):1872-83.
Bencherif et al., Influence of cross-linker chemistry on release kinetics of PEG-co-PGA hydrogels. J Biomed Mater Res A. Jul. 2009;90(1):142-53.
Bencherif et al., Influence of the degree of methacrylation on hyaluronic acid hydrogels properties. Biomaterials. Apr. 2008;29(12):1739-49.
Bencherif et al., Injectable preformed scaffolds with shape-memory properties. Proc Natl Acad Sci U S A. Nov. 27, 2012;109(48):19590-5.
Bencherif et al., Nanostructured hybrid hydrogels prepared by a combination of atom transfer radical polymerization and free radical polymerization. Biomaterials. Oct. 2009;30(29):5270-8.
Bencherif et al., Synthesis by AGET ATRP of degradable nanogel precursors for in situ formation of nanostructured hyaluronic acid hydrogel. Biomacromolecules. Sep. 14, 2009;10(9):2499-507.
Benton et al., Photocrosslinking of gelatin macromers to synthesize porous hydrogels that promote valvular interstitial cell function. Tissue Eng Part A. Nov. 2009;15(11):3221-30.

(56) References Cited

OTHER PUBLICATIONS

Berg et al., Il-10 is a central regulator of cyclooxygenase-2 expression and prostaglandin production. J Immunol. Feb. 15, 2001;166(4):2674-80.
Bergstraesser et al., Stimulation and inhibition of human mammary epithelial cell duct morphogenesis in vitro. Proc Assoc Am Physicians. Mar. 1996;108(2):140-54.
Bianco et al., The meaning, the sense and the significance: translating the science of mesenchymal stem cells into medicine. Nat Med. Jan. 2013;19(1):35-42.
Bierer et al., T cell receptors: adhesion and signaling. Adv Cancer Res. 1991;56:49-76.
Bilodeau et al., Regular Pyramid Punch Problem. J Appl Mech. 1992;59(3):519-523.
Bischoff, Proliferation of muscle satellite cells on intact myofibers in culture. Dev Biol. May 1986;115(1):129-39.
Bjork et al., Tuning the shape of mesoporous silica particles by alterations in parameter space: from rods to platelets. Langmuir. Nov. 5, 2013;29(44):13551-61.
Blumenthal et al., Polyurethane scaffolds seeded with genetically engineered skeletal myoblasts: a promising tool to regenerate myocardial function. Artif Organs. Feb. 2010;34(2):E46-54.
Boateng et al., Wound healing dressings and drug delivery systems: a review. J Pharm Sci. Aug. 2008;97(8):2892-923.
Boerckel et al., Mechanical regulation of vascular growth and tissue regeneration in vivo. Proc Natl Acad Sci U S A. Sep. 13, 2011;108(37):E674-80.
Bohl et al., Role of synthetic extracellular matrix in development of engineered dental pulp. J Biomater Sci Polym Ed. 1998;9(7):749-64.
Bojarova et al., Sugared biomaterial binding lectins: achievements and perspectives. Biomater Sci. Jul. 19, 2016;4(8):1142-60.
Bonauer et al., MicroRNA-92a controls angiogenesis and functional recovery of ischemic tissues in mice. Science. Jun. 26, 2009;324(5935):1710-3.
Boontheekul et al., Controlling alginate gel degradation utilizing partial oxidation and bimodal molecular weight distribution. Biomaterials. May 2005;26(15):2455-65.
Boontheekul et al., Regulating myoblast phenotype through controlled gel stiffness and degradation. Tissue Eng. Jul. 2007;13(7):1431-42.
Borselli et al., Functional muscle regeneration with combined delivery of angiogenesis and myogenesis factors. Proc Natl Acad Sci U S A. Feb. 23, 2010;107(8):3287-92.
Bouhadir et al., Degradation of partially oxidized alginate and its potential application for tissue engineering. Biotechnol Prog. Sep.-Oct. 2001;17(5):945-50.
Bouhadir et al., Synthesis of Cross-Linked Poly(aldehyde guluronate) Hydrogels. Polymer. Jun. 1999;40(12):3575-3584.
Bowne et al., Injection of DNA encoding granulocyte-macrophage colony-stimulating factor recruits dendritic cells for immune adjuvant effects. Cytokines Cell Mol Ther. Dec. 1999;5(4):217-25.
Brignone et al., A phase I pharmacokinetic and biological correlative study of IMP321, a novel MHC class II agonist, in patients with advanced renal cell carcinoma. Clin Cancer Res. Oct. 1, 2009;15(19):6225-31.
Brinkman et al., Photo-cross-linking of type I collagen gels in the presence of smooth muscle cells: mechanical properties, cell viability, and function. Biomacromolecules. Jul.-Aug. 2003;4(4):890-5.
Brinkmann et al., Neutrophil extracellular traps kill bacteria. Science. Mar. 5, 2004;303(5663):1532-5.
Bristol-Myers Squibb, Investigational Anti-PD-1 Immunotherapy BMS-936558 Showed Clinical Activity in Phase 1 Trial of Patients with Previously-Treated non-Small-Cell Lung Cancer, Metastatic Melanoma adn Renal Cell Cancer. Financial Times. 3 pages, Jun. 2, 2012.
Brodie et al., In vivo migration and function of transferred HIV-1-specific cytotoxic T cells. Nat Med. Jan. 1999;5(1):34-41.
Brouwers et al., Can the growth factors PTHrP, Ihh and VEGF, together regulate the development of a long bone? J Biomech. 2006;39(15):2774-82.
Broxmeyer, Insights into the biology of cord blood stem/progenitor cells. Cell Prolif. Apr. 2011;44 Suppl 1:55-9.
Brunner et al., Enhanced dendritic cell maturation by TNF-alpha or cytidine-phosphate-guanosine DNA drives T cell activation in vitro and therapeutic anti-tumor immune responses in vivo. J Immunol. Dec. 1, 2000;5(11):6278-86.
Bryant et al., Photo-patterning of porous hydrogels for tissue engineering. Biomaterials. Jul. 2007;28(19):2978-86.
Buckwalter et al., Form of Antigen Dictates Immunity: Irradiated Cell vs. Whole Cell Lysate Vaccination. J Immunol. Apr. 1, 2007;178(1 Suppl):S77.
Bullard et al., Fetal wound healing: current biology. World J Surg. Jan. 2003;27(1):54-61.
Buonaguro et al., Translating tumor antigens into cancer vaccines. Clin Vaccine Immunol. Jan. 2011;18(1):23-34.
Burdick et al., Controlled degradation and mechanical behavior of photopolymerized hyaluronic acid networks. Biomacromolecules. Jan.-Feb. 2005;6(1):386-91.
Burdick et al., Photoencapsulation of osteoblasts in injectable RGD-modified PEG hydrogels for bone tissue engineering. Biomaterials. Nov. 2002;23(22):4315-23.
Burdick et al., Stimulation of neurite outgrowth by neurotrophins delivered from degradable hydrogels. Biomaterials. Jan. 2006;27(3):452-9.
Burger et al., Effect of VEGF and its receptor antagonist SU-5416, an inhibitor of angiogenesis, on processing of the beta-amyloid precursor protein in primary neuronal cells derived from brain tissue of Tg2576 mice. Int J Dev Neurosci. Nov. 2010;28(7):597-604.
Bégué et al., Vaccination against human papillomavirus. Implementation and efficacy against cervical cancer control. Bull Acad Natl Med. Dec. 2007;191(9):1805-16.
Callahan et al., At the bedside: CTLA-4- and PD-1-blocking antibodies in cancer immunotherapy. J Leukoc Biol. Jul. 2013;94(1):41-53.
Calvert, Electroactive Polymer Gels. Electroactive Polymer (EAP) Acutators as Artificial Muscle: Reality, Potential, and Challenges. Bar-Cohen, (Ed.), Spie Press, Bellingham, WA. 151-170. (2004).
Calvert, Gel Sensors and Actuators. MRS Bullet. 2008;33(3):207-212.
Cameron et al., The influence of substrate creep on mesenchymal stem cell behaviour and phenotype. Biomaterials. Sep. 2011;32(26):5979-93.
Cao et al., Promoting angiogenesis via manipulation of VEGF responsiveness with notch signaling. Biomaterials. Sep. 2009;30(25):4085-93.
care.diabetesjournals.org, Standards of Medical Care in Diabetes. Diabetes Care. Jan. 2013;36(Suppl 1):S1-S2.
Carlson et al., Notch signaling pathway and tissue engineering. Front Biosci. Sep. 1, 2007;12:5143-56.
Carmeliet et al., Angiogenesis in cancer and other diseases. Nature. Sep. 14, 2000;407(6801):249-57.
Carmeliet, Mechanisms of angiogenesis and arteriogenesis. Nat Med. Apr. 2000;6(4):389-95.
Caulfield et al., Regulation of major histocompatibility complex class II antigens on human alveolar macrophages by granulocyte-macrophage colony-stimulating factor in the presence of glucocorticoids. Immunology. Sep. 1999;98(1):104-10.
Ceriello et al., Clinical review 2: The "metabolic memory": is more than just tight glucose control necessary to prevent diabetic complications? J Clin Endocrinol Metab. Feb. 2009;94(2):410-5.
Ceriello et al., The emerging challenge in diabetes: the "metabolic memory". Vascul Pharmacol. Nov.-Dec. 2012;57(5-6):133-8.
Champion et al., Shape induced inhibition of phagocytosis of polymer particles. Pharm Res. Jan. 2009;26(1):244-9.
Chan et al., Antifibrotic effects of suramin in injured skeletal muscle after laceration. J Appl Physiol. Sep. 2003;95(2):771-80.
Chan et al., Helix induction in antimicrobial peptides by alginate in biofilms. J Biol Chem. Sep. 10, 2004;279(37):38749-54.
Chan et al., Traction dynamics of filopodia on compliant substrates. Science. Dec. 12, 2008;322(5908):1687-91.

(56) References Cited

OTHER PUBLICATIONS

Chang, Mouse models for studies of retinal degeneration and diseases. Methods Mol Biol. 2013;935:27-39.
Chapman, Endosomal proteases in antigen presentation. Curr Opin Immunol. Feb. 2006;18(1):78-84.
Chen et al., Adipogenic differentiation of adipose tissue-derived human mesenchymal stem cells: effect of gastric bypass surgery. Surg Endosc. Dec. 2012;26(12):3449-56.
Chen et al., Functional Human Vascular Network Generated in Photocrosslinkable Gelatin Methacrylate Hydrogels. Adv Funct Mater. May 23, 2012;22(10):2027-2039.
Chen et al., Integrated approach to designing growth factor delivery systems. FASEB J. Dec. 2007;21(14):3896-903.
Chen et al., Polymeric growth factor delivery strategies for tissue engineering. Pharm Res. Aug. 2003;20(8):1103-12.
Chen et al., Skeletal muscle stem cells. Reprod Biol Endocrinol. Nov. 13, 2003;1:101. 7 pages.
Chen et al., Spatio-temporal VEGF and PDGF delivery patterns blood vessel formation and maturation. Pharm Res. Feb. 2007;24(2):258-64.
Chiang et al., Whole tumor antigen vaccines. Semin Immunol. Jun. 2010;22(3):132-43.
Choi et al., In vitro mineralization by preosteoblasts in poly(DL-lactide-co-glycolide) inverse opal scaffolds reinforced with hydroxyapatite nanoparticles. Langmuir. Jul. 20, 2010;26(14):12126-31.
Choi et al., Three-dimensional scaffolds for tissue engineering: the importance of uniformity in pore size and structure. Langmuir. Dec. 21, 2010;26(24):19001-6.
Choi, Replacement Organs, Hot Off the Press. New Scientist. 2003;177(2379):16.
Chou et al., Characterization of Photocross Linked Alginate Hydrogels for Nucleus Pulposus Cell Encapsulation. J Biomed Mater Res A. 2009;91 A(1):187-194.
Chromiak et al., Bioreactor perfusion system for the long-term maintenance of tissue-engineered skeletal muscle organoids. In Vitro Cell Dev Biol Anim. Oct. 1998;34(9):694-703.
Clark et al.. Myosin II and mechanotransduction: a balancing act. Trends Cell Biol. Apr. 2007;17(4):178-86.
Clauss et al., Interstitial transport of rabbit and sheep antibodies in normal and neoplastic tissues. Cancer Res. Jun. 15, 1990;50(12):3487-92.
ClinicalTrials.gov, NCT00729664, Multiple Ascending Dose (MDX1105-01) (Anti-PDL1). 4 pages, Sep. 3, 2015.
ClinicalTrials.gov, NCT00730639, A Phase 1 Study of Nivolumab (BMS-936558) in Subjects with Advanced or Recurrent Malignancies (MDX1106-03). 5 pages, Mar. 24, 2016.
ClinicalTrials.gov, NCT01352884, Study to Assess the Safety, and Pharmacokinetics of AMP-224 in Patients with Advanced Cancer. 3 pages, Sep. 2, 2016.
ClinicalTrials.gov, NCT01391143, Safety Study of MGA271 in Refractory Cancer. 4 pages, Sep. 28, 2016.
Cohen et al., Controlled delivery systems for proteins based on poly(lactic/glycolic acid) microspheres. Pharm Res. Jun. 1991;8(6):713-20.
Comisar et al., Engineering RGD nanopatterned hydrogels to control preosteoblast behavior: a combined computational and experimental approach. Biomaterials. Oct. 2007;28(30):4409-17.
Conboy et al., The regulation of Notch signaling controls satellite cell activation and cell fate determination in postnatal myogenesis. Dev Cell. Sep. 2002;3(3):397-409.
Conconi et al., In vitro and in vivo evaluation of acellular diaphragmatic matrices seeded with muscle precursors cells and coated with VEGF silica gels to repair muscle defect of the diaphragm. J Biomed Mater Res A. May 2009;89(2):304-16.
Conn et al., Purification of a glycoprotein vascular endothelial cell mitogen from a rat glioma-derived cell line. Proc Natl Acad Sci U S A. Feb. 1990;87(4):1323-7.
Cook et al., A sialomucopeptide liberated by trypsin from the human erythrocyte. Nature. Dec. 17, 1960;188:1011-2.
Cooper et al., Extended amplification in vitro and replicative senescence: key factors implicated in the success of human myoblast transplantation. Hum Gene Ther. Aug. 10, 2003;14(12):1169-79.
Cooper, Metabolic memory: implications for diabetic vascular complications. Pediatr Diabetes. Aug. 2009;10(5):343-6.
Corcione et al., CCL19 and CXCL12 trigger in vitro chemotaxis of human mantle cell lymphoma B cells. Clin Cancer Res. Feb. 1, 2004;10(3):964-71.
Cornelison et al., Single-cell analysis of regulatory gene expression in quiescent and activated mouse skeletal muscle satellite cells. Dev Biol. Nov. 15, 1997;191(2):270-83.
Cornelison et al., Syndecan-3 and syndecan-4 specifically mark skeletal muscle satellite cells and are implicated in satellite cell maintenance and muscle regeneration. Dev Biol. Nov. 1, 2001;239(1):79-94.
Coulson et al., Flow of Fluids through Granular Beds and Packed Columns. Chemical Engineering, vol. 2. Third Edition. Pergamon Press. Chapter 4, pp. 125-171, (1978).
Crameri et al., Improved green fluorescent protein by molecular evolution using DNA shuffling. Nat Biotechnol. Mar. 1996;14(3):315-9.
Cuda et al., In vitro actin filament sliding velocities produced by mixtures of different types of myosin. Biophys J. Apr. 1997;72(4):1767-79.
Cukierman et al., Taking cell-matrix adhesions to the third dimension. Science. Nov. 23, 2001;294(5547):1708-12.
Cullen et al., Investigation of vascular endothelial growth factor effects on pulmonary endothelial monolayer permeability and neutrophil transmigration. Gen Pharmacol. Sep. 2000;35(3):149-57.
Curiel et al., Tumor immunotherapy: inching toward the finish line. J Clin Invest. Feb. 2002;109(3):311-2.
Curran et al., PD-1 and CTLA-4 combination blockade expands infiltrating T cells and reduces regulatory T and myeloid cells within B16 melanoma tumors. Proc Natl Acad Sci U S A. Mar. 2, 2010;107(9):4275-80.
D'Amico et al., The early progenitors of mouse dendritic cells and plasmacytoid predendritic cells are within the bone marrow hemopoietic precursors expressing Flt3. J Exp Med. Jul. 21, 2003;198(2):293-303.
Dainiak et al., Gelatin-fibrinogen cryogel dermal matrices for wound repair: preparation, optimisation and in vitro study. Biomaterials. Jan. 2010;31(1):67-76.
Damle et al., Stimulation via the CD3 and CD28 molecules induces responsiveness to IL-4 in CD4+CD29+CD45R-memory T lymphocytes. J Immunol. Sep. 15, 1989;143(6):1761-7.
Dar et al., Optimization of cardiac cell seeding and distribution in 3D porous alginate scaffolds. Biotechnol Bioeng. Nov. 5, 2002;80(3):305-12.
Daro et al., Polyethylene glycol-modified GM-CSF expands CD11b(high)CD11c(high) but not CD11b(low)CD11c(high) murine dendritic cells in vivo: a comparative analysis with Flt3 ligand. J Immunol. Jul. 1, 2000;165(1):49-58.
David et al., The in vitro Desensitization of Sensitive Cells by Trypsin. J Exp Med. Dec. 1, 1964;120:1189-200.
Davies et al., Antibody-antigen complexes. Annu Rev Biochem. 1990;59:439-73.
De Jong et al., Regulation of Notch signaling genes during BMP2-induced differentiation of osteoblast precursor cells. Biochem Biophys Res Commun. Jul. 16, 2004;320(1):100-7.
De Temmerman et al., Particulate vaccines: on the quest for optimal delivery and immune response. Drug Discov Today. Jul. 2011;16(13-14):569-82.
Dembo et al., Stresses at the cell-to-substrate interface during locomotion of fibroblasts. Biophys J. Apr. 1999;76(4):2307-16.
Den Haan et al., CD8(+) but not CD8(-) dendritic cells cross-prime cytotoxic T cells in vivo. J Exp Med. Dec. 18, 2000;192(12):1685-96.
Dennis et al., Excitability and contractility of skeletal muscle engineered from primary cultures and cell lines. Am J Physiol Cell Physiol. Feb. 2001;280(2):C288-95.
Dennis et al., Excitability and isometric contractile properties of mammalian skeletal muscle constructs engineered in vitro. In Vitro Cell Dev Biol Anim. May 2000;36(5):327-35.

(56) References Cited

OTHER PUBLICATIONS

Deshmane et al., Monocyte chemoattractant protein-1 (MCP-1): an overview. J Interferon Cytokine Res. Jun. 2009;29(6):313-26.

Dexter et al., Conditions controlling the proliferation of haemopoietic stem cells in vitro. J Cell Physiol. Jun. 1977;91(3):335-44.

Diduch et al., Two cell lines from bone marrow that differ in terms of collagen synthesis, osteogenic characteristics, and matrix mineralization. J Bone Joint Surg Am. Jan. 1993;75(1):92-105.

Dieu et al., Selective recruitment of immature and mature dendritic cells by distinct chemokines expressed in different anatomic sites. J Exp Med. Jul. 20, 1998;188(2):373-86.

Diridollou et al., Skin ageing: changes of physical properties of human skin in vivo. Int J Cosmet Sci. Dec. 2001;23(6):353-62.

Discher et al., Tissue cells feel and respond to the stiffness of their substrate. Science. Nov. 18, 2005;310(5751):1139-43.

Disis et al., Granulocyte-macrophage colony-stimulating factor: an effective adjuvant for protein and peptide-based vaccines. Blood. Jul. 1, 1996;88(1):202-10.

Doan et al., Antigens and Receptors. Lippincott's Illustrated Reviews: Immunology. Wolters Kluwer/Lippincott Williams & Wilsons, Philadelphia. Chapter 12, pp. 11-23, (2008).

Doan et al., Subcellular localization of a sporulation membrane protein is achieved through a network of interactions along and across the septum. Mol Microbiol. Mar. 2005;55(6):1767-81.

Donati et al., New hypothesis on the role of alternating sequences in calcium-alginate gels. Biomacromolecules. Mar.-Apr. 2005;6(2):1031-40.

Dong et al., Antitumor effect of secreted Flt3-ligand can act at distant tumor sites in a murine model of head and neck cancer. Cancer Gene Ther. Feb. 2003;10(2):96-104.

Dor et al., Making vascular networks in the adult: branching morphogenesis without a roadmap. Trends Cell Biol. Mar. 2003;13(3):131-6.

Douay et al., Ex vivo production of human red blood cells from hematopoietic stem cells: what is the future in transfusion? Transfus Med Rev. Apr. 2007;21(2):91-100.

Dranoff et al., Vaccination with irradiated tumor cells engineered to secrete murine granulocyte-macrophage colony-stimulating factor stimulates potent, specific, and long-lasting anti-tumor immunity. Proc Natl Acad Sci U S A. Apr. 15, 1993;90(8):3539-43.

Dranoff, Cytokines in cancer pathogenesis and cancer therapy. Nat Rev Cancer. Jan. 2004;4(1):11-22.

Dranoff, GM-CSF-based cancer vaccines. Immunol Rev. Oct. 2002;188:147-54.

Dudley et al. Adoptive cell transfer therapy following non-myeloablative but lymphodepleting chemotherapy for the treatment of patients with refractory metastatic melanoma. J Clin Oncol. Apr. 1, 2005;23(10):2346-57.

Dudley et al., CD8+ enriched "young" tumor infiltrating lymphocytes can mediate regression of metastatic melanoma. Clin Cancer Res. Dec. 15, 2010;16(24):6122-31.

Dufort et al., Balancing forces: architectural control of mechanotransduction. Nat Rev Mol Cell Biol. May 2011;12(5):308-19.

Dupont et al., Role of YAP/TAZ in mechanotransduction. Nature. Jun. 8, 2011;474(7350):179-83.

Duraiswamy et al., Dual blockade of PD-1 and CTLA-4 combined with tumor vaccine effectively restores T-cell rejection function in tumors—response. Cancer Res. Jan. 15, 2014;74(2):633-4.

Duraiswamy et al., Dual blockade of PD-1 and CTLA-4 combined with tumor vaccine effectively restores T-cell rejection function in tumors. Cancer Res. Jun. 15, 2013;73(12):3591-603.

Edwards et al.. Evaluation of biomechanical properties of human skin. Clin Dermatol. Jul.-Aug. 1995;13(4):375-80.

Egholm et al., Peptide Nucleic Acids (PNA). Oligonucleotide Analogues with an Achiral Peptide Backbone. J Am Chem Soc. 1992;114(5):1895-1897.

Egholm et al., PNA hybridizes to complementary oligonucleotides obeying the Watson-Crick hydrogen-bonding rules. Nature. Oct. 7, 1993;365(6446):566-8.

Ehrbar et al., Endothelial cell proliferation and progenitor maturation by fibrin-bound VEGF variants with differential susceptibilities to local cellular activity. J Control Release. Jan. 3, 2005;101(1-3):93-109.

Eiselt et al., Porous carriers for biomedical applications based on alginate hydrogels. Biomaterials. Oct. 2000;21(19):1921-7.

El-Backly et al., Regeneration of dentine/pulp-like tissue using a dental pulp stem cell/poly(lactic-co-glycolic) acid scaffold construct in New Zealand white rabbits. Aust Endod J. Aug. 2008;34(2):52-67.

El-Behi et al., The encephalitogenicity of T(H)17 cells is dependent on IL-1- and IL-23-induced production of the cytokine GM-CSF. Nat Immunol. Jun. 2011;12(6):568-75.

Eldar et al., Elucidating mechanisms underlying robustness of morphogen gradients. Curr Opin Genet Dev. Aug. 2004;14(4):435-9.

Eldar et al., Robustness of the BMP morphogen gradient in *Drosophila* embryonic patterning. Nature. Sep. 1, 2002;419(6904):304-8.

Eldar et al., Self-enhanced ligand degradation underlies robustness of morphogen gradients. Dev Cell. Oct. 2003;5(4):635-46.

Eming et al., Inflammation in wound repair: molecular and cellular mechanisms. J Invest Dermatol. Mar. 2007;127(3):514-25.

Engler et al., Matrix elasticity directs stem cell lineage specification. Cell. Aug. 25, 2006;126(4):677-89.

Engler et al., Microtissue elasticity: measurements by atomic force microscopy and its influence on cell differentiation. Methods Cell Biol. 2007;83:521-45.

Engler et al., Substrate compliance versus ligand density in cell on gel responses. Biophys J. Jan. 2004;86(1 Pt 1):617-28.

Ennett et al., Temporally regulated delivery of VEGF in vitro and in vivo. J Biomed Mater Res A. Oct. 2006;79(1):176-84.

Exposito et al., The fibrillar collagen family. Int J Mol Sci. Jan. 28, 2010;11(2):407-26.

Fadel et al., A carbon nanotube-polymer composite for T-cell therapy. Nat Nanotechnol. Aug. 2014;9(8):639-47.

Fadel et al., Enhanced cellular activation with single walled carbon nanotube bundles presenting antibody stimuli. Nano Lett. Jul. 2008;8(7):2070-6.

Faissner et al., Boundaries and inhibitory molecules in developing neural tissues. Glia. Apr. 1995;13(4):233-54.

Falanga, Wound healing and its impairment in the diabetic foot. Lancet. Nov. 12, 2005;366(9498):1736-43.

Falsey et al., Peptide and small molecule microarray for high throughput cell adhesion and functional assays. Bioconjug Chem. May-Jun. 2001;12(3):346-53.

Farrar et al., T helper subset development: roles of instruction, selection, and transcription. J Clin Invest. Feb. 2002;109(4):431-5.

Fauquemberque et al., HLA-A*0201-restricted CEA-derived peptide CAP1 is not a suitable target for T-cell-based immunotherapy. J Immunother. May 2010;33(4):402-13.

Ferrara et al., Angiogenesis as a therapeutic target. Nature. Dec. 15, 2005;438(7070):967-74.

Ferrara et al., Discovery and development of bevacizumab, an anti-VEGF antibody for treating cancer. Nat Rev Drug Discov. May 2004;3(5):391-400.

Fesnak et al., Engineered T cells: the promise and challenges of cancer immunotherapy. Nat Rev Cancer. Aug. 23, 2016;16(9):566-81.

Fischbach et al., Polymeric Systems for Bioinspired Delivery of Angiogenic Molecules. Adv Polym Sci. 2006;203:191-221.

Fischer et al., A brilliant monomeric red fluorescent protein to visualize cytoskeleton dynamics in Dictyostelium. FEBS Lett. Nov. 5, 2004;577(1-2):227-32.

Fischer et al., Visualizing cytoskeleton dynamics in mammalian cells using a humanized variant of monomeric red fluorescent protein. FEBS Lett. May 1, 2006;580(10):2495-502.

Fisher et al., The study of protein mechanics with the atomic force microscope. Trends Biochem Sci. Oct. 1999;24(10):379-84.

Folkman, Angiogenesis. Annu Rev Med. 2006;57:1-18.

Fonseca et al., Capitalizing on the immunogenicity of dying tumor cells. Clin Cancer Res. Mar. 15, 2008;14(6):1603-8.

Fontaine et al., Surgical treatment of peripheral circulation disorders. Helv Chir Acta. Dec. 1954;21(5-6):499-533.

(56) References Cited

OTHER PUBLICATIONS

Fox, Management of worsening multiple sclerosis with mitoxantrone: a review. Clin Ther. Apr. 2006;28(4):461-74.
Fransen et al., Local immunomodulation for cancer therapy: Providing treatment where needed. Oncoimmunology. Nov. 1, 2013;2(11):e26493.
Friedenstein et al., Fibroblast precursors in normal and irradiated mouse hematopoietic organs. Exp Hematol. Sep. 1976;4(5):267-74.
Friedrich et al., Promoter traps in embryonic stem cells: a genetic screen to identify and mutate developmental genes in mice. Genes Dev. Sep. 1991;5(9):1513-23.
Fukushima et al., The use of an antifibrosis agent to improve muscle recovery after laceration. Am J Sports Med. Jul.-Aug. 2001;29(4):394-402.
Furqan et al., STAT inhibitors for cancer therapy. J Hematol Oncol. Dec. 5, 2013;6:90. 11 pages.
Gamvrellis et al., Vaccines that facilitate antigen entry into dendritic cells. Immunol Cell Biol. Oct. 2004;82(5):506-16.
Gardel et al., Traction stress in focal adhesions correlates biphasically with actin retrograde flow speed. J Cell Biol. Dec. 15, 2008;183(6):999-1005.
Garlie et al., T cells coactivated with immobilized anti-CD3 and anti-CD28 as potential immunotherapy for cancer. J Immunother. Jul. 1999;22(4):336-45.
Gasic et al., Removal and regeneration of the cell coating in tumour cells. Nature. Oct. 13, 1962;196:170.
Gauthier et al., Temporary increase in plasma membrane tension coordinates the activation of exocytosis and contraction during cell spreading. Proc Natl Acad Sci U S A. Aug. 30, 2011;108(35):14467-72.
Geerligs et al., Linear viscoelastic behavior of subcutaneous adipose tissue. Biorheology. 2008;45(6):677-88.
GenBank Accession No. 000082.2, May 10, 2014.
GenBank Accession No. 000091.4, May 10, 2014.
GenBank Accession No. 000230.2, Dec. 17, 2012.
GenBank Accession No. 000514.3, Aug. 19, 2012.
GenBank Accession No. 000572.2, May 18, 2014.
GenBank Accession No. 000601.4, Nov. 25, 2012.
GenBank Accession No. 000614.3, Sep. 9, 2012.
GenBank Accession No. 000629.3, May 4, 2014.
GenBank Accession No. 000638.3, May 4, 2014.
GenBank Accession No. 000660.4, Dec. 9, 2012.
GenBank Accession No. 000749.2, May 4, 2014.
GenBank Accession No. 000758.3, May 4, 2014.
GenBank Accession No. 000800.3, Mar. 4, 2012.
GenBank Accession No. 000876.3, Apr. 13, 2014.
GenBank Accession No. 000885.4, Apr. 13, 2014.
GenBank Accession No. 000954.1, Jun. 13, 2014.
GenBank Accession No. 000963.3, Jun. 13, 2014.
GenBank Accession No. 001001522.1, May 18, 2014.
GenBank Accession No. 001096124.1, Dec. 16, 2012.
GenBank Accession No. 001102654.1, Dec. 16, 2012.
GenBank Accession No. 001111283.1, Dec. 9, 2012.
GenBank Accession No. 001171630.1, Dec. 9, 2012.
GenBank Accession No. 001202.3, Nov. 18, 2012.
GenBank Accession No. 001836.2, May 3, 2014.
GenBank Accession No. 001845.4, May 3, 2014.
GenBank Accession No. 001892.1, May 18, 2014.
GenBank Accession No. 001901.2, May 18, 2014.
GenBank Accession No. 002010.2, Dec. 9, 2012.
GenBank Accession No. 002421.3. May 11, 2014.
GenBank Accession No. 002506.2, Dec. 9, 2012.
GenBank Accession No. 002632.4, May 4, 2011.
GenBank Accession No. 002973.1, May 3, 2014.
GenBank Accession No. 002982.3, May 3, 2014.
GenBank Accession No. 003236.2, Aug. 21, 2011.
GenBank Accession No. 003239.2, Feb. 18, 2014.
GenBank Accession No. 003254.2, Jan. 5, 2013.
GenBank Accession No. 003255.2, Jan. 6, 2013.
GenBank Accession No. 003259.2, Nov. 25, 2012.
GenBank Accession No. 003263.3, Jan. 5, 2013.
GenBank Accession No. 003264.3, Jan. 6, 2013.
GenBank Accession No. 003268.5, Nov. 25, 2012.
GenBank Accession No. 003368.1, May 5, 2014.
GenBank Accession No. 003377.4, May 5, 2014.
GenBank Accession No. 003383.2, May 5, 2014.
GenBank Accession No. 003392.4, May 5, 2014.
GenBank Accession No. 004460.1, May 25, 2014.
GenBank Accession No. 004469.4, May 25, 2014.
GenBank Accession No. 005420.1, May 11, 2014.
GenBank Accession No. 005429.3, Mar. 31, 2014.
GenBank Accession No. 006059.2, Oct. 28, 2012.
GenBank Accession No. 006068.4, Oct. 28, 2012.
GenBank Accession No. 015719.3, Feb. 26, 2014.
GenBank Accession No. 016562.3, Jan. 6, 2013.
GenBank Accession No. 030956.3, Oct. 28, 2012.
GenBank Accession No. 033023.4, Nov. 18, 2012.
GenBank Accession No. 056534.2, Feb. 26, 2014.
GenBank Accession No. 057646.1, Jan. 6, 2013.
GenBank Accession No. 112218.2, Oct. 28, 2012.
GenBank Accession No. 138554.4, Dec. 29, 2012.
GenBank Accession No. 138636.4, Dec. 23, 2012.
GenBank Accession No. 170731.4, Dec. 9, 2012.
GenBank Accession No. 205819.3, Dec. 6, 2012.
GenBank Accession No. 205820.1, Jan. 5, 2013.
GenBank Accession No. 205823.2, Jan. 6, 2013.
GenBank Accession No. 570912.2, Nov. 18, 2012.
GenBank Accession No. 612564.1, Dec. 29, 2012.
GenBank Accession No. 619542.1, Dec. 23, 2012.
GenBank Accession No. 991388.2, Dec. 6, 2012.
GenBank Accession No. 991389.1, Jan. 5, 2013.
GenBank Accession No. 991392.1, Jan. 6, 2013.
GenBank Accession No. A32848.1, Jul. 5, 2002.
GenBank Accession No. AAA35789.1, Apr. 27, 1993.
GenBank Accession No. AAA36738.1, Aug. 3, 1993.
GenBank Accession No. AAA56738.1, Dec. 7, 1994.
GenBank Accession No. AAA60022.1, Jan. 7, 1995.
GenBank Accession No. AAA60552.1, Nov. 24, 2003.
GenBank Accession No. AAA64239.1, Mar. 23, 1995.
GenBank Accession No. AAA64297.1, Mar. 24, 1995.
GenBank Accession No. AAB18786.3, Jul. 12, 1999.
GenBank Accession No. AAB21432.2, Jun. 5, 2000.
GenBank Accession No. AAB29057.2, Mar. 6, 2001.
GenBank Accession No. AAB31818.1, Jan. 25, 1995.
GenBank Accession No. AAC16450.1, May 15, 1998.
GenBank Accession No. AAH07789.1, Jun. 9, 2008.
GenBank Accession No. AAH32517.2, Jun. 9, 2008.
GenBank Accession No. AAH93731.1, Jul. 17, 2006.
GenBank Accession No. AAH94877.1, May 20, 2005.
GenBank Accession No. AAI44040, Mar. 18, 2009.
GenBank Accession No. ABC86910, Jan. 3, 2011.
GenBank Accession No. AEO22039.1, Sep. 17, 2011.
GenBank Accession No. AF344424.1, Apr. 8, 2002.
GenBank Accession No. AF414120.1, Sep. 26, 2001.
GenBank Accession No. AF450242.1, Feb. 11, 2002.
GenBank Accession No. AJ583695.1, Oct. 7, 2008.
GenBank Accession No. AY291313.1, Apr. 26, 2004.
GenBank Accession No. BC094887.1, Jul. 21, 2006.
GenBank Accession No. CAA01954.1, Jun. 15, 1995.
GenBank Accession No. CAA01955.1, Nov. 14, 2006.
GenBank Accession No. CAA40093.1, Oct. 7, 2008.
GenBank Accession No. CAA62632.1, Sep. 15, 1995.
GenBank Accession No. CAG29322.1, Oct. 16, 2008.
GenBank Accession No. CAG33149.1, Oct. 21, 2008.
GenBank Accession No. CAG46721.1, Jun. 29, 2004.
GenBank Accession No. CBI71013.1, Feb. 2, 2010.
GenBank Accession No. DQ103757.1, Jul. 25, 2005.
GenBank Accession No. EF064765.1, Nov. 13, 2006.
GenBank Accession No. EU826563.1, Jul. 23, 2008.
GenBank Accession No. JN602184.1, Sep. 17, 2011.
GenBank Accession No. M16006.1, Jan. 7, 1995.
GenBank Accession No. M24902.1, January?, 1995.
GenBank Accession No. M73239.1, Mar. 23, 1995.

(56) References Cited

OTHER PUBLICATIONS

GenBank Accession No. U76381.2, Jul. 12, 1999.
Genes et al., Effect of substrate mechanics on chondrocyte adhesion to modified alginate surfaces. Arch Biochem Biophys. Feb. 15, 2004;422(2):161-7.
Gerhardt et al., VEGF guides angiogenic sprouting utilizing endothelial tip cell filopodia. J Cell Biol. Jun. 23, 2003;161(6):1163-77.
Gilboa, DC-based cancer vaccines. J Clin Invest. May 2007;117(5):1195-203.
Gimmi et al., B-cell surface antigen B7 provides a costimulatory signal that induces T cells to proliferate and secrete interleukin 2. Proc Natl Acad Sci U S A. Aug. 1, 1991;88(15):6575-9.
Glasbey et al., Image Analysis and Three-Dimensional Modelling of Pores in Soil Aggregates. Eur J Soil Sci. Sep. 1991;42(3):479-486.
Gnjatic et al., Toll-like receptor agonists: are they good adjuvants? Cancer J. Jul.-Aug. 2010;16(4):382-91.
Godbey et al. Tracking the intracellular path of poly(ethylenimine)/DNA complexes for gene delivery. Proc Natl Acad Sci U S A. Apr. 27, 1999;96(9):5177-81.
Goddard et al., Polymer surface modification for the attachment of bioactive compounds. Progress in Polymer Science. Jul. 2007;32(7):698-725.
Gospodarowicz et al., Effect of fibroblast growth factor on the division and fusion of bovine myoblasts. J Cell Biol. Aug. 1976;70(2 pt 1):395-405.
Graessley, Entangled Linear, Branched and Network Polymer Systems—Molecular Theories. Adv Poly Sci. 1982;47:67-117.
Griffith et al., Tissue engineering—current challenges and expanding opportunities. Science. Feb. 8, 2002;295(5557):1009-14.
Grimmer et al., Tracheal reconstruction using tissue-engineered cartilage. Arch Otolaryngol Head Neck Surg. Oct. 2004;130(10):1191-6.
Gros et al., A common somitic origin for embryonic muscle progenitors and satellite cells. Nature. Jun. 16, 2005;435(7044):954-8.
Guillaume et al., Two abundant proteasome subtypes that uniquely process some antigens presented by HLA class I molecules. Proc Natl Acad Sci U S A. Oct. 26, 2010;107(43):18599-604.
Gullberg et al., Extracellular matrix and its receptors during development. Int J Dev Biol. Oct. 1995;39(5):845-54.
Guo et al., Droplet microfluidics for high-throughput biological assays. Lab Chip. Jun. 21, 2012;12(12):2146-55.
Gupta et al., Magnetically controlled targeted micro-carrier systems. Life Sci. 1989;44(3):175-86.
Gurkan et al., The mechanical environment of bone marrow: a review. Ann Biomed Eng. Dec. 2008;36(12):1978-91.
Gussoni et al., Dystrophin expression in the mdx mouse restored by stem cell transplantation. Nature. Sep. 23, 1999;401(6751):390-4.
Halim et al., Biologic and synthetic skin substitutes: An overview. Indian J Plast Surg. Sep. 2010;43(Suppl):S23-8.
Hamby et al., Small molecule inhibitors of tumor-promoted angiogenesis, including protein tyrosine kinase inhibitors. Pharmacol Ther. May-Jun. 1999;82(2-3):169-93.
Hamdy et al., Targeting dendritic cells with nano-particulate PLGA cancer vaccine formulations. Adv Drug Deliv Rev. Sep. 10, 2011;63(10-11):943-55.
Hamilton et al., GM-CSF Biology. Growth Factors. Dec. 2004;22(4):225-31.
Hamilton, GM-CSF in inflammation and autoimmunity. Trends Immunol. Aug. 2002;23(8):403-8.
Hanada, Efficacy of rehabilitative therapy in regional musculoskeletal conditions. Best Pract Res Clin Rheumatol. Feb. 2003;17(1):151-66.
Hansen et al., Comparison of clinical grade type 1 polarized and standard matured dendritic cells for cancer immunotherapy. Vaccine. Jan. 11, 2013;31(4):639-46.
Hansen et al., Integrin binding and cell spreading on extracellular matrix act at different points in the cell cycle to promote hepatocyte growth. Mol Biol Cell. Sep. 1994;5(9):967-75.
Harding et al., CD28-mediated signalling co-stimulates murine T cells and prevents induction of anergy in T-cell clones. Nature. Apr. 16, 1992;356(6370):607-9.
Harris et al., Open pore biodegradable matrices formed with gas foaming. J Biomed Mater Res. Dec. 5, 1998;42(3):396-402.
Harrison, What is the status of reaction-diffusion theory thirty-four years after turing? J Theor Biol. Apr. 21, 1987;125(4):369-84.
Hartgerink et al., Peptide-amphiphile nanofibers: a versatile scaffold for the preparation of self-assembling materials. Proc Natl Acad Sci U S A. Apr. 16, 2002;99(8):5133-8.
Hartmann et al., CpG DNA: a potent signal for growth, activation, and maturation of human dendritic cells. Proc Natl Acad Sci U S A. Aug. 3, 1999;96(16):9305-10.
Hasan et al., Artificial Antigen Presenting Cells: An Off the Shelf Approach for Generation of Desirable T-Cell Populations for Broad Application of Adoptive Immunotherapy. Advancements in Genetic Engineering. 2015;4(3):1-10.
Hashimoto et al., Development of alginate wound dressings linked with hybrid peptides derived from laminin and elastin. Biomaterials. Mar.-Apr. 2004;25(7-8):1407-14.
Haso et al., Anti-CD22-chimeric antigen receptors targeting B-cell precursor acute lymphoblastic leukemia. Blood. Feb. 14, 2013;121(7):1165-74.
Hawke et al., Myogenic satellite cells: physiology to molecular biology. J Appl Physiol (1985). Aug. 2001;91(2):534-51.
Heath, Cells for tissue engineering. Trends Biotechnol. Jan. 2000;18(1):17-9.
Helm et al., Synergy between interstitial flow and VEGF directs capillary morphogenesis in vitro through a gradient amplification mechanism. Proc Natl Acad Sci U S A. Nov. 1, 2005;102(44):15779-84.
Henry et al., VIVA Investigators. The VIVA trial: Vascular endothelial growth factor in Ischemia for Vascular Angiogenesis. Circulation. Mar. 18, 2003;107(10):1359-65.
Hermanson, Bioconjugate Techniques. Academic Press, New York. pp. 152-186, (1996).
Heslop et al., Transplanted primary neonatal myoblasts can give rise to functional satellite cells as identified using the Myf5nlacZl+ mouse. Gene Ther. May 2001;8(10):778-83.
Hildner et al., Batf3 deficiency reveals a critical role for CD8alpha+ dendritic cells in cytotoxic T cell immunity. Science. Nov. 14, 2008;322(5904):1097-100.
Hill et al., Designing scaffolds to enhance transplanted myoblast survival and migration. Tissue Eng. May 2006;12(5):1295-304.
Hill et al., Muscle satellite (stem) cell activation during local tissue injury and repair. J Anat. Jul. 2003;203(1):89-99.
Hill, Macroporous Scaffold Architecture, Peptide, HGF/FGF and Myoblast Incorporation Enhance Myogenesis. IADR/AADR/CADR 83rd General Session. Mar. 9-12, 2005. Poster #2829.
Hirano et al., Peptide and Protein Presenting Materials for Tissue Engineering. Adv Mat. Jan. 16, 2004;16(1):17-25.
Hodge-Dufour et al., Inhibition of interferon gamma induced interleukin 12 production: a potential mechanism for the anti-inflammatory activities of tumor necrosis factor. Proc Natl Acad Sci U S A. Nov. 10, 1998;95(23):13806-11.
Hodi et al., Immunologic and clinical effects of antibody blockade of cytotoxic T lymphocyte-associated antigen 4 in previously vaccinated cancer patients. Proc Natl Acad Sci U S A. Feb. 26, 2008;105(8):3005-10.
Hodi et al., Improved survival with ipilimumab in patients with metastatic melanoma. N Engl J Med. Aug. 19, 2010;363(8):711-23.
Holland et al., Dual growth factor delivery from degradable oligo(poly(ethylene glycol) fumarate) hydrogel scaffolds for cartilage tissue engineering. Journal of Controlled Release. 2005;101:111-125.
Holland et al., Transforming growth factor-beta 1 release from oligo(poly(ethylene glycol) fumarate) hydrogels in conditions that model the cartilage wound healing environment. J Control Release. Jan. 8, 2004;94(1):101-14.
Hollyman et al., Manufacturing validation of biologically functional T cells targeted to CD19 antigen for autologous adoptive cell therapy. J Immunother. Feb.-Mar. 2009;32(2):169-80.

(56) References Cited

OTHER PUBLICATIONS

Horsley et al., IL-4 acts as a myoblast recruitment factor during mammalian muscle growth. Cell. May 16, 2003;113(4):483-94.
Hsiong et al., Differentiation stage alters matrix control of stem cells. J Biomed Mater Res A. Apr. 2008;85A(1):145-56.
Huang et al., Fabrication and in vitro Testing of Polymeric Delivery Systems for Condensed DNA. J Biomed Mater Res. 2003;67:1384-1392.
Huang et al., Long-Term In Vivo Gene Expression via Delivery of PEI-DNA Condensates From Porous Polymer Scaffolds. Hum Gene Ther. 2005;16(5):609-617.
Hubbell et al., Materials Engineering for Immunomodulation. Nature. 2009;462:449-460.
Hubbell, Biomaterials in tissue engineering. Biotechnology (N Y). Jun. 1995;13(6):565-76.
Huebsch et al., Harnessing traction-mediated manipulation of the cell/matrix interface to control stem-cell fate. Nat Mater. Jun. 2010;9(6):518-26.
Humphries et al., Integrin ligands at a glance. J Cell Sci. Oct. 1, 2006;119(Pt 19):3901-3.
Huppa et al., T-cell-antigen recognition and the immunological synapse. Nat Rev Immunol. Dec. 2003;3(12):973-83.
Huston et al., Protein engineering of antibody binding sites: recovery of specific activity in an anti-digoxin single-chain Fv analogue produced in *Escherichia coli*. Proc Natl Acad Sci U S A. Aug. 1988;85(16):5879-83.
Hutson et al., Synthesis and characterization of tunable poly(ethylene glycol): gelatin methacrylate composite hydrogels. Tissue Eng Part A. Jul. 2011;17(13-14):1713-23.
Hwang et al., Fabrication of three-dimensional porous cell-laden hydrogel for tissue engineering. Biofabrication. Sep. 2010;2(3):035003. 12 pages.
Ichida et al., A small-molecule inhibitor of tgf-Beta signaling replaces sox2 in reprogramming by inducing nanog. Cell Stem Cell. Nov. 6, 2009;5(5):491-503.
Iellem et al., Unique chemotactic response profile and specific expression of chemokine receptors CCR4 and CCR8 by CD4(+)CD25(+) regulatory T cells. J Exp Med. Sep. 17, 2001;194(6):847-53.
Ihnat et al., Hypothesis: the 'metabolic memory', the new challenge of diabetes. Diabet Med. Jun. 2007;24(6):582-6.
Il et al., A novel cyclohexene derivative, ethyl (6R)-6-[N-(2-Chloro-4-fluorophenyl)sulfamoyl]cyclohex-1-ene-1-carboxylate (TAK-242), selectively inhibits toll-like receptor 4-mediated cytokine production through suppression of intracellular signaling. Mol Pharmacol. Apr. 2006;69(4):1288-95.
Irintchev et al., Formation of Skeletal Muscle After Subcutaneous Implantation of Cultured Myoblasts. Bio/Technology. p. 366, Abstract 153.06, Jun. 1995.
Irvine et al., Engineering synthetic vaccines using cues from natural immunity. Nat Mater. Nov. 2013;12(11):978-90.
Isern et al., Self-renewing human bone marrow mesenspheres promote hematopoietic stem cell expansion. Cell Rep. May 30, 2013;3(5):1714-24.
Ishihara et al., Roles of bradykinin in vascular permeability and angiogenesis in solid tumor. Int Immunopharmacol. Mar. 2002;2(4):499-509.
Iwamoto et al., Preparation of an Ionic Polymer Gel Microactuator and Measurement of its Periodic Motions. Nippon Kagaku Kaishi. 1997;9:609-614.
Jain, Molecular Regeneration of Vessel Maturation. Nat Med. Jun. 1, 2003;9:685-693.
Jain, The manufacturing techniques of various drug loaded biodegradable poly(lactide-co-glycolide) (PLGA) devices. Biomaterials. Dec. 2000;21(23):2475-90.
Jankovic et al., In the absence of IL-12, CD4(+) T cell responses to intracellular pathogens fail to default to a Th2 pattern and are host protective in an IL-10(-/-) setting. Immunity. Mar. 2002;16(3):429-39.

Janmey et al., From tissue mechanics to transcription factors. Differentiation. Oct. 2013;86(3):112-20.
Jego et al., Plasmacytoid dendritic cells induce plasma cell differentiation through type I interferon and interleukin 6. Immunity. Aug. 2003;19(2):225-34.
Jiang et al. Two-piconewton slip bond between fibronectin and the cytoskeleton depends on talin. Nature. Jul. 17, 2003;424(6946):334-7.
Jiang et al., Click hydrogels, microgels and nanogels: emerging platforms for drug delivery and tissue engineering. Biomaterials. Jun. 2014;35(18):4969-85.
Jiang et al., Self-organization of periodic patterns by dissociated feather mesenchymal cells and the regulation of size, number and spacing of primordia. Development. Nov. 1999;126(22):4997-5009.
Jinushi et al., Enhancing the clinical activity of granulocyte-macrophage colony-stimulating factor-secreting tumor cell vaccines. Immunol Rev. Apr. 2008;222:287-98.
Jinushi et al., MFG-E8-mediated uptake of apoptotic cells by APCs links the pro- and antiinflammatory activities of GM-CSF. J Clin Invest. Jul. 2007;117(7):1902-13.
Johnson et al., Activation of skeletal muscle satellite cells and the role of fibroblast growth factor receptors. Exp Cell Res. Aug. 1995;219(2):449-53.
Jokinen et al., Integrin-mediated cell adhesion to type I collagen fibrils. J Biol Chem. Jul. 23, 2004;279(30):31956-63.
Jugdutt et al., Aging and defective healing, adverse remodeling, and blunted post-conditioning in the reperfused wounded heart. J Am Coll Cardiol. Apr. 8, 2008;51(14):1399-403.
June et al., Adoptive cellular therapy: a race to the finish line. Sci Transl Med. Mar. 25, 2015;7(280):280ps7.
June et al., The B7 and CD28 receptor families. Immunol Today. Jul. 1994;15(7):321-31.
Juntanon et al., Electrically controlled release of sulfosalicylic acid from crosslinked poly(vinyl alcohol) hydrogel. Int J Pharm. May 22, 2008;356(1-2):1-11.
Kang et al., Effect of Porous Structure on the Degradation of Freeze-Dried Gelatin Hydrogels. J Bioact Compat Poly. Jul. 1, 1999;14(4):331-343.
Kanzler et al., Therapeutic targeting of innate immunity with Toll-like receptor agonists and antagonists. Nat Med. May 2007;13(5):552-9.
Kared et al., Treatment with granulocyte colony-stimulating factor prevents diabetes in NOD mice by recruiting plasmacytoid dendritic cells and functional CD4(+)CD25(+) regulatory T-cells. Diabetes. Jan. 2005;54(1):78-84.
Katayama et al., Integrated analysis of the genome and the transcriptome by FANTOM. Brief Bioinform. Sep. 2004;5(3):249-58.
Kathuria et al., Synthesis and characterization of elastic and macroporous chitosan-gelatin cryogels fortissue engineering. Acta Biomater. Jan. 2009;5(1):406-18.
Kawai et al., Innate immune recognition of viral infection. Nat Immunol. Feb. 2006;7(2):131-7.
Kawashima et al., Pulmonary delivery of insulin with nebulized DL-lactide/glycolide copolymer (PLGA) nanospheres to prolong hypoglycemic effect. J Control Release. Nov. 1, 1999;62(1-2):279-87.
Kearney et al., Macroscale delivery systems for molecular and cellular payloads. Nat Mater. Nov. 2013;12(11):1004-17.
Kennedy et al., Rapid and extensive collapse from electrically responsive macroporous hydrogels. Adv Healthc Mater. Apr. 2014;3(4):500-7.
Khetan et al., Degradation-mediated cellular traction directs stem cell fate in covalently crosslinked three-dimensional hydrogels. Nat Mater. May 2013;12(5):458-65.
Khownium et al., Novel endotoxin-sequestering compounds with terephthalaldehyde-bis-guanylhydrazone scaffolds. Bioorg Med Chem Lett. Mar. 1, 2006;16(5):1305-8.
Kim et al., An overview of cartilage tissue engineering. Yonsei Med J. Dec. 2000;41(6):766-73.
Kim et al., Injectable, spontaneously assembling, inorganic scaffolds modulate immune cells in vivo and increase vaccine efficacy. Nat Biotechnol. Jan. 2015;33(1):64-72.

(56) References Cited

OTHER PUBLICATIONS

Kim et al., Multifunctional capsule-in-capsules for immunoprotection and trimodal imaging. Angew Chem Int Ed Engl. Mar. 1, 2011;50(10):2317-21.
Kim et al., The effect of VEGF on the myogenic differentiation of adipose tissue derived stem cells within thermosensitive hydrogel matrices. Biomaterials. Feb. 2010;31(6):1213-8.
Kinoshita et al., Successive injections in mdx mice of myoblasts grown with bFGF. Neuromuscul Disord. May 1996;6(3):187-93.
Kisak et al. The vesosome—a multicompartment drug delivery vehicle. Curr Med Chem. Jan. 2004;11(2):199-219.
Klebanoff et al., CD8+ T-cell memory in tumor immunology and immunotherapy. Immunol Rev. Jun. 2006;211:214-24.
Klein et al., Cell-Cycle Control by Physiological Matrix Elasticity and In Viivo Tissue Stiffening. Curr Biol. Sep. 29, 2009:19:1511-1518.
Klinman, Immunotherapeutic uses of CpG oligodeoxynucleotides. Nat Rev Immunol. Apr. 2004;4(4):249-58.
Kohane, Microparticles and nanoparticles for drug delivery. Biotechnol Bioeng. Feb. 1, 2007;96(2):203-9.
Kondo et al., A reaction-diffusion wave on the skin of the marine angelfish Pomacanthus. Nature. Aug. 31, 1995;376(6543):765-8.
Kong et al., Controlling Degradation of Hydrogels via the Size of Cross-Linked Junctions. Adv Mater. Nov. 30, 2004;16(21):1917-1921.
Kong et al., Controlling rigidity and degradation of alginate hydrogels via molecular weight distribution. Biomacromolecules. Sep.-Oct. 2004;5(5):1720-7.
Kong et al., Decoupling the Dependence of Rheological/Mechanical Properties of Hydrogels from Solids Concentration. Polymer. 2002;43(23):6239-6246.
Kong et al., Design of biodegradable hydrogel for the local and sustained delivery of angiogenic plasmid DNA. Pharm Res. May 2008;25(5):1230-8.
Kong et al., Designing alginate hydrogels to maintain viability of immobilized cells. Biomaterials. Oct. 2003;24(22):4023-9.
Kong et al., FRET measurements of cell-traction forces and nano-scale clustering of adhesion ligands varied by substrate stiffness. Proc Natl Acad Sci U S A. Mar. 22, 2005;102(12):4300-5.
Kong et al., Non-viral gene delivery regulated by stiffness of cell adhesion substrates. Nat Mater. Jun. 2005;4(6):460-4.
Koo et al., Bioorthogonal copper-free click chemistry in vivo for tumor-targeted delivery of nanoparticles. Angew Chem Int Ed Engl. Nov. 19, 2012;51(47):11836-40.
Kratky et al., Direct activation of antigen-presenting cells is required for CD8+ T-cell priming and tumor vaccination. Proc Natl Acad Sci U S A. Oct. 18, 2011;108(42):17414-9.
Kratz, Albumin as a drug carrier: design of prodrugs, drug conjugates and nanoparticles. J Control Release. Dec. 18, 2008;132(3):171-83.
Krieg, Development of TLR9 agonists for cancer therapy. J Clin Invest. May 2007;117(5):1184-94.
Krishnamachari et al., PLGA Microparticles that Co-deliver Antigen and Toll Like Receptor Ligand Adjuvants for Applications in Cancer Immunotherapy. AAPS Annual Meeting and Exposition. Nov. 9, 2009. 1 page.
Kumamoto et al., Induction of tumor-specific protective immunity by in situ Langerhans cell vaccine. Nat Biotechnol. Jan. 2002;20(1):64-9.
Kumar et al., Toll-like receptors and innate immunity. Biochem Biophys Res Commun. Oct. 30, 2009;388(4):621-5.
Kupferschmidt et al., Mesoporous silica particles potentiate antigen-specific T-cell responses. Nanomedicine (Lond). 2014;9(12):1835-46.
Kuwahara et al., Cell delivery using an injectable and adhesive transglutaminase-gelatin gel. Tissue Eng Part C Methods. Aug. 2010;16(4):609-18.
Kwon et al., Electrically erodible polymer gel for controlled release of drugs. Nature. Nov. 28, 1991;354(6351):291-3.

Kwon et al., In vivo targeting of dendritic cells for activation of cellular immunity using vaccine carriers based on pH-responsive microparticles. Proc Natl Acad Sci U S A. Dec. 20, 2005;102(51):18264-8.
Kyi et al., Checkpoint blocking antibodies in cancer immunotherapy. FEBS Lett. Jan. 21, 2014;588(2):368-76.
Langenkamp et al., Kinetics of dendritic cell activation: impact on priming of TH1, TH2 and nonpolarized T cells. Nat Immunol. Oct. 2000;1(4):311-6.
Langer et al., Tissue engineering. Science. May 14, 1993;260(5110):920-6.
Lanzavecchia et al., Regulation of T cell immunity by dendritic cells. Cell. Aug. 10, 2001;106(3):263-6.
Lao et al., Magnetic and hydrogel composite materials for hyperthermia applications. J Mater Sci Mater Med. Oct. 2004;15(10):1061-4.
Latorre et al., Applications of magnetic nanoparticles in medicine: magnetic fluid hyperthermia. P R Health Sci J. Sep. 2009;28(3):227-38.
Latz et al., TLR9 signals after translocating from the ER to CpG DNA in the lysosome. Nat Immunol. Feb. 2004;5(2):190-8.
Lauterbach et al., Mouse CD8alpha+ DCs and human BDCA3+ DCs are major producers of IFN-lambda in response to poly IC. J Exp Med. Nov. 22, 2010;207(12):2703-17.
Leach et al., Coating of VEGF-releasing scaffolds with bioactive glass for angiogenesis and bone regeneration. Biomaterials. Jun. 2006;27(17):3249-55.
Lee et al., Controlling Mechanical and Swelling Properties of Alginate Hydrogels Independently by Cross-Linker Type and Cross-Linking Density. Macromolecules. Apr. 2000;33(11):4291-4294.
Lee et al., Engineering liver tissue spheroids with inverted colloidal crystal scaffolds. Biomaterials. Sep. 2009;30(27):4687-94.
Lee et al., Hydrogel Formation via Vell Crosslinking. Advanced Materials. Nov. 2003;15(21):1828-1832.
Lee et al., Hydrogels for tissue engineering. Chem Rev. Jul. 2001;101(7):1869-79.
Lee et al., Intravenous hMSCs improve myocardial infarction in mice because cells embolized in lung are activated to secrete the anti-inflammatory protein TSG-6. Cell Stem Cell. Jul. 2, 2009;5(1):54-63.
Lee et al., The immunological synapse balances T cell receptor signaling and degradation. Science. Nov. 14, 2003;302(5648):1218-22.
Lefaucheur et al., The cellular events of injured muscle regeneration depend on the nature of the injury. Neuromuscul Disord. Nov. 1995;5(6):501-9.
Lele et al., Investigating complexity of protein-protein interactions in focal adhesions. Biochem Biophys Res Commun. May 9, 2008;369(3):929-34.
Lensch et al., Scientific and clinical opportunities for modeling blood disorders with embryonic stem cells. Blood. Apr. 1, 2006;107(7):2605-12.
Leor et al., Cells, scaffolds, and molecules for myocardial tissue engineering. Pharmacol Ther. Feb. 2005;105(2):151-63.
Leshem et al., Hepatocyte growth factor (HGF) inhibits skeletal muscle cell differentiation: a role for the bHLH protein twist and the cdk inhibitor p27. J Cell Physiol. Jul. 2000;184(1):101-9.
Letsinger et al., Phosphoramidate analogs of oligonucleotides. J Org Chem. Nov. 1970;35(11):3800-3.
Levental et al., Soft biological materials and their impact on cell function. Soft Matter. 2007;3:299-306.
Levine et al., Effects of CD28 costimulation on long-term proliferation of CD4+ T cells in the absence of exogenous feeder cells. J Immunol. Dec. 15, 1997;159(12):5921-30.
Li et al., Effect of growth factors and extracellular matrix materials on the proliferation and differentiation of microencapsulated myoblasts. J Biomater Sci Polym Ed. 2003;14(6):533-49.
Li et al., Effects of Three-Dimensional Scaffolds on Cell Organization and Tissue Development. Biotechnology and Bioprocess Engineering. Oct. 2001;6(5):311-325.
Li et al., Mesoporous silica nanoparticles in biomedical applications. Chem Soc Rev. Apr. 7, 2012;41(7):2590-605.

(56) References Cited

OTHER PUBLICATIONS

Li et al., pH sensitive Laponite/alginate hybrid hydrogels: swelling behaviour and release mechanism. Soft Matter. 2011;7:6231-6238.
Li et al., Purified hybrid cells from dendritic cell and tumor cell fusions are superior activators of antitumor immunity. Cancer Immunol Immunother. Nov. 2001;50(9):456-62.
Li et al., Recent advances of biomaterials in biotherapy. Regen Biomater. Jun. 2016;3(2):99-105.
Li et al., The effect of surface modification of mesoporous silica micro-rod scaffold on immune cell activation and infiltration. Biomaterials. Mar. 2016;83:249-56.
Li, TNF-alpha is a mitogen in skeletal muscle. Am J Physiol Cell Physiol. Aug. 2003;285(2):C370-6.
Liao et al., Synthesis of mesoporous silica nanoparticle-encapsulated alginate microparticles for sustained release and targeting therapy. J Biomed Mater Res B Appl Biomater. Feb. 2014;102(2):293-302.
Liederer et al., Enzymes involved in the bioconversion of ester-based prodrugs. J Pharm Sci. Jun. 2006;95(6):1177-95.
Lin et al., Transdermal regulation of vascular network bioengineering using a photopolymerizable methacrylated gelatin hydrogel. Biomaterials. Sep. 2013;34(28):6785-96.
Lindstein et al., Regulation of lymphokine messenger RNA stability by a surface-mediated T cell activation pathway. Science. Apr. 21, 1989;244(4902):339-43.
Linsley et al., The role of the CD28 receptor during T cell responses to antigen. Annu Rev Immunol. 1993;11:191-212.
Lipton et al., Developmental fate of skeletal muscle satellite cells. Science. Sep. 21, 1979;205(4412):1292-4.
Liu et al., Heterobifunctional poly(ethylene glycol)-tethered bone morphogenetic protein-2-stimulated bone marrow mesenchymal stromal cell differentiation and osteogenesis. Tissue Eng. May 2007;13(5):1113-24.
Liu et al., Immunostimulatory CpG oligodeoxynucleotides enhance the immune response to vaccine strategies involving granulocyte-macrophage colony-stimulating factor. Blood. Nov. 15, 1998;92(10):3730-6.
Liu et al., Nanostructured materials designed for cell binding and transduction. Biomacromolecules. 2001 Summer;2(2):362-8.
Liu et al., On the viscoelastic character of liver tissue: experiments and modelling of the linear behaviour. Biorheology. 2000;37(3):191-201.
Liu et al., Preparation of uniform calcium alginate gel beads by membrane emulsification coupled with internal gelation. Journal of Applied Polymer Science. Nov. 22, 2002;87(5):848-852.
Liu, Dendritic cell subsets and lineages, and their functions in innate and adaptive immunity. Cell. Aug. 10, 2001;106(3):259-62.
Lo et al., Cell movement is guided by the rigidity of the substrate. Biophys J. Jul. 2000;79(1):144-52.
Lodish et al., Collagen: The Fibrous Proteins of the Matrix. Molecular Cell Biology. W.H. Freeman, New York. 2000;Section 22.3:979-985.
Lopez et al., Magnetic Applications of Polymer Gels. Macromol Symp. 2001;166(1):173-178.
Lu et al., Muscle-derived stem cells seeded into acellular scaffolds develop calcium-dependent contractile activity that is modulated by nicotinic receptors. Urology. Jun. 2003;61(6):1285-91.
Lubeck, The costs of musculoskeletal disease: health needs assessment and health economics. Best Pract Res Clin Rheumatol. Jun. 2003;17(3):529-39.
Ludewig et al., Immunotherapy with dendritic cells directed against tumor antigens shared with normal host cells results in severe autoimmune disease. J Exp Med. Mar. 6, 2000;191(5):795-804.
Lumelsky et al., Differentiation of embryonic stem cells to insulin-secreting structures similar to pancreatic islets. Science. May 18, 2001;292(5520):1389-94.
Lutolf et al., Repair of bone defects using synthetic mimetics of collagenous extracellular matrices. Nat Biotechnol. May 2003;21(5):513-8.
Lutterotti et al., Antigen-specific tolerance by autologous myelin peptide-coupled cells: a phase 1 trial in multiple sclerosis. Sci Transl Med. Jun. 5, 2013;5(188):188ra75.
Mach et al., Differences in dendritic cells stimulated in vivo by tumors engineered to secrete granulocyte-macrophage colony-stimulating factor or Flt3-ligand. Cancer Res. Jun. 15, 2000;60(12):3239-46.
Magram et al., IL-12-deficient mice are defective but not devoid of type 1 cytokine responses. Ann N Y Acad Sci. Oct. 31, 1996;795:60-70.
Mahony et al., Mesoporous silica nanoparticles act as a self-adjuvant for ovalbumin model antigen in mice. Small. Sep. 23, 2013;9(18):3138-46.
Maini, Spatial and spatio-temporal patterns in a cell-haptotaxis model. J Math Biol. 1989;27(5):507-22.
Majeti et al., Identification of a hierarchy of multipotent hematopoietic progenitors in human cord blood. Cell Stem Cell. Dec. 13, 2007;1(6):635-45.
Maldonado et al., How tolerogenic dendritic cells induce regulatory T cells. Adv Immunol. 2010;108:111-65.
Maley et al., Extracellular matrix, growth factors,genetics: their influence on cell proliferation and myotube formation in primary cultures of adult mouse skeletal muscle. Exp Cell Res. Jul. 1995;219(1):169-79.
Malhotra et al., Use of an oncolytic virus secreting GM-CSF as combined oncolytic and immunotherapy for treatment of colorectal and hepatic adenocarcinomas. Surgery. Apr. 2007;141(4):520-9.
Malmqvist, Biospecific interaction analysis using biosensor technology. Nature. Jan. 14, 1993;361(6408):186-7.
Mammoto et al., Mechanical control of tissue and organ development. Development. May 2010;137(9):1407-20.
Manavski et al., Vascular niche controls organ regeneration. Circ Res. Mar. 28, 2014;114(7):1077-9.
Mandal et al., Polymer-based synthetic dendritic cells for tailoring robust and multifunctional T cell responses. ACS Chem Biol. Feb. 20, 2015;10(2):485-92.
Mangsbo et al., Enhanced tumor eradication by combining CTLA-4 or PD-1 blockade with CpG therapy. J Immunother. Apr. 2010;33(3):225-35.
Mansoor et al., Engineering T cells for cancer therapy. Br J Cancer. Nov. 14, 2005;93(10):1085-91.
Martinsen et al., Alginate as immobilization material: I. Correlation between chemical and physical properties of alginate gel beads. Biotechnol Bioeng. Jan. 5, 1989;33(1):79-89.
Marui et al., Simultaneous application of basic fibroblast growth factor and hepatocyte growth factor to enhance the blood vessels formation. J Vasc Surg. Jan. 2005;41(1):82-90.
Masedunskas et al., Role for the actomyosin complex in regulated exocytosis revealed by intravital microscopy. Proc Natl Acad Sci U S A. Aug. 16, 2011;108(33):13552-7.
Massia et al., An RGD spacing of 440 nm is sufficient for integrin alpha V beta 3-mediated fibroblast spreading and 140 nm for focal contact and stress fiber formation. J Cell Biol. Sep. 1991;114(5):1089-100.
Matthew et al., Subperiosteal behaviour of alginate and cellulose wound dressing materials. Biomaterials. Mar. 1995;16(4):275-8.
Maus et al., Ex vivo expansion of polyclonal and antigen-specific cytotoxic T lymphocytes by artificial APCs expressing ligands for the T-cell receptor, CD28 and 4-1BB. Nat Biotechnol. Feb. 2002;20(2):143-8.
McColl, Chemokines and dendritic cells: a crucial alliance. Immunol Cell Biol. Oct. 2002;80(5):489-96.
McConnell et al., Vaccination with outer membrane complexes elicits rapid protective immunity to multidrug-resistant Acinetobacter baumannii. Infect Immun. Jan. 2011;79(1):518-26.
McDonald et al., Early fracture callus displays smooth muscle-like viscoelastic properties ex vivo: implications for fracture healing. J Orthop Res. Nov. 2009;27(11):1508-13.
McKay et al., Click chemistry in complex mixtures: bioorthogonal bioconjugation. Chem Biol. Sep. 18, 2014;21(9):1075-101.
McKinney-Freeman et al., Muscle-derived hematopoietic stem cells are hematopoietic in origin. Proc Natl Acad Sci U S A. Feb. 5, 2002;99(3):1341-6.

(56) References Cited

OTHER PUBLICATIONS

McKinnon et al., Biophysically defined and cytocompatible covalently adaptable networks as viscoelastic 3D cell culture systems. Adv Mater. Feb. 12, 2014;26(6):865-72.
McPherron et al., Regulation of skeletal muscle mass in mice by a new TGF-beta superfamily member. Nature. May 1, 1997;387(6628):83-90.
McQualter et al., Granulocyte macrophage colony-stimulating factor: a new putative therapeutic target in multiple sclerosis. J Exp Med. Oct. 1, 2001;194(7):873-82.
McWhorter et al., Modulation of macrophage phenotype by cell shape. Proc Natl Acad Sci U S A. Oct. 22, 2013;110(43):17253-8.
Mehta et al., Engineering New Approaches to Cancer Vaccines. Cancer Immunol Res. Aug. 2015;3(8):836-43.
Meier et al., Peptide Nucleic Acids(PNAs)—Unusual Properties of Noionic Oligonucleotide Analogues. Angewandte Chemie, Int'l Edition. Aug. 1992;31(8):1008-1010.
Melero-Martin et al., Engineering robust and functional vascular networks in vivo with human adult and cord blood-derived progenitor cells. Circ Res. Jul. 18, 2008;103(2):194-202. Includes supplementary materials.
Melief et al., Immunotherapy of established (pre)malignant disease by synthetic long peptide vaccines. Nat Rev Cancer. May 2008;8(5):351-60.
Melief et al., T-cell immunotherapy of tumors by adoptive transfer of cytotoxic T lymphocytes and by vaccination with minimal essential epitopes. Immunol Rev. Jun. 1995;145:167-77.
Mellman et al., Dendritic cells: specialized and regulated antigen processing machines. Cell. Aug. 10, 2001;106(3):255-8.
Menetry et al., Suturing Versus Immobilization of a Muscle Laceration: A Morphological and Functional Study in a Mouse Model. Am J Sports Med. 1999;27(2):222-229.
Meng et al., Use of a lipid-coated mesoporous silica nanoparticle platform for synergistic gemcitabine and paclitaxel delivery to human pancreatic cancer in mice. ACS Nano. 2015;9(4):3540-57.
Meraz et al., Mesoporous Silicon Particles for the Presentation of Tumor Antigens and Adjuvant for Anti-Cancer Immunity. Cancer Res. 2011;71(S24):159s-160s, Abstract #P1-01-12.
Merck, Merck Announces Presentation of Interim Data from Phase 1B Study of MK-3475, Investigational anti-PD-1 Immunotherapy, in Previously-Treated Patients with Non-Small Cell Lung Cancer (NSCLC) at 15th World Conference on Lung Cancer. Merck Newsroom Home. 3 pages, Oct. 29, 2013.
Merkel et al., Using mechanobiological mimicry of red blood cells to extend circulation times of hydrogel microparticles. Proc Natl Acad Sci U S A. Jan. 11, 2011;108(2):586-91.
Merriam-Webster, Transient. Merriam-Webster Dictionary. Web. Jul. 18, 2014. www.merriam-webster.com/dictionary/transient. 3 pages.
Metters et al., Fundamental studies of biodegradable hydrogels as cartilage replacement materials. Biomed Sci Instrum. 1999;35:33-8.
Meyer et al., Biodegradable nanoellipsoidal artificial antigen presenting cells for antigen specific T-cell activation. Small. Apr. 2015;11(13):1519-25.
Meyer et al., Clinical investigations of Toll-like receptor agonists. Expert Opin Investig Drugs. Jul. 2008;17(7):1051-65.
Meylan et al., Intracellular pattern recognition receptors in the host response. Nature. Jul. 6, 2006;442(7098):39-44.
MGI, Mouse Facts. Retrieved online at: http://www.informatics.jax.org/mgihome/other/mouse_facts1.shtml. 2 pages. Jul. 31, 2018.
Miljkovic et al., Chondrogenesis, bone morphogenetic protein-4 and mesenchymal stem cells. Osteoarthritis Cartilage. Oct. 2008;16(10):1121-30.
Miller et al., Hepatocyte growth factor affects satellite cell activation and differentiation in regenerating skeletal muscle. Am J Physiol Cell Physiol. Jan. 2000;278(1):C174-81.
Miller et al., Lipopolysaccharide sequestrants: structural correlates of activity and toxicity in novel acylhomospermines. J Med Chem. Apr. 7, 2005;48(7):2589-99.
Miller et al., Melanoma. N Engl J Med. Jul. 6, 2006;355(1):51-65.

Miralles et al., Actin dynamics control SRF activity by regulation of its coactivator MAL. Cell. May 2, 2003;113(3):329-42.
Mitchell et al., The exogenous administration of basic fibroblast growth factor to regenerating skeletal muscle in mice does not enhance the process of regeneration. Growth Factors. 1996;13(1-2):37-55.
Miyata et al., Biomolecule-sensitive hydrogels. Adv Drug Deliv Rev. Jan. 17, 2002;54(1):79-98.
Mohan et al., Novel Porous, Polysaccharide Scaffolds for Tissue Engineering Applications. Trends Biomater Artif Organs. 2005;18(2):219-224.
Moioli et al., Matrices and scaffolds for drug delivery in dental, oral and craniofacial tissue engineering. Adv Drug Deliv Rev. May 30, 2007;59(4-5):308-24.
Molinari et al., Modification of surface membrane antigens by trypsin. Proc Soc Exp Biol Med. Apr. 1975;148(4):991-4.
Molloy et al., Movement and force produced by a single myosin head. Nature. Nov. 9, 1995;378(6553):209-12.
Mooney et al., Cytoskeletal filament assembly and the control of cell spreading and function by extracellular matrix. J Cell Sci. Jun. 1995;108 (Pt 6):2311-20.
Mooney et al., Switching from differentiation to growth in hepatocytes: control by extracellular matrix. J Cell Physiol. Jun. 1992;151(3):497-505.
Moser et al., Dendritic cell regulation of TH1-TH2 development. Nat Immunol. Sep. 2000;1(3):199-205.
Mulder et al., Wound Management: Past, Present, and Future. Clinicians' Pocket Guide to Chronic Wound Repair. Springhouse Corporation, Springhouse, Pennsylvania. 1998:85-90.
Muralidharan-Chari et al., ARF6-regulated shedding of tumor cell-derived plasma membrane microvesicles. Curr Biol. Dec. 1, 2009;19(22):1875-85.
Murdan, Electro-responsive drug delivery from hydrogels. J Control Release. Sep. 19, 2003;92(1-2):1-17.
Nagai et al., A variant of yellow fluorescent protein with fast and efficient maturation for cell-biological applications. Nat Biotechnol. Jan. 2002;20(1):87-90.
Naik et al., Development of plasmacytoid and conventional dendritic cell subtypes from single precursor cells derived in vitro and in vivo. Nat Immunol. Nov. 2007;8(11):1217-26.
NCBI Accession No. 000749.2, Apr. 1, 2012.
NCBI Accession No. 000758, Apr. 1, 2012.
NCBI Accession No. 001020537, Jan. 30, 2011.
NCBI Accession No. 001020538, Jan. 30, 2011.
NCBI Accession No. 001020539, Jan. 30, 2011.
NCBI Accession No. 001020540, Jan. 30, 2011.
NCBI Accession No. 001028928, Jan. 30, 2011.
NCBI Accession No. 001193, May 3, 2014.
NCBI Accession No. 001552.2, Mar. 16, 2014.
NCBI Accession No. 001561.5, Mar. 16, 2014.
NCBI Accession No. 003237.2, May 25, 2014.
NCBI Accession No. 003265, Dec. 30, 2012.
NCBI Accession No. 003318.1, May 4, 2014.
NCBI Accession No. 003327.3, May 4, 2014.
NCBI Accession No. 003367, Jan. 30, 2011.
NCBI Accession No. 004119, Apr. 14, 2013.
NCBI Accession No. 004448.3, Apr. 23, 2014.
NCBI Accession No. 005009.2, Apr. 27, 2014.
NCBI Accession No. 005018.2, Apr. 27, 2014.
NCBI Accession No. 006274.2, Mar. 31, 2013.
NCBI Accession No. 017442, Apr. 14, 2012.
NCBI Accession No. 059138, Apr. 14, 2012.
NCBI Accession No. 181780.3, Jan. 27, 2014.
NCBI Accession No. 861445.3, Jan. 27, 2014.
NCBI, MeSH. Nivolumab. Retrieved online at: https://www.ncbi.nlm.nih/gov/mesh/?term=nivolumab. 3 pages, (2010).
Nehls et al., A novel, microcarrier-based in vitro assay for rapid and reliable quantification of three-dimensional cell migration and angiogenesis. Microvasc Res. Nov. 1995;50(3):311-22.
Nestle et al., Vaccination of melanoma patients with peptide- or tumorlysate-pulsed dendritic cells. Nature Medicine. Mar. 1, 1998;4(3):328-32.

(56) References Cited

OTHER PUBLICATIONS

Niamlang et al., Electrically controlled release of salicylic acid from poly(p-phenylene vinylene)/polyacrylamide hydrogels. Int J Pharm. Apr. 17, 2009;371(1-2):126-33.

Nichol et al., Cell-laden microengineered gelatin methacrylate hydrogels. Biomaterials. Jul. 2010;31(21):5536-44.

Nicodemus et al., Cell encapsulation in biodegradable hydrogels for tissue engineering applications. Tissue Eng Part B Rev. Jun. 2008;14(2):149-65.

Niessen et al., The alpha 6 beta 4 integrin is a receptor for both laminin and kalinin. Exp Cell Res. Apr. 1994;211(2):360-7.

NIH—National Cancer Institute, AMP-224, anti-PD-1 fusion protein AMP-224. Retrieved online at: https://www.cancer/gov/publications/dictionaries/cancer-drug/def/anti-pd-1-fusion-protein-amp-224. 1 page, (2019).

Noguera-Troise et al., Blockade of Dll4 inhibits tumour growth by promoting non-productive angiogenesis. Nature. Dec. 21, 2006;444(7122):1032-7.

Nuttelman et al., Dexamethasone-functionalized gels induce osteogenic differentiation of encapsulated hMSCs. J Biomed Mater Res A. Jan. 2006;76(1):183-95.

Ní Annaidh et al., Characterization of the anisotropic mechanical properties of excised human skin. J Mech Behav Biomed Mater. Jan. 2012;5(1):139-48.

O'Garra et al., Are dendritic cells afraid of commitment? Nat Immunol. Dec. 2004;5(12):1206-8.

O'Shea et al., Type 1 IFNs and regulation of TH1 responses: enigmas both resolved and emerge. Nat Immunol. Jul. 2000;1(1):17-9.

Ohashi et al., Surgical excision combined with autologous whole tumor cell vaccination is an effective therapy for murine neuroblastoma. J Pediatr Surg. Aug. 2006;41(8):1361-8.

Ohlstein et al., The stem cell niche: theme and variations. Curr Opin Cell Biol. Dec. 2004;16(6):693-9.

Oldenburg et al., TLR13 recognizes bacterial 23S rRNA devoid of erythromycin resistance-forming modification. Science. Aug. 31, 2012;337(6098):1111-5.

Oldenhove et al., Decrease of Foxp3+ Treg cell number and acquisition of effector cell phenotype during lethal infection. Immunity. Nov. 20, 2009;31(5):772-86.

Oneto et al., Implantable biomaterial based on click chemistry for targeting small molecules. Acta Biomaterialia. 2014;10:5099-5105.

Orner et al., Arrays for the combinatorial exploration of cell adhesion. J Am Chem Soc. Sep. 8, 2004;126(35):10808-9.

Osunkoya et al., Synthesis and fate of immunological surface receptors on cultured Burkitt lymphoma cells. Int J Cancer. Mar. 15, 1969;4(2):159-65.

Ota et al., Percutaneous subxiphoid access to the epicardium using a miniature crawling robotic device. Innovations (Phila). 2006 Fall;1(5):227-31.

Overwijk et al., Tumor regression and autoimmunity after reversal of a functionally tolerant state of self-reactive CD8+ T cells. J Exp Med. Aug. 18, 2003;198(4):569-80.

Ozawa et al., Microenvironmental VEGF concentration, not total dose, determines a threshold between normal and aberrant angiogenesis. J Clin Invest. Feb. 2004;113(4):516-27.

Padilla et al., Insufficient TLR activation contributes to the slow development of CD8+ T cell responses in Trypanosoma cruzi infection. J Immunol. Jul. 15, 2009;183(2):1245-52.

Page-McCaw et al., Matrix metalloproteinases and the regulation of tissue remodelling. Nat Rev Mol Cell Biol. Mar. 2007;8(3):221-33.

Pailler-Mattei et al., In vivo measurements of the elastic mechanical properties of human skin by indentation tests. Med Eng Phys. Jun. 2008;30(5):599-606.

Pajonk et al., From sol-gel to aerogels and cryogels. J Non Cryst Solids. May 1990;121(1-3):66-67.

Palacio et al., Interleukin 10 and tumor necrosis factor alpha gene expression in respiratory and peripheral muscles. Relation to sarcolemmal damage. Arch Bronconeumol. Jul. 2002;38(7):311-6.

Paradee et al., Effects of crosslinking ratio, model drugs, and electric field strength on electrically controlled release for alginate-based hydrogel. J Mater Sci Mater Med. Apr. 2012;23(4):999-1010.

Pardoll, The blockade of immune checkpoints in cancer immunotherapy. Nat Rev Cancer. Mar. 22, 2012;12(4):252-64.

Parekh et al., Modulus-driven differentiation of marrow stromal cells in 3D scaffolds that is independent of myosin-based cytoskeletal tension. Biomaterials. Mar. 2011;32(9):2256-64.

Parekkadan et al., Mesenchymal stem cell-derived molecules reverse fulminant hepatic failure. PLoS One. Sep. 26, 2007;2(9):e941.

Park et al., Photopolymerized hyaluronic acid-based hydrogels and interpenetrating networks. Biomaterials. Mar. 2003;24(6):893-900.

Parker et al., Effect of mitoxantrone on outcome of children with first relapse of acute lymphoblastic leukaemia (ALL R3): an open-label randomised trial. Lancet. Dec. 11, 2010;376(9757):2009-17.

Partridge et al., Conversion of mdx myofibres from dystrophin-negative to-positive by injection of normal myoblasts. Nature. Jan. 12, 1989;337(6203):176-9.

Patterson et al., Differential binding of chemokines to macrophages and neutrophils in the human inflamed synovium. Arthritis Res. 2002;4(3):209-14.

Pawlaczyk et al., Age-dependent biomechanical properties of the skin. Postepy Dermatol Alergol. Oct. 2013;30(5):302-6.

Pedersen et al., Induction of regulatory dendritic cells by dexamethasone and 1alpha,25-Dihydroxyvitamin D(3). Immunol Lett. Jan. 30, 2004;91(1):63-9.

Pek et al., The effect of matrix stiffness on mesenchymal stem cell differentiation in a 3D thixotropic gel. Biomaterials. Jan. 2010;31(3):385-91.

Pelinkovic et al., Tissue engineering and gene therapy of the musculoskeletal system with muscle cells. Z Orthop Ihre Grenzgeb. Sep.-Oct. 2000;138(5)402-6.

Pena et al., Effects of TGF-beta and TGF-beta neutralizing antibodies on fibroblast-induced collagen gel contraction: implications for proliferative vitreoretinopathy. Invest Ophthalmol Vis Sci. May 1994;35(6):2804-8.

Perica et al., Enrichment and Expansion with Nanoscale Artificial Antigen Presenting Cells for Adoptive Immunotherapy. ACS Nano. Jul. 28, 2015;9(7):6861-71.

Peters et al., Engineering vascular networks in porous polymer matrices. J Biomed Mater Res. Jun. 15, 2002;60(4):668-78.

Peyton et al., The use of poly(ethylene glycol) hydrogels to investigate the impact of ECM chemistry and mechanics on smooth muscle cells. Biomaterials. Oct. 2006;27(28):4881-93.

Phillippi, Patterning of Multiple Cell Lineages from a Single Stem Cell Population. Annual Meeting of the American Society for Cell Biology. Dec. 10, 2006.

Pinho et al., PDGFRa and CD51 mark human nestin+ sphere-forming mesenchymal stem cells capable of hematopoietic progenitor cell expansion. J Exp Med. Jul. 1, 2013;210(7):1351-67.

Platten et al., Cancer Immunotherapy by Targeting IDO1/TDO and Their Downstream Effectors. Front Immunol. Jan. 12, 2015;5:673. 7 pages.

Pluen et al., Role of tumor-host interactions in interstitial diffusion of macromolecules: cranial vs. subcutaneous tumors. Proc Natl Acad Sci U S A. Apr. 10, 2001;98(8):4628-33.

Pooyan et al., Conjugates bearing multiple formyl-methionyl peptides display enhanced binding to but not activation of phagocytic cells. Bioconjug Chem. Mar.-Apr. 2002;13(2):216-23.

Pope et al., Organ-specific regulation of the CD8 T cell response to Listeria monocytogenes infection. J Immunol. Mar. 1, 2001;166(5):3402-9.

Porter et al., Separation of Natural Populations of Coliform Bacteria from Freshwater and Sewage by Magnetic-Bead Cell Sorting. J Microbiol Meth. 1998;33(3):221-226.

Pouzet et al., Factors affecting functional outcome after autologous skeletal myoblast transplantation. Ann Thorac Surg. Mar. 2001;71(3):844-50; discussion 850-1.

PRnewswire, GlaxoSmithKline and Amplimmune Form Global Strategic Collaboration. Alliance to Focus on AMP-224 for Cancer and Other Diseases. 3 pages, Aug. 4, 2010.

(56) References Cited

OTHER PUBLICATIONS

Pulendran et al., Flt3-ligand and granulocyte colony-stimulating factor mobilize distinct human dendritic cell subsets in vivo. J Immunol. Jul. 1, 2000;165(1):566-72.
Qi et al., Patterned differentiation of individual embryoid bodies in spatially organized 3D hybrid microgels. Adv Mater. Dec. 7, 2010;22(46):5276-81.
Qin et al., CD22-Targeted Chimeric Antigen Receptor (CAR) T Cells Containing The 4-1BB Costimulatory Domain Demonstrate Enhanced Persistence and Superior Efficacy Against B-Cell Precursor Acute Lymphoblastic Leukemia (ALL) Compared to Those Containing CD28. Blood. 2013:122:1431.
Qin et al., Soft lithography for micro- and nanoscale patterning. Nat Protoc. Mar. 2010;5(3):491-502.
Qiu et al., Environment-sensitive hydrogels for drug delivery. Adv Drug Deliv Rev. Dec. 31, 2001;53(3):321-39.
Qu et al., Development of approaches to improve cell survival in myoblast transfer therapy. J Cell Biol. Sep. 7, 1998;142(5):1257-67.
Qu-Petersen et al., Identification of a novel population of muscle stem cells in mice: potential for muscle regeneration. J Cell Biol. May 27, 2002;157(5):851-64.
Quezada et al., CTLA4 blockade and GM-CSF combination immunotherapy alters the intratumor balance of effector and regulatory T cells. J Clin Invest. Jul. 2006;116(7):1935-45.
Quintana et al., Autoantibody patterns in diabetes-prone NOD mice and in standard C57BL/6 mice. J Autoimmun. Nov. 2001;17(3):191-7.
Raeber et al., Molecularly engineered PEG hydrogels: a novel model system for proteolytically mediated cell migration. Biophys J. Aug. 2005;89(2):1374-88.
Rajagopalan et al., Regional angiogenesis with vascular endothelial growth factor in peripheral arterial disease: a phase II randomized, double-blind, controlled study of adenoviral delivery of vascular endothelial growth factor 121 in patients with disabling intermittent claudication. Circulation. Oct. 21, 2003;108(16):1933-8.
Ramón-Azcón et al., Gelatin methacrylate as a promising hydrogel for 3D microscale organization and proliferation of dielectrophoretically patterned cells. Lab on a Chip. Aug. 21, 2012;12(16):2959-69.
Randolph et al., Migration of dendritic cell subsets and their precursors. Annu Rev Immunol. 2008;26:293-316.
Ranganath et al., Harnessing the mesenchymal stem cell secretome for the treatment of cardiovascular disease. Cell Stem Cell. Mar. 2, 2012;10(3):244-58.
Raposo et al., Extracellular vesicles: exosomes, microvesicles, and friends. J Cell Biol. Feb. 18, 2013;200(4):373-83.
Rappolee et al., Macrophage-derived growth factors. Curr Top Microbiol Immunol. 1992;181:87-140.
Rapraeger, Syndecan-regulated receptor signaling. J Cell Biol. May 29, 2000;149(5):995-8.
Reddy et al., Exploiting lymphatic transport and complement activation in nanoparticle vaccines. Nat Biotechnol. Oct. 2007;25(10):1159-64.
Reimann et al., Satellite Cells in Normal and Regenerated Soleus Muscles of mdx and Control Mice. Eur J Neurosci. 1998;10:366, Abstract No. 153.07.
Reis E Sousa., Activation of dendritic cells: translating innate into adaptive immunity. Curr Opin Immunol. Feb. 2004;16(1):21-5.
Research Results of National Institute of Advanced Industrial Science and Technology, retrieved online at: http://www.aist.go.jp/aist_j/press_release/pr2006/pr20060719.html. 4 pages, (2006).
Rhoads et al., Satellite cell-mediated angiogenesis in vitro coincides with a functional hypoxia-inducible factor pathway. Am J Physiol Cell Physiol. Jun. 2009;296(6):C1321-8.
Ribas et al., Phase III randomized clinical trial comparing tremelimumab with standard-of-care chemotherapy in patients with advanced melanoma. J Clin Oncol. Feb. 10, 2013;31(5):616-22.
Richards Grayson et al., Multi-pulse drug delivery from a resorbable polymeric microchip device. Nat Mater. Nov. 2003;2(11):767-72.
Richardson et al., Polymeric system for dual growth factor delivery. Nat Biotechnol. Nov. 2001;19(11):1029-34.
Riddell et al., Phase I Study of Cellular Adoptive Immunotherapy Using Genetically Modified CD8+ HIV-Specific T Cells for HIV Seropositive Patients Undergoing Allogeneic Bone Marrow Transplant. Fred Hutchinson Cancer Research Center and the University of Washington. Human Gene Therapy. Jun. 1992;3(3):319-338.
Riddell et al., Principles for adoptive T cell therapy of human viral diseases. Annu Rev Immunol. 1995;13:545-86.
Riddell et al., Restoration of viral immunity in immunodeficient humans by the adoptive transfer of T cell clones. Science. Jul. 10, 1992;257(5067):238-41.
Riddell et al., The use of anti-CD3 and anti-CD28 monoclonal antibodies to clone and expand human antigen-specific T cells. J Immunol Methods. Apr. 17, 1990;128(2):189-201.
Riddle et al., Role of poly(lactide-co-glycolide) particle size on gas-foamed scaffolds. J Biomater Sci Polym Ed. 2004;15(12):1561-70.
Ridgway et al., Inhibition of Dll4 signalling inhibits tumour growth by deregulating angiogenesis. Nature. Dec. 21, 2006;444(7122):1083-7.
Rinderknecht et al., The amino acid sequence of human insulin-like growth factor I and its structural homology with proinsulin. J Biol Chem. Apr. 25, 1978;253(8):2769-76.
Rizzo et al., An improved cyan fluorescent protein variant useful for FRET. Nat Biotechnol. Apr. 2004;22(4):445-9.
Roccaro et al., BM mesenchymal stromal cell-derived exosomes facilitate multiple myeloma progression. J Clin Invest. Apr. 2013;123(4):1542-55.
Rodriguez et al., Minimal "Self" peptides that inhibit phagocytic clearance and enhance delivery of nanoparticles. Science. Feb. 22, 2013;339(6122):971-5.
Rosenberg et al., Adoptive cell transfer as personalized immunotherapy for human cancer. Science. Apr. 3, 2015;348(6230):62-8.
Rosenberg et al., Cancer immunotherapy: moving beyond current vaccines. Nat Med. Sep. 2004;10(9):909-15.
Rosenberg et al., Durable complete responses in heavily pretreated patients with metastatic melanoma using T-cell transfer immunotherapy. Clin Cancer Res. Jul. 1, 2011;17(13):4550-7.
Roth et al., SC68896, a novel small molecule proteasome inhibitor, exerts antiglioma activity in vitro and in vivo. Clin Cancer Res. Nov. 1, 2009;15(21):6609-18.
Rowlands et al., Directing osteogenic and myogenic differentiation of MSCs: interplay of stiffness and adhesive ligand presentation. Am J Physiol Cell Physiol. Oct. 2008;295(4):C1037-44.
Rowley et al., Alginate hydrogels as synthetic extracellular matrix materials. Biomaterials. Jan. 1999;20(1):45-53.
Rowley et al., Alginate type and RGD density control myoblast phenotype. J Biomed Mater Res. May 2002;60(2):217-23.
Rowley et al., Biomaterials to Spatially Regulate Cell Fate. Adv Mater. Jun. 2002;14(12):886-889.
Rubbi et al., Evidence of surface antigen detachment during incubation of cells with immunomagnetic beads. J Immunol Methods. Dec. 3, 1993;166(2):233-41.
Rubin et al., Dissociation of heparan sulfate and receptor binding domains of hepatocyte growth factor reveals that heparan sulfate-c-met interaction facilitates signaling. J Biol Chem. Aug. 31, 2001;276(35):32977-83.
Ryten et al., ATP regulates the differentiation of mammalian skeletal muscle by activation of a P2X5 receptor on satellite cells. J Cell Biol. Jul. 22, 2002;158(2):345-55.
Ryu et al., The construction of three-dimensional micro-fluidic scaffolds of biodegradable polymers by solvent vapor based bonding of micro-molded layers. Biomaterials. Feb. 2007;28(6):1174-84.
Sacchetti et al., Self-renewing osteoprogenitors in bone marrow sinusoids can organize a hematopoietic microenvironment. Cell. Oct. 19, 2007;131(2):324-36.
Sakai et al., An injectable, in situ enzymatically gellable, gelatin derivative for drug delivery and tissue engineering. Biomaterials. Jul. 2009;30(20):3371-7.
Salem et al., Defining the antigen-specific T-cell response to vaccination and poly(I:C)/TLR3 signaling: evidence of enhanced pri-

(56) References Cited

OTHER PUBLICATIONS mary and memory CD8 T-cell responses and antitumor immunity. J Immunother. May-Jun. 2005;28(3):220-8.
Salvador et al., Combination of immune stimulating adjuvants with poly(lactide-co-glycolide) microspheres enhances the immune response of vaccines. Vaccine. Jan. 11, 2012;30(3):589-96.
Salvay et al., Inductive tissue engineering with protein and DNA-releasing scaffolds. Mol Biosyst. Jan. 2006;2(1):36-48.
Sano et al., Swift development of protective effector functions in naive CD8(+) T cells against malaria liver stages. J Exp Med. Jul. 16, 2001;194(2):173-9.
Sansonetti, The innate signaling of dangers and the dangers of innate signaling. Nat Immunol. Dec. 2006;7(12):1237-42.
Sarkar et al., Condensation of oligonucleotides assembled into nicked and gapped duplexes: potential structures for oligonucleotide delivery. Nucleic Acids Res. Jan. 7, 2005;33(1):143-51.
Sato, Human dendritic cells. Biotherapy. Nov. 2004;18(6):467-77.
Saxena et al., Skeletal muscle tissue engineering using isolated myoblasts on synthetic biodegradable polymers: preliminary studies. Tissue Eng. Dec. 1999;5(6):525-32.
Schaefer et al., Innate immunity in the human female reproductive tract: antiviral response of uterine epithelial cells to the TLR3 agonist poly(I:C). J Immunol. Jan. 15, 2005;174(2):992-1002.
Scheel et al., Toll-like receptor-dependent activation of several human blood cell types by protamine-condensed mRNA. Eur J Immunol. May 2005;35(5):1557-66.
Schijns et al., Mice lacking IL-12 develop polarized Th1 cells during viral infection. J Immunol. Apr. 15, 1998;160(8):3958-64.
Schnorrer et al., The dominant role of CD8+ dendritic cells in cross-presentation is not dictated by antigen capture. Proc Natl Acad Sci U S A. Jul. 11, 2006;103(28):10729-34.
Schofield, The relationship between the spleen colony-forming cell and the haemopoietic stem cell. Blood Cells. 1978;4(1-2):7-25.
Schuler et al., The use of dendritic cells in cancer immunotherapy. Curr Opin Immunol. Apr. 2003;15(2):138-47.
Schwartz, A cell culture model for T lymphocyte clonal anergy. Science. Jun. 15, 1990;248(4961):1349-56.
Schwartz, Integrins and extracellular matrix in mechanotransduction. Cold Spring Harb Perspect Biol. Dec. 2010;2(12):a005066.
Seale et al., Pax7 is required for the specification of myogenic satellite cells. Cell. Sep. 15, 2000;102(6):777-86.
Sensi et al., Unique tumor antigens: evidence for immune control of genome integrity and immunogenic targets for T cell-mediated patient-specific immunotherapy. Clin Cancer Res. Sep. 1, 2006;12(17):5023-32.
Shakweh et al., Design and characterisation of poly(lactide-co-glycolide) small particulate systems for the delivery of immunostimulant CpG oligonucleotide. J Nanosci Nanotechnol. Sep.-Oct. 2006;6(9-10):2811-20.
Shaner et al., Improved monomeric red, orange and yellow fluorescent proteins derived from *Discosoma* sp. red fluorescent protein. Nat Biotechnol. Dec. 2004;22(12):1567-72.
Shansky et al., A simplified method for tissue engineering skeletal muscle organoids in vitro. In Vitro Cell Dev Biol Anim. Oct. 1997;33(9):659-61.
Shapiro et al., Sizing it up: cellular MRI using micron-sized iron oxide particles. Magn Reson Med. Feb. 2005;53(2):329-38.
Sheehan et al., Skeletal muscle satellite cell proliferation in response to members of the fibroblast growth factor family and hepatocyte growth factor. J Cell Physiol. Dec. 1999;181(3):499-506.
Sheppard et al., Polyethyleneimine is a potent systemic adjuvant for glycoprotein antigens. Int Immunol. Oct. 2014;26(10):531-8.
Sheridan et al., Bioabsorbable polymer scaffolds for tissue engineering capable of sustained growth factor delivery. J Control Release. Feb. 14, 2000;64(1-3):91-102.
Shi et al., A novel Toll-like receptor that recognizes vesicular stomatitis virus. J Biol Chem. Feb. 11, 2011;286(6):4517-24.
Shi et al., Granulocyte-macrophage colony-stimulating factor (GM-CSF) and T-cell responses: what we do and don't know. Cell Res. Feb. 2006;16(2):126-33.

Shibuya et al., Anti-CD3/anti-CD28 bead stimulation overcomes CD3 unresponsiveness in patients with head and neck squamous cell carcinoma. Arch Otolaryngol Head Neck Surg. Apr. 2000;126(4):473-9.
Shin et al., Contractile forces sustain and polarize hematopoiesis from stem and progenitor cells. Cell Stem Cell. Jan. 2, 2014;14(1):81-93.
Shin et al., Lamins regulate cell trafficking and lineage maturation of adult human hematopoietic cells. Proc Natl Acad Sci U S A. Nov. 19, 2013;110(47):18892-7.
Shin et al., Myosin-II inhibition and soft 2D matrix maximize multinucleation and cellular projections typical of platelet-producing megakaryocytes. Proc Natl Acad Sci U S A. Jul. 12, 2011;108(28):11458-63.
Shoichet et al., Stability of hydrogels used in cell encapsulation: An in vitro comparison of alginate and agarose. Biotechnol Bioeng. May 20, 1996;50(4):374-81.
Shortman et al., Steady-state and inflammatory dendritic-cell development. Nat Rev Immunol. Jan. 2007;7(1):19-30.
Sick et al., WNT and DKK determine hair follicle spacing through a reaction-diffusion mechanism. Science. Dec. 1, 2006;314(5804):1447-50.
Siegwart et al., Synthesis, characterization, and in vitro cell culture viability of degradable poly(N-isopropylacrylamide-co-5,6-benzo-2-methylene-1,3-dioxepane)-based polymers and crosslinked gels. J Biomed Mater Res A. Nov. 2008;87(2):345-58.
Silva et al., Effects of VEGF temporal and spatial presentation on angiogenesis. Biomaterials. Feb. 2010;31(6):1235-41.
Silva et al., Material-based deployment enhances efficacy of endothelial progenitor cells. Proc Natl Acad Sci U S A. Sep. 23, 2008;105(38):14347-52.
Silva et al., Spatiotemporal control of vascular endothelial growth factor delivery from injectable hydrogels enhances angiogenesis. J Thromb Haemost. Mar. 2007;5(3):590-8.
Simmons et al., GM-CSF as a systemic adjuvant in a phase II prostate cancer vaccine trial. Prostate. Jun. 1, 1999;39(4):291-7.
Simpson et al., Fc-dependent depletion of tumor-infiltrating regulatory T cells co-defines the efficacy of anti-CTLA-4 therapy against melanoma. J Exp Med. Aug. 26, 2013;210(9):1695-710.
Singer et al., Cutaneous wound healing. N Engl J Med. Sep. 2, 1999;341(10):738-46.
Skokos et al., CD8-DCs induce IL-12-independent Th1 differentiation through Delta 4 Notch-like ligand in response to bacterial LPS. J Exp Med. Jul. 9, 2007;204(7):1525-31.
Skuk et al., Efficacy of myoblast transplantation in nonhuman primates following simple intramuscular cell injections: toward defining strategies applicable to humans. Exp Neurol. May 2002;175(1):112-26.
Skuk et al., Myoblast transplantation: the current status of a potential therapeutic tool for myopathies. J Muscle Res Cell Motil. 2003;24(4-6):285-300.
Sletten et al., A hydrophilic azacyclooctyne for Cu-free click chemistry. Org Lett. Jul. 17, 2008;10(14):3097-9.
Smidsrød et al., Alginate as immobilization matrix for cells. Trends Biotechnol. Mar. 1990;8(3):71-8.
Sohier et al., Critical factors in the design of growth factor releasing scaffolds for cartilage tissue engineering. Expert Opin Drug Deliv. May 2008;5(5):543-66.
Solon et al., Fibroblast adaptation and stiffness matching to soft elastic substrates. Biophys J. Dec. 15, 2007;93(12):4453-61.
Sonawane et al., Chloride accumulation and swelling in endosomes enhances DNA transfer by polyamine-DNA polyplexes. J Biol Chem. Nov. 7, 2003;278(45):44826-31.
Springer et al., The lymphocyte function-associated LFA-1, CD2, and LFA-3 molecules: cell adhesion receptors of the immune system. Annu Rev Immunol. 1987;5:223-52.
Stachowiak et al., Inverse opal hydrogel-collagen composite scaffolds as a supportive microenvironment for immune cell migration. J Biomed Mater Res A. Jun. 1, 2008;85(3):815-28.
Steenblock et al., A comprehensive platform for ex vivo T-cell expansion based on biodegradable polymeric artificial antigen-presenting cells. Mol Ther. Apr. 2008;16(4):765-72.

(56) References Cited

OTHER PUBLICATIONS

Steenblock et al., An artificial antigen-presenting cell with paracrine delivery of IL-2 impacts the magnitude and direction of the T cell response. J Biol Chem. Oct. 7, 2011;286(40):34883-92.
Steinman et al., Taking dendritic cells into medicine. Nature. Sep. 27, 2007;449(7161):419-26.
Stockmann et al., Exploring isonitrile-based click chemistry for ligation with biomolecules. Organic & Biomolecular Chemistry. 2011;9:7300-7302.
Storrie et al., Sustained delivery of plasmid DNA from polymeric scaffolds for tissue engineering. Adv Drug Deliv Rev. Jul. 7, 2006;58(4):500-14.
Straub et al., Animal models for muscular dystrophy show different patterns of sarcolemmal disruption. J Cell Biol. Oct. 20, 1997;139(2):375-85.
Sun et al., Biomimetic interpenetrating polymer network hydrogels based on methacrylated alginate and collagen for 3D pre-osteoblast spreading and osteogenic differentiation. Soft Matter. Jan. 12, 2012;8:2398-2404.
Sun et al., Highly stretchable and tough hydrogels. Nature. Sep. 6, 2012;489(7414):133-6.
Sun et al., Sustained vascular endothelial growth factor delivery enhances angiogenesis and perfusion in ischemic hind limb. Pharm Res. Jul. 2005;22(7):1110-6.
Sunshine et al., Particle shape dependence of CD8+ T cell activation by artificial antigen presenting cells. Biomaterials. Jan. 2014;35(1):269-277.
Suri et al., Photopatterned collagen-hyaluronic acid interpenetrating polymer network hydrogels. Acta Biomater. Sep. 2009;5(7):2385-97.
Suzuki et al., A novel small-molecule inhibitor of transforming growth factor beta type I receptor kinase (SM16) inhibits murine mesothelioma tumor growth in vivo and prevents tumor recurrence after surgical resection. Cancer Res. Mar. 1, 2007;67(5):2351-9.
Swift et al., Nuclear lamin-A scales with tissue stiffness and enhances matrix-directed differentiation. Science. Aug. 30, 2013;341(6149):1240104. 17 pages.
Syed et al., Stem cell therapy market. Nat Rev Drug Discov. Mar. 2013;12(3):185-6.
Tabata et al., Enhanced Vascularization and Tissue Granulation by Basic Fibroblast Growth Factor Impregnated in Gelatin Hydrogels. Journal of Controlled Release. Sep. 1994;31(2):189-199.
Takahashi et al., Induction of pluripotent stem cells from adult human fibroblasts by defined factors. Cell. Nov. 30, 2007;131(5):861-72.
Takeshita et al., Therapeutic angiogenesis. A single intraarterial bolus of vascular endothelial growth factor augments revascularization in a rabbit ischemic hind limb model. J Clin Invest. Feb. 1994;93(2):662-70.
Tamura et al., Immunotherapy of tumors with autologous tumor-derived heat shock protein preparations. Science. Oct. 3, 1997;278(5335):117-20.
Tanaka et al., Collapse of gels in an electric field. Science. Oct. 29, 1982;218(4571):467-9.
Tang et al., Combining radiation and immunotherapy: a new systemic therapy for solid tumors? Cancer Immunol Res. Sep. 2014;2(9):831-8.
Tannous, Gaussia luciferase reporter assay for monitoring biological processes in culture and in vivo. Nat Protoc. 2009;4(4):582-91.
Tatsumi et al., HGF/SF is present in normal adult skeletal muscle and is capable of activating satellite cells. Dev Biol. Feb. 1, 1998;194(1):114-28.
Ten Dijke et al., Growth Factors for Wound Healing. Nat Biotechnol. 1989;7:793-798.
Thelin et al., In Vivo Enrichment of Diabetogenic T Cells. Diabetes. Aug. 2017;66(8):2220-2229.
Thomas et al., Intravenous infusion of bone marrow in patients receiving radiation and chemotherapy. N Engl J Med. Sep. 12, 1957;257(11):491-6.
Thornton et al., Shape retaining injectable hydrogels for minimally invasive bulking. J Urol. Aug. 2004;172(2)763-8.
Thurner et al., Vaccination with mage-3A1 peptide-pulsed mature, monocyte-derived dendritic cells expands specific cytotoxic T cells and induces regression of some metastases in advanced stage IV melanoma. J Exp Med. Dec. 6, 1999;190(11):1669-78.
Thurston et al., The Delta paradox: DLL4 blockade leads to more tumour vessels but less tumour growth. Nat Rev Cancer. May 2007;7(5):327-31.
Tidball, Inflammatory cell response to acute muscle injury. Med Sci Sports Exerc. Jul. 1995;27(7):1022-32.
Tomer et al., Electrically Controlled Release of Macromolecules from Cross-Linked Hyaluronic Acid Hydrogels. Journal of Controlled Release. Mar. 1995:33(3):405-413.
Tong et al., Engineering interpenetrating network hydrogels as biomimetic cell niche with independently tunable biochemical and mechanical properties. Biomaterials. Feb. 2014;35(6):1807-15.
Tourniaire et al., Polymer microarrays for cellular adhesion. Chem Commun (Camb). May 28, 2006;(20):2118-20.
Trappmann et al., Extracellular-matrix tethering regulates stem-cell fate. Nat Mater. May 27, 2012;11(7):642-9.
Trappmann et al., How cells sense extracellular matrix stiffness: a material's perspective. Curr Opin Biotechnol. Oct. 2013;24(5):948-53.
Tripathi et al., Elastic and macroporous agarose-gelatin cryogels with isotropic and anisotropic porosity for tissue engineering. J Biomed Mater Res A. Sep. 1, 2009;90(3):680-94.
Tsien, The green fluorescent protein. Annu Rev Biochem. 1998;67:509-44.
Turing, Discussion: Turing's Theory of Morphogenesis—Its Influence on Modelling Biological Pattern and Form. Bull Math Biol. 1990;52(1-2):119-159.
Turing, The Chemical Basis of Morphogenesis. Philosophical Transactions of the Royal Society of London. Series B. 1952;237(641):37-72.
Turtle et al., Anti-CD19 Chimeric Antigen Receptor-Modified T Cell Therapy for B Cell Non-Hodgkin Lymphoma and Chronic Lymphocytic Leukemia: Fludarabine and Cyclophosphamide Lymphodepletion Improves In Vivo Expansion and Persistence of CAR-T Cells and Clinical Outcomes. Blood. 2015;126:184.
Turtle et al., CD19 CAR-T cells of defined CD4+:CD8+ composition in adult B cell ALL patients. J Clin Invest. Jun. 1, 2016;126(6):2123-38.
Uchida et al., Immunization by particle bombardment of antigen-loaded poly-(DL-lactide-co-glycolide) microspheres in mice. Vaccine. Mar. 15, 2006;24(12):2120-30.
Ugarte et al., Notch signaling enhances osteogenic differentiation while inhibiting adipogenesis in primary human bone marrow stromal cells. Exp Hematol. Jul. 2009;37(7):867-875.
Uhlenbruck, Action of proteolytic enzymes on the human erythrocyte surface. Nature. Apr. 8, 1961;190:181.
Ulrich et al., Probing cellular mechanobiology in three-dimensional culture with collagen-agarose matrices. Biomaterials. Mar. 2010;31(7):1875-84.
UniProtKB/Swiss-Prot Accession No. P02751.4, Apr. 16, 2014.
UniProtKB/Swiss-Prot Accession No. P02778.2, Jun. 11, 2014.
UniProtKB/Swiss-Prot Accession No. P04626.1, Apr. 16, 2014.
UniProtKB/Swiss-Prot Accession No. P05121.1, Apr. 16, 2014.
UniProtKB/Swiss-Prot Accession No. P05231.1, Jun. 11, 2014.
UniProtKB/Swiss-Prot Accession No. P09038.3, Jun. 11, 2014.
UniProtKB/Swiss-Prot Accession No. P10145.1, Jun. 11, 2014.
UniProtKB/Swiss-Prot Accession No. P13500.1, Jun. 11, 2014.
UniProtKB/Swiss-Prot Accession No. P14210.2, Jun. 11, 2014.
UniProtKB/Swiss-Prot Accession No. P14780.3, Jun. 11, 2014.
UniProtKB/Swiss-Prot Accession No. P14902.1, May 14, 2014.
UniProtKB/Swiss-Prot Accession No. P15692.2, Jun. 11, 2014.
UniProtKB/Swiss-Prot Accession No. P16035.2, Jun. 11, 2014.
UniProtKB/Swiss-Prot Accession No. P16410.3, Apr. 16, 2014.
UniProtKB/Swiss-Prot Accession No. P48061.1, Jun. 18, 2014.
UniProtKB/Swiss-Prot Accession No. P80162.4, Jun. 11, 2014.
UniProtKB/Swiss-Prot Accession No. P98066.2, Feb. 19, 2014.
UniProtKB/Swiss-Prot Accession No. Q8TDQ0.3, Mar. 19, 2014.
UniProtKB/Swiss-Prot Accession No. Q96HF1.2, May 14, 2014.

(56) References Cited

OTHER PUBLICATIONS

UniProtKB/Swiss-Prot Accession No. Q9BQ51.2, Mar. 19, 2014.
UniProtKB/Swiss-Prot Accession No. Q9HCB6.2, Jun. 11, 2014.
UniProtKB/Swiss-Prot Accession No. Q9NZQ7.1, Apr. 16, 2014.
Urbanek et al., Stem cell niches in the adult mouse heart. Proc Natl Acad Sci U S A. Jun. 13, 2006;103(24):9226-31.
Van Berkel et al., Metal-free triazole formation as a tool for bioconjugation. Chembiochem. Sep. 3, 2007;8(13):1504-8.
Van Der Bruggen et al., Peptide Database: T cell-defined tumor antigens. Cancer Immunity. Retrieved online at: http://www.cancerimmunity.org/peptide/ 59 pages. (2013).
Van Duin et al., Triggering TLR signaling in vaccination. Trends Immunol. Jan. 2006;27(1):49-55.
Van Elsas et al., Combination immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation. J Exp Med. Aug. 2, 1999;190(3):355-66.
Van Elsas et al., Elucidating the autoimmune and antitumor effector mechanisms of a treatment based on cytotoxic T lymphocyte antigen-4 blockade in combination with a B16 melanoma vaccine: comparison of prophylaxis and therapy. J Exp Med. Aug. 20, 2001;194(4):481-9.
Vandenburgh et al., Tissue-engineered skeletal muscle organoids for reversible gene therapy. Hum Gene Ther. Nov. 10, 1996;7(17):2195-200.
Venturoni et al., Investigations into the polymorphism of rat tail tendon fibrils using atomic force microscopy. Biochem Biophys Res Commun. Apr. 4, 2003;303(2):508-13.
Vieira et al., Polysaccharide-based hydrogels: preparation, characterization, and drug interaction behaviour. Biomacromolecules. Apr. 2008;9(4):1195-9.
Vieira et al., The bulk of endogenously produced IgG2a is eliminated from the serum of adult C57BL/6 mice with a half-life of 6-8 days. Eur J Immunol. Jul. 1986;16(7):871-4.
Vieira et al., The half-lives of serum immunoglobulins in adult mice. Eur J Immunol. Feb. 1988;18(2):313-6.
Villadangos et al., Intrinsic and cooperative antigen-presenting functions of dendritic-cell subsets in vivo. Nat Rev Immunol. Jul. 2007;7(7):543-55.
Villadangos, Presentation of antigens by MHC class II molecules: getting the most out of them. Mol Immunol. Sep. 2001;38(5):329-46.
Vincent et al., Stem cell differentiation: Post-degradation forces kick in. Nat Mater. May 2013;12(5):384-6.
Vogel et al., Local force and geometry sensing regulate cell functions. Nat Rev Mol Cell Biol. Apr. 2006;7(4):265-75.
Von Dassow et al., The segment polarity network is a robust developmental module. Nature. Jul. 13, 2000;406(6792):188-92.
W.H.O., World Health Organization, Global Burden of Musculo-skeletal Disease Revealed in new WHO Report. Bull World Health Organ. 2003;81(11):853-854.
W.H.O., World Health Organization, The World Health Report 2004: Changing History. The World Health Report. 2004:1-169.
Wakim et al., Dendritic cell-induced memory T cell activation in nonlymphoid tissues. Science. Jan. 11, 2008;319(5860):198-202.
Wan et al., Peritoneal macrophage uptake, pharmacokinetics and biodistribution of macrophage-targeted PEG-fMLF (N-formyl-methionyl-leucyl-phenylalanine) nanocarriers for improving HIV drug delivery. Pharm Res. Nov. 2007;24(11):2110-9.
Wang et al., Biological activity of bevacizumab, a humanized anti-VEGF antibody in vitro. Angiogenesis. 2004;7(4):335-45.
Wang et al., Evolution of new nonantibody proteins via iterative somatic hypermutation. Proc Natl Acad Sci U S A. Nov. 30, 2004;101(48):16745-9.
Wang et al., Mechanotransduction at a distance: mechanically coupling the extracellular matrix with the nucleus. Nat Rev Mol Cell Biol. Jan. 2009;10(1):75-82.

Wang et al., Mouse CD229 Ligation Co-stimulates T Cell Activation. The Journal of Immunology. May 2012;188(suppl 1):176.7.
Wang et al., Photothermal effects of supramolecularly assembled gold nanoparticles for the targeted treatment of cancer cells. Angew Chem Int Ed Engl. May 17, 2010;49(22):3777-81.
Wang-Gillam et al., A phase I study of IMP321 and gemcitabine as the front-line therapy in patients with advanced pancreatic adenocarcinoma. Invest New Drugs. Jun. 2013;31(3):707-13.
Warner et al., Cyclooxygenases: new forms, new inhibitors, and lessons from the clinic. FASEB J. May 2004;18(7):790-804.
Weeks et al., The effects of chemokine, adhesion and extracellular matrix molecules on binding of mesenchymal stromal cells to poly(l-lactic acid). Cytotherapy. Oct. 2012;14(9):1080-8.
Wegmann et al., Polyethyleneimine is a potent mucosal adjuvant for viral glycoprotein antigens. Nat Biotechnol. Sep. 2012;30(9):883-8.
Wei et al., Global mapping of H3K4me3 and H3K27me3 reveals specificity and plasticity in lineage fate determination of differentiating CD4+ T cells. Immunity. Jan. 16, 2009;30(1):155-67.
Weiner et al., Immunostimulatory oligodeoxynucleotides containing the CpG motif are effective as immune adjuvants in tumor antigen immunization. Proc Natl Acad Sci U S A. Sep. 30, 1997;94(20):10833-7.
Weiner, Induction and mechanism of action of transforming growth factor-beta-secreting Th3 regulatory cells. Immunol Rev. Aug. 2001;182:207-14.
Weisenberger et al., Comprehensive DNA Methylation Analysis on the Illumina® Infinium® Assay Platform. Illumina, Inc., 4 pages, Mar. 25, 2008.
Weiss et al., The demonstration of rupture of cell surfaces by an immunological technique. Exp Cell Res. Apr. 1963;30:331-8.
Wen et al., Mechanically Robust Gelatin-Alginate IPN Hydrogels by a Combination of Enzymatic and Ionic Crosslinking Approaches. Macromol Mater Eng. Apr. 2014;299(4):504-513.
Wernig et al., Function of skeletal muscle tissue formed after myoblast transplantation into irradiated mouse muscles. J Physiol. Jan. 15, 2000;522 Pt 2:333-45.
White et al., Leukemia inhibitory factor enhances regeneration in skeletal muscles after myoblast transplantation. Muscle Nerve. May 2001;24(5):695-7.
Wieland et al., Engineering molecular circuits using synthetic biology in mammalian cells. Annu Rev Chem Biomol Eng. 2012;3:209-34.
Wipff et al., Myofibroblast contraction activates latent TGF-beta1 from the extracellular matrix. J Cell Biol. Dec. 17, 2007;179(6):1311-23.
Wong et al., Focal adhesion kinase links mechanical force to skin fibrosis via inflammatory signaling. Nat Med. Dec. 11, 2011;18(1):148-52.
Wong et al., Mechanical force prolongs acute inflammation via T-cell-dependent pathways during scar formation. FASEB J. Dec. 2011;25(12):4498-510.
Wong et al., Pushing back: wound mechanotransduction in repair and regeneration. J Invest Dermatol. Nov. 2011;131(11):2186-96.
Wozniak et al., Mechanotransduction in development: a growing role for contractility. Nat Rev Mol Cell Biol. Jan. 2009;10(1):34-43.
Wright et al., Muscle-based gene therapy and tissue engineering for the musculoskeletal system. Drug Discov Today. Jul. 1, 2001;6(14):728-733.
Wu et al., Intraperitoneal administration of poly(I:C) with polyethylenimine leads to significant antitumor immunity against murine ovarian tumors. Cancer Immunol Immunother. Aug. 2011;60(8):1085-96.
Xie et al., Preparation and Application of Surface-Coated Superparamagnetic Nanobeads in the Isolation of Genomic DNA. J Magn Magnetic Mater. Jun. 2004;277(1-2):16-23.
Xiong et al., Transcription Factor STAT3 as a Novel Molecular Target for Cancer Prevention. Cancers (Basel). Apr. 16, 2014;6(2):926-57.
Yamazaki et al., CD8+ CD205+ splenic dendritic cells are specialized to induce Foxp3+ regulatory T cells. J Immunol. Nov. 15, 2008;181(10):6923-33.
Yancopoulos et al., Vascular-specific growth factors and blood vessel formation. Nature. Sep. 14, 2000;407(6801):242-8.

(56) References Cited

OTHER PUBLICATIONS

Yang et al., The effect of incorporating RGD adhesive peptide in polyethylene glycol diacrylate hydrogel on osteogenesis of bone marrow stromal cells. Biomaterials. Oct. 2005;26(30):5991-8.

Yee et al., Melanocyte destruction after antigen-specific immunotherapy of melanoma: direct evidence of t cell-mediated vitiligo. J Exp Med. Dec. 4, 2000;192(11):1637-44.

Yeung et al., Effects of substrate stiffness on cell morphology, cytoskeletal structure, and adhesion. Cell Motil Cytoskeleton. Jan. 2005;60(1):24-34.

Yoo et al., Bio-inspired, bioengineered and biomimetic drug delivery carriers. Nat Rev Drug Discov. Jul. 1, 2011;10(7):521-35.

Yoon, Hidden Markov Models and their Applications in Biological Sequence Analysis. Curr Genomics. Sep. 2009;10(6):402-15.

Young et al., Gelatin as a delivery vehicle for the controlled release of bioactive molecules. J Control Release. Dec. 5, 2005;109(1-3):256-74.

Yu et al., Induced pluripotent stem cell lines derived from human somatic cells. Science. Dec. 21, 2007;318(5858):1917-20.

Yuen et al., Mimicking nature by codelivery of stimulant and inhibitor to create temporally stable and spatially restricted angiogenic zones. Proc Natl Acad Sci U S A. Oct. 19, 2010;107(42):17933-8.

Yuk et al., Electric current-sensitive drug delivery systems using sodium alginate/polyacrylic acid composites. Pharm Res. Jul. 1992;9(7):955-7.

Zammit et al., Kinetics of myoblast proliferation show that resident satellite cells are competent to fully regenerate skeletal muscle fibers. Exp Cell Res. Nov. 15, 2002;281(1):39-49.

Zammit et al., Muscle satellite cells adopt divergent fates: a mechanism for self-renewal? J Cell Biol. Aug. 2, 2004;166(3):347-57.

Zappasodi et al., The effect of artificial antigen-presenting cells with preclustered anti-CD28/-CD3/-LFA-1 monoclonal antibodies on the induction of ex vivo expansion of functional human antitumor T cells. Haematologica. Oct. 2008;93(10):1523-34.

Zeltinger et al., Effect of pore size and void fraction on cellular adhesion, proliferation, and matrix deposition. Tissue Eng. Oct. 2001;7(5):557-72.

Zemel et al. Optimal matrix rigidity for stress fiber polarization in stem cells. Nat Phys. Jun. 1, 2010;6(6):468-473.

Zhang et al., A comparative study of the antigen-specific immune response induced by co-delivery of CpG ODN and antigen using fusion molecules or biodegradable microparticles. J Pharm Sci. Dec. 2007;96(12):3283-92.

Zhang et al., A tension-induced mechanotransduction pathway promotes epithelial morphogenesis. Nature. Mar. 3, 2011;471(7336):99-103.

Zhang et al., Generation of a syngeneic mouse model to study the effects of vascular endothelial growth factor in ovarian carcinoma. Am J Pathol. Dec. 2002;161(6):2295-309.

Zhang et al., Talin depletion reveals independence of initial cell spreading from integrin activation and traction. Nat Cell Biol. Sep. 2008;10(9):1062-8.

Zhao et al., A cell-permeable Stat3 SH2 domain mimetic inhibits Stat3 activation and induces antitumor cell effects in vitro. J Biol Chem. Nov. 12, 2010;285(46):35855-65.

Zhao et al., Active scaffolds for on-demand drug and cell delivery. Proc Natl Acad Sci U S A. Jan. 4, 2011;108(1):67-72.

Zhao et al., Directed cell migration via chemoattractants released from degradable microspheres. Biomaterials. Aug. 2005;26(24):5048-63.

Zhao et al., Stress-relaxation behavior in gels with ionic and covalent crosslinks. J Appl Phys. Mar. 15, 2010;107(6):63509.

Zhou et al., Instability of the transcription factor Foxp3 leads to the generation of pathogenic memory T cells in vivo. Nat Immunol. Sep. 2009;10(9):1000-7.

Zhou et al., Microstructure and Mechanical Properties of Poly(L-lactide) Scaffolds Fabricated by Gelatin Particle Leaching Method. J Appl Polymer Sci. Nov. 5, 2005;98(3):1373-1379.

Zizzari et al., The Macrophage Galactose-Type C-Type Lectin (MGL) Modulates Regulatory T Cell Functions. PLoS One. Jul. 6, 2015;10(7):e0132617. 12 pages.

U.S. Appl. No. 15/564,905, filed Oct. 6, 2017, 2018-0164298, Allowed.

U.S. Appl. No. 17/381,031, filed Jul. 20, 2021, Pending.

U.S. Appl. No. 15/935,392, filed Mar. 26, 2018, 2018-0344821, Published.

Andersson et al., HSP70 promoter-driven activation of gene expression for immunotherapy using gold nanorods and near infrared light. Vaccines (Basel). Mar. 25, 2014;2(2):216-27.

Bhardwaj et al., TLR Agonists: Are They Good Adjuvants? Cancer J. 2010;16(4):382-391.

Casanova et al., Human Mannose-binding Lectin in Immunity: Friend, Foe, or Both?. J Exp Med. 2004;199 (10):1295-1299.

Chao et al., Morphological control on SBA-15 mesoporous silicas via a slow self-assembling rate. J Mater Sci. 2009;44:6453-62.

Che et al., Synthesis and characterization of chiral mesoporous silica. Nature. May 20, 2004;429(6989):281-4.

Chen et al., Enhanced humoral and cell-mediated immune responses generated by cationic polymer-coated PLA microspheres with adsorbed HBsAg. Mol Pharm. Jun. 2, 2014;11(6):1772-84.

Chen et al., Morphological control of mesoporous silica SBA-15 synthesized at low temperature without additives. J Porous Mater. 2011;18:211-6.

Chen et al., Quantitative proteomic profiling of pancreatic cancer juice. Proteomics. Jul. 2006;6(13):3871-9.

Cheung et al., Engineered Materials for Cancer Immunotherapy. Nano Today. Aug. 1, 2015;10(4):511-531.

Cheung et al., Scaffolds that mimic antigen-presenting cells enable ex vivo expansion of primary T cells. Nat Biotechnol. Feb. 2018;36(2):160-169.

Choi et al., Facile synthesis of high quality mesoporous SBA-15 with enhanced control of the porous network connectivity and wall thickness. Chem Commun (Camb). Jun. 21, 2003;(12):1340-1.

Cooper, A Genetic Pathogen Capture Technology for Sepsis Diagnosis. Submitted to the Department of Chemical Engineering in Partial Fulfillment of the Requirements for the Degree of Doctor of Philosophy in Medical and Engineering Physics at the Massachusetts Institute of Technology. 130 pages, May 1, 2013.

Del Chiaro et al., Early detection and prevention of pancreatic cancer: is it really possible today? World J Gastroenterol. Sep. 14, 2014;20(34):12118-31.

Dengler et al., Mesoporous silica-supported lipid bilayers (protocells) for DNA cargo delivery to the spinal cord. J Control Release. Jun. 10, 2013;168(2):209-24.

Drury et al., Hydrogels for tissue engineering: scaffold design variables and applications. Biomaterials. Nov. 2003;24(24):4337-51.

Egea et al., Role of secreted glyceraldehyde-3-phosphate dehydrogenase in the infection mechanism of enterohemorrhagic and enteropathogenic *Escherichia coli*: interaction of the extracellular enzyme with human plasminogen and fibrinogen. Int J Biochem Cell Biol. 2007;39(6):1190-203.

Eggermont et al., Towards efficient cancer immunotherapy: advances in developing artificial antigen-presenting cells. Trends Biotechnol. Sep. 2014;32(9):456-65.

Ennett, Temporal Delivery of Multiple Growth Factors from Polymer Scaffolds to Enhance Neovascularization. A dissertation submitted in partial fulfillment of the requirements for the degree of Doctor of Philosophy (Biomedical Engineering) in the University of Michigan. 186 pages, (2004).

Gao et al., Immune cell recruitment and cell-based system for cancer therapy. Pharm Res. Apr. 2008;25(4):752-68.

Grabowska et al., Systemic in vivo delivery of siRNA to tumours using combination of polyethyleneimine and transferrin-polyethyleneimine conjugates. Biomater Sci. Nov. 2015,3(11):1439-48.

Han et al., Synthesis of rod-like mesoporous silica using mixed surfactants of cetyltrimethylammonium bromide and cetyltrimethylammonium chloride as templates. Materials Letters. 2003;57:4520-4.

(56) References Cited

OTHER PUBLICATIONS

Jiang, Application of polymers in nucleic acid delivery. Thesis in partial fulfillment of the requirements for the Doctor of Philosophy degree in Pharmacy in the Graduate College of The University of Iowa. 138 pages, Dec. 2011.
Johansson, Controlling the Pore Size and Morphology of Mesoporous Silica. Linkoping Studies in Science and Technology Licentiate Thesis No. 1451, 53 pages, (2010).
John et al., Passive and active mechanisms trap activated CD8+ T cells in the liver. J Immunol. May 1, 2004;172 (9):5222-9.
Kosuge et al., Morphological Control of Rod- and Fiberlike SBA-15 Type Mesoporous Silica Using Water-Soluble Sodium Silicate. Chem Mater. 2004;16:899-905.
Lacy et al., Cytokine release from innate immune cells: association with diverse membrane trafficking pathways. Blood. 2011;118(1):9-18.
Lauw et al., Proinflammatory effects of IL-10 during human endotoxemia. J Immunol. Sep. 1, 2000;165(5):2783-9.
Liu et al., Porous nanoparticle supported lipid bilayers (protocells) as delivery vehicles. J Am Chem Soc. Feb. 4, 2009;131(4):1354-5.
Millar et al., Prediction of local recurrence, distant metastases, and death after breast-conserving therapy in early-stage invasive breast cancer using a five-biomarker panel. J Clin Oncol. Oct. 1, 2009;27(28):4701-8.
Milone et al., Powered and controlled T-cell production. Nat Biomed Eng. Mar. 2018;2(3):148-150.
Mu et al., Identification and characterization of a mannose-binding lectin from Nile tilapia (*Oreochromis niloticus*). Fish Shellfish Immunol. 2017;67:244-253.
Qiao et al., Synthesis and Bio-adsorptive Properties of Large-Pore Periodic Mesoporous Organosilica Rods. Chem Mater. 2005;17:6172-6.
Singh et al., Hydrogels and scaffolds for immunomodulation. Adv Mater. Oct. 2014;26(38):6530-41.
Stanley et al., Transjugular intrahepatic portosystemic shunt as a treatment for protein-losing enteropathy caused by portal hypertension. Gastroenterology. Dec. 1996;111(6):1679-82.
Stephen et al., Biopolymer implants enhance the efficacy of adoptive T-cell therapy. Nat Biotechnol. Jan. 2015;33 (1):97-101.
Sunshine et al., Nanoengineering approaches to the design of artificial antigen-presenting cells. Nanomedicine. 2013;8(7):1173-89.
Takamura et al., Regulatory role of lymphoid chemokine CCL19 and CCL21 in the control of allergic rhinitis. J Immunol. 2007;179(9):5897-5906.
Thielemann et al., Pore structure and surface area of silica SBA-15: influence of washing and scale-up. Beilstein J Nanotechnol. 2011;2:110-8.
Veldhoen et al., TGFbeta1, a "Jack of all trades": the link with pro-inflammatory IL-17-producing T cells. Trends Immunol. Aug. 2006;27(8):358-61.
Yu, Designed synthesis of mono-dispersed silica-based nanostructures and their applications in drug/gene delivery. A thesis submitted for the degree of Doctor of Philosophy at The University of Queensland in 2014, 196 pages.
Beduer et al., A compressible scaffold for minimally invasive delivery of large intact neuronal networks. Adv Healthc Mater. Jan. 28, 2015;4(2):301-12.
Furdui et al., Immunomagnetic T cell capture from blood for PCR analysis using microfluidic systems. Lab Chip. Dec. 2004;4(6):614-8.
Jain et al., Macroporous interpenetrating cryogel network of poly(acrylonitrile) and gelatin for biomedical applications. J Mater Sci Mater Med. Dec. 2009;20 Suppl 1:S173-9.
Lee et al., Chemical tumor-targeting of nanoparticles based on metabolic glycoengineering and click chemistry. ACS Nano. Mar. 25, 2014;8(3):2048-63.
Lee et al., Effect of dual treatment with SDF-1 and BMP-2 on ectopic and orthotopic bone formation. PLoS One. Mar. 17, 2015;10(3):e0120051, 15 pages.
Lipson et al., Ipilimumab: an anti-CTLA-4 antibody for metastatic melanoma. Clin Cancer Res. Nov. 15, 2011;17 (22):6958-62.
Lungu et al., Linear and Branched PEIs (Polyethylenimines) and Their Property Space. Int J Mol Sci. Apr. 13, 2016;17(4):555.
MeSH, Nivolumab. Retrieved online at: https://www.ncbi.nlm.nih.gov/mesh/?term=nivolumab. 2 pages, (2010).
Sahdev et al., Biomaterials for nanoparticle vaccine delivery systems. Pharm Res. Oct. 2014;31(10):2563-82.
Shah et al., An injectable bone marrow-like scaffold enhances T cell immunity after hematopoietic stem cell transplantation. Nat Biotechnol. Mar. 2019;37(3):293-302.
Shukla, Controlled Generation of Progenitor T-cells from Hematopoietic Stem Cells and Pluripotent Stem Cells. A thesis submitted in conformity with the requirements for the degree of Doctorate of Philosophy, Institute of Biomaterials and Biomedical Engineering, University of Toronto. 214 pages, (2017).
Sobral et al., Antigen-free cancer vaccine to treat poorly immunogenic tumors. Cancer Immunol Res. 2019;7(2 Suppl):Abstract B045.
Super et al., Biomaterial vaccines capturing pathogen-associated molecular patterns protect against bacterial infections and septic shock. Nat Biomed Eng. Jan. 2022;6(1):8-18.
Titan et al., Growth Factor Delivery to a Bovine Defect Using Leukocyte-Rich Platelet-Rich Concentrates on a Hyaluronic Acid Scaffold. Arthroscopy: The Journal of Arthroscopic and Related Surgery. Pre-publication edition, 33 pages, Dec. 2019.
Wikipedia, Matrigel. Retrieved online at: https://en.wikipedia.org/wiki/Matrigel. 4 pages, Oct. 10, 2018.
Wolchok et al., Nivolumab plus ipilimumab in advanced melanoma. N Engl J Med. Jul. 11, 2013;369(2):122-33.
U.S. Appl. No. 15/434,781, filed Feb. 16, 2017, U.S. Pat. No. 10,813,988, Issued.
U.S. Appl. No. 17/015,177, filed Sep. 9, 2020, 2021-0170007, Published.
U.S. Appl. No. 13/386,950, filed Jan. 25, 2012, U.S. Pat. No. 8,728,456, Issued.
U.S. Appl. No. 14/185,494, filed Feb. 20, 2014, U.S. Pat. No. 9,381,235, Issued.
U.S. Appl. No. 15/147,442, filed May 5, 2016, U.S. Pat. No. 10,080,789, Issued.
U.S. Appl. No. 16/121,988, filed Sep. 5, 2018, 2019-0183992, Abandoned.
U.S. Appl. No. 15/564,905, filed Oct. 6, 2017, U.S. Pat. No. 11,150,242, Issued.
U.S. Appl. No. 17/501,821, filed Oct. 14, 2021, 2022-0107308, Published.
U.S. Appl. No. 11/638,796, filed Dec. 13, 2006, U.S. Pat. No. 8,067,237, Issued.
U.S. Appl. No. 13/305,088, filed Nov. 28, 2011, U.S. Pat. No. 8,932,583, Issued.
U.S. Appl. No. 14/223,759, filed Mar. 24, 2014, U.S. Pat. No. 9,132,210, Issued.
U.S. Appl. No. 14/750,423, filed Jun. 25, 2015, U.S. Pat. No. 9,446,107, Issued.
U.S. Appl. No. 15/085,858, filed Mar. 30, 2016, 2016-0271298, Abandoned.
U.S. Appl. No. 15/135,207, filed Apr. 21, 2016, U.S. Pat. No. 10,149,897, Issued.
U.S. Appl. No. 15/135,213, filed Apr. 21, 2016, U.S. Pat. No. 10,137,184, Issued.
U.S. Appl. No. 16/170,313, filed Oct. 25, 2018, U.S. Pat. No. 11,096,997, Issued.
U.S. Appl. No. 17/381,031, filed Jul. 20, 2021, Abandoned.
U.S. Appl. No. 13/877,572, filed Nov. 19, 2013, U.S. Pat. No. 11,202,759, Issued.
U.S. Appl. No. 17/522,297, filed Nov. 9, 2021, 2022-0192986, Published.
U.S. Appl. No. 14/112,096, filed Dec. 27, 2013, U.S. Pat. No. 10,045,947, Issued.
U.S. Appl. No. 14/166,689, filed Jan. 28, 2014, U.S. Pat. No. 9,675,561, Issued.
U.S. Appl. No. 15/617,837, filed Jun. 8, 2017, 2018-0243231, Abandoned.

(56) References Cited

OTHER PUBLICATIONS

U.S. Appl. No. 16/033,025, filed Jul. 11, 2018, 2019-0076373, Published.
U.S. Appl. No. 17/083,720, filed Oct. 29, 2020, 2021-0205233, Published.
U.S. Appl. No. 14/394,552, filed Oct. 15, 2014, U.S. Pat. No. 9,937,249, Issued.
U.S. Appl. No. 15/935,392, filed Mar. 26, 2018, U.S. Pat. No. 11,278,604, Issued.
U.S. Appl. No. 17/693,017, filed Mar. 11, 2022, Pending.
U.S. Appl. No. 15/303,985, filed Oct. 13, 2016, U.S. Pat. No. 10,682,400, Issued.
U.S. Appl. No. 16/877,274, filed May 18, 2020, 2020-0276290, Published.
U.S. Appl. No. 16/263,098, filed Jan. 31, 2019, 2019-0216910, Published.
U.S. Appl. No. 12/867,426, filed Jan. 13, 2012, U.S. Pat. No. 10,328,133, Issued.
U.S. Appl. No. 15/135,255, filed Apr. 21, 2016, U.S. Pat. No. 10,258,677, Issued.
U.S. Appl. No. 15/135,290, filed Apr. 21, 2016, 2016-0228543, Abandoned.
U.S. Appl. No. 15/135,294, filed Apr. 21, 2016, 2016-0220668, Abandoned.
U.S. Appl. No. 13/510,356, filed May 17, 2012, Abandoned.
U.S. Appl. No. 14/123,615, filed Mar. 17, 2014, U.S. Pat. No. 9,486,512, Issued.
U.S. Appl. No. 15/345,131, filed Nov. 7, 2016, U.S. Pat. No. 10,406,216, Issued.
U.S. Appl. No. 13/741,271, filed Jan. 14, 2013, U.S. Pat. No. 9,370,558, Issued.
U.S. Appl. No. 15/135,216, filed Apr. 21, 2016, 9,821,045, Issued.
U.S. Appl. No. 15/818,509, filed Nov. 20, 2017, U.S. Pat. No. 10,568,949, Issued.
U.S. Appl. No. 15/563,878, filed Oct. 2, 2017, 2018-0117171, Abandoned.
U.S. Appl. No. 15/546,852, filed Jul. 27, 2017, 2018-0021253, Published.
U.S. Appl. No. 16/075,937, filed Aug. 6, 2018, 2019-0060525, Published.
U.S. Appl. No. 16/708,218, filed Dec. 9, 2019, 2020-0206333, Published.
U.S. Appl. No. 17/414,037, filed Jun. 15, 2021, 2022-0047778, Published.
U.S. Appl. No. 17/701,270, filed Mar. 22, 2022, Pending.

* cited by examiner

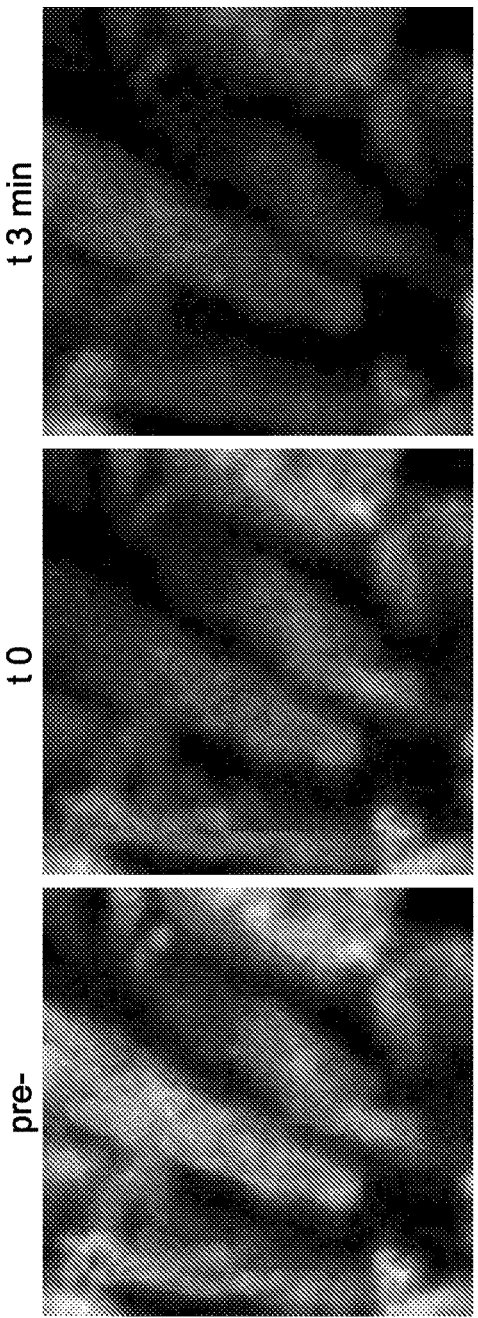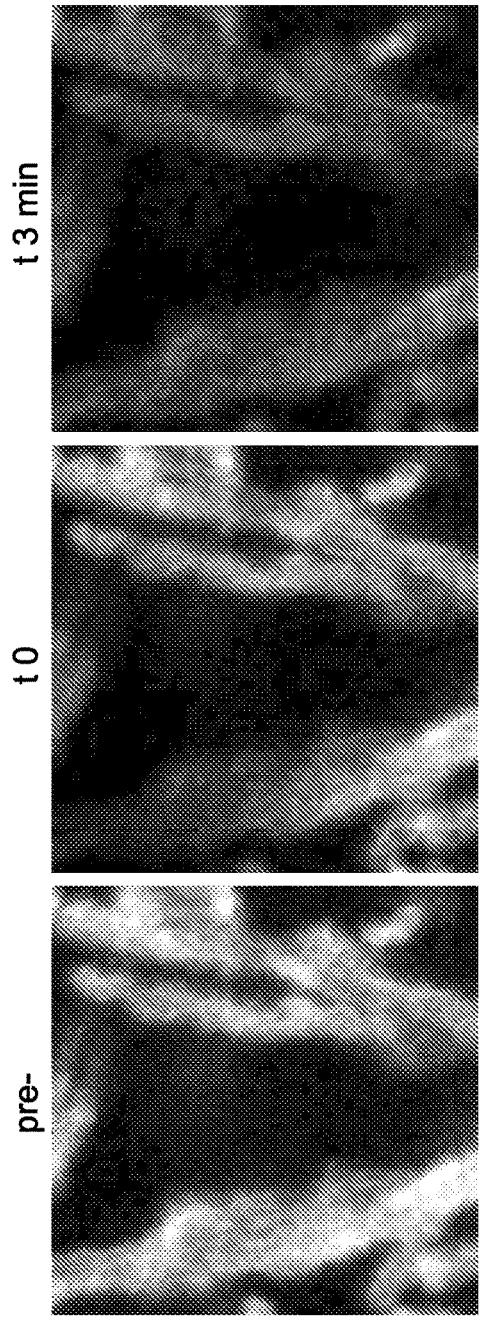

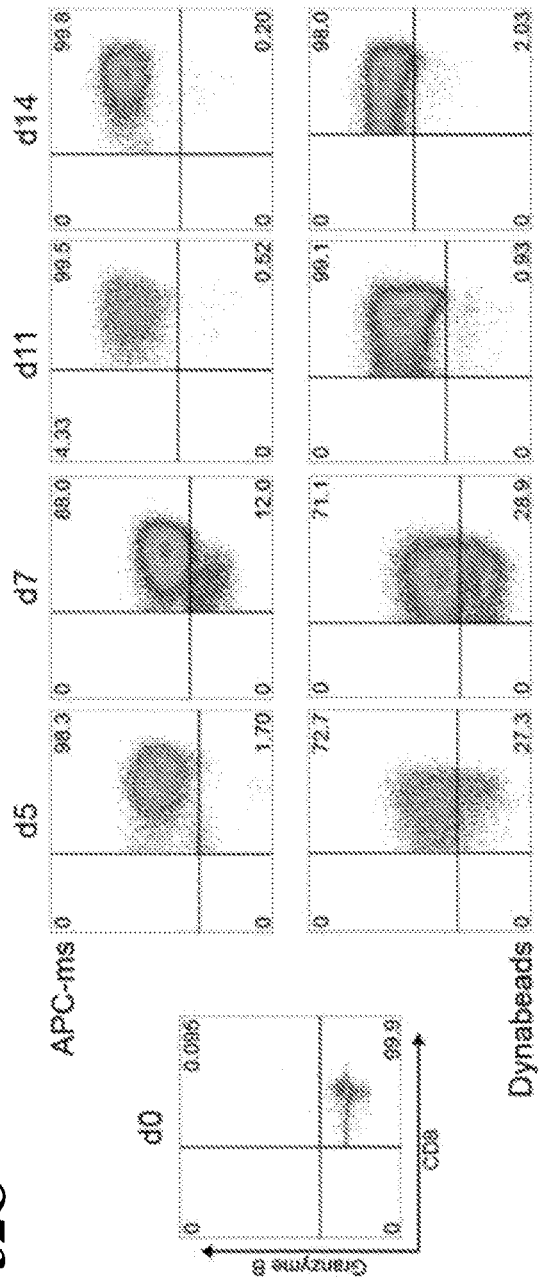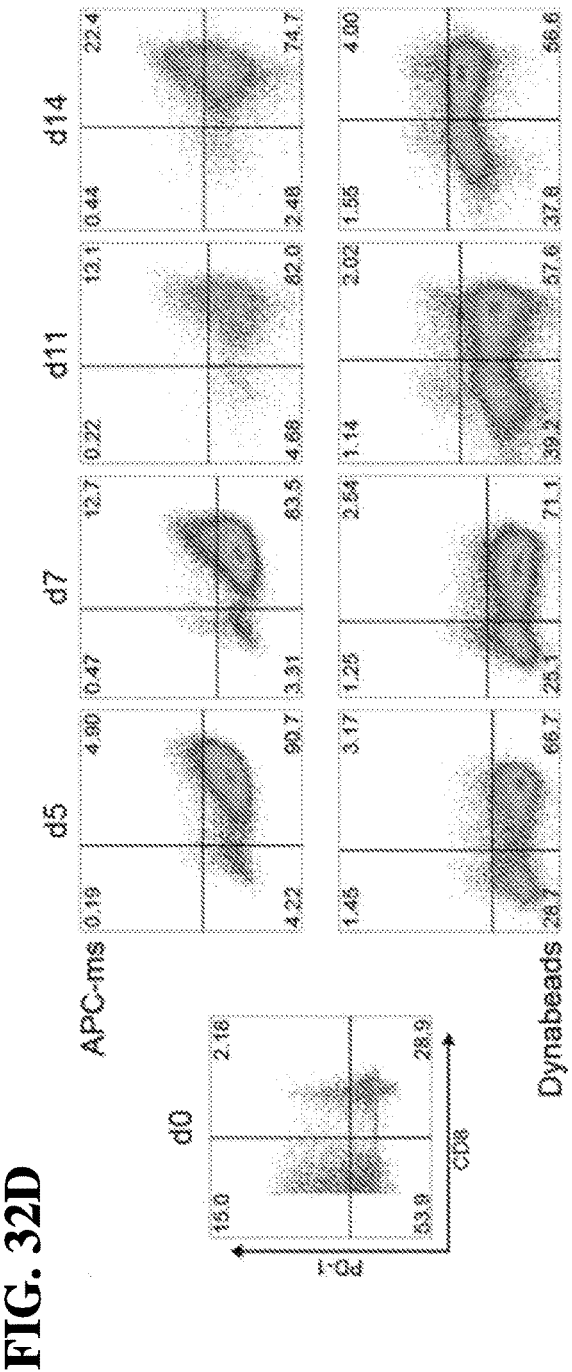

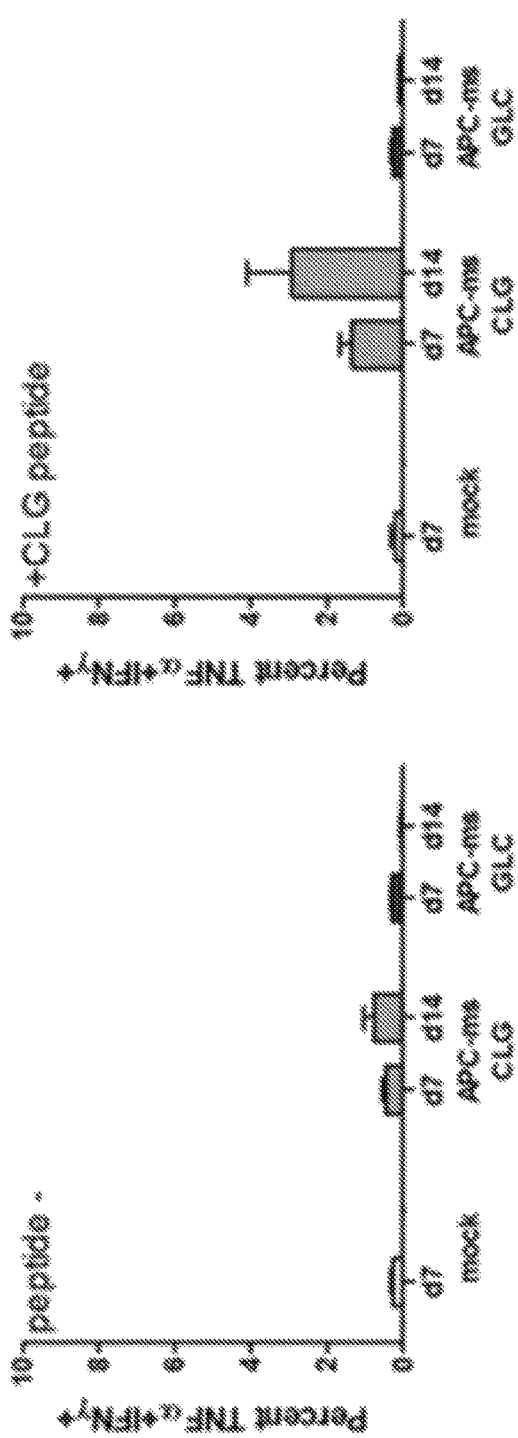
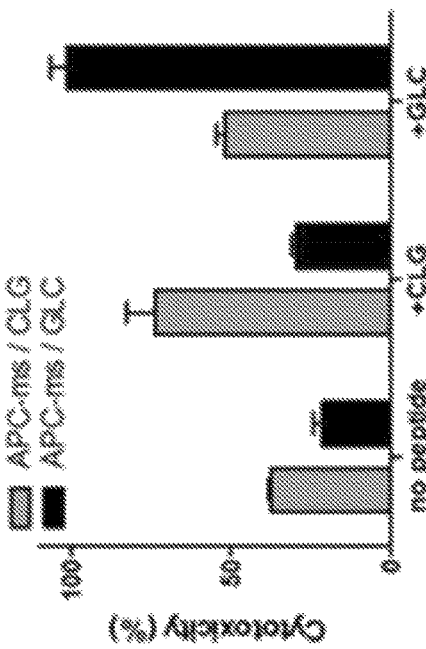
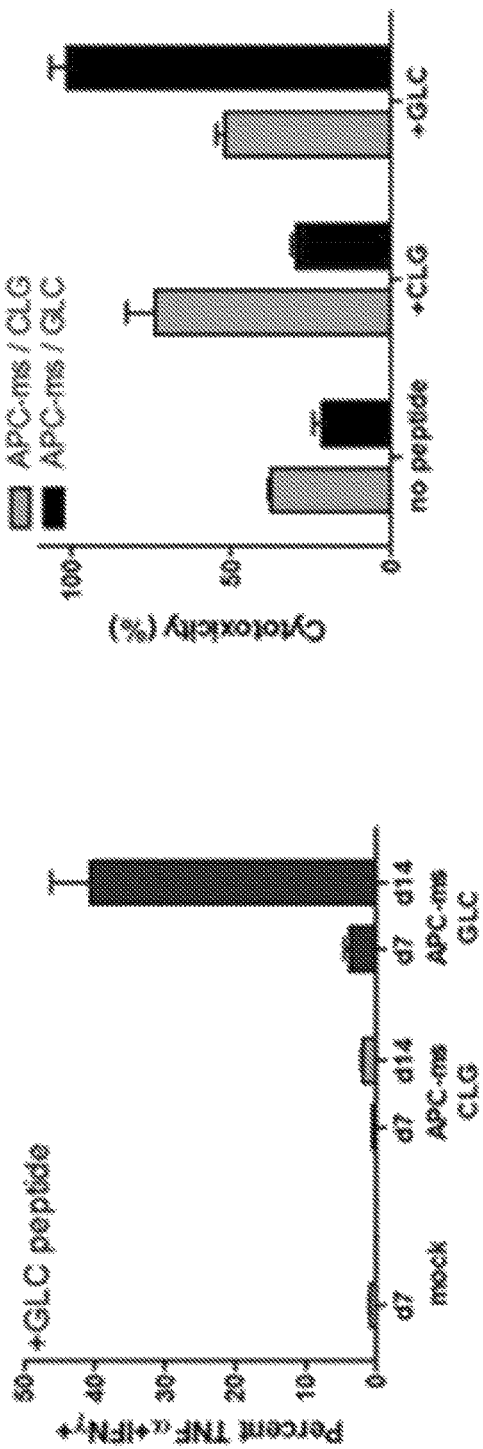
FIG. 36G
FIG. 36H
FIG. 36I
FIG. 36J

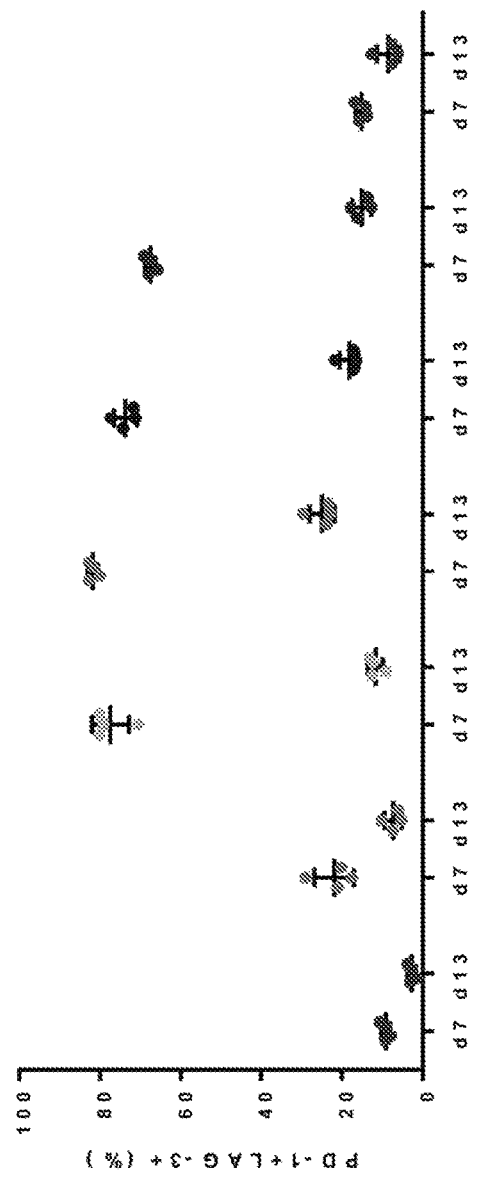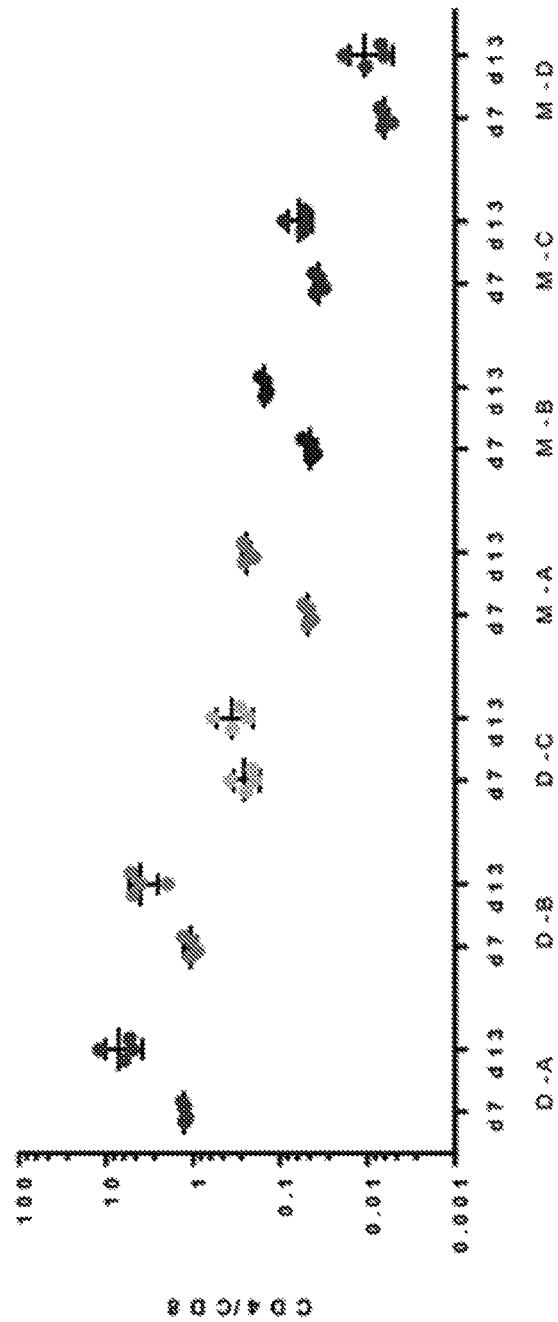
FIG. 40C
FIG. 40D

SEQUENCE LISTING

<160> NUMBER OF SEQ ID NOS: 7

<210> SEQ ID NO 1
<211> LENGTH: 9
<212> TYPE: PRT
<213> ORGANISM: Epstein-Barr virus

<400> SEQUENCE: 1

Cys Leu Gly Gly Leu Leu Thr Met Val
1               5

<210> SEQ ID NO 2
<211> LENGTH: 9

-continued

```
<212> TYPE: PRT
<213> ORGANISM: Epstein-Barr virus

<400> SEQUENCE: 2

Gly Leu Cys Thr Leu Val Ala Met Leu
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ser Val Tyr Asp Phe Phe Val Trp Leu
1               5

<210> SEQ ID NO 4
<211> LENGTH: 8
<212> TYPE: PRT
<213> ORGANISM: Gallus gallus

<400> SEQUENCE: 4

Ser Ile Ile Asn Phe Glu Lys Leu
1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 5

His His His His His His
1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Tyr Ile Gly Ser Arg
1               5

<210> SEQ ID NO 7
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (26)..(26)
<223> OTHER INFORMATION: Hydroxyproline

<400> SEQUENCE: 7

Gly Gly Tyr Gly Gly Gly Pro Cys Gly Pro Pro Gly Pro Pro Gly Pro
1               5                   10                  15
```

-continued

```
Pro Gly Pro Pro Gly Pro Pro Gly Phe Pro Gly Glu Arg Gly Pro Pro
            20              25              30
Gly Pro Pro Gly Pro Pro Gly Pro Pro Gly Pro Pro Gly Pro Cys
        35              40              45
```

ANTIGEN-PRESENTING CELL-MIMETIC SCAFFOLDS AND METHODS FOR MAKING AND USING THE SAME

RELATED APPLICATIONS

This application is a 35 U.S.C. § 371 national stage filing of International Application No. PCT/US2017/041912, filed on Jul. 13, 2017, which in turn claims priority to U.S. Provisional Patent Application No. 62/361,891, filed on Jul. 13, 2016. The entire contents of each of the aforementioned applications are expressly incorporated herein by reference.

SEQUENCE LISTING

The instant application contains a Sequence Listing which has been submitted electronically in ASCII format and is hereby incorporated by reference in its entirety. Said ASCII copy, created on Jan. 9, 2019, is named 117823-13402-117823-13420_SL.txt and is 1.96 KB (2,009 bytes) in size.

STATEMENT OF GOVERNMENT SUPPORT

This invention was made with Government support under Grant Nos. EB015498, EB014703, and DE013033, awarded by the U.S. National Institutes of Health. The Government has certain rights in the invention.

BACKGROUND OF THE INVENTION

Immunotherapy involving the priming and expansion of T lymphocytes (T cells) holds promise for the treatment of cancer and infectious diseases, particularly in humans (Melief et al., *Immunol. Rev.* 145: 167-177 (1995); Riddell et al., *Annu. Rev. Immunol.* 13:545-586 (1995)). Current studies of adoptive transfer in patients with viral infections and/or cancer involve the infusion of T cells that have been stimulated, cloned and expanded for many weeks in vitro on autologous dendritic cells (DC), virally infected B cells, and/or allogeneic feeder cells (Riddell et al., *Science* 257: 238-241 (1992); Yee et al., *J. Exp. Med.* 192:1637-1644 (2000), Brodie et al., *Nat. Med.* 5:34-41 (1999); Riddell et al., *Hum. Gene Ther.* 3:319-338 (1992), Riddell et al., *J. Immunol. Methods* 128:189-201 (1990)). However, since adoptive T cell immunotherapy clinical trials often require billions of cells (Riddell et al., 1995), existing in vitro T-cell expansion protocols are often inadequate to meet the demands of such trials.

Furthermore, optimal engraftment requires use of functional, and not senescent, T-cells, at the time of re-infusion. For clinical applications, it is important to ensure that the T cells have the desired functionality, i.e., that they proliferate, perform effector functions and produce cytokines in a desirable manner (Liebowitz et al., *Current Opinion Oncology,* 10, 533-541, 1998). In the natural setting, T cell activation is initiated by the engagement of the T cell receptor/CD3 complex (TCR/CD3) by a peptide-antigen bound to a major histocompatibility complex (MHC) molecule on the surface of an antigen-presenting cell (APC) (Schwartz, *Science* 248:1349 (1990)). While this is the primary signal in T cell activation, other receptor-ligand interactions between APCs and T cells are also required for complete activation. For example, TCR stimulation in the absence of other molecular interactions can induce a state of anergy, such that these cells cannot respond to full activation signals upon re-stimulation (Schwartz, 1990; Harding, et al., *Nature* 356:607, 1992; Dudley et al., *Clinical Cancer Research.,* 16, 6122-6131, 2010; Rosenberg et al., *Clinical Cancer Research.,* 17, 4550-4557, 2011). In the alternative, T cells may die by programmed cell death (apoptosis) when activated by TCR engagement alone (Webb et al., *Cell* 63:1249, 1990; Kawabe et al., *Nature* 349:245, 1991; Kabelitz et al., *Int. Immunol.* 4:1381, 1992; Groux et al., *Eur J. Immunol.* 23:1623, 1993).

Accordingly, optimal functionality may be conferred via use of a second signaling molecule, e.g., a membrane-bound protein or a secreted product of the APC. In the context of membrane-bound proteins, such secondary interactions are usually adhesive in nature, reinforcing the contact between the two cells (Springer et al., *Ann. Rev. Immunol.* 5:223, 1987). Other signaling molecules, such as transduction of additional activation signals from the APC to the T cell may also be involved (Bierer et al., *Adv. Cancer Res.* 56:49, 1991)). For example, CD28 is a surface, glycoprotein present on 80% of peripheral T cells in humans and is present on both resting and activated T cells. CD28 binds to B7-1 (CD80) or B7-2 (CD86) and is one of the most potent of the known co-stimulatory molecules (June et al., *Immunol. Today* 15:321 (1994), Linsley et al., *Ann. Rev. Immunol.* 11:191 (1993)). CD28 ligation on T cells in conjunction with TCR engagement induces the production of interleukin-2 (IL-2) (June et al., 1994; Jenkins et al., 1993; Schwartz, 1992). Secreted IL-2 is an important factor for ex vivo T cell expansion (Smith et al., *Ann. N.Y. Acad. Sci.* 332:423-432 (1979); Gillis et al., *Nature* 268:154-156 (1977)).

Co-stimulation of T cells has been shown to affect multiple aspects of T cell activation (June et al., 1994). It lowers the concentration of anti-CD3 required to induce a proliferative response in culture (Gimmi et al., *Proc. Natl. Acad. Sci. USA* 88:6575 (1991)). CD28 co-stimulation also markedly enhances the production of lymphokines by helper T cells through transcriptional and post-transcriptional regulation of gene expression Lindsten et al., *Science* 244:339 (1989); Fraser et al., *Science* 251:313 (1991)), and can activate the cytolytic potential of cytotoxic T cells. Inhibition of CD28 co-stimulation in vivo can block xenograft rejection, and allograft rejection is significantly delayed (Lenschow et, al., *Science* 257:789 (1992); Turka et al., *Proc. Natl. Acad. Sci. USA* 89:11102 (1992)).

More importantly, the aforementioned effectors for stimulatory/co-stimulatory simulation have been widely applied in the context of manipulation of T-cells in vitro. In this context, a combination of anti-CD3 monoclonal antibody (first signal) and anti-CD28 monoclonal antibody (second signal) is most commonly used to simulate the APCs. The signals provided by anti-CD3 and anti-CD28 monoclonal antibodies are best-delivered to T-cells when the antibodies are immobilized on a solid surface such as plastic plates (Baroja et al., *Cellular Immunology, vol.* 120, 205-217, 1989; Damle et al., *The Journal of Immunology, vol.* 143, 1761-1767, 1989) or sepharose beads (Anderson et al., *Cellular Immunology, vol.* 115, 246-256, 1988). See also U.S. Pat. No. 6,352,694 issued to June et al.

A variety of surfaces and reagents containing anti-CD3 and anti-CD28 monoclonal antibodies have been developed for obtaining and expanding T cells for various applications. For instance, Levine et al. (*The Journal of Immunology*, vol. 159, No. 12: pp. 5921-5930, 1997) disclose tosyl-activated paramagnetic beads with a 4.5 micron (μM) diameter containing anti-CD3 and anti-CD28 monoclonal antibodies, which can be utilized to stimulate and proliferate T-cells and induce them to produce pro-inflammatory cytokines. It has also been shown that T-cells activated with these beads exhibit properties, such as cytokine production, that make them potentially useful for adoptive immunotherapy (Garlie et al., *J Immunother* 22(4): 336-45, 1999; Shibuya et al., *Arch Otolaryngol Head Neck Surg*, vol. 126, No. 4: 473-479, 2000). These beads are commercially available from Thermo-Fisher Scientific, Inc. under the trade name DYNA-BEADS CD3/CD28 T-cell expansion.

The use of paramagnetic beads with immobilized monoclonal antibodies for expansion of T-cells in cell therapy requires separation and removal of the beads from the T-cells prior to patient infusion. This is a very labor-intensive process and results in cell loss, cell damage, increased risk of contamination and increased cost of processing. Because of the tight association of the immobilized monoclonal antibodies on the beads with the corresponding ligands on the surface of the target T-cells, the removal of the beads from the T-cells is difficult. The bead-cell conjugates are often separated by waiting until the T-cells internalize the target antigens and then using mechanical disruption techniques to separate the beads from the T-cells. This technique can cause damage to the T-cells and can also cause the ligated antigens on the T-cells to be removed from the cell surface (Rubbi et al., *Journal of Immunology Methods*, 166, 233-241, 1993). In addition, since activated T-cells are often most-desired for use in cell therapy protocols and the desirable properties of the cells are lost during the 24-72 hour waiting time, paramagnetic separation has a limited use in the adoptive cell-therapy setting.

Techniques for separation and purification of cells attached to paramagnetic beads are also unusable in the clinical context. For instance, the process of removing the paramagnetic beads after separation from the T-cells requires the passing of the cell/bead solution over a magnet. This process, while greatly reducing the number of beads remaining with the T-cells, does not completely eliminate the beads. Implantation of compositions containing beads into patients can cause toxic effects. The bead removal process also reduces the number of T-cells available for therapy, as many T-cells remain associated with the paramagnetic beads, even after mechanical disassociation. Some cell loss also occurs with respect to the T-cells that are manipulated but otherwise not bound to the beads because these cells are washed away prior to the internalization and/or mechanical removal step(s).

There is, therefore, an unmet need for compositions and methods that allow isolation of T-cells, which can be readily utilized for the therapy of human diseases, such as immunodeficiency disorders, autoimmune disorders, and cancers. Embodiments of the instant invention, which are described in detail below, address these needs.

SUMMARY OF THE INVENTION

The present invention provides compositions and methods for manipulating, e.g., activating, stimulating, expanding, proliferating, or energizing, T-cells. In this context, embodiments of the present invention provide methods for generating large numbers (or substantially pure sub-populations) of activated T cells that express certain markers and/or cell-surface receptors or produce certain cytokines that are optimal for T cell-mediated immune responses. Such manipulated T cells may be used in the treatment and prevention of many diseases, such as cancer, infectious diseases, autoimmune diseases, allergies, immune dysfunction related to aging, or any other disease state where T cells are desired for treatment. Further embodiments described herein relate to methods and compositions for the effective therapy of any the aforementioned diseases by utilizing T-cells with optimal reactivity, which cells are selected or screened using the compositions and/or methods of the instant invention. The compositions and methods of the present invention are more effective over existing compositions and methods not only with respect to the ability to generate larger number of activated T-cells but also with regard to the significantly improved effectiveness of such T-cells in the in vivo setting. Accordingly, the compositions and methods of the instant invention are useful for the generation of highly desirable human T lymphocytes for engraftment, autologous transfers, and for therapeutic applications.

Accordingly, in one embodiment, the instant invention provides antigen presenting cell-mimetic scaffolds (APC-MS), comprising a base layer comprising high surface area mesoporous silica micro-rods (MSR); a continuous, fluid supported lipid bilayer (SLB) layered on the MSR base layer; a plurality of T-cell activating molecules and T-cell co-stimulatory molecules adsorbed onto the scaffold; and a plurality of T-cell homeostatic agents adsorbed onto the scaffold.

In one embodiment, the present invention provides antigen presenting cell-mimetic scaffolds (APC-MS) that sequester T-cells selected from the group consisting of natural killer (NK) cells, CD3+ T-cells, CD4+ T-cells, CD8+ T-cells, and regulatory T-cells (Tregs), or a combination thereof.

In one embodiment, the present invention provides antigen presenting cell-mimetic scaffolds (APC-MS) containing the plurality of T-cell homeostatic agents which are adsorbed onto the SLB layer.

In one embodiment, the present invention provides antigen presenting cell-mimetic scaffolds (APC-MS) containing the plurality of T-cell homeostatic agents which are adsorbed onto the MSR layer.

In one embodiment, the present invention provides antigen presenting cell-mimetic scaffolds (APC-MS) containing the plurality of T-cell homeostatic agents which are released from the scaffold in a controlled-release manner. In some embodiments, the T-cell homeostatic agent is released from the scaffold in a controlled release manner over a period of 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 30 days, 35 days, 40 days, 45 days, 50 days, 60 days, 1 month, 2 months, 3 months, 4 months, 5 months, 6 months, 7 months, 8 months, 9 months, or more.

In one embodiment, the present invention provides antigen presenting cell-mimetic scaffolds (APC-MS) containing the plurality of T-cell homeostatic agents which are released from the scaffold in a sustained manner for up to 15 days. In some embodiments, the T-cell homeostatic agent is released from the scaffold in a sustained manner for up to 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 30 days, 35 days, 40 days, 45 days, 50 days, 60 days, 1 month, 2 months, 3 months, 4 months, 5 months, 6 months, 7 months, 8 months, 9 months, or more. In some embodiments, the T-cell homeostatic agent is released from the scaffold in a sustained manner for at least 30 days. In some embodiments, the T-cell homeostatic agent is released from the scaffold in a sustained manner for at least 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 30 days, 35 days, 40 days, 45 days, 50 days, 60 days, 1 month, 2 months, 3 months, 4 months, 5 months, 6 months, 7 months, 8 months, 9 months, or more.

In one embodiment, the present invention provides antigen presenting cell-mimetic scaffolds (APC-MS) containing the plurality of T-cell homeostatic agents which are selected from the group consisting of IL-1, IL-2, IL-4, IL-5, IL-7, IL-10, IL-12, IL-15, IL-17, IL-21, and transforming growth factor beta (TGF-β), or an agonist thereof, a mimetic thereof, a variant thereof, a functional fragment thereof, or a combination thereof.

In one embodiment, the present invention provides antigen presenting cell-mimetic scaffolds (APC-MS) containing a plurality of the T-cell homeostatic agents which are IL-2, an agonist thereof, a mimetic thereof, a variant thereof, a functional fragment thereof, or a combination thereof with a second homeostatic agent selected from the group consisting of IL-7, IL-21, IL-15, and IL-15 superagonist. In one embodiment, the T-cell homeostatic agent may be selected from the group consisting of an N-terminal IL-2 fragment comprising the first 30 amino acids of IL-2 (p1-30), an IL-2 superkine peptide, and an IL-2 partial agonist peptide, or a combination thereof.

In another embodiment, the present invention relates to antigen presenting cell-mimetic scaffolds (APC-MS) containing a plurality of activating and co-stimulatory molecules, wherein the T-cell activating molecules and the T-cell co-stimulatory molecules are each, independently, adsorbed onto the fluid supported lipid bilayer (SLB). In one embodiment, the T-cell activating molecules and the T-cell co-stimulatory molecules may be adsorbed via affinity pairing or chemical coupling. In some embodiments, the chemical coupling comprises a click chemistry reagent (e.g., DBCO or azide). In one embodiment, the T-cell activating molecules and the T-cell co-stimulatory molecules may be adsorbed via affinity pairing comprising a biotin-streptavidin pair, an antibody-antigen pair, an antibody-hapten pair, an aptamer affinity pair, a capture protein pair, an Fc receptor-IgG pair, a metal-chelating lipid pair, a metal-chelating lipid-histidine (HIS)-tagged protein pair, or a combination thereof. In one embodiment, the T-cell activating molecules and the T-cell co-stimulatory molecules may be adsorbed via chemical coupling comprising azide-alkyne chemical (AAC) reaction, dibenzo-cyclooctyne ligation (DCL), or tetrazine-alkene ligation (TAL).

In another embodiment, the present invention relates to antigen presenting cell-mimetic scaffolds (APC-MS) containing a plurality of activating and co-stimulatory molecules, wherein the T-cell activating molecules and the T-cell co-stimulatory molecules are each, independently, coated onto the fluid supported lipid bilayer (SLB). Alternately, in another embodiment, the present invention relates to antigen presenting cell-mimetic scaffolds (APC-MS) containing a plurality of activating and co-stimulatory molecules, wherein the T-cell activating molecules and the T-cell co-stimulatory molecules are each, independently, partly embedded onto the fluid supported lipid bilayer (SLB).

In another embodiment, the present invention relates to antigen presenting cell-mimetic scaffolds (APC-MS) containing a plurality of activating and co-stimulatory molecules, wherein the T-cell activating molecules and the T-cell co-stimulatory molecules are each, independently, adsorbed onto the mesoporous silica micro-rods (MSR).

In another embodiment, the present invention relates to antigen presenting cell-mimetic scaffolds (APC-MS) containing a plurality of activating and co-stimulatory molecules, wherein the T-cell activating molecules and the T-cell co-stimulatory molecules are each, independently, antibody molecules or antigen-binding fragments thereof.

In another embodiment, the present invention relates to antigen presenting cell-mimetic scaffolds (APC-MS) containing a plurality of activating and co-stimulatory molecules, wherein the T-cell activating molecules are selected from the group consisting of an anti-CD3 antibody or an antigen-binding fragment thereof, an anti-CD2 antibody or an antigen-binding fragment thereof, an anti-CD47 antibody or an antigen-binding fragment thereof, anti-macrophage scavenger receptor (MSR1) antibody or an antigen-binding fragment thereof, an anti-T-cell receptor (TCR) antibody or an antigen-binding fragment thereof, a major histocompatibility complex (MHC) molecule or a multimer thereof loaded with an MHC peptide, and an MHC-immunoglobulin (Ig) conjugate or a multimer thereof, or a combination thereof.

In another embodiment, the present invention relates to antigen presenting cell-mimetic scaffolds (APC-MS) containing a plurality of activating and co-stimulatory molecules, wherein the T-cell co-stimulatory molecules are antibodies, or an antigen-binding fragments thereof, which specifically bind to a co-stimulatory antigen selected from the group consisting of CD28, 4.1BB (CD137), OX40 (CD134), CD27 (TNFRSF7), GITR (CD357), CD30 (TNFRSF8), HVEM (CD270), LTβR (TNFRSF3), DR3 (TNFRSF25), ICOS (CD278), CD226 (DNAM1), CRTAM (CD355), TIM1 (HAVCR1, KIM1), CD2 (LFA2, OX34), SLAM (CD150, SLAMF1), 2B4 (CD244, SLAMF4), Ly108 (NTBA, CD352, SLAMF6), CD84 (SLAMFS), Ly9 (CD229, SLAMF3), CD279 (PD1) and CRACC (CD319, BLAME).

In another embodiment, the present invention relates to antigen presenting cell-mimetic scaffolds (APC-MS) containing a plurality of activating and co-stimulatory molecules, wherein the T-cell activating molecules and T-cell co-stimulatory molecules comprise bispecific antibodies or antigen binding fragments thereof.

In another embodiment, the present invention relates to antigen presenting cell-mimetic scaffolds (APC-MS) containing a plurality of activating and co-stimulatory molecules, wherein the T-cell activating molecules and T-cell co-stimulatory molecules comprise a pair selected from the group consisting of CD3/CD28, CD3/ICOS optionally together with CD28, CD3/CD27 optionally together with CD28, and CD3/CD137 optionally together with CD28, or a combination thereof.

In another embodiment, the present invention relates to antigen presenting cell-mimetic scaffolds (APC-MS) which further comprise an immunoglobulin molecule that binds specifically to an Fc-fusion protein.

In another embodiment, the present invention relates to antigen presenting cell-mimetic scaffolds (APC-MS) which further comprise a recruitment compound selected from the group consisting of granulocyte macrophage-colony stimulating factor (GM-CSF), chemokine (C-C motif) ligand 21 (CCL-21), chemokine (C-C motif) ligand 19 (CCL-19), a C-X-C motif chemokine ligand 12 (CXCL12), Interferon gamma (IFNγ), or a FMS-like tyrosine kinase 3 (Flt-3) ligand, or an agonist thereof, a mimetic thereof, a variant thereof, a functional fragment thereof, or a combination thereof. In one embodiment, the scaffolds further comprise a recruitment compound which is granulocyte macrophage colony stimulating factor (GM-CSF), or an agonist thereof, a mimetic thereof, a variant thereof, or a functional fragment thereof.

In another embodiment, the present invention relates to antigen presenting cell-mimetic scaffolds (APC-MS) which further comprise an antigen. In one embodiment, the antigen comprises a tumor antigen. Still further under this embodiment, the tumor antigen is selected from the group consisting of MAGE-1, MAGE-2, MAGE-3, CEA, Tyrosinase, midkin, BAGE, CASP-8, β-catenin, β-catenin, γ-catenin, CA-125, CDK-1, CDK4, ESO-1, gp75, gp100, MART-1, MUC-1, MUM-1, p53, PAP, PSA, PSMA, ras, trp-1, HER-2, TRP-1, TRP-2, IL13Ralpha, IL13Ralpha2, AIM-2, AIM-3, NY-ESO-1, C9orf 112, SART1, SART2, SART3, BRAP, RTN4, GLEA2, TNKS2, KIAA0376, ING4, HSPH1, C13orf24, RBPSUH, C6orf153, NKTR, NSEP1, U2AF1L, CYNL2, TPR, SOX2, GOLGA, BMI1, COX-2, EGFRvIII, EZH2, LICAM, Livin, Livinβ, MRP-3, Nestin, OLIG2, ART1, ART4, B-cyclin, Gli1, Cav-1, cathepsin B, CD74, E-cadherin, EphA2/Eck, Fra-1/Fosl 1, GAGE-1, Ganglioside/GD2, GnT-V, β1,6-N, Ki67, Ku70/80, PROX1, PSCA, SOX10, SOX11, Survivin, UPAR, WT-1, Dipeptidyl peptidase IV (DPPIV), adenosine deaminase-binding protein (AD Abp), cyclophilin b, Colorectal associated antigen (CRC)-C017-1A/GA733, T-cell receptor/CD3-zeta chain, GAGE-family of tumor antigens, RAGE, LAGE-I, NAG, GnT-V, RCAS1, α-fetoprotein, p120ctn, Pmel117, PRAME, brain glycogen phosphorylase, SSX-I, SSX-2 (HOM-MEL-40), SSX-I, SSX-4, SSX-5, SCP-I, CT-7, cdc27, adenomatous polyposis coli protein (APC), fodrin, P1A, Connexin 37, Ig-idiotype, p15, GM2, GD2 gangliosides, Smad family of tumor antigens, imp-1, EBV-encoded nuclear antigen (EBNA)-I, UL16-binding protein-like transcript 1 (Multi), RAE-1 proteins, H60, MICA, MICB, c-erbB-2, a neoantigen identified in a patient specific manner, or an immunogenic peptide thereof, or a combination thereof.

In a related embodiment, the present invention relates to antigen presenting cell-mimetic scaffolds (APC-MS), comprising a base layer comprising high surface area mesoporous silica micro-rods (MSR); a continuous, fluid supported lipid bilayer (SLB) layered on the MSR base layer; a plurality of T-cell activating molecules and T-cell co-stimulatory molecules adsorbed onto the scaffold; and a plurality of T-cell homeostatic agents adsorbed onto the scaffold, wherein the weight ratio of the supported lipid bilayer (SLB) to the mesoporous silica micro-rods (MSR) is between about 10:1 and about 1:20. In one embodiment, the weight ratio reflects the ratio of SLB to MSR prior to loading. In another embodiment, the weight ratio is adjusted to achieve the desired scaffold composition. In one embodiment, the weight ratio of the SLB to the MSR may be between about 9:1 and about 1:15, between about 5:1 and about 1:10, between about 3:1 and about 1:5, including all ratios in between, e.g., about 3; 1, about 2:1, about 1:1, about 1:2, about 1:3, about 1:4, about 1:5, about 1:6, about 1:7, about 1:8, about 1:9, about 1:10.

In another embodiment, the present invention relates to antigen presenting cell-mimetic scaffolds (APC-MS), comprising a base layer comprising high surface area mesoporous silica micro-rods (MSR); a continuous, fluid supported lipid bilayer (SLB) layered on the MSR base layer; a plurality of T-cell activating molecules and T-cell co-stimulatory molecules adsorbed onto the scaffold; and a plurality of T-cell homeostatic agents adsorbed onto the scaffold, wherein the continuous, fluid supported lipid bilayer (SLB) comprises a lipid comprising 14 to 23 carbon atoms. In one embodiment, the lipid is phosphatidylethanolamine (PE), phosphatidylcholine (PC), phosphatidic acid (PA), phosphatidylserine (PS), or phosphoinositide, or a derivative thereof. In one embodiment, the APC-MS comprises fluid supported lipid bilayer (SLB) comprises a lipid which is selected from the group consisting of dimyristoylphosphatidylcholine (DMPC), dipalmitoylphosphatidylcholine (DPPC), distearoylphosphatidylcholine (DSPC), palmitoyl-oleoylphosphatidylcholine (POPC), dioleoylphosphatidylcholine (DOPC), dioleoylphosphatidylethanolamine (DOPE), dimyristoylphosphatidylethanolamine (DMPE), and dipalmitoylphosphatidylethanolamine (DPPE) or a combination thereof. In some embodiments, the lipid bilayer comprises a lipid composition that mimics the lipid composition of a mammalian cell membrane (e.g., a human cell plasma membrane). The lipid composition of many mammalian cell membranes have been characterized and are readily ascertainable by one of skill in the art (see, e.g., Essaid et al. *Biochim. Biophys. Acta* 1858(11): 2725-36 (2016), the entire contents of which are incorporated herein by reference). In some embodiments, the lipid bilayer comprises cholesterol. In some embodiments, the lipid bilayer comprises a sphingolipid. In some embodiments, the lipid bilayer comprises a phospholipid. In some embodiments, the lipid is a phosphatidylethanolamine, a phosphatidylcholine, a phosphatidylserine, a phosphoinositide a phosphosphingolipid with saturated or unsaturated tails comprising 6-20 carbons, or a combination thereof.

In another embodiment, the present invention relates to antigen presenting cell-mimetic scaffolds (APC-MS), comprising a base layer comprising high surface area mesoporous silica micro-rods (MSR); a continuous, fluid supported lipid bilayer (SLB) layered on the MSR base layer; a plurality of T-cell activating molecules and T-cell co-stimulatory molecules adsorbed onto the scaffold; and a plurality of T-cell homeostatic agents adsorbed onto the scaffold, wherein the mesoporous silica microrod-lipid bilayer (MSR-SLB) scaffold retains a continuous, fluid architecture for at least 14 days. In some embodiments, the MSR-SLB scaffold retains a continuous, fluid architecture for 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 25 days, 30 days, 35 days, 40 days, 50 days, or more. In some embodiments, the MSR of the MSR-SLB scaffold degrade in about 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 25 days, 30 days, 35 days, 40 days, 50 days, or more. In some embodiments, the lipid bilayer of the MSR-SLB scaffold degrades in about 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 25 days, 30 days, 35 days, 40 days, 50 days, or more.

In another embodiment, the present invention relates to antigen presenting cell-mimetic scaffolds (APC-MS), comprising a base layer comprising high surface area mesoporous silica micro-rods (MSR); a continuous, fluid supported lipid bilayer (SLB) layered on the MSR base layer; a plurality of T-cell activating molecules and T-cell co-stimulatory molecules adsorbed onto the scaffold; and a plurality of T-cell homeostatic agents adsorbed onto the scaffold, wherein the dry weight ratio of the mesoporous silica micro-rods (MSR) to the T-cell activating/co-stimulatory molecules is between about 1:1 to about 50:1. In one embodiment, the ratio of MSR to T-cell activating/co-stimulatory molecules is reflective of the weight of the MSR to the weight of the antibodies which are used as T-cell activating/co-stimulatory molecules. In another embodiment, the MSR:antibody weight ratio is adjusted to achieve the desired scaffold composition. In one embodiment, the weight ratio of the SLB to the antibody composition is between about 2:1 and about 20:1, between about 3:1 and about 10:1, between about 4:1 and about 8:1, including all ratios in between, e.g., about 1:1, about 2:1, about 3:1, about 4:1, about 5:1, about 6:1, about 7:1, about 8:1, about 9:1, about 10:1, about 15:1, about 20:1, about 25:1, about 30:1, about 40:1.

In another embodiment, the present invention relates to antigen presenting cell-mimetic scaffolds (APC-MS), comprising a base layer comprising high surface area mesoporous silica micro-rods (MSR); a continuous, fluid supported lipid bilayer (SLB) layered on the MSR base layer; a plurality of T-cell activating molecules and T-cell co-stimulatory molecules adsorbed onto the scaffold; and a plurality of T-cell homeostatic agents adsorbed onto the scaffold, wherein the scaffolds are stacked to selectively permit infiltration of T-cells into the mesoporous silica micro-rods (MSR). In one embodiment, the instant invention further provides APC-MS wherein the T-cell activating and/or co-stimulatory molecules are present on the scaffolds at a concentration sufficient to permit in situ manipulation of T-cells.

In another aspect, the present invention relates to pharmaceutical compositions comprising antigen presenting cell-mimetic scaffolds (APC-MS) comprising a base layer comprising high surface area mesoporous silica micro-rods (MSR); a continuous, fluid supported lipid bilayer (SLB) layered on the MSR base layer; a plurality of T-cell activating molecules and T-cell co-stimulatory molecules adsorbed onto the scaffold; and a plurality of T-cell homeostatic agents adsorbed onto the scaffold; and a pharmaceutically acceptable carrier. In one embodiment, the instant invention further provides pharmaceutical compositions that are formulated for intravenous administration, subcutaneous administration, intraperitoneal administration, or intramuscular administration.

In another aspect, the present invention relates to compositions comprising antigen presenting cell-mimetic scaffolds (APC-MS) comprising a base layer comprising high surface area mesoporous silica micro-rods (MSR); a continuous, fluid supported lipid bilayer (SLB) layered on the MSR base layer; a plurality of T-cell activating molecules and T-cell co-stimulatory molecules adsorbed onto the scaffold; and a plurality of T-cell homeostatic agents adsorbed onto the scaffold; and T-cells clustered therein. In one embodiment, the instant invention further provides compositions that contain APC-MS and T-cells selected from the group consisting of natural killer (NK) cells, a CD3+ T-cells, CD4+ T-cells, CD8+ T-cells, and regulatory T-cells (Tregs), or a combination thereof.

Still further, embodiments of the instant invention relate to methods of treating a disease in a subject in need thereof, comprising contacting a sample comprising a T-cell population obtained from the subject with the antigen presenting cell-mimetic scaffold (APC-MS), thereby activating, co-stimulating and homeostatically maintaining the population of T-cells; optionally expanding the population of T-cells; and administering the activated, co-stimulated, maintained and optionally expanded T-cells into the subject, thereby treating the disease in the subject. In one embodiment, the instant invention further provides methods of treating a disease in a subject in need thereof, wherein the method further comprises re-stimulating the population of T-cells prior to the administration step. In one embodiment, the method includes expanding the population of T-cells after contacting with the scaffold for a period between 2 days to 5 days.

In another therapeutic embodiment, the instant invention relate to methods of treating a disease in a subject in need thereof, comprising contacting a sample which is a blood sample, a bone marrow sample, a lymphatic sample or a splenic sample comprising a T-cell population obtained from the subject with the antigen presenting cell-mimetic scaffold (APC-MS), thereby activating, co-stimulating and homeostatically maintaining the population of T-cells; optionally expanding the population of T-cells; and administering the activated, co-stimulated, maintained and optionally expanded T-cells into the subject, thereby treating the disease in the subject. In one embodiment, the subject is a human subject. In one embodiment, the method provides for the treatment of a cancer and the scaffold comprises at least one cytotoxic T-cell specific activating molecules and at least one cytotoxic T-cell specific co-stimulatory molecule.

In another therapeutic embodiment, the instant invention relate to methods of treating a cancer in a subject in need thereof, comprising contacting a sample comprising a T-cell population obtained from the subject with the antigen presenting cell-mimetic scaffold (APC-MS), thereby activating, co-stimulating and homeostatically maintaining the population of T-cells; optionally expanding the population of T-cells; and administering the activated, co-stimulated, maintained and optionally expanded T-cells into the subject, thereby treating the cancer in the subject. In one embodiment, the cancer is selected from the group consisting of head and neck cancer, breast cancer, pancreatic cancer, prostate cancer, renal cancer, esophageal cancer, bone cancer, testicular cancer, cervical cancer, gastrointestinal cancer, glioblastoma, leukemia, lymphoma, mantle cell lymphoma, pre-neoplastic lesions in the lung, colon cancer, melanoma, and bladder cancer. In one embodiment, the method may further include sorting and optionally enriching cytotoxic T-cells from the sample and/or the expanded cell population.

In yet another therapeutic embodiment, the instant invention relate to methods of treating an immunodeficiency disorder in a subject in need thereof, comprising contacting a sample comprising a T-cell population obtained from the subject with the antigen presenting cell-mimetic scaffold (APC-MS), thereby activating, co-stimulating and homeostatically maintaining the population of T-cells; optionally expanding the population of T-cells; and administering the activated, co-stimulated, maintained and optionally expanded T-cells into the subject, thereby treating the immunodeficiency disorder in the subject. In one embodiment, the scaffold comprises at least one helper T-cell (Th) specific activating molecule and at least one helper T-cell (Th) specific co-stimulatory molecule. In one embodiment, the method may be used to treat an immunodeficiency disorder selected from the group consisting of primary immunodeficiency disorder and acquired immunodeficiency disorder. In one embodiment, the method may be used to treat acquired immunodeficiency syndrome (AIDS) or a hereditary disorder selected from the group consisting of DiGeorge syndrome (DGS), chromosomal breakage syndrome (CBS), ataxia telangiectasia (AT) and Wiskott-Aldrich syndrome (WAS), or a combination thereof.

In another embodiment, the instant invention relates to methods of treating a disease in a subject in need thereof, comprising contacting a sample comprising a T-cell population obtained from the subject with the antigen presenting cell-mimetic scaffold (APC-MS), thereby activating, co-stimulating and homeostatically maintaining the population of T-cells; optionally expanding the population of T-cells; further sorting and optionally enriching the T-cells from the sample and/or the expanded cell population; and administering the activated, co-stimulated, maintained and optionally expanded T-cells into the subject, thereby treating the disease in the subject. In one embodiment, the T-cells may be selected from the group consisting of natural killer (NK) cells, a CD3+ T-cells, CD4+ T-cells, CD8+ T-cells, and regulatory T-cells (Tregs), or a combination thereof.

In another embodiment, the instant invention relates to methods of treating an autoimmune disorder in a subject in need thereof, comprising contacting a sample comprising a T-cell population obtained from the subject with the antigen presenting cell-mimetic scaffold (APC-MS), thereby activating, co-stimulating and homeostatically maintaining the population of T-cells; optionally expanding the population of T-cells; further optionally sorting and enriching the T-cells from the sample and/or the expanded cell population; and administering the activated, co-stimulated, maintained and optionally expanded T-cells into the subject, thereby treating the autoimmune disorder in the subject.

In another embodiment, the instant invention relates to methods of treating a disease in a subject in need thereof, comprising contacting a sample comprising a T-cell population obtained from the subject with the antigen presenting cell-mimetic scaffold (APC-MS), thereby activating, co-stimulating and homeostatically maintaining the population of T-cells; optionally expanding the population of T-cells; further optionally sorting and enriching the T-cells from the sample and/or the expanded cell population; and subcutaneously or intravenously administering the activated, co-stimulated, maintained and optionally expanded T-cells into the subject, thereby treating the disease in the subject. In one embodiment, the T-cells may be activated, co-stimulated, homeostatically maintained, and optionally expanded by contacting the sample with the scaffold for a period between about 1 day to about 20 days.

In another embodiment, the instant invention relates to methods for the manipulation of T-cells, comprising contacting the antigen presenting cell-mimetic scaffold (APC-MS) with a subject's biological sample, thereby activating, co-stimulating, homeostatically maintaining and optionally expanding a population of T-cells present within the sample, thereby manipulating the T-cells. In one embodiment, the manipulation may include stimulation, activation, changes in viability, promotion of growth, division, differentiation, expansion, proliferation, exhaustion, anergy, quiescence, apoptosis, death of T-cells. In one embodiment, the manipulation preferably includes promoting expansion or proliferation of T-cells. In an additional embodiment, the manipulated T-cells may be further transformed. In a specific embodiment, the T-cells may be transformed to express a chimeric antigen receptor (CAR). The CAR T-cell product may be further expanded by incubating with the antigen presenting cell-mimetic scaffolds (APC-MS) containing an antigen which is specific to the CAR T-cell. In certain embodiments, the CAR T-cell-specific antigen is selected from the group consisting of CD19, CD22, or a fragment thereof or a variant thereof. In some embodiments, the CAR T-cell-specific antigen is a tumor antigen. Tumor antigens are well known in the art and include, for example, a glioma-associated antigen, carcinoembryonic antigen (CEA), β-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor and mesothelin. In some embodiments, a CAR T-cell product may be expanded polyclonally post-production to generate a larger population of CAR T-cells.

In another embodiment, the instant invention relates to methods for the manipulation of T-cells, comprising contacting the antigen presenting cell-mimetic scaffold (APC-MS), wherein the method confers increased expansion of the population of T-cells after about 1 week of contact with the scaffold compared to a control scaffold comprising the base layer comprising high surface area mesoporous silica micro-rods (MSR) and the continuous, fluid supported lipid bilayer (SLB) but not containing the T-cell activating molecules and the T-cell co-stimulatory molecules. In one embodiment, the method confers about a 50-fold to 800-fold increase in the expansion of the population of T-cells after about 1 week of contact with the scaffold compared to a control scaffold comprising the base layer comprising high surface area mesoporous silica micro-rods (MSR) and the continuous, fluid supported lipid bilayer (SLB) but not containing the T-cell activating molecules and the T-cell co-stimulatory molecules.

In another embodiment, the instant invention relates to methods for the manipulation of T-cells, comprising contacting the antigen presenting cell-mimetic scaffold (APC-MS), wherein the method confers increased expansion of the population of T-cells after about 1 week of contact with the scaffold compared to a superparamagnetic spherical polymer particle (DYNABEAD) comprising the T-cell activating molecules and the T-cell co-stimulatory molecules. In one embodiment, the method confers about a 5-fold to 20-fold increase in the expansion of the population of T-cells after about 1 week of contact with the scaffold compared to a superparamagnetic spherical polymer particle (DYNABEAD) comprising the T-cell activating molecules and the T-cell co-stimulatory molecules.

In another embodiment, the instant invention relates to methods for improving the metabolic activity of T-cells, comprising contacting the antigen presenting cell-mimetic scaffold (APC-MS) with a subject's biological sample, thereby activating, co-stimulating, homeostatically maintaining and optionally expanding a population of T-cells present within the sample, thereby improving the metabolic activity of T-cells. In one embodiment, the method confers improved metabolic activity of the population of T-cells after about 1 week of contact with the scaffold compared to a control scaffold comprising the base layer comprising high surface area mesoporous silica micro-rods (MSR) and the continuous, fluid supported lipid bilayer (SLB) but not containing the T-cell activating molecules and the T-cell co-stimulatory molecules. In one embodiment, the method confers about a 5-fold to 20-fold improved metabolic activity of the population of T-cells after about 1 week of contact with the scaffold compared to a control scaffold comprising the base layer comprising high surface area mesoporous silica micro-rods (MSR) and the continuous, fluid supported lipid bilayer (SLB) but not containing the T-cell activating molecules and the T-cell co-stimulatory molecules. In one embodiment, the method confers improved metabolic activity of the population of T-cells after about 1 week of contact with the scaffold compared to a superparamagnetic spherical polymer particle (DYNABEAD) comprising the T-cell activating molecules and the T-cell co-stimulatory molecules. In one embodiment, the method further confers about a 1-fold to 10-fold increase in the expansion of the population of T-cells after about 1 week of contact with the scaffold compared to a superparamagnetic spherical polymer particle (DYNABEAD) comprising the T-cell activating molecules and the T-cell co-stimulatory molecules.

In another embodiment, the instant invention relates to methods for screening metabolically active T-cells, comprising contacting the antigen presenting cell-mimetic scaffold (APC-MS) with a subject's biological sample, thereby activating, co-stimulating, homeostatically maintaining and optionally expanding a population of T-cells present within the sample; identifying metabolically active cells in the population of activated, co-stimulated, homeostatically maintained and optionally expanded T-cells; thereby screening metabolically-active T-cells. In one embodiment, the expanded T-cells are metabolically active for at least about 7 days post-contact with the scaffold. In one embodiment, the expanded T-cells form aggregates for at least about 7 days post-contact with the scaffold.

Yet in another embodiment, the instant invention relates to methods for generating a polyclonal population of T-cells, comprising contacting the antigen presenting cell-mimetic scaffold (APC-MS) with a subject's biological sample, thereby activating, co-stimulating, homeostatically maintaining and optionally expanding a population of T-cells present within the sample; identifying a specific population of T-cells from the expanded population of T-cells based on the expression of a plurality of markers in the expanded T-cells; optionally isolating or purifying the identified population of T-cells, thereby generating a polyclonal population of T-cells. In one embodiment, the method may be adapted for the generation of a polyclonal population of CD4+ cells or CD8+ cells. In a related embodiment, the method may be adapted for the generation of a polyclonal population of CD4+/FOXP3+ T-cells. Still further, the method may be adapted for the generation of a polyclonal population of CD44+/CD62L− T-cells (effector memory and/or effector T-cells). In another embodiment, the method may be adapted for the generation of a polyclonal population of CD8+/CD69+ T-cells (activated T-cells). In another embodiment, the method may be adapted for the generation of a polyclonal population of granzyme B+ CD8+ T-cells (cytotoxin-secreting T-cells). In yet another embodiment, the method may be adapted for the generation of a polyclonal population of IFNγ+ T-cells (activator cytokine-secreting T-cells). In yet another embodiment, the method may be adapted for the generation of a polyclonal population of CD62L+/CCR7+ T-cells (memory T-cells).

In another embodiment, the instant invention relates to methods for generating a polyclonal sub-population of T-cells, comprising contacting the antigen presenting cell-mimetic scaffold (APC-MS) with a subject's biological sample, thereby activating, co-stimulating, homeostatically maintaining and optionally expanding a population of T-cells present within the sample; identifying a specific population of exhausted T-cells from the expanded population of T-cells based on the expression of a plurality of markers in the expanded T-cells; optionally removing the identified population of T-cells, thereby generating a polyclonal sub-population of T-cells. In one embodiment, the exhausted T-cells are identified or isolated based on cell-surface expression of CD8+/PD-1+. In another embodiments, the exhausted T-cells are identified or isolated based on cell-surface expression of LAG3+/TIM3+.

In another embodiment, the instant invention relates to methods for manipulation of T-cells ex vivo, comprising contacting the antigen presenting cell-mimetic scaffold (APC-MS) with a subject's biological sample ex vivo, thereby activating, co-stimulating, homeostatically maintaining and optionally expanding a population of T-cells present within the sample, thereby manipulating the T-cells ex vivo. In one embodiment, the sample is contacted with the scaffold for a period from about 1 day to about 20 days. In one embodiment, the method may involve detecting the production of one or more cytokines or cytotoxins produced by the manipulated T-cells. In one embodiment, the method involves further detecting the production of a cytokine selected from the group consisting of interferon gamma (IFNγ), tissue necrosis factor alpha (TNFα), IL-2, IL-1, IL-4, IL-5, IL-10, and IL-13, IL-17 or a combination thereof by the manipulated T-cells.

In a related embodiment, the instant invention relates to methods for the manipulation of T-cells ex vivo in accordance with the foregoing methods, wherein the manipulated T-cells are T-helper 1 (Th1) cells and the method comprises detecting the production of a cytokine selected from the group consisting of IL-2, interferon gamma (IFNγ) and tissue necrosis factor alpha (TNFα), or a combination thereof. Alternately, in a related embodiment, the instant invention relates to methods for the manipulation of T-cells ex vivo in accordance with the foregoing methods, wherein the manipulated T-cells are T-helper 2 (Th2) cells and the method comprises detecting the production of a cytokine selected from the group consisting of IL-4, IL-5, IL-10 and IL-13, or a combination thereof. Still further in a related embodiment, the instant invention relates to methods for the manipulation of T-cells ex vivo in accordance with the foregoing methods, wherein the manipulated T-cells are cytotoxic T (Tc) cells and the method comprises detecting the production of a cytokine selected from the group consisting of interferon gamma (IFNγ) and lymphotoxin alpha (LTα/TNFβ), or a combination thereof. In one embodiment, the manipulated T-cells are cytotoxic T (Tc) cells and the method comprises detecting the secretion of a cytotoxin selected from the group consisting of a granzyme or a perforin, or a combination thereof.

In a related embodiment, the instant invention relates to methods for the manipulation of T-cells ex vivo in accordance with the foregoing methods, wherein the method further comprising detecting the expression of a cell-surface marker in the manipulated T-cells. In one embodiment, the cell surface marker is selected from the group consisting of CD69, CD4, CD8, CD25, CD62L, FOXP3, HLA-DR, CD28, and CD134, or a combination thereof. Alternately or additionally, in one embodiment, the cell-surface marker is a non-T-cell marker selected from the group consisting of CD36, CD40, and CD44, or a combination thereof.

In another related embodiment, the instant invention relates to methods for the manipulation of T-cells ex vivo in accordance with the foregoing methods, wherein the subject is a human subject.

In another related embodiment, the instant invention relates to methods for the manipulation of T-cells in vivo in accordance with the foregoing methods, wherein the scaffold is administered to the subject to permit the biological sample comprising T-cells to come into contact with the scaffold in vivo. In one embodiment, the scaffold may be maintained in the subject for a period between about 3 days to about 15 days, preferably for a period between about 7 days to about 11 days. In some embodiments, the scaffold may be maintained in the subject for a period of at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 25 days, at least 30 days, at least 35 days, at least 40 days, at least 50 days, or more.

In yet another embodiment, the instant invention relates to methods for making the antigen presenting cell-mimetic scaffold (APC-MS), comprising (a) providing a base layer comprising high surface area mesoporous silica micro-rods (MSR); (b) optionally loading the T-cell homeostatic agents on the MSR; (c) layering a continuous, fluid supported lipid bilayer (SLB) on the base layer comprising the MSRs, thereby generating an MSR-SLB scaffold; (d) loading the T-cell homeostatic agents on the MSR-SLB scaffold if step (b) is not carried out; (e) optionally blocking one or more non-specific integration sites in the MSR-SLB scaffold with a blocker; and (f) loading the T-cell activating molecules and the T-cell co-stimulatory molecules onto the MSR-SLB scaffold, thereby making the APC-MS. In one embodiment, the methods may further involve assembling a plurality of scaffolds to generate stacks with sufficient porosity to permit infiltration of T cells. In one embodiment, the method may include loading at least one additional agent selected from the group consisting of a growth factor, a cytokine, an interleukin, an adhesion signaling molecule, an integrin signaling molecule, or a fragment thereof or a combination thereof.

Other features and advantages of the invention will be apparent from the following detailed description and the drawings.

BRIEF DESCRIPTION OF THE DRAWINGS

FIG. 2A shows chemical structures of various lipids. Abbreviations: DOPC—dioleoylphosphatidylcholine; POPC—palmitoyl-oleoylphosphatidylcholine; and DSPC—distearoylphosphatidylcholine. FIG. 2B shows the percentage of lipid that is retained in various compositions containing mesoporous silica microrods (MSR) and fluid supported, lipid bilayer (SLB). In this experiment, a payload of 250 μg lipid was inputted into a 500 μg MSR composition. FIG. 2C shows changes in relative florescence of various MSR-SLB compositions containing DOPC, POPC or DSPC in phosphate-buffered saline (PBS) over a two-week (14-day) period at 37° C. FIG. 2D shows changes in relative florescence of various MSR-SLB compositions containing DOPC, POPC or DSPC in complete Roswell Park Memorial Institute medium (cRPMI) over a two-week (14-day) period at 37° C.

FIGS. 4A, 4B, 4C, 4D, and 4E show changes in the assembly and the characteristics of MSR-SLB fluid structures over time. FIG. 4A shows phase-contrast and fluorescence microscope images of lipids in association with mesoporous silica microrods (MSRs) taken at high magnification (scale=2 μM) prior to bleaching (pre), right after bleaching (t=0) and 5 minutes post-bleaching (t=5 min) the lipid composition. FIG. 4B shows changes in fluorescence recovery after photo-bleaching (FRAP) with time. The fluorescence "source" is depicted in region (2), the fluorescence "sink" is depicted in region (3), and the normalization point is indicated by region (1). The differential distribution was best seen at early time points after seeding and achieved an equilibrium at around 2 mins (120 s). FIG. 4C shows smooth-fitting curves depicting average changes in FRAP, as derived from normalized images, over time. FIGS. 4D and 4E show two sets of high resolution images of MSR-SLB fluid structures prior to bleaching (pre), right after bleaching (t=0) and 3 minutes post-bleaching (t=3 min) the lipid composition.

FIG. 5A shows a schematic representation of the structure of APC-MS containing a lipid bilayer of POPC containing phycoerythrin biotin (biotin PE), which is conjugated to a streptavidin molecule (e.g., a streptavidin dimer), which in turn is conjugated to a biotinylated antibody (e.g., a biotinylated anti-CD3 antibody or a biotinylated anti-CD28 antibody or another specific or non-specific antibody). FIG. 5B shows spectrophotometric analysis of B3Z reporter cell β-galactosidase expression following treatment with combinations of MPS (silica), POPC (lipid), MPS-POPC composite, biotinylated MPS-POPC composite (in the presence or absence of streptavidin) and the MPS-POPC composite together with the biotinylated antibody in the presence or absence of phycoerythrin biotin (biotin PE) and/or streptavidin. Significant increase in absorbance is observed in MSR-SLB compositions containing all the individual components—phosphoethanolamine biotin (biotin PE) conjugated to a biotinylated antibody via a streptavidin linker (dark bars; ** indicates statistical significance ($p<0.001$, analyzed using one-way ANOVA, followed by Tukey HSD post-hoc test; data represents mean±s.d. of three experimental replicates and are representative of at least two independent experiments).

FIG. 6A shows an electron micrograph of porous structure of MSR containing IL-2 (scale bar=100 nm). FIG. 6B shows a plot of cumulative release of IL-2 levels over a 15-day period. FIG. 7A shows cells that have been stained with two different dyes. FIG. 7B shows cells that have been stained with a single dye (indicating live cells).

FIG. 9A shows polyclonal expansion of T-cells after a 3 day stimulation of T-cells with control scaffolds (mock; free; POPC lipid only; and a combination of POPC and IL-2) and experimental scaffolds (containing a combination of POPC and IL-2, along with antibody). Three different doses of the antibody (MSR: antibody ratio of 1:50, 1:25 and 1:10) were studied. FIG. 9B shows secretion of IFNγ after a 3 day stimulation of T-cells with control scaffolds (mock; free; POPC lipid only; and a combination of POPC and IL-2) and experimental scaffolds (containing a combination of POPC and IL-2, along with antibody). Three different doses of the antibody (MSR: antibody ratio of 1:50, 1:25 and 1:10) were studied.

FIG. 10 shows fold-expansion of primary T-cells upon incubation with control (mock; free; SLB+IL-2; DYNABEAD+IL-2) or experimental compositions. Incubation of primary T-cells with the composition of the instant invention significantly induced T-cell expansion (with or without re-stimulation) compared to mock compositions or compositions free of SLB. More importantly, compared to a composition of DYNABEADS and IL-2, incubation of primary T-cells with the scaffolds of the invention resulted in a measurably stronger proliferation upon re-stimulation at day 7. FIG. 11 shows a bar-chart of cellular metabolic activity of T-cells (as measured by relative fluorescence units (RFU) of Alamar Blue reduction normalized to the cell number) that were incubated with the scaffolds of the instant invention loaded with IL-2 (SLB/IL2/ABS) or DYNABEADS loaded with IL-2 (DYNABEADS-IL2).

FIG. 12A shows photomicrographs (at 4× magnification) of aggregates of splenic T cells upon incubation with DYNABEADS or APC-MS at day 0, day 3, and day 7. FIG. 12B shows photomicrographs (at 10× magnification) of aggregates of splenic T cells upon incubation with DYNABEADS or APC-MS at day 0, day 3, and day 7. (White scale bars=100 µM).

FIG. 13A shows flow cytometric (FACS) scatter plots of T-cell population(s) at various time-points (t=0 days, 5 days, 7 days, 11 days and 13 days) following incubation with APC-MS or DYNABEADS (with re-stimulation or IL-2 treatment after 7 days of incubation), wherein the values on the X-axis depict intensity of CD8+ staining and the values on the Y-axis depict intensity of CD4+ staining. Flow data were gated on Fluorescence Minus ONE (FMO) controls for each sample, at each timepoint. Data is representative of at least two independent experiments. FIG. 13B is a line-graph showing changes in percentage of CD4+ versus CD8+ T-cell sub-populations after incubation with APC-MS (squares) or DYNABEADS (triangles) at various time-points (t=0 days, 5 days, 7 days, 11 days and 13 days). After 7-days of incubation, the cells were divided into two sub-populations, wherein the first sub-population was re-stimulated (dashed line) and the second sub-population was treated with IL-2 (solid line). APC-MS was used for restimulation of APC-MS conditions, DYNABEADS were used to restimulate DYNABEADS conditions.

FIG. 20A shows a line graph of the polyclonal expansion of primary T cells that were incubated with control scaffolds or experimental scaffolds at various time-points (t=0 days, 5 days, 7 days, 11 days and 13 days). The control scaffolds include sham ("mock"; black line) compositions and compositions that are free of SLB ("free"; red line). The experimental scaffolds include (1) DYNABEADS (blue line) and (2) lipid bilayers (SLB) of the present invention (green line). FIG. 20B shows a bar graph showing metabolic activity of primary T cells (measured with standard Alamar Blue staining assay) that were incubated with control scaffolds or experimental scaffolds at various time-points (t=0 days, 5 days, 7 days, 11 days and 13 days). The control scaffolds include sham compositions ("mock"; "m") and compositions that are free of SLB ("free"; "f"). The experimental scaffolds include (1) DYNABEADS ("d") and (2) lipid bilayers (SLB) of the present invention ("s").

FIG. 23 shows CD62L and CCR7 expression on live T cells expanded for 14 days using the APC-MS containing IL-2 and the aforementioned anti-CD3 antibodies—OKT3 (left panels), HIT3a (middle panels) and UCHT1 (right panels) and anti-CD28 antibody at a 1:1 ratio, at 1× loading concentration (about 5 µg). The expression of CD62L and CCR7 in total live cells is shown in the top panels and the expression of these markers in gated CD8+ cells is shown in the bottom panels. A majority of cells expanded with the APC-MS of the instant invention remain CD62L+CCR7+ after incubation for 14 days, which has been shown to be important for in vivo functionality in human patients. Additionally, APC-MS scaffolds containing OKT3 were particularly effective in expanding and/or retaining CD62L+CCR7+ T-cells compared to scaffolds containing UCHT1 and/or HIT3a.

FIG. 25A depicts an exemplary process for preparing APC-MS: 1) Mesoporous silica micro-rods (MSRs) are synthesized; 2) MSRs are adsorbed with IL-2; 3) IL-2-adsorbed MSRs are coated with liposomes, forming MSR-SLBs; 4) T cell activation cues are attached to the surface of MSR-SLBs; 5) MSR-SLBs are cultured with T cells; and 6) MSR-SLBs settle and stack to form a scaffold that is infiltrated by T cells. Scaffolds formed from MSR-SLBs that were loaded with IL-2 and surface-functionalized with T cell activation cues are referred to as APC-MS. FIG. 25B depicts exemplary structures and functions of distinct APC-MS formulations. IL-2 is released from APC-MS over time, resulting in paracrine delivery of IL-2 to local T cells. Incorporation of predefined amounts of a biotinylated phospholipid into liposome formulations enables the precise surface attachment of biotinylated T cell activation cues via streptavidin-biotin interactions, mimicking the cell surface presentation of cues by natural APCs to T cells. For polyclonal T cell expansion, activating antibodies against CD3 (αCD3) and CD28 (αCD28) are attached (left). For antigen-specific T cell expansion, peptide-loaded MHC (pMHC) and αCD28 are attached (right).

FIG. 26A shows a representative brightfield microscopy image of MSRs. Scale bar=100 µm. FIG. 26B depicts the size distribution of POPC liposomes as measured by dynamic light scattering (DLS). Data in FIG. 26B represents the mean size distribution of 3 samples.

FIG. 27A is a microscopy image showing the aggregation of MSRs at low lipid:MSR. Representative microscopy images of lipid-coated MSRs (lipid:MSR 1:20 w/w) showing brightfield image of MSRs (left), fluorophore-tagged phospholipid (1 mol % of total lipid; middle), and co-localization of MSRs and lipid (right). Scale bar=200 µm. FIG. 27B is a microscopy image of lipid-coated MSRs (lipid:MSR 1:4 w/w) showing brightfield image of MSRs (left), fluorophore-tagged phospholipid (1 mol % of total lipid; middle), and co-localization of MSRs and lipid (right). Scale bar=200 µm.

FIG. 28A depicts the retention of lipid coating (containing 1 mol % fluorophore-tagged lipid) on MSRs over time in either PBS or RPMI media containing 10% serum (cRPMI), maintained at cell culture conditions. FIG. 28B is a representative overlaid fluorescence microscopy images of lipid-coated MSRs (MSRs, brightfield; lipid (1 mol % fluorophore-tagged lipid), green), maintained in cRPMI under standard cell culture conditions, over time. Scale bar=100 µm. Data represents mean±s.d. of three experimental replicates and are representative of at least two independent experiments. FIG. 28C is a graph depicting the quantification of IL-2 released from MSR-SLBs (500 µg of MSRs) in vitro over time (data points) with one phase exponential fit (dashed line; $R^2$=0.98). Data represents mean±s.d. of three experimental replicates and are representative of at least two independent experiments. FIG. 28D is a graph depicting the quantification of attachment of various inputs of biotinylated IgG onto MSRs coated with lipid formulations containing 0.01 mol %, 0.1 mol %, or 1 mol % biotinylated lipid. Values above bars indicate concentration (μg) of IgG attached for each respective condition. Data represents mean±s.d. of four experimental replicates and are representative of at least two independent experiments. FIG. 28E is a SEM image showing close association of primary human T cells with APC-MS. Scale bar=10 μm.

FIG. 30A are representative brightfield microscopy images of primary mouse T cells cultured with DYNABEADS or APC-MS, at various timepoints, at low magnification (left) or high magnification with APC-MS (right). Scale bars=100 μm. FIG. 30B shows the expansion of primary mouse T cells that were either untreated (mock), or cultured with free cues (110 nM αCD3, 110 nM αCD28, 1.3 μg/ml IL-2), commercial CD3/CD28 mouse T cell expansion beads and exogenous IL-2 (DYNABEADS), IL-2-loaded MSR-SLBs without T cell cues presented on the bilayer surface (MSR-SLB (cue-)), or APC-MS (loaded with αCD3, αCD28, IL-2). Curves for mock and free were indistinguishable from the MSR-SLB (cue-) curve. FIG. 30C depicts the frequencies of CD4+ and CD8+ cells among live single cells over time in APC-MS or Dynabead cultures, measured using FACS. Data was analyzed using two-way ANOVA, followed by Tukey HSD post-hoc test. FIG. 30D are representative brightfield microscopy images of primary human T cells cultured with DYNABEADS or APC-MS formulations, at various timepoints. Scale bars=100 μm. (F1) APC-MS presenting αCD3 and αCD28 saturating 1 mol % biotinylated lipid, input at 333 μg/ml of MSRs to initial culture, (F2) APC-MS presenting αCD3 and αCD28 saturating 1 mol % biotinylated lipid, input at 33 μg/ml of MSRs to initial culture, (F3) APC-MS presenting αCD3 and αCD28 saturating 0.1 mol % biotinylated lipid, input at 333 μg/ml of MSRs to initial culture, and (F4) APC-MS presenting αCD3 and αCD28 saturating 0.1 mol % biotinylated lipid, input at 33 μg/ml of MSRs to initial culture. FIG. 30E shows the expansion of primary human T cells that were either untreated (mock), or cultured with commercial CD3/CD28 human T cell expansion beads and exogenous IL-2 (DYNABEADS), or with various APC-MS formulations. FIG. 30F depicts the FACS quantification of CD4 and CD8 single positive cells among live single CD3+ cells, in samples expanded for 14 days either with DYNABEADS or with various APC-MS formulations. FIG. 30G depicts the FACS quantification of cells co-expressing PD-1 and LAG-3 among live single cells, in samples expanded either with DYNABEADS or with various APC-MS formulations. Data in FIGS. 30F and 30G represent mean±s.d. of three experimental replicates and are representative of at least two independent experiments. Data in FIG. 30E represent mean±s.d. of at least three different donor samples from two independent experiments. Data in FIG. 30F and 30G represent mean±s.d. of three different donor samples and are representative of at least two independent experiments. p<0.01, *p<0.001.

FIGS. 32A, 32B, 32C and 32D depict the extended phenotypic characterization of polyclonally expanded primary mouse T cells. FIG. 32A depicts the FACS quantification of Granzyme B positive cells among live single CD8+ cells, in samples expanded either with DYNABEADS or with APC-MS (left), and representative FACS plots (right). FIG. 32B depicts the FACS quantification of FoxP3 positive cells among live single CD4+ cells, in samples expanded either with DYNABEADS or with APC-MS. FIGS. 32C and 32D shows representative FACS plots showing PD-1 expression on live single cells, as a function of CD8 expression. Flow data were gated on Fluorescence Minus One (FMO) controls for each sample, at each timepoint. Data represent mean±s.d. of three experimental replicates and are representative of at least two independent experiments.

FIG. 34A shows representative brightfield microscopy images of primary CD8+ OT-I T cells cultured for two days with APC-MS presenting an irrelevant peptide (SVYDFFVWL (SEQ ID NO: 3); left) or the relevant peptide (SIINFEKL (SEQ ID NO: 4); right) in H-2K(b). Scale bar=100 μm. FIG. 34B shows the expansion of primary CD8+ OT-I T cells that were either untreated (mock), or cultured with various APC-MS formulations. (F1) APC-MS presenting SIINFEKL (SEQ ID NO: 4)/H-2K(b) and αCD28 saturating 1 mol % biotinylated lipid, input at 333 μg/ml of MSRs to initial culture, (F2) APC-MS presenting SIINFEKL (SEQ ID NO: 4)/H-2K(b) and αCD28 saturating 1 mol % biotinylated lipid, input at 33 μg/ml of MSRs to initial culture, (F3) APC-MS presenting SIINFEKL (SEQ ID NO: 4)/H-2K(b) and αCD28 saturating 0.1 mol % biotinylated lipid, input at 333 μg/ml of MSRs to initial culture, and (F4) APC-MS presenting SIINFEKL (SEQ ID NO: 4)/H-2K(b) and αCD28 saturating 0.1 mol % biotinylated lipid, input at 33 μg/ml of MSRs to initial culture. FIG. 34C depicts the FACS quantification of IFNγ and TNFα expression by live single CD8+ OT-I T cells expanded for 13 days with various APC-MS formulations and then co-cultured with B16-F10 cells that were either mock pulsed (−), or pulsed with SIINFEKL (SEQ ID NO: 4) peptide (+). FIG. 34D depicts the quantification of in vitro killing of mock-pulsed (−) or SIINFEKL (SEQ ID NO: 4)-pulsed (+) B16-F10 target cells by CD8+ OT-I T cells that were expanded for 13 days with various APC-MS formulations, and then co-cultured at various effector:target cell ratios. FIG. 34E depicts the quantification of IFNγ secretion by CD8+ OT-I T cells expanded for 13 days with various APC-MS formulations in response to co-culture at various effector:target cell ratios with B16-F10 cells that were either mock pulsed (pep−), or pulsed with SIINFEKL (SEQ ID NO: 4) peptide (pep+). Data in FIGS. 34B, 34C, 34D, and 34E represent mean±s.d. of three experimental replicates and are representative of at least two independent experiments.

FIG. 35A shows the total expansion of primary human CD8+ T cell isolates that were mock treated (30 U/ml IL-2), or cultured with APC-MS (loaded with pMHC, αCD28, IL-2) either presenting the CLG or GLC peptide in HLA-A2. Data for mock-treated cells only available for days 0 and 7. FIGS. 35B, 35C and 35D show the quantification of IFNγ secretion of CD8+ T cell isolates that were mock treated (30 U/ml IL-2), or cultured with APC-MS presenting either the CLG peptide (APC-MS CLG) or GLC peptide (APC-MSGLC), following co-culture with T2 cells that were either unpulsed (peptide-) (FIG. 35B), pulsed with CLG peptide (+CLG peptide) (FIG. 35C), or pulsed with GLC peptide (+GLC peptide) (FIG. 35D). Data for mock-treated cells only available for day 7. FIG. 35E shows representative FACS plots showing IFNγ and TNFα expression, of CD8+ T cell isolates that were cultured with APC-MS presenting either the CLG peptide (APC-MS/CLG) or GLC peptide (APC-MS/GLC), following co-culture with T2 cells that were either unpulsed (no peptide; top), pulsed with CLG peptide (+CLG peptide; middle), or pulsed with GLC peptide (+GLC peptide; bottom). Data in FIGS. 35A and 35B represent mean±s.d. of three experimental replicates and are representative of two experiments with two different donor samples.

FIGS. 36A, 35B, 36C, 36D, 36E, 36F, 36G, 36H, 36I, 36J, 36K, 36L, 36M, and 36N show the antigen-specific expansion of primary human T cells. FIGS. 36A, 36B, 36C, 36D, 36E, 36F, 36G, 36H, 36I, and 36J depict the antigen-specific expansion of primary human T cells from CD8+ T cell isolates. FIGS. 36A, 36B and 36D depict the tetramer analysis of live CD8+ single cells specific for the EBV-derived peptides CLGGLLTMV (SEQ ID NO: 1) (CLG; FIGS. 36A and 36B) and GLCTLVAML (SEQ ID NO: 2) (GLC; FIGS. 36D and 36E). Representative FACS plots with numbers in gates denoting the percent of live single CD8+ cells that are positive for the respective tetramer (FIGS. 36A and 36D), and quantification of FACS data at various timepoints (FIGS. 36B and 36E), of primary HLA-A2+ human CD8+ T cells that were mock treated (30 U/ml IL-2), or cultured with APC-MS (loaded with pMHC, αCD28, IL-2) either presenting the CLG or GLC peptide in HLA-A2. Data for mock-treated cells only available for days 0 and 7. FIG. 36F shows the expansion of primary human CD8+ T cells specific for CLG (FIG. 36C) or GLC (FIG. 36F) that were either mock treated, or cultured with APC-MS either presenting the CLG or GLC peptide in HLA-A2. Data for mock-treated cells only available for days 0 and 7. FIGS. 36G, 36H and 36I depict the frequencies of TNFα+IFNγ+ cells among live single CD8+ T cells that were mock treated, or cultured with APC-MS either presenting the CLG or GLC peptide in HLA-A2, following co-culture with T2 cells that were either unpulsed (peptide−; FIG. 36G), pulsed with CLG peptide (+CLG peptide; FIG. 36H), or pulsed with GLC peptide (+GLC peptide; FIG. 36I). Data for mock-treated cells only available for day 7. FIG. 36J shows the quantification of in vitro killing of T2 target cells that were mock-pulsed (no peptide), or pulsed with either the CLG peptide (+CLG) or GLC peptide (+GLC), by primary human CD8+ T cells expanded for 14 days with APC-MS either presenting the CLG or GLC peptide in HLA-A2. FIGS. 36K, 36L, 36M and 36N show the antigen-specific expansion of primary human T cells from PBMCs. FIG. 36K depicts the frequency of GLC-specific cells among live single CD8+ T cells, within PBMCs cultured for 7 days in 30 U/ml IL-2 (mock), or with APC-MS presenting the GLC peptide in HLA-A2. FIG. 36L shows the number of GLC-specific CD8+ T cells within PBMCs cultured for 7 days in 30 U/ml IL-2 (mock), or with APC-MS presenting the GLC peptide in HLA-A2. Numbers above bars denote fold expansion (mean±s.d.). FIGS. 36M and 36N show the frequency of TNFα+IFNγ+ cells among live single CD8+ T cells (FIG. 36M), and IFNγ secretion (FIG. 36N), from PBMCs that were cultured for 7 days in 30 U/ml IL-2 (mock), or with APC-MS presenting the GLC peptide in HLA-A2, following co-culture with T2 cells that were either unpulsed (no peptide), pulsed with CLG peptide (+CLG), or pulsed with GLC peptide (+GLC). All data represent mean±s.d. of three experimental replicates and are representative of two experiments with two different donor samples.

FIG. 39A are representative images of three independent FRAP events. Images show fluorescently-tagged MSR-SLB before photobleaching (left), immediately after photobleaching (middle), and after fluorescence recovery (right). Photobleached regions are indicated by red arrows. FIG. 39B shows the quantification of fluorescence recovery over time. Fluorescence recovery of 8 independent photobleaches on different MSR-SLBs are shown in dashed black and the average trend is shown in solid.

FIGS. 40A, 40B, 40C, and 40D depict the results of T-cell expansion experiments performed using APC-MSs as compared to DYNABEADs, wherein the amount of DYNABEADs was normalized to comprise the same amount of anti-CD3 and anti-CD28 antibodies as the APC-MSs. FIG. 40A. Bicinchoninic acid assay (BCA) analysis for total protein quantification performed to determine the amount of protein bound on the surface of commercial mouse or human CD3/CD28 T cell activator DYNABEADS. DYNABEAD stock solutions were washed thoroughly, and DYNABEAD antibody load was evaluated via BCA assay. DYNABEADs targeted to mouse and human T-cells were found to have similar antibody loads (~20 μg/ml). On a per cell basis, a DYNABEAD:cell of 5:1 ratio (condition D-B) corresponded to the same dose of anti-CD28/anti-CD3 antibodies as APC-MS presenting 0.1% T cell cues input at 16.7 μg (condition M-D). FIG. 40B. Dose-dependent expansion of primary mouse T-cells was observed with APC-MS over 13-day culture period, but not with DYNABEADs within the dose range tested. APC-MS significantly promoted enhanced T cell expansion compared to DYNABEADS presenting the same amount of anti-CD3 and anti-CD28 antibodies (see condition M-D vs D-B). FIG. 40C. Despite greater expansion, cells expanded with APC-MS condition M-D did not show enhanced co-expression of exhaustion markets PD-1 and LAG-3 as compared to cells expanded with DYNABEADs presenting the same amount of anti-CD3 and anti-CD28 antibodies (condition D-B). FIG. 40D. T cells expanded with low-to-moderate doses of DYNABEADs showed primarily CD4-biased skewing (conditions D-A, D-B). When DYNABEADs were added at extremely high doses, moderate CD8-biased skewing was observed (condition D-C). In contrast, APC-MS tended to show heavy CD8-biased skewing with the degree of skewing dependent on the formulation of the APC-MS. Data in FIGS. 40B, 40C and 40D represent mean±s.d. of samples from four different mice and are representative of at least two independent experiments. ***$p<0.001$, (b) analyzed using two-way ANOVA, followed by Tukey HSD post-hoc test.

FIG. 41A shows the expansion of primary mouse T cells treated with either APC-MS loaded with IL-2 (M-D), APC-MS and IL-2 added to media (M-D bIL2); DYNABEADs (D-B) or DYNABEADs and IL-2 added to media (D-B bIL-2). D-B: DYNABEAD 5:1; D-B-bIL-2: DYNABEAD 5:1+ IL-2 bolus; M-D: 0.1% T cell cues/1:10× material/loaded IL-2; M-S/bIL-2: 0.1% T cell cues/1L10× material/IL-2 bolus. FIG. 41B shows the co-expression of exhaustion markers PD-1 and LAG-3 in primary mouse T-cells cells expanded with either APC-MS loaded with IL-2 (M-D); APC-MS and IL-2 added to media (M-D bIL2); DYNABEADs (D-B); or DYNABEADs and IL-2 added to media (D-B bIL-2). Data represent mean±s.d. of samples from four different mice and are representative of at least two independent experiments. ***$p<0.001$, analyzed using two-way ANOVA, followed by Tukey HSD post-hoc test.

FIG. 42A. Varying amounts of azide-modified IgG (as indicated) were incubated with MSR-SLBs containing varying amounts of DBCO-modified lipid (as indicated). Values above bars represent ug of azide-modified IgG that was attached to MSR-SLBs. FIG. 42B shows the broader dose titration of azide-modified IgG input to MSR-SLBs containing varying amounts of DBCO-modified lipid. nIgG represents IgG that was not azide-modified. Values above bars represent μg of azide-modified IgG that was attached to the MSR-SLBs.

DETAILED DESCRIPTION OF THE INVENTION

Figure 1:
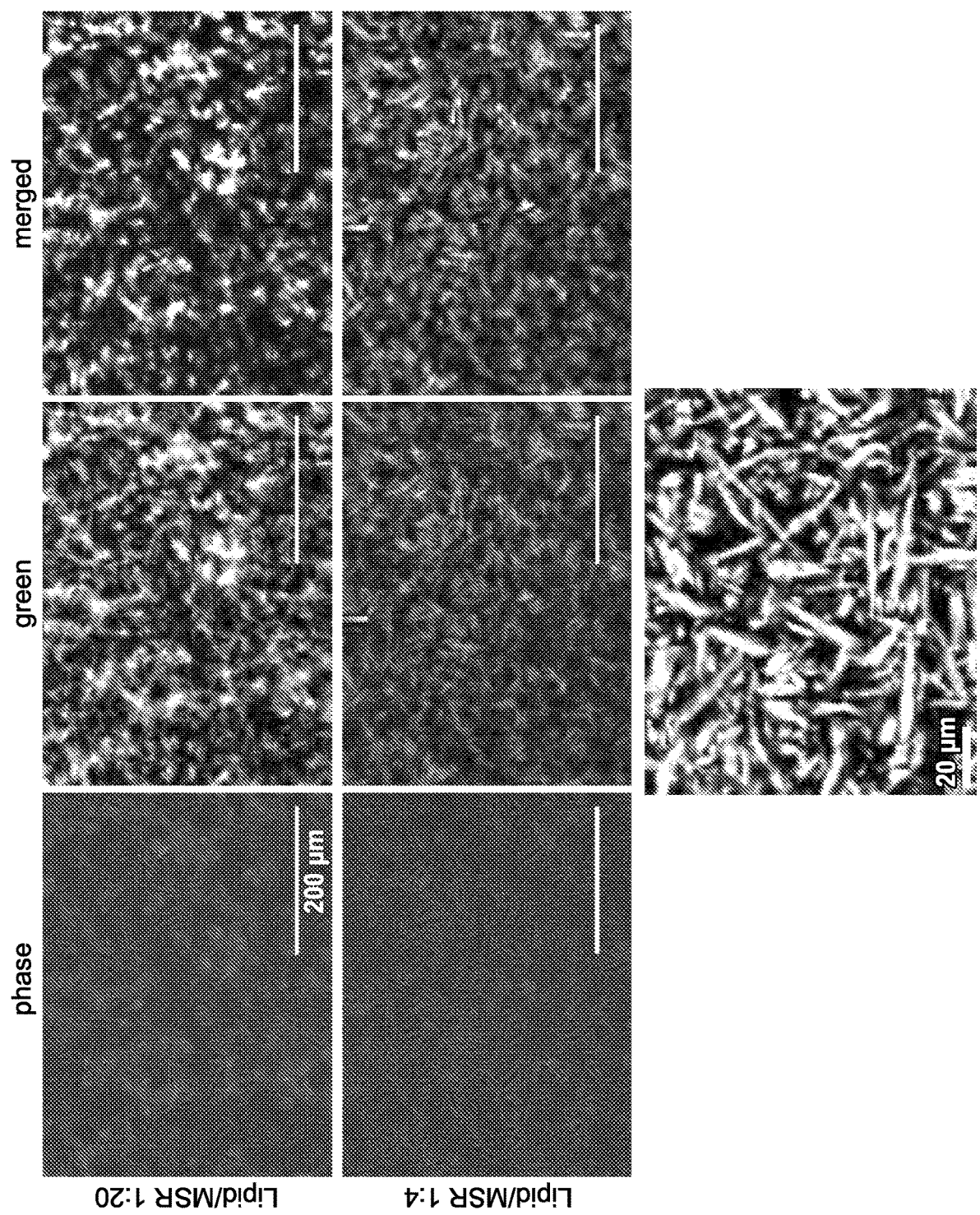
FIG. 1 shows phase-contrast and fluorescence microscope images of lipids in association with mesoporous silica microrods (MSRs). The top panel shows merged pictures of the lipids and mesoporous silica microrods at a lipid:MSR ratio of 1:20 (Scale=200 μm). The middle panel shows merged pictures of the lipids and mesoporous silica microrods at a lipid:MSR ratio of 1:4 (Scale=200 μm). The bottom panel shows a merged phase-contrast microscope image of lipids in association with MSRs at a higher magnification (Scale=20 μm).

The present invention provides a solution to the problem of manipulating T-cells. Specifically, the present invention provides antigen presenting cell-mimetic scaffolds (APC-MS), which are useful in the manipulation of such cells. The scaffolds include mesoporous silica rods (MSR), which incorporate or are coated with a continuous, fluid supported lipid bilayer (SLB) thereby forming MSR-SLB scaffolds. The MSR-SLB scaffold further contains a plurality of T-cell activating and T-cell co-stimulatory molecules, along with a plurality of T-cell homeostatic agents, which together make up a structure that mimics antigen-presenting cells (APC) and allows the scaffolds to elicit various effector functions on target cells, e.g., T-cells. In some embodiments, the scaffold mediates these effects via direct or indirect interaction between the cell surface molecules residing in target cells and the various binding partners presented by the scaffolds. Depending on the application for which the scaffold is used, the scaffold regulates survival and growth of the targeted cells through the physical or chemical characteristics of the scaffold itself. Depending upon application, the scaffold composition may be modified to contain certain activating and co-stimulatory signals, as well as homeostatic signaling molecules, which act together to mediate various effector functions, e.g., activation, division, promote differentiation, growth, expansion, reprogramming, anergy, quiescence, senescence, apoptosis or death, of target cells. In these applications, the scaffolds were found to surprisingly improve cell metabolic activity and growth of targeted cells. Moreover, the improvement in growth and metabolic activity conferred by the scaffolds of the invention was unexpectedly superior to existing platforms, such as magnetic beads.

In order to permit manipulation of specific cells, such as T-cells, the permeability of the scaffold composition may be regulated, for example, by selecting or engineering a material for greater or smaller pore size, density, polymer cross-linking, stiffness, toughness, ductility, or elasticity. The scaffold composition may contain physical channels or paths through which targeted cells interact with the scaffold and/or move into a specific compartment or region of the scaffold. To facilitate the compartmentalization, the scaffold composition may be optionally organized into compartments or layers, each with a different permeability, so that cells are sorted or filtered to allow access to only a certain sub-population of cells. Sequestration of target cell populations in the scaffold may also be regulated by the degradation, de- or re-hydration, oxygenation, chemical or pH alteration, or ongoing self-assembly of the scaffold composition. Following their capture, the targeted cells may be allowed to grow or expand within the scaffold with the help of stimulatory molecules, cytokines, and other co-factors present in the scaffold. In other instances, non-targeted cells which have otherwise infiltrated the scaffold may be rejected or removed using negative selection agents.

The cells that are contained or sequestered within the scaffolds of the invention are primarily immune cells. In certain embodiments, the invention relates to scaffolds for sequestering and/or manipulating T cells. In other embodiments, the invention relates to scaffolds that are permeable to other lymphocytes, e.g., B-cells. Yet in other embodiments, the invention relates to a combination of scaffolds, e.g., a combination of T-cell scaffolds and B-cell scaffolds. The immune cells, e.g., T-cells, are optionally harvested and analyzed to identify distinct sub-populations that are useful in the diagnosis or therapy of diseases. The harvested cells may also be reprogrammed or expanded for developing compositions or formulations that are to be used in therapy.

The invention is further described in more detail in the subsections below.

I. Antigen Presenting Cell-Mimetic Scaffolds (APC-MS)

In one embodiment, the present invention provides antigen-presenting cell-mimetic scaffolds (APC-MS). The scaffolds contain a base layer comprising high surface area mesoporous silica micro-rods (MSR); a continuous, fluid supported lipid bilayer (SLB) layered on the MSR base layer; a plurality of T-cell activating molecules and T-cell co-stimulatory molecules adsorbed onto the scaffold; and a plurality of T-cell homeostatic agents adsorbed onto the scaffold.

A. Mesoporous Silica

In one embodiment, the components of the scaffolds of the invention include mesoporous silica. Mesoporous silica is a porous body with hexagonal close-packed, cylinder-shaped, uniform pores. This material is synthesized by using a rod-like micelle of a surfactant as a template, which is formed in water by dissolving and hydrolyzing a silica source such as alkoxysilane, sodium silicate solution, kanemite, silica fine particle in water or alcohol in the presence of acid or basic catalyst. See, US Pub. No. 2015-0072009 and Hoffmann et al., *Angewandte Chemie International Edition*, 45, 3216-3251, 2006. Many kinds of surfactants such as cationic, anionic, and nonionic surfactants have been examined as the surfactant and it has been known that generally, an alkyl trimethylammonium salt of cationic surfactant leads to a mesoporous silica having the greatest specific surface area and a pore volume. See, U.S. Publication No. 2013/0052117 and Katiyar et al. (*Journal of Chromatography* 1122 (1-2): 13-20). The terms "mesoscale," "mesopore," "mesoporous" and the like, as used in this specification, may refer to structures having feature sizes in the range of 5 nm to 100 nm, in particular in the range of 2 nm to 50 nm. Hence, in some embodiments, a mesoporous material includes pores, which may be ordered or randomly distributed, having a diameter in the range of 5 nm to 100 nm.

The mesoporous silica used in the scaffolds of the invention may be provided in various forms, e.g., microspheres, irregular particles, rectangular rods, round nanorods, etc., although structured rod forms (MSR) are particularly preferred. The particles can have various pre-determined shapes, including, e.g., a spheroid shape, an ellipsoid shape, a rod-like shape, or a curved cylindrical shape. Methods of assembling mesoporous silica to generate microrods are known in the art. See, Wang et al., *Journal of Nanoparticle Research*, 15:1501, 2013. In one embodiment, mesoporous silica nanoparticles are synthesized by reacting tetraethyl orthosilicate with a template made of micellar rods. The result is a collection of nano-sized spheres or rods that are filled with a regular arrangement of pores. The template can then be removed by washing with a solvent adjusted to the proper pH. In this example, after removal of surfactant templates, hydrophilic silica nanoparticles characterized by a uniform, ordered, and connected mesoporosity are prepared with a specific surface area of, for example, about 600 $m^2/g$ to about 1200 $m^2/g$, particularly about 800 $m^2/g$ to about 1000 $m^2/g$ and especially about 850 $m^2/g$ to about 950 $m^2/g$. In another embodiment, the mesoporous particle could be synthesized using a simple sol-gel method or a spray drying method. Tetraethyl orthosilicate is also used with an additional polymer monomer (as a template). In yet another embodiment, one or more tetraalkoxy-silanes and one or more (3-cyanopropyl)trialkoxy-silanes may be co-condensed to provide the mesoporous silicate particles as rods. See, US Publication Nos. 2013-0145488, 2012-0264599 and 2012-0256336, which are incorporated by reference.

The mesoporous silica rods may comprise pores of between 2-50 nm in diameter, e.g., pores of between 2-5 nm, 10-20 nm, 10-30 nm, 10-40 nm, 20-30 nm, 30-50 nm, 30-40 nm, 40-50 nm. In particular embodiments, the microrods comprise pores of approximately 5 nm, 6 nm, 7 nm, 8 nm, 9 nm, 10 nm, 11 nm, 12 nm, or more in diameter. The pore size may be altered depending on the type of application.

In another embodiment, the length of the micro rods is in the micrometer range, ranging from about 5 μm to about 500 μm. In one example, the microrods comprise a length of 5-50 μm, e.g., 10-20 μm, 10-30 μm, 10-40 μm, 20-30 μm, 30-50 μm, 30-40 μm, 40-50 μm. In other embodiment, the rods comprise length of 50 μm to 250 μm, e.g., about 60 μm, 70 μm, 80 μm, 90 μm, 100 μm, 120 μm, 150 μm, 180 μm, 200 μm, 225 μm, or more. For recruitment of cells, it may be preferable to employ MSR compositions having a higher aspect ratio, e.g., with rods comprising a length of 50 μm to 200 μm, particularly a length of 80 μm to 120 μm, especially a length of about 100 μm or more.

In yet another embodiment, the MSR provide a high surface area for attachment and/or binding to target cells, e.g., T-cells. Methods of obtaining high surface area mesoporous silcates are known in the art. See, e.g., U.S. Pat. No. 8,883,308 and US Publication No. 2011-0253643, the entire contents of which are incorporated by reference herein. In one embodiment, the high surface area is due to the fibrous morphology of the nanoparticles, which makes it possible to obtain a high concentration of highly dispersed and easily accessible moieties on the surface. In certain embodiments, the high surface area MSRs have a surface area of at least about 100 $m^2/g$, at least 150 $m^2/g$, or at least 300 $m^2/g$. In other embodiments, the high surface area MSRs have a surface area from about 100 $m^2/g$ to about 1000 $m^2/g$, including all values or sub-ranges in between, e.g., 50 $m^2/g$, 100 $m^2/g$, 200 $m^2/g$, 300 $m^2/g$, 400 $m^2/g$, 600 $m^2/g$, 800 $m^2/g$, 100-500 $m^2/g$, 100-300 $m^2/g$, 500-800 $m^2/g$ or 500-1000 $m^2/g$.

B. Lipids

The scaffolds of the invention comprise a continuous, fluid supported lipid bilayer (SLB) on the MSR base layer. The term "lipid" generally denotes a heterogeneous group of substances associated with living systems which have the common property of being insoluble in water, can be extracted from cells by organic solvents of low polarity such as chloroform and ether. In one embodiment, "lipid" refers to any substance that comprises long, fatty-acid chains, preferably containing 10-30 carbon units, particularly containing 14-23 carbon units, especially containing 16-18 carbon units.

In one embodiment, the lipid is provided as a monolayer. In another embodiment, the lipid is provided as a bilayer. A lipid bilayer is a thin polar membrane made of two layers of lipid molecules. Preferably, the lipid bilayer is fluid, wherein individual lipid molecules able to diffuse rapidly within the monolayer. The membrane lipid molecules are preferably amphipathic.

In one embodiment, the lipid layers are continuous bilayers, e.g., resembling those found in natural biological membranes such as cellular plasma membranes. In another embodiment, the lipid is provided in the form of a supported bilayer (SLB). An SLB is a planar structure sitting on a solid support, e.g., mesoporous silica rods (MSR). In such an arrangement, the upper face of the supported bilayer is exposed, while the inner face of the supported bilayer is in contact with the support. MSR-SLB scaffolds are stable and remain largely intact even when subject to high flow rates or vibration and can withstand holes, e.g., holes that are aligned with the pores of the mesoporous silica base layer. Because of this stability, experiments lasting weeks and even months are possible with supported bilayers. SLBs are also amenable to modification, derivatization and chemical conjugation with many chemical and/or biological moieties.

In one embodiment, the SLB may be immobilized on the MSR base layer using any known methods, including covalent and non-covalent interactions. Types of non-covalent interactions include, for example, electrostatic interactions, van der Waals' interactions, 7r-effects, hydrophobic interactions, etc. In one embodiment, the lipids are adsorbed on the MSR base layer. In another embodiment, the SLBs are attached or tethered to the MSR base layer via covalent interactions. Methods for attaching lipids to silicates are known in the art, e.g., surface absorption, physical immobilization, e.g., using a phase change to entrap the substance in the scaffold material. In one embodiment, the lipid bilayers are layered onto the MSR base layer. For example, a lipid film (containing for example, a solution of DPPC/cholesterol/DSPE-PEG at a molar ratio of 77.5:20:2.5 in chloroform) may be spotted onto the mesoporous silica and the solvent is evaporated using a rotary evaporator. See Meng et al., ACS Nano, 9 (4), 3540-3557, 2015. In one embodiment, the lipid bilayer can be prepared, for example, by extrusion of hydrated lipid films through a filter with pore size of, for example, about 100 nm, using standard protocols. The filtered lipid bilayer films can then be fused with the porous particle cores, for example, by a pipette mixing.

Alternatively, covalent coupling via alkylating or acylating agents may be used to provide a stable, structured and long-term retention of the SLB on the MSR layer. In such embodiments, the lipid bilayers may be reversibly or irreversibly immobilized onto the MSR layers using known techniques. For example, the MSR base layer can be hydrophilic and can be further treated to provide a more hydrophilic surface, e.g., with ammonium hydroxide and hydrogen peroxide. The lipid bilayer can be fused, e.g., using known coupling techniques, onto the porous MSR base layer to form the MSR-SLB scaffolds. The scaffolds may be further processed and derivatized with additional moieties to allow attachment and/or immobilization of other secondary agents onto the structure.

Accordingly, in one embodiment, the instant invention provides MSR-SLB scaffolds, wherein the SLB component is a phospholipid. Representative examples of such lipids include, but are not limited to, amphoteric liposomes described in U.S. Pat. Nos. 9,066,867 and 8,3676,28. For example, the lipid bilayer may comprise a lipid selected from dimyristoylphosphatidylcholine (DMPC), dipalmitoylphosphatidylcholine (DPPC), distearoylphosphatidylcholine (DSPC), palmitoyl-oleoylphosphatidylcholine (POPC), dioleoylphosphatidylcholine (DOPC), dioleoylphosphatidylethanolamine (DOPE), dimyristoyl-phosphatidylethanolamine (DMPE) and dipalmitoyl-phosphatidylethanolamine (DPPE) or a combination thereof. In some embodiments, the lipid bilayer comprises a lipid composition that mimics the lipid composition of a mammalian cell membrane (e.g., a human cell plasma membrane). The lipid composition of many mammalian cell membranes have been characterized and are readily ascertainable by one of skill in the art (see, e.g., Essaid et al. Biochim. Biophys. Acta 1858(11): 2725-36 (2016), the entire contents of which are incorporated herein by reference). The composition of the lipid bilayer may be altered to modify the charge or fluidity of the lipid bilayer. In some embodiments, the lipid bilayer comprises cholesterol. In some embodiments, the lipid bilayer comprises a sphingolipid. In some embodiments, the lipid bilayer comprises a phospholipid. In some embodiments, the lipid is a phosphatidylethanolamine, a phosphatidylcholine, a phosphatidylserine, a phosphoinositide a phosphosphingolipid with saturated or unsaturated tails comprising 6-20 carbons, or a combination thereof.

In another embodiment, the lipid is DIYNE PC lipid. Representative examples of such lipids include, but are not limited to, 1-Palmitoyl-2-10,12 Tricosadiynoyl-sn-Glycero-3-Phosphocholine (16:0-23:2 DIYNE PC) and 1,2-bis(10,12-tricosadiynoyl)-SN-Glycero-3-Phosphocholine (23:2 Diyne PC).

In one embodiment, the MSR-SLB scaffold of the invention retains a continuous, fluid architecture for at least 1 day, at least 2 days, at least 3 days, at least 4 days, at least 5 days, at least 6 days, at least 7 days, at least 8 days, at least 9 days, at least 10, at least 11 days, at least 12 days, at least 13 days, at least 14 days, at least 15 days, at least 16 days, at least 17 days, at least 18 days, at least 19 days, at least 20 days, at least 21 days, at least 25 days, at least 30 days, at least 35 days, at least 40 days, at least 50 days, or more.

The architecture of the MSR-SLB scaffold may be studied with any known techniques, including, the microscopic visualization techniques illustrated in the Examples below.

C. Functional Molecules

In an embodiment of the instant invention, the MSR-SLB scaffold may contain one or more functional molecules. The term "functional molecule" includes any molecule which possesses biologically desirable properties. In the context of the invention, examples of such functional molecules include proteins, peptides, antigens, antibodies, DNA, RNA, carbohydrates, haptens, and other small molecules, e.g., drugs. In one embodiment, the functional molecule is a T-cell activating molecule. In another embodiment, the functional molecule is a T-cell co-stimulatory molecule. Still further, in one embodiment, the functional molecule is a T-cell homeostatic agent. In certain embodiments, the MSR-SLB scaffolds comprise a plurality of functional molecules, e.g., at least one T-cell activating molecule, at least one T-cell co-stimulatory molecule, and at least one T-cell homeostatic agent.

T-Cell Activating Molecules

In one embodiment, the instant invention provides for MSR-SLB scaffolds containing a plurality of T-cell activating molecules. These activating molecules may mediate direct, indirect, or semi-direct activation of a target population of T-cells. See, Benichou et al., Immunotherapy, 3(6): 757-770, 2011. Preferably, the T-cell activating molecules mediate direct activation of T-cells.

In one embodiment, the instant invention provides for MSR-SLB scaffolds containing molecules which directly activate T-cells, e.g., via binding to cell surface receptors on target T-cells. Particularly, the direct activation may be mediated via cluster of differentiation-3 (CD3), which is a T-cell co-receptor that helps to activate cytotoxic T-cells. In another embodiment, T-cells may be directly activated without concomitant participation of CD3, e.g., in a CD3-independent manner.

In one embodiment, the target T-cells are activated in a CD3-dependent manner. It is generally believed that T cell activation requires a T cell receptor (TCR) to recognize its cognate peptide in the context of an MHC molecule. In addition, the association of CD3 with the TCR-peptide-MHC complex transmits the activation signal to intracellular signaling molecules to initiate a signaling cascade in the T cell. See, Ryan et al., Nature Reviews Immunology 10, 7, 2010. The CD3 receptor complex found on T-cells contains a CD3γ chain, a CD3δ chain, and two CD3ε chains, which associate with TCR and the ξ-chain (zeta-chain; CD247) to generate an activation signal in T cells. The TCR, ξ-chain, and CD3 molecules together constitute the T cell receptor (TCR) complex. Binding of an activating molecule, e.g., an antibody, to one or more of the members of the TCR complex may activate the T-cell.

In one embodiment, the T-cell activating molecule is an antibody or an antigen binding fragment thereof. Where the T-cell activating molecule acts in a CD3-dependent manner, the T-cell activating molecule is preferably an anti-CD3 antibody or an antigen-binding fragment thereof. In another embodiments, the T-cell activating molecule may include, for example, an anti-CD2 antibody or an antigen-binding fragment thereof, an anti-CD47 antibody or an antigen-binding fragment thereof, anti-macrophage scavenger receptor (MSR1) antibody or an antigen-binding fragment thereof, an anti-T-cell receptor (TCR) antibody or an antigen-binding fragment thereof, etc. In another embodiment, the T-cell activating molecule is a major histocompatibility complex (MHC) molecule or a multimer thereof that is optionally loaded with an MHC peptide. Still further, the T-cell activating molecule is a conjugate containing MHC and immunoglobulin (Ig) or a multimer thereof.

The term "antibody", as used herein, broadly refers to any immunoglobulin (Ig) molecule comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art. Non-limiting embodiments of which are discussed herein. In one embodiment, the T-cell activating antibody used in the compositions and methods of the disclosure is the anti-CD3 antibody selected from the group consisting of muromonab (OKT3), otelixizumab (TRX4), teplizumab (hOKT3γ1(Ala-Ala)), visilizumab, an antibody recognizing 17-19 kD ε-chain of CD3 within the CD3 antigen/T cell antigen receptor (TCR) complex (HIT3a), and an antibody recognizing a 20 kDa subunit of the TCR complex within CD3e (UCHT1), or an antigen-binding fragment thereof. Other anti-CD3 antibodies, including, antigen-binding fragments thereof are described in US patent pub. No. 2014-0088295, which is incorporated by reference.

Embodiments of the invention include "full-length" antibodies. In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG 1, IgG2, IgG 3, IgG4, IgA1 and IgA2) or subclass.

The term "antigen-binding portion" of an antibody (or simply "antibody portion"), as used herein, refers to one or more fragments of an antibody that retain the ability to specifically bind to an antigen (e.g., IL-13). It has been shown that the antigen-binding function of an antibody can be performed by fragments of a full-length antibody. Such antibody embodiments may also be bispecific, dual specific, or multi-specific formats; specifically binding to two or more different antigens. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546, Winter et al., PCT publication WO 90/05144 A1 herein incorporated by reference), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger et al., *Proc. Natl. Acad. Sci. USA* 90:6444-6448 (1993); Poljak et al., *Structure* 2:1121-1123 (1994)). Such antibody binding portions are known in the art (Kontermann and Dubel eds., *Antibody Engineering* (2001) Springer-Verlag. New York. 790 pp. (ISBN 3-540-41354-5).

"Antibody fragments" comprise only a portion of an intact antibody, wherein the portion preferably retains at least one, and typically most or all, of the functions normally associated with that portion when present in an intact antibody. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half-life modulation, ADCC function and complement binding. In one embodiment, an antibody fragment is a monovalent antibody that has an in vivo half-life substantially similar to an intact antibody. For example, such an antibody fragment may comprise on antigen binding arm linked to an Fc sequence capable of conferring in vivo stability to the fragment.

The term "antibody construct" as used herein refers to a polypeptide comprising one or more the antigen binding portions of the disclosure linked to a linker polypeptide or an immunoglobulin constant domain. Linker polypeptides comprise two or more amino acid residues joined by peptide bonds and are used to link one or more antigen binding portions. Such linker polypeptides are well known in the art (see e.g., Holliger et al., *Proc. Natl. Acad. Sci. USA* 90:6444-6448 (1993); Poljak et al., *Structure* 2:1121-1123 (1994)). An immunoglobulin constant domain refers to a heavy or light chain constant domain Human IgG heavy chain and light chain constant domain amino acid sequences are known in the art and disclosed in Table 2 of U.S. Pat. No. 7,915,388, the entire contents of which are incorporated herein by reference.

Still further, an antibody or antigen-binding portion thereof may be part of a larger immunoadhesion molecules, formed by covalent or noncovalent association of the antibody or antibody portion with one or more other proteins or peptides. Examples of such immunoadhesion molecules include use of the streptavidin core region to make a tetrameric scFv molecule (Kipriyanov et al., *Human Antibodies and Hybridomas* 6:93-101 (1995)) and use of a cysteine residue, a marker peptide and a C-terminal polyhistidine tag to make bivalent and biotinylated scFv molecules (Kipriyanov et al., Mol. Immunol. 31:1047-1058 (1994)). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

An "isolated antibody", as used herein, is intended to refer to an antibody that is substantially free of other antibodies having different antigenic specificities (e.g., an isolated antibody that specifically binds CD3 is substantially free of antibodies that specifically bind antigens other than CD3). An isolated antibody that specifically binds CD3 may, however, have cross-reactivity to other antigens, such as CD3 molecules from other species. Moreover, an isolated antibody may be substantially free of other cellular material and/or chemicals.

The term "human antibody", as used herein, is intended to include antibodies having variable and constant regions derived from human germline immunoglobulin sequences. The human antibodies of the disclosure may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further in U.S. Pat. No. 7,915,388, the contents of which are incorporated herein by reference), antibodies isolated from a recombinant, combinatorial human antibody library (Hoogenboom et al., *TIB Tech.* 15:62-70 (1994); Azzazy et al., *Clin. Biochem.* 35:425-445 (2002); Gavilondo et al., *BioTechniques* 29:128-145 (2002); Hoogenboom et al., *Immunology Today* 21:371-378 (2000)), antibodies isolated from an animal (e g, a mouse) that is transgenic for human immunoglobulin genes (see e.g., Taylor et al., *Nucl. Acids Res.* 20:6287-6295 (1992); Kellermann et al., *Current Opinion in Biotechnology* 13:593-597 (2002); Little et al., *Immunology Today* 21:364-370 (2002)) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. One embodiment provides fully human antibodies capable of binding human CD3 which can be generated using techniques well known in the art, such as, but not limited to, using human Ig phage libraries such as those disclosed in Jermutus et al., PCT publication No. WO 2005/007699 A2.

The term "chimeric antibody" refers to antibodies which comprise heavy and light chain variable region sequences from one species and constant region sequences from another species, such as antibodies having murine heavy and light chain variable regions linked to human constant regions. Methods for producing chimeric antibodies are known in the art and discussed in to detail in Example 2.1. See e.g., Morrison, *Science* 229:1202 (1985); Oi et al., *BioTechniques* 4:214 (1986); Gillies et al., (1989) *J. Immunol. Methods* 125:191-202; U.S. Pat. Nos. 5,807,715; 4,816,567; and 4,816,397, which are incorporated herein by reference in their entireties. In addition, "chimeric antibodies" may be produced by art-known techniques. See, Morrison et al., 1984, *Proc. Natl. Acad. Sci.* 81:851-855; Neuberger et al., 1984, *Nature* 312:604-608; Takeda et al., 1985, *Nature* 314:452-454 which are incorporated herein by reference in their entireties.

The terms "specific binding" or "specifically binding", as used herein, in reference to the interaction of an antibody, a protein, or a peptide with a second chemical species, mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The antibodies used in the scaffolds of the present invention may be "monospecific," "bi-specific," or "multispecific." As used herein, the expression "antibody" herein is intended to include both monospecific antibodies (e.g., anti-CD3 antibody) as well as bispecific antibodies comprising an arm that binds to an antigen of interest (e.g., a CD3-binding arm) and a second arm that binds a second target antigen. The target antigen that the other arm of the CD3 bispecific antibody binds can be any antigen expressed on or in the vicinity of a cell, tissue, organ, microorganism or virus, against which a targeted immune response is desired. In certain embodiments, the CD3-binding arm binds human CD3 and induces human T cell proliferation. Also included within the meaning of the term are antibodies which bind to different regions of the CD3 molecule, e.g., an arm that binds to a 17-19 kD ε-chain of CD3 within the CD3 antigen/T cell antigen receptor (TCR) complex (e.g., derived from HIT3a), and arm that binds to a 20 kDa subunit of the TCR complex within CD3e (e.g., derived from UCHT1). Preferably, the anti-CD3 antibody is OKT3 or a CD3-binding fragment thereof.

In one embodiment, the antibody molecule used in the scaffolds of the invention is a bispecific antibody. Bispecific antibodies may be employed in the context of the invention to bring a cell of interest, e.g., a cancer cell or a pathogen, in close proximity with the target effector cell of the invention, e.g., a cytotoxic T-cell, such that the effector function of the target effector cell is mediated specifically upon the cell of interest. Thus, in one embodiment, the invention provides scaffolds containing bispecific antibodies, wherein one arm of the antibody binds CD3 and the other arm binds a target antigen which is a tumor-associated antigen. Non-limiting examples of specific tumor-associated antigens include, e.g., AFP, ALK, BAGE proteins, β-catenin, brc-abl, BRCA1, BORIS, CA9, carbonic anhydrase IX, caspase-8, CCR5, CD19, CD20, CD30, CD40, CDK4, CEA, CTLA4, cyclin-B1, CYP1 B1, EGFR, EGFRv111, ErbB2/Her2, ErbB3, ErbB4, ETV6-AML, EpCAM, EphA2, Fra-1, FOLR1, GAGE proteins (e.g., GAGE-1, -2), GD2, GD3, GloboH, glypican-3, GM3, gp100, Her2, HLA/B-raf, HLA/k-ras, H LA/MAG E-A3, hTERT, LMP2, MAGE proteins (e.g., MAGE-1, -2, -3, -4, -6, and -12), MART-1, mesothelin, ML-IAP, Mud, Muc2, Muc3, Muc4, Muc5, Muc16 (CA-125), MUM1, NA17, NY-BR1, NY-BR62, NY-BR85, NY-ES01, OX40, p15, p53, PAP, PAX3, PAX5, PCTA-1, PLAC1, PRLR, PRAME, PSMA (FOLHI), RAGE proteins, Ras, RGS5, Rho, SART-1, SART-3, Steap-1, Steap-2, survivin, TAG-72, TGF-β, TMPRSS2, Tn, TRP-1, TRP-2, tyrosinase, and uroplakin-3.

In one specific embodiment, the cancer antigen is a member of the epidermal growth factor receptor (EGFR) family, e.g., a receptor selected from the group consisting of EGFR (ErbB-1), HER2/c-neu (ErbB-2), Her 3 (ErbB-3) and Her 4 (ErbB-4), or a mutant thereof.

In another embodiment, the invention relates to scaffolds containing a bispecific T-cell engager (BiTE) molecule. The BiTE molecule is specifically an antibody that recognizes at least one of the aforementioned tumor antigens and at least one T-cell cell surface molecule, e.g., CD3. Representative examples of such bispecific T-cell engager molecules include, but are not limited to, solitomab (CD3×EpCAM), blinatumomab (CD3×CD19), MAB MT-111 (CD3×CEA), and BAY-2010112 (CD3×PSMA).

Bispecific antibodies may also be used in the context of the invention to target effector cells such as T-cells or B-cells to mediate effect on pathogens, e.g., bacteria, viruses, fungus, protists, and other microbes, either directly or indirectly. In one embodiment, the pathogen is a virus. In another embodiment, the pathogen is a bacterium. Bispecific antibodies have been used to treat bacterial infections, e.g., drug resistant *Pseudomonas aeruginosa*. See, DiGiandomenico et al., *Sci Transl Med.*, 6(262), 2014; Kingwell et al., *Nat Rev Drug Discov.*, 14(1):15, 2015. Other bispecific have been developed to redirect cytotoxic T lymphocytes to kill HIV (Berg et al., *Proc Natl Acad Sci.*, 88(11):4723-7,1991), protect against HBV infection (Park et al., *Mol Immunol.*, 37(18):1123-30, 2000), and other prototypical pathogens (Taylor et al., *J Immunol.*, 159(8):4035-44, 1997).

Accordingly, in one embodiment, the invention provides scaffolds containing bispecific antibodies, wherein one arm of the antibody binds CD3 and the other arm binds a target antigen which is an infectious disease-associated antigen (e.g., a bacterial, protozoal, viral, or fungal antigen). Non-limiting examples of infectious disease-associated antigens include, e.g., an antigen that is expressed on the surface of a virus particle, or preferentially expressed on a cell that is infected with a virus, wherein the virus is selected from the group consisting of HIV, hepatitis (A, B or C), herpes virus (e.g., HSV-1, HSV-2, CMV, HAV-6, VZV, Epstein Barr virus), adenovirus, influenza virus, flavivirus, echovirus, rhinovirus, coxsackie virus, coronavirus, respiratory syncytial virus, mumps virus, rotavirus, measles virus, rubella virus, parvovirus, vaccinia virus, HTLV, dengue virus, pap- illomavirus, molluscum virus, poliovirus, rabies virus, JC virus, and arboviral encephalitis virus. Alternatively, the target antigen can be an antigen that is expressed on the surface of a bacterium, or preferentially expressed on a cell that is infected with a bacterium, wherein the bacterium is from a genus selected from the group consisting of *Chlamydia, Rickettsia, Mycobacteria, Staphylococci, Streptococci, Pneumonococci, Meningococci, Gonococci, Klebsiella, Proteus, Serratia, Pseudomonas, Legionella, Diphtheria, Salmonella, Bacilli, Clostridium*, and *Leptospira*. In some embodiments, the bacteria causes cholera, tetanus, botulism, anthrax, plague, or Lyme disease. In certain embodiments, the target antigen is an antigen that is expressed on the surface of a fungus, or preferentially expressed on a cell that is infected with a fungus, wherein the fungus is selected from the group consisting of *Candida* (e.g., *C. albicans, C. krusei, C. glabrata, C. tropicalis*, etc.), *Crytococcus neoformans, Aspergillus* (e.g., *A. fumigatus, A. niger*, etc.), *Mucorales* (e.g., *M. mucor, M. absidia, M. rhizopus*, etc.), *Sporothrix schenkii, Blastomyces dermatitidis, Paracoccidioides brasiliensis, Coccidioides immitis*, and *Histoplasma capsulatum*. In certain embodiments, the target antigen is an antigen that is expressed on the surface of a parasite, or preferentially expressed on a cell that is infected with a parasite, wherein the parasite is selected from the group consisting of *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondii, Nippostrongylus brasiliensis, Taenia crassiceps*, and *Brugia malayi*. Non-limiting examples of specific pathogen-associated antigens include, e.g., HIV gp120, HIV CD4, hepatitis B glycoprotein L, hepatitis B glycoprotein M, hepatitis B glycoprotein S, hepatitis C E1, hepatitis C E2, hepatocyte-specific protein, herpes simplex virus gB, cytomegalovirus gB, and HTLV envelope protein.

In some embodiments, the scaffold of the invention may be used for the treatment and/or prevention of an allergic reaction or allergic response. For example, in some embodiments the scaffold may be used to generate T-cells (e.g., Tregs) that suppress an allergic response or reaction. For example, in some embodiments, the scaffolds comprise an anti-CD3 antibody and TGF-β. in some embodiments, the scaffolds comprise an anti-CD3 antibody and IL-10. in some embodiments, the scaffolds comprise an anti-CD3 antibody and rapamycin. In some embodiments, the scaffolds comprise an anti-CD3 antibody, TGF-β, IL-10 and rapamycin. In some embodiments, the scaffolds comprise an anti-CD3 antibody TGF-β, and IL-10. In some embodiments, the scaffolds comprise an anti-CD3 antibody and TGF-β and rapamycin. In some embodiments, the scaffolds comprise an anti-CD3 antibody and IL-10 and rapamycin.

In some embodiments, the scaffold of the invention may be used to selectively expand allergen reactive T-cells (e.g., Tregs). In some embodiments the scaffold comprises a peptide derived from an allergen. In some embodiments, the peptide derived from an allergen is presented on (e.g., complexed with) an MHC molecule (e.g., an MHC class I or MHC class II molecule). In some embodiments, the MHC molecule is a monomer. In some embodiments the allergen is a food allergen (e.g., a banana, milk, legumes, shellfish, tree nut, stone fruit, egg, fish, soy, or wheat allergen). In one embodiment, the allergen is selected from the group consisting of a food allergen, a plant allergen, an insect allergen, an animal allergen, a fungal allergen, a viral allergen, a latex allergen, and a mold spore allergen. In one embodiment, the allergen polypeptide is an insect allergen. In one embodiment, the insect allergen is a dust mite allergen (e.g., an allergen from *Dermatophagoides farina* or *Dermatophagoides pteronyssinus*). In one embodiment, the allergen polypeptide is an ovalbumin polypeptide. In one embodiment, the allergen polypeptide is a food allergen polypeptide. In some embodiments, the scaffold comprises a peptide derived from an allergen and a Th1-skewing cytokine (e.g., IL-12 or IFNγ). In one embodiment, the allergen polypeptide is a food allergen polypeptide. In some embodiments, the scaffold comprises a peptide derived from an allergen presented on an MHC molecule and a Th1-skewing cytokine (e.g., IL-12 or IFNγ). According to certain exemplary embodiments, the present invention includes bispecific antigen-binding molecules that specifically bind CD3 and CD28. Such molecules may be referred to herein as, e.g., "anti-CD3/anti-CD28," or "anti-CD3×CD28" or "CD3×CD28" bispecific molecules, or other similar terminology.

The term "CD28," as used herein, refers to the human CD28 protein unless specified as being from a non-human species (e.g., "mouse CD28," "monkey CD28," etc.). The human CD28 protein has the amino acid sequence shown in GENBANK accession Nos. NP_001230006.1, NP_001230007.1, or NP_006130.1. The mouse CD28 protein has the amino acid sequence shown in GENBANK accession No. NP_031668.3. The various polypeptide sequences encompassed by the aforementioned accession numbers, include, the corresponding mRNA and gene sequences, are incorporated by reference herein in their entirety. As used herein, the expression "antigen-binding molecule" means a protein, polypeptide or molecular complex comprising or consisting of at least one complementarity determining region (CDR) that alone, or in combination with one or more additional CDRs and/or framework regions (FRs), specifically binds to a particular antigen. In certain embodiments, an antigen-binding molecule is an antibody or a fragment of an antibody, as those terms are defined elsewhere herein.

As used herein, the expression "bispecific antigen-binding molecule" means a protein, polypeptide or molecular complex comprising at least a first antigen-binding domain and a second antigen-binding domain. Each antigen-binding domain within the bispecific antigen-binding molecule comprises at least one CDR that alone, or in combination with one or more additional CDRs and/or FRs, specifically binds to a particular antigen. In the context of the present invention, the first antigen-binding domain specifically binds a first antigen (e.g., CD3), and the second antigen-binding domain specifically binds a second, distinct antigen (e.g., CD28).

The first antigen-binding domain and the second antigen-binding domain of the bispecific antibodies may be directly or indirectly connected to one another. Alternatively, the first antigen-binding domain and the second antigen-binding domain may each be connected to a separate multimerizing domain. The association of one multimerizing domain with another multimerizing domain facilitates the association between the two antigen-binding domains, thereby forming a bispecific antigen-binding molecule. As used herein, a "multimerizing domain" is any macromolecule, protein, polypeptide, peptide, or amino acid that has the ability to associate with a second multimerizing domain of the same or similar structure or constitution. For example, a multimerizing domain may be a polypeptide comprising an immunoglobulin CH3 domain. A non-limiting example of a multimerizing component is an Fc portion of an immunoglobulin (comprising a CH2-CH3 domain), e.g., an Fc domain of an IgG selected from the isotypes IgG1, IgG2, IgG3, and IgG4, as well as any allotype within each isotype group.

Bispecific antigen-binding molecules of the present invention will typically comprise two multimerizing domains, e.g., two Fc domains that are each individually part of a separate antibody heavy chain. The first and second multimerizing domains may be of the same IgG isotype such as, e.g., lgG1/lgG1, 1gG2/1gG2, 1gG4/1gG4. Alternatively, the first and second multimerizing domains may be of different IgG isotypes such as, e.g., 1gG1/1gG2, 1gG1/1gG4, 1gG2/1gG4, etc.

In certain embodiments, the multimerizing domain is an Fc fragment or an amino acid sequence of 1 to about 200 amino acids in length containing at least one cysteine residues. In other embodiments, the multimerizing domain is a cysteine residue, or a short cysteine-containing peptide. Other multimerizing domains include peptides or polypeptides comprising or consisting of a leucine zipper, a helix-loop motif, or a coiled-coil motif.

Any bispecific antibody format or technology may be used to make the bispecific antigen-binding molecules of the present invention. For example, an antibody or fragment thereof having a first antigen binding specificity can be functionally linked (e.g., by chemical coupling, genetic fusion, noncovalent association or otherwise) to one or more other molecular entities, such as another antibody or antibody fragment having a second antigen-binding specificity to produce a bispecific antigen-binding molecule. Specific exemplary bispecific formats that can be used in the context of the present invention include, without limitation, e.g., scFv-based or diabody bispecific formats, IgG-scFv fusions, dual variable domain (DVD)-1g, Quadroma, knobs-into-holes, common light chain (e.g., common light chain with knobs-into-holes, etc.), CrossMab, CrossFab, (SEED)body, leucine zipper, Duobody, 1gG1/1gG2, dual acting Fab (DAF)-1gG, and Mab2 bispecific formats (see, e.g., Klein et al., mAbs 4:6, 1-11, 2012 and references cited therein, for a review of the foregoing formats).

Multispecific antibodies may be specific for different epitopes of one target polypeptide or may contain antigen-binding domains specific for more than one target polypeptide. See, e.g., Tutt et al., 1991, *J. Immunol.* 147:60-69; Kufer et al., 2004, *Trends Biotechnol.* 22:238-244. The anti-CD3 antibodies of the present invention can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multispecific antibody with a second binding specificity. A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art. the multispecific antigen-binding molecules of the invention are derived from chimeric, humanized or fully human antibodies. Methods for making multispecic antibodies are well known in the art. For example, one or more of the heavy and/or light chains of the bispecific antigen-binding molecules of the present invention can be prepared using VELOCIMMUNE™ technology. Using VELOCIMMUNE™ technology (or any other human antibody generating technology), high affinity chimeric antibodies to a particular antigen (e.g., CD3 or CD28) are initially isolated having a human variable region and a mouse constant region. The antibodies are characterized and selected for desirable characteristics, including affinity, selectivity, epitope, etc. The mouse constant regions are replaced with a desired human constant region to generate fully human heavy and/or light chains that can be incorporated into the bispecific antigen-binding molecules of the present invention.

In the context of bispecific antigen-binding molecules of the present invention, the multimerizing domains, e.g., Fc domains, may comprise one or more amino acid changes (e.g., insertions, deletions or substitutions) as compared to the wild-type, naturally occurring version of the Fc domain. For example, the invention includes bispecific antigen-binding molecules comprising one or more modifications in the Fc domain that results in a modified Fc domain having a modified binding interaction (e.g., enhanced or diminished) between Fc and FcRn. In one embodiment, the bispecific antigen-binding molecule comprises a modification in a CH2 or a CH3 region, wherein the modification increases the affinity of the Fc domain to FcRn in an acidic environment (e.g., in an endosome where pH ranges from about 5.5 to about 6.0). Non-limiting examples are provided in, for example, US Publication No. 2014-0088295. The present invention also includes bispecific antigen-binding molecules comprising a first CH3 domain and a second Ig CH3 domain, wherein the first and second Ig CH3 domains differ from one another by at least one amino acid, and wherein at least one amino acid difference reduces binding of the bispecific antibody to Protein A as compared to a bi-specific antibody lacking the amino acid difference. In certain embodiments, the Fc domain may be chimeric, combining Fc sequences derived from more than one immunoglobulin isotype.

In another embodiment, the T-cell activating molecule is a major histocompatibility complex (MHC) molecule which binds to CD3. Representative examples include, but are not limited to, MHC type I which binds to TCR and CD8 or MHC type II which binds to TCR and CD4. The MHC molecules may be optionally loaded with antigens, e.g., biotinylated peptides. In other embodiments, the MHC molecules may be conjugated to immunoglobulins, e.g., Fc portion of an immunoglobulin G (IgG) chain. In another embodiment, a plurality of MHC-peptide complexes may be employed. In the latter case, multiple copies of MHC-peptide complexes may be attached, covalently or non-covalently, to multimerization domains. Known examples of such MHC multimers include, but are not limited to, MHC-dimers (contains two copies of MHC-peptide; IgG is used as multimerization domain, and one of the domains of the MHC protein is covalently linked to IgG); MHC-tetramers (contains four copies of MHC-peptide, each of which is biotinylated and the MHC complexes are held together in a complex by the streptavidin tetramer protein, providing a non-covalent linkage between a streptavidin monomer and the MHC protein); MHC pentamers (contains five copies of MHC-peptide complexes are multimerised by a self-assembling coiled-coil domain), MHC dextramers (typically contains more than ten MHC complexes which are attached to a dextran polymer) and MHC streptamers (contains 8-12 MHC-peptide complexes attached to streptactin). MHC tetramers are described in U.S. Pat. No. 5,635,363; MHC pentamers are described in the US patent 2004209295; MHC-dextramers are described in the patent application WO 02/072631. MHC streptamers are described in Knabel M et al., *Nature Medicine* 6. 631-637, 2002).

The target T-cells may also be activated in a CD3-independent manner, for example, via binding and/or ligation of one or more cell-surface receptors other than CD3. Representative examples of such cell-surface molecules include, e.g., CD2, CD47, CD81, MSR1, etc.

In this context, CD2 is found on virtually all T cells (and also natural killer (NK) cells) and is important in T-lymphocyte function. CD2 is associated with several proteins including CD3, CD5 and CD45. CD2-CD58 interaction facilitates cell-cell contact between T cells and APC, thereby enhancing antigen recognition through the TCR/CD3 complex. CD2 also serves a signal transduction role. Co-stimulation blockade using antibodies directed against CD2 may be a potent immunosuppressive strategy in organ transplantation. Thus, in one embodiment, the T-cells are activated via the use of an antibody or an antigen binding fragment thereof that specifically binds to CD2. Representative examples of anti-CD2 antibodies include, for example, siplizumab (MEDI-507) and LO-CD2b (ATCC accession No. PTA-802; deposited Jun. 22, 1999).

CD47 (IAP) belongs to the immunoglobulin superfamily and partners with membrane integrins and also binds the ligands thrombospondin-1 (TSP-1) and signal-regulatory protein alpha (SIRPα). See Barclay et al., *Curr. Opin. Immunol.* 21 (1): 47-52, 2009; *Br. J. Pharmacol.*, 167 (7): 1415-30, 2012. CD47 interacts with signal-regulatory protein alpha (SIRPα), an inhibitory transmembrane receptor present on myeloid cells. The CD47/SIRPα interaction leads to bidirectional signaling, resulting in different cell-to-cell responses including inhibition of phagocytosis, stimulation of cell-cell fusion, and T-cell activation. See, Reinhold et al., *J Exp Med.*, 185(1): 1-12, 1997. In accordance with the present invention, in one embodiment, the T-cells are activated via the use of an antibody or an antigen binding fragment thereof that specifically binds to CD47. Representative examples of anti-CD47 antibodies include, for example, monoclonal antibody Hu5F9-G4, which is being investigated in various clinical trials against myeloid leukemia and monoclonal antibodies MABL-1 and MABL-2 (FERM Deposit Nos. BP-6100 and BP-6101). See, e.g., WO1999/12973, the disclosure in which is incorporated by reference herein.

CD81 is a member of the tetraspanin superfamily of proteins. It is expressed on a broad array of tissues, including T cells and hematopoietic cells. CD81 is known to play an immunomodulatory role. In particular, cross-linking of CD81 enhances CD3 mediated activation of αβ and γδ T-lymphocytes and induces TCR-independent production of cytokines by γδ T cells in vitro. In accordance with the present invention, in one embodiment, the T-cells are activated via the use of an antibody or an antigen binding fragment thereof that specifically binds to CD81. See, Menno et al., *J. Clin. Invest.*, 4:1265, 2010. Representative examples of anti-CD81 antibodies include, for example, monoclonal antibody 5A6. See, e.g., Maecker et al., *BMC Immunol.*, 4:1, 2003., the disclosure in which is incorporated by reference herein.

MSR1 (CD204) belongs to the family of class A macrophage scavenger receptors, which include three different types (1, 2, 3) generated by alternative splicing of the MSR1 gene. These receptors or isoforms are trimeric integral membrane glycoproteins and have been implicated in many macrophage-associated physiological and pathological processes including atherosclerosis, Alzheimer's disease, and host defense. See, Matsumoto et al., *Proc. Natl. Acad. Sci. U.S.A.* 87 (23): 9133-7, 1990. Recent studies demonstrate that dendritic (DC) MSR1 impacts the activation and proliferation of CD8 T cells and antibody-mediated blocking of MSR1 increased proliferation and expansion of T-cells in vitro. Lerret et al., *PLoS One.*, 7(7):e41240, 2012. In accordance with the present invention, in one embodiment, the T-cells are activated via the use of an antibody or an antigen binding fragment thereof that specifically binds to MSR1. Representative examples of anti-MSR1 antibodies include, for example, rat anti-human CD204 antibody (Thermo Catalog No. MA5-16494) and goat anti-human CD204/MSR1 antibody (Biorad Catalog No. AHP563).

In another embodiment, the T-cells are activated by ligating/binding to a T-cell receptor (TCR) molecule, which is expressed ubiquitously in T-cells. The TCR is a heterodimer composed of two different protein chains. In humans, in 95% of T cells the TCR consists of an alpha ($\alpha$) and beta ($\beta$) chain, whereas in 5% of T cells the TCR consists of gamma and delta ($\gamma/\delta$) chains. When the TCR engages with antigenic peptide and MHC (peptide/MHC), the T lymphocyte is activated through signal transduction. In accordance with the present invention, in one embodiment, the T-cells are activated via the use of an antibody or an antigen binding fragment thereof that specifically binds to TCR. Representative examples of anti-TCR antibodies include, for example, mouse anti-human TCR monoclonal antibody IMMU510 (Immunotech, Beckman Coulter, Fullerton, Calif.) (described in Zhou et al., *Cell Mol Immunol.*, 9(1): 34-44, 2012) and monoclonal antibody defining alpha/beta TCR WT31 (described in Gupta et al., *Cell Immunol.*, 132(1):26-44, 1991).

In another embodiment, the T-cell activating molecule is a major histocompatibility complex (MHC) molecule that is optionally loaded with an MHC peptide. There are two general classes of MHC molecules. Class I MHC (pMHC) molecules are found on almost all cells and present peptides to cytotoxic T lymphocytes (CTL). Class II MHC molecules are found mainly on antigen-presenting immune cells (APCs), which ingest polypeptide antigens (in, for example, microbes) and digest them into peptide fragments. The MHC-II molecules then present the peptide fragments to helper T cells, which, after activation, provide generally required helper activity for responses of other cells of the immune system (e.g., CTL or antibody-producing B cells). The interaction between the peptide bound in the binding cleft of the heavy chain of MHC class I (pMHC) and the complementary determining regions (CDR) of the T cell receptor (TCR) determines the potential for T cell activation during the afferent and efferent stages of cellular immunity. The affinity that exists between TCR and MHC-peptide complex regulates T cell fate during development, initial activation, and during execution of effector functions.

Accordingly, in one embodiment, the instant invention relates to MSR-SLB scaffolds containing a human MHC molecule optionally loaded with a peptide. Representative examples of such MHC molecules include HLA-A, HLA-B, HLA-C, DP, DQ and DR, or a combination thereof. The MHC molecules may be monovalent or bivalent. In some embodiments, bivalency or multivalency of the MHC molecules is desirable for signal delivery (either activation or inhibition signals) to the T cell. Therefore, in some embodiments, the MSR-SLB scaffolds of the present invention include at least two identical MHC molecules attached to a linker.

The linker of the bivalent MHC molecule serves three functions. First, the linker contributes the required bivalency or multivalency. Second, the linker increases the half-life of the entire fusion protein in vivo. Third, the linker determines whether the fusion protein will activate or suppress T cells. T cell priming requires stimulation via the TCR and an additional second signal generally delivered by the APC. In the absence of a second signal, T cell hyporesponsiveness may result. By constructing a fusion protein in which the linker allows delivery of a second signal, T cell stimulation results in enhanced T cell immunity. By constructing a fusion protein in which the linker does not provide for delivery of a second signal, T cell suppression results in immunosuppression. A fusion protein with T cell stimulatory properties can be constructed by using a linker which allows for delivery of a second signal to the T cell in addition to the signal delivered via the TCR. This can be accomplished by using a linker that has binding affinity for a cell surface structure on another cell, that cell being capable of delivering a second signal to the T cell. Thus, the linker serves to bridge the T cell and the other cell. By bringing the other cell into close proximity to the T cell, the other cell can deliver a second signal to the T cell.

Examples include linkers that can bind to Fc receptors on other cells such as certain immunoglobulin chains or portions of immunoglobulin chains. Specific examples include IgG, IgA, IgD, IgE, and IgM. When an immunoglobulin is used, the entire protein is not required. For example, the immunoglobulin gene can be cleaved at the hinge region and only the gene encoding the hinge, CH2, and CH3 domains of the heavy chain is used to form the fusion protein. The linker may bind other cell surface structures. For example, the linker can include a cognate moiety for many cell surface antigens which can serve as a bridge to bring the second cell into close proximity with the T cell. The linker might also deliver a second signal independently. For example, a linker with binding affinity for the T cell antigen CD28 can deliver a second signal. In addition, the linker can increase the half-life of the entire fusion protein in vivo. A fusion protein with T cell inhibitory properties can be constructed by using a linker that does not result in delivery of a second signal. Examples include Ig chains that do not bind Fc receptor, Ig F(ab')2 fragments, a zinc finger motif, a leucine zipper, and non-biological materials. Examples of non-biological materials include plastic microbeads, or even a larger plastic member such as a plastic rod or tube, as well as other physiologically acceptable carriers which are implantable in vivo.

In some embodiments, the MHC molecules are not attached to a linker. Without wishing to be bound by any particular theory, it is believed that the fluid nature of the lipid bilayer allows T cells to reorganize the membrane and form multivalent clusters. These clusters can subsequently be disassembled, which would not be possible if the signaling molecules were attached together with a linker. Inability to un-form these multivalent clusters can potentially lead to overstimulation and T cell exhaustion or anergy (see, e.g., Lee K-H et al. *Science* 302(5648): 1218-22 (2003)).

In some embodiments, the lipid bilayer of the APC-MS comprises a lipid composition that favor the spontaneous partitioning of lipid species into liquid-ordered domains (see, e.g., Wang T-Y et al. *Biochemistry* 40(43):13031-40 (2001)).

Optionally, the MHC molecules may be loaded with a specific peptide (e.g., a peptide derived from a viral antigen, a bacterial antigen, or an allergen). The specific peptide of the fusion protein can be loaded into the MHC molecules after the fusion protein has been made. The peptide may also be subsequently covalently attached to the MHC, for example by UV cross-linking. Alternatively, a peptide sequence can be incorporated into the DNA sequence encoding the fusion protein such that the peptide is loaded into the MHC molecules during generation of the fusion protein. In the latter case, the peptide can be attached with a tether, such as polylysine, which allows it to complex with the MHC portion of the fusion protein. The specific peptides to be loaded into the MHC molecules are virtually limitless and are determined based on the desired application. For example, to enhance T cell immunity, peptides from various sources, e.g., viral, fungal and bacterial infections, or to tumors, can be used. To suppress T cell immunity in autoimmunity, autoreactive peptides can be used. To suppress T cell immunity to transplanted tissues, self-peptides which are presented by alloantigens can be used.

Toxins, such as ricin and diphtheria toxin, and radioisotopes, may be complexed to the fusion protein (for example, using 5-methyl-2-iminothiolane) to kill the specific T cell clones. These toxins can be chemically coupled to the linker or to the MHC portion of the fusion protein, or they can be incorporated into the DNA sequence encoding the fusion protein such that the toxin is complexed to the fusion protein during generation of the fusion protein.

The MHC-peptide/immunoglobulin fusion protein can be prepared by constructing a gene which encodes for the production of the fusion protein. Alternatively, the components of the fusion protein can be assembled using chemical methods of conjugation. Sources of the genes encoding the MHC molecules and the linkers can be obtained from various databases. In the case of MHC class I fusion proteins, the MHC fragment can be attached to the linker and β2 microglobulin can be allowed to self-associate. Alternatively, the fusion protein gene can be constructed such that β2 microglobulin is attached to the MHC fragment by a tether. In the case of MHC class II fusion protein, either the alpha or the beta chain can be attached to the linker and the other chain can be allowed to self-associate. Alternatively, the fusion protein gene can be constructed such that the alpha and beta chains are connected by a tether. Peptides can be prepared by encoding them into the fusion protein gene construct or, alternatively, with peptide synthesizers using standard methodologies available to one of ordinary skill in the art. The resultant complete fusion proteins can be administered using routine techniques.

T-Cell Co-Stimulatory Molecules

In one embodiment, the instant invention provides MSR-SLB scaffolds containing a plurality of T-cell co-stimulatory molecules. These co-stimulatory molecules may mediate direct, indirect, or semi-direct stimulation of a target population of T-cells. Preferably, the co-stimulatory molecules mediate activation of T-cells in the presence of one or more T-cell activating molecules.

The term "co-stimulatory molecule" is used herein in accordance with its art recognized meaning in immune T cell activation. Specifically, a "co-stimulatory molecule" refers to a group of immune cell surface receptor/ligands which engage between T cells and antigen presenting cells and generate a stimulatory signal in T cells which combines with the stimulatory signal (i.e., "co-stimulation") in T cells that results from T cell receptor ("TCR") recognition of antigen on antigen presenting cells. As used herein, a soluble form of a co-stimulatory molecule "derived from an APC" refers to a co-stimulatory molecule normally expressed by B cells, macrophages, monocytes, dendritic cells and other APCs. See, Huppa et al., *Nature Reviews Immunology.* 3, 973-983 (2003). A "co-stimulator of T cells activation" refers to the ability of a co-stimulatory ligand to bind and to activate T cells which have been activated via any of the aforementioned mechanisms or pathways, e.g., via CD3-dependent or CD3-independent T-cell activation. Co-stimulatory activation can be measured for T cells by the production of cytokines as is well known and by proliferation assays that are well known (e.g., CFSE staining) and/or as described in the examples below.

In one embodiment, the instant invention provides for MSR-SLB scaffolds containing molecules that specifically bind to a co-stimulatory antigen. Particularly, the MSR-SLB scaffolds contain a plurality of T-cell costimulatory molecules which specifically bind to CD28, 4.1BB (CD137), OX40 (CD134), CD27 (TNFRSF7), GITR (CD357), CD30 (TNFRSF8), HVEM (CD270), LTβR (TNFRSF3), DR3 (TNFRSF25), ICOS (CD278), CD226 (DNAM1), CRTAM (CD355),TIM1 (HAVCR1, KIM1), CD2 (LFA2, OX34), SLAM (CD150, SLAMF1), 2B4 (CD244, SLAMF4), Ly108 (NTBA, CD352, SLAMF6), CD84 (SLAMFS), Ly9 (CD229, SLAMF3), CD279 (PD-1) and/or CRACC (CD319, BLAME).

In one embodiment, the co-stimulatory molecule is an antibody or an antigen binding fragment thereof which binds specifically to one or more of the aforementioned co-stimulatory antigens. In this context, CD28 is the prototypic T cell co-stimulatory antigen and binds to molecules of the B7 family expressed on APCs such as dendritic cells and activated B cells. Human CD28 is found on all CD4+ T cells and on about half of CD8+ T cells. T cell activities attributed to CD28 include prevention of energy, induction of cytokine gene transcription, stabilization of cytokine mRNA and activation of CD8+ cytotoxic T lymphocytes. The ligands for CD28 identified as CD80(B7-1) and CD86(B7-2) are immunoglobulin superfamily monomeric transmembrane glycoproteins of 60 kDa and 80 kDa respectively.

In one embodiment, the instant invention relates to MSR-SLB scaffolds containing an antibody or an antigen-binding fragment thereof which binds specifically to CD28. Representative examples of anti-CD28 antibodies include, for example, lulizumab pegol and TGN1412. See also U.S. Pat. No. 8,785,604.

In another embodiment, the instant invention relates to MSR-SLB scaffolds containing an antibody or an antigen-binding fragment thereof which binds specifically to ICOS (CD278). ICOS is a CD28-superfamily costimulatory molecule that is expressed on activated T cells. It is thought to be important for Th2 cells in particular. Representative examples of anti-ICOS antibodies include, for example, monoclonal antibody 2C7, which recognizes the ICOS molecule expressed on activated T cells and induces the activation as well as proliferation of T cells prestimulated by anti-human CD3 monoclonal antibodies. See Deng et al., *Hybrid Hybridomics.,* 23(3):176-82, 2004.

In another embodiment, the instant invention provides for MSR-SLB scaffolds containing an antibody or an antigen-binding fragment thereof which binds specifically to CD152 (CTLA4). The antibody is preferably a neutralizing antibody or a blocking antibody. CD152 is expressed on activated CD4+ and CD8+ T cells, and on regulatory T-cells (Tregs). Its functions in T-cell biology, during immune responses to infection, and as a target for cancer immunotherapy have been well described (Egen et al., *Nat. Immunol.,* 3(7):611-618, 2002). CTLA-4 is a homologous counterpart to CD28, both of which bind to CD80 and CD86 on APCs. The importance of CTLA-4 for immune tolerance is clear (Waterhouse et al., *Science,* 270(5238):985-988, 1995). These include out-competing lower affinity CD28 molecules for ligand binding to minimize T-cell co-stimulation, recruitment of inhibitory phosphatases to the TCR complex to disrupt positive signaling cascades, and removing CD80 and CD86 from the surface of APC by trans-endocytosis, thereby diminishing the ability of APC to properly activate otherwise responsive T-cells. Accordingly, exploitation of the CTLA-4 receptor/pathway is an attractive strategy to modulate T-cell immunity. Indeed, anti-CTLA-4 was the first monoclonal antibody (ipilimumab) to be FDA-approved for checkpoint blockade treatment in cancer patients. Other examples of CTLA-4 antibodies that may be employed in accordance with the instant invention include tremelimumab and antigen-binding fragments thereof.

In another embodiment, the instant invention provides for MSR-SLB scaffolds containing an antibody or an antigen-binding fragment thereof which binds specifically to programmed death-1 (PD-1; CD279). PD1 is a member of the same family of receptors as CD28 and CTLA-4, and is broadly expressed on lymphoid and myeloid cells. PD-1 binds uniquely to the B7 ligands PD-L1 and PD-L2 on APC and other surrounding tissues, greatly influencing the fate of responding CD8+ T cells in settings of chronic infections. On T-cells, PD-1 is expressed after antigen encounter, but acts almost immediately to impede T-cell activation by recruiting the phosphatases SHP-1 and SHP-2 through signaling motifs in the PD-1 cytoplasmic tail, which reduces Akt phosphorylation, and diminishes T-cell metabolism, proliferation and survival. Accordingly, the antibody is preferably a neutralizing antibody or a blocking antibody. Representative examples of such anti-PD-1 antibodies include, for example, nivolumab, lambrolizumab (MK-3475), pidilizumab (CT-011) and AMP-224.

In another embodiment, the instant invention relates to MSR-SLB scaffolds containing an antibody or an antigen-binding fragment thereof which binds specifically to CD81. Engagement of CD81 lowers the signaling threshold required to trigger T-Cell/CD3 mediated proviral DNA in CD4+ T cells (Tardif et al., *J. Virol.* 79 (7): 4316-28, 2005). Representative examples of anti-CD81 antibodies include, for example, monoclonal antibody 5A6. See, e.g., Maecker et al., *BMC Immunol.*, 4:1, 2003, the disclosure in which is incorporated by reference herein.

In another embodiment, the instant invention relates to MSR-SLB scaffolds containing an antibody or an antigen-binding fragment thereof which binds specifically to CD137. Crosslinking of CD137 enhances T cell proliferation, IL-2 secretion, survival and cytolytic activity. Further, it can enhance immune activity to eliminate tumors in vivo. Accordingly, the antibodies that bind to CD137 are preferably agonistic antibodies. Representative examples of anti-CD137 antibodies include, for example, monoclonal antibody utomilumab, which is a human IgG that is currently being investigated in clinical trials. See National Clinical Trials ID: NCT01307267.

In another embodiment, the instant invention relates to MSR-SLB scaffolds containing an antibody or an antigen-binding fragment thereof which binds specifically to OX40 (CD134). OX4OL binds to OX40 receptors on T-cells, preventing them from dying and subsequently increasing cytokine production. OX40 has a critical role in the maintenance of an immune response beyond the first few days and onwards to a memory response due to its ability to enhance survival. OX40 also plays a crucial role in both Th1 and Th2 mediated reactions in vivo. Accordingly, the antibodies that bind to OX40 are preferably agonistic antibodies. Representative examples of anti-OX40 antibodies include, for example, anti-OX40 monoclonal antibody utomilumab, which is being investigated in various clinical trials (see National Clinical Trials ID: NCT01644968, NCT01303705 and NCT01862900).

In another embodiment, the instant invention relates to MSR-SLB scaffolds containing an antibody or an antigen-binding fragment thereof which binds specifically to CD27 (TNFRSF7). CD27 a member of the TNF-receptor superfamily and is required for generation and long-term maintenance of T cell immunity. It binds to ligand CD70, and plays a key role in regulating immunoglobulin synthesis. CD27 supports antigen-specific expansion (but not effector cell maturation) of naïve T cells, independent of the cell cycle-promoting activities of CD28 and IL2 (Hendriks et al., *Nature Immunology* 1, 433-440, 2000)). As such, the MSR-SLB scaffolds of the invention preferably include agonistic antibodies that bind to CD27. Representative examples of anti-CD27 antibodies include, for example, the monoclonal antibody varlilumab. See Ramakrishna et al., *Journal for ImmunoTherapy of Cancer,* 3:37, 2015.

In another embodiment, the instant invention relates to MSR-SLB scaffolds containing an antibody or an antigen-binding fragment thereof which binds specifically to glucocorticoid-induced TNF receptor family-regulated gene (GITR or CD357). GITR is a 25 kD TNF receptor superfamily member which is expressed on activated lymphocytes. GITR is upregulated by T cell receptor engagement. The cytoplasmic domain of GITR is homologous to CD40, 4-1BB and CD27. GITR signaling has been shown to regulate T cell proliferation and TCR-mediated apoptosis, and to break immunological self-tolerance. GITR further binds GITRL and is involved in the development of regulatory T cells and to regulate the activity of Th1 subsets. Modulation of GITR with agonistic antibodies has been shown to amplify the antitumor immune responses in animal models via multiple mechanisms. Anti-GITR antibodies are designed to activate the GITR receptor thereby increasing the proliferation and function of effector T cells. At the same time, ligation of GITR on surface of Tregs could abrogate suppressive function of these cells on tumor specific effector T-cells thus further augmenting T-cell immune response. Representative examples of anti-GITR antibodies include, for example, humanized, Fc disabled anti-human GITR monoclonal antibody TRX518, which induces both the activation of tumor-antigen-specific T effector cells, as well as abrogating the suppression induced by inappropriately activated T regulatory cells. TRX518 is being investigated in various clinical trials (see National Clinical Trials ID: NCT01239134).

In another embodiment, the instant invention relates to MSR-SLB scaffolds containing an antibody or an antigen-binding fragment thereof which binds specifically to CD30 (TNFRSF8). CD30 antigen is a trans-membrane glycoprotein belonging to the tumor necrosis factor receptor superfamily, which, when stimulated, exerts pleiotropic effects on cell growth and survival. In normal or inflamed tissues, CD30 expression is restricted to medium/large activated B and/or T-lymphocytes. It is expressed by activated, but not by resting, T and B cells (Guo et al., *Infect. Immun.*, 81 (10), 3923-3934, 2013). Stimulation of CD3OL/CD30 signaling by in vivo administration of agonistic anti-CD30 monoclonal antibody (MAb) restored IL-17A production by Vγ1-Vγ4-γδ T cells in CD30L knockout mice. Representative examples of anti-CD30 antibodies include, for example, brentuximab vedotin (Adcetris).

In another embodiment, the instant invention relates to MSR-SLB scaffolds containing an antibody or an antigen-binding fragment thereof which binds specifically to HVEM (CD270). CD270 is a member of the TNF-receptor superfamily. This receptor was identified as a cellular mediator of herpes simplex virus (HSV) entry. Mutations in this gene have been recurrently been associated to cases of diffuse large B-cell lymphoma. Representative examples of anti-CD270 antibodies include, for example, the monoclonal antibody HVEM-122. See, Cheung et al., *J. Immunol.*, 185:1949, 2010; Hobo et al., *J Immunol.*, 189:39, 2012.

In another embodiment, the instant invention relates to MSR-SLB scaffolds containing an antibody or an antigen-binding fragment thereof which binds specifically to lymphotoxin beta receptor (LTβR; TNFRSF3). LTβR is involved in CD4+ T-cell priming (Summers deLuca et al., *J Exp Med.*, 204(5):1071-81, 2007). Representative examples of anti-LTβR antibodies include, for example, the monoclonal antibody BBF6 antibody. See also WO2010/078526, which is incorporated by reference.

In another embodiment, the instant invention relates to MSR-SLB scaffolds containing an antibody or an antigen-binding fragment thereof which binds specifically to DR3 (TNFRSF25). DR3 is thought to be involved in controlling lymphocyte proliferation induced by T-cell activation. Specifically, activation of DR3 is dependent upon previous engagement of the T cell receptor. Following binding to TL1A, DR3 signaling increases the sensitivity of T cells to endogenous IL-2 via the IL-2 receptor and enhances T cell proliferation. Because the activation of the receptor is T cell receptor dependent, the activity of DR3 in vivo is specific to those T cells that are encountering cognate antigen. At rest, and for individuals without underlying autoimmunity, the majority of T cells that regularly encounter cognate antigen are FoxP3+ regulatory T cells. Stimulation of TNFRSF25, in the absence of any other exogenous signals, stimulates profound and highly specific proliferation of FoxP3+ regulatory T cells from their 8-10% of all CD4+ T cells to 35-40% of all CD4+ T cells within 5 days. Representative examples of DR3 agonists include, for example, antibodies binding specifically to DR3 (Reddy et al., *J. Virol.*, 86 (19) 10606-10620, 2012) and the agonist 4C12 (Wolf et al., *Transplantation*, 27; 94(6):569-74, 2012).

In another embodiment, the instant invention relates to MSR-SLB scaffolds containing an antibody or an antigen-binding fragment thereof which binds specifically to CD226 (DNAM1). CD226 is a ~65 kDa glycoprotein expressed on the surface of natural killer cells, platelets, monocytes and a subset of T cells. It is a member of the immunoglobulin superfamily and mediates cellular adhesion to other cells bearing its ligands, CD112 and CD155. Cross-linking CD226 with antibodies causes cellular activation and ligation of CD226 and LFA-1 with their respective ligands cooperates in triggering cytotoxicity and cytokine secretion by T and NK cells (Tahara et al., *Int. Immunol.* 16 (4): 533-8, 2004).

In another embodiment, the instant invention relates to MSR-SLB scaffolds containing an antibody or an antigen-binding fragment thereof which binds specifically to CRTAM (CD355). CTRAM is an MHC-class-I-restricted T-cell-associated molecule, which regulates late phase of cell polarity in some CD4+ T cells. CTRAM also regulates interferon-γ (IFNγ) and interleukin-22 (IL-22) production. In one embodiment, the MSR-SLB scaffolds comprise a monoclonal anti-CTRAM antibody. Representative examples of CTRAM antibodies include, for example, the mouse anti human CTRAM antibody 21A9 (GENTEX Inc. USA, Irvine, Calif.).

In another embodiment, the instant invention relates to MSR-SLB scaffolds containing an antibody or an antigen-binding fragment thereof which binds specifically to TIM1 (HAVCR1, KIM1). TIM genes belong to type I cell-surface glycoproteins, which include an N-terminal immunoglobulin (Ig)-like domain, a mucin domain with distinct length, a single transmembrane domain, and a C-terminal short cytoplasmic tail. The localization and functions of TIM genes are divergent between each member. TIM-1 is preferentially expressed on Th2 cells and has been identified as a stimulatory molecule for T-cell activation (Umetsu et al., *Nat. Immunol.* 6 (5): 447-54, 2005). In one embodiment, the MSR-SLB scaffolds comprise a monoclonal anti-TIM1 antibody. Representative examples of TIM1 antibodies include, for example, the rabbit anti human TIM1 antibody ab47635 (ABCAM, Cambridge, Mass.).

In another embodiment, the instant invention relates to MSR-SLB scaffolds containing an antibody or an antigen-binding fragment thereof which binds specifically to SLAM (CD150, SLAMF1). SLAM (CD150) is a self-ligand and cell surface receptor that functions as a costimulatory molecule and also a microbial sensor that controlled the killing of Gram-negative bacteria by macrophages. In particular, SLAM regulated activity of the NADPH oxidase NOX2 complex and phagolysosomal maturation after entering the phagosome, following interaction with the bacterial outer membrane proteins (Berger et al., *Nature Immunology* 11, 920-927, 2010). Slamf1 is expressed on the surface of activated and memory T cells as well as on activated B cells, dendritic cells, macrophages and platelets (Calpe et al., *Adv. Immunol.* 2008; 97:177). In one embodiment, the MSR-SLB scaffolds comprise a monoclonal anti-SLAM1 antibody or an antigen-binding fragment thereof.

Representative examples of SLAM1 antibodies include, e.g., the rabbit anti human SLAM1 antibody 600-401-EN3 (Rockland Antibodies, Limerick, Pa.).

In another embodiment, the instant invention relates to MSR-SLB scaffolds containing an antibody or an antigen-binding fragment thereof which binds specifically to 2B4 (CD244, SLAMF4). CD244 is a cell surface receptor expressed on natural killer cells (NK cells) (and some T cells) mediating non-major histocompatibility complex (MHC) restricted killing. The interaction between NK-cell and target cells via this receptor is thought to modulate NK-cell cytolytic activity. CD244 is a co-inhibitory SLAM family member which attenuates primary antigen-specific CD8(+) T cell responses in the presence of immune modulation with selective CD28 blockade. Recent studies reveal a specific up-regulation of 2B4 on antigen-specific CD8(+) T cells in animals in which CD28 signaling was blocked (Liu et al., *J Exp Med.* 2014 Feb. 10; 211(2):297-311). In one embodiment, the MSR-SLB scaffolds comprise a monoclonal anti-CD244 antibody or an antigen-binding fragment thereof. Representative examples of CD244 antibodies include, e.g., anti-2B4 antibody C1.7 or PE-conjugated anti-2B4 (C1.7), which have been characterized in Sandusky et al. (*Eur J Immunol.* 2006 December; 36(12):3268-76).

In another embodiment, the instant invention relates to MSR-SLB scaffolds containing an antibody or an antigen-binding fragment thereof which binds specifically to Ly108 (NTBA, CD352, SLAMF6). SLAMF6 is a type I transmembrane protein, belonging to the CD2 subfamily of the immunoglobulin superfamily, which is expressed on natural killer (NK), T, and B lymphocytes. Co-stimulation of T lymphocytes through the SLAMF3/SLAMF6 pathways mediates more potent effects on IL-17A expression when compared with the canonical CD28 pathway. SLAMF3/SLAMF6 signaling mediates increased nuclear abundance and recruitment of RORγt to the proximal IL17A promoter, resulting in increased trans-activation and gene expression (Chatterjee et al., *J Biol Chem.*, 287(45): 38168-38177, 2012). In one embodiment, the MSR-SLB scaffolds comprise a monoclonal anti-CD244 antibody or an antigen-binding fragment thereof. Representative examples of CD244 antibodies include, e.g., anti NTB-A antibodies characterized in Flaig et al. (*J. Immunol.* 2004. 172: 6524-6527) and Stark et al. (*J. Immunol. Methods* 2005. 296: 149-158).

In another embodiment, the instant invention relates to MSR-SLB scaffolds containing an antibody or an antigen-binding fragment thereof which binds specifically to CD84 (SLAMF5). CD84 is a member of the CD2 subgroup of the immunoglobulin receptor superfamily Members of this family have been implicated in the activation of T cells and NK cells. CD84 increases proliferative responses of activated T-cells and homophilic interactions enhance interferon gamma secretion in lymphocytes. CD84 may also serve as a marker for hematopoietic progenitor cells. See the disclosure in the references with the PUBMED ID Nos. 11564780, 12115647, 12928397, 12962726, 16037392, which indicate that it is required for a prolonged T-cell: B-cell contact, optimal Th function, and germinal center formation. In one embodiment, the MSR-SLB scaffolds comprise a monoclonal anti-CD84 antibody or an antigen-binding fragment thereof. Representative examples of CD84 antibodies include, e.g., PE anti-human CD84 antibody CD84.1.21, which is able to enhance CD3 induced IFN-γ production and partially block CD84-Ig binding to lymphocytes (BioLegend, San Diego, Calif.; Catalog No. 326008).

In another embodiment, the instant invention relates to MSR-SLB scaffolds containing an antibody or an antigen-binding fragment thereof which binds specifically to Ly9 (CD229, SLAMF3). CD229 participates in adhesion reactions between T lymphocytes and accessory cells by homophilic interaction. It also promotes T-cell differentiation into a helper T-cell Th17 phenotype leading to increased IL-17 secretion; the costimulatory activity requires SH2D1A (Chatterjee et al., *J Biol Chem.*, 287(45): 38168-38177, 2012). In particular, concurrent ligation of CD229 and TCR with immobilized CD229-His protein and anti-CD3 antibody significantly enhanced cell proliferation and IFN-γ secretion in murine CD3+ splenocytes in a dose-dependent manner (Wang et al., *The Journal of Immunology*, 188 (sup. 1) 176.7, May 2012). Accordingly, in one embodiment, the MSR-SLB scaffolds comprise a monoclonal anti-CD229 antibody or an antigen-binding fragment thereof. Representative examples of CD229 antibodies include, e.g., PE anti-human CD229 antibody HLy-9.1.25 (BIOLEGEND, San Diego, Calif.; Catalog No. 326108) or mouse anti-human CD229 antibody (R&D Systems Catalog No. AF1898).

In another embodiment, the instant invention relates to MSR-SLB scaffolds containing an antibody or an antigen-binding fragment thereof which binds specifically to CD279 (PD-1). PD-1 functions as an immune checkpoint and plays an important role in down regulating the immune system by preventing the activation of T-cells, which in turn reduces autoimmunity and promotes self-tolerance. The inhibitory effect of PD-1 is accomplished through a dual mechanism of promoting apoptosis (programmed cell death) in antigen specific T-cells in lymph nodes while simultaneously reducing apoptosis in regulatory T cells (suppressor T cells). Representative examples of CD229 antibodies include, e.g., nivolumab, pembrolizumab, pidilizumab (CT-011, Cure Tech), BMS936559, and atezolizumab.

In another embodiment, the instant invention relates to MSR-SLB scaffolds containing an antibody or an antigen-binding fragment thereof which binds specifically to CRACC (CD319, BLAME). CD319 mediates NK cell activation through a SH2D1A-independent extracellular signal-regulated ERK-mediated pathway (Bouchon et al., *J Immunol.* 2001 Nov. 15; 167(10):5517-21). CD319 also positively regulates NK cell functions and may contribute to the activation of NK cells. Accordingly, in one embodiment, the MSR-SLB scaffolds comprise a monoclonal anti-CD319 antibody or an antigen-binding fragment thereof. Representative examples of CD319 antibodies include, e.g., elotuzumab or an antigen-binding fragment thereof.

In certain embodiments, the instant invention provides for MSR-SLB scaffolds containing a binding pair containing at least one T-cell activating molecule and at least one T-cell co-stimulatory molecule. Representative examples of such pairs include, but are not limited to, for example, antibodies binding to CD3/CD28, CD3/ICOS, CD3/CD27, and CD3/CD137, or a combination thereof. In this context, depending on the desired modulation of activity of co-stimulatory molecules, it may be desirable to employ an agonist antibody for the first component (CD3) and an agonist or antagonist antibody for the second component.

In certain embodiments, the instant invention provides for MSR-SLB scaffolds containing a binding pair containing at least one T-cell activating molecule which is an antibody binding to CD3 and at least one T-cell co-stimulatory molecule which is an antibody binding to CD28, optionally together with a second co-stimulatory molecule which is an antibody binding to an antigen selected from the group consisting of ICOS, CD27, and CD137. In one embodiment, the MSR-SLB scaffold contains a combination of functional molecules selected from the following combinations: (a) antibodies which bind to CD3, CD28 and ICOS, (b) antibodies which bind to CD3, CD28 and CD27, (c) antibodies which bind to CD3, CD28 and CD137, (d) antibodies which bind to CD3, CD28, ICOS and CD27. In this regard, experimental data suggests that stimulation of these secondary T-cell co-stimulation factors may stimulate differentiation of certain types of T-cells when applied with appropriate activation stimuli such as CD3+CD28. For example, ICOS stimulation favors differentiation of Th effector cells when cooperates with CD3+CD28+ stimulation, whereas it supports differentiation of regulatory T cells when costimulatory signals are insufficient. See, Mesturini et al., *Eur J Immunol.*, 36(10):2601-12, 2006 Similarly, anti-CD27 antibodies may be used to fine-tune the system. In this context, anti-CD27 antibody 1F5 (when used together with anti-CD3 antibodies) did not trigger potentially dangerous polyclonal T-cell activation—a phenomena observed with co-stimulatory CD28-specific super-agonistic antibodies. See, Thomas et al., *Oncoimmunology*, 3: e27255, 2014.

In one embodiment, the binding pair includes monospecific antibodies, wherein a first antibody binds to a first member of the pair, e.g., CD3, and a second antibody binds to a second member of the pair, e.g., CD28. In another embodiment, the pair includes bispecific antibodies, wherein a single antibody binds to the individual pair members, e.g., a bispecific antibody binding to CD3 and CD28. In this context, bispecific antibodies are preferred due to their ability to confer enhanced T-cell activation. See, Willems et al., *Cancer Immunol Immunother.* 2005 November; 54(11): 1059-71.

Alternately, the binding pair includes monospecific antibodies, wherein a first antibody binds to CD3 and a second antibody binds to ICOS. In the context of the antibody binding to ICOS, insofar as the molecule has been implicated in the etiology of graft-versus-host diseases (see, Sato et al., *Transplantation*, 96(1): 34-41, 2013), it may be preferable to employ an antagonistic antibody that neutralizes ICOS. A bispecific antibody containing an agonist CD3-binding antibody fragment and an antagonist ICOS-binding antibody fragment, may also be employed.

Alternately, the binding pair includes monospecific antibodies, wherein a first antibody binds to CD3 and a second antibody binds to CD27. In this embodiment, both antibodies are preferably stimulatory or agonist antibodies. It has been reported that CD27 costimulation augments the survival and antitumor activity of redirected human T cells in vivo (Song et al., *Blood*, 119(3):696-706, 2012). A bispecific antibody containing an agonist CD3-binding antibody fragment and an agonist CD27-binding antibody fragment, may also be employed.

Alternately, the binding pair includes monospecific antibodies, wherein a first antibody binds to CD3 and a second antibody binds to CD137. In this embodiment, both antibodies are preferably stimulatory or agonist antibodies. It has been reported that CD137 costimulation improves the expansion and function of CD8(+) melanoma tumor-infiltrating lymphocytes for adoptive T-cell therapy (Chacon et al., *PLoS One*. 2013; 8(4):e60031, 2013). A bispecific antibody containing an agonist CD3-binding antibody fragment and an agonist CD27-binding antibody fragment, may also be employed.

T-Cell Homeostatic Agents

In one embodiment, the MSR-SLB scaffolds and/or the antigen-presenting cell mimetic scaffolds contains a homeostatic agent is selected from the group consisting of IL-1, IL-2, IL-4, IL-5, IL-7, IL-10, IL-12, IL-15, IL-17, IL-21, and transforming growth factor beta (TGF-β), or an agonist thereof, a mimetic thereof, a variant thereof, a functional fragment thereof, or a combination thereof. In some embodiments, the MSR-SLB scaffolds and/or the antigen-presenting cell mimetic scaffolds contains a plurality of homeostatic agents selected from the group consisting of IL-1, IL-2, IL-4, IL-5, IL-7, IL-10, IL-12, IL-15, IL-17, IL-21, and transforming growth factor beta (TGF-β), or an agonist thereof, a mimetic thereof, a variant thereof, a functional fragment thereof, or a combination thereof. Functional fragments of these homeostatic agents, which are characterized by their ability to modulate the activity of target cells, may also be employed. Representative types of homeostatic agents, including, NCBI accession numbers of human and/or mouse homologs thereof, are provided in Table 1.

TABLE 1

Types of T-cell homeostatic agents that may be employed in the scaffolds.

| T-cell homeostats | NCBI Accession Nos. |
|---|---|
| IL-1 (IL-1α) | NP_000566.3 (human) |
| | NP_034684.2 (mouse) |
| IL-1 (IL-1β) | NP_000567.1 (human) |
| | NP_032387.1 (mouse) |
| IL-2 | NP_000577.2 (human) |
| | NP_032392.1 (mouse) |
| IL-4 | NP_000580.1; NP_758858.1 (human) |
| | NP_067258.1 (mouse) |
| IL-5 | NP_000870.1 (human) |
| | NP_034688.1 (mouse) |
| IL-7 | NP_000871.1; NP_001186815.1; NP_001186816.1; NP_001186817.1 (human) NP_032397.1 (mouse) |
| IL 10 | NP_000563.1 (human) |
| | NP_034678.1 (mouse) |

TABLE 1-continued

Types of T-cell homeostatic agents that may be employed in the scaffolds.

| T-cell homeostats | NCBI Accession Nos. |
|---|---|
| IL 12A | NP_000873.2 (human) |
| | NP_001152896.1; NP_032377.1 (mouse) |
| IL-12B | NP_002178.2 (human) |
| | NP_001290173.1 (mouse) |
| IL-15 | NP_000576.1; NP_751915.1 (human) |
| | NP_001241676.1; NP_032383.1 (mouse) |
| IL-17 (A) | NP_002181.1; NP_034682.1 (human) |
| | NP_002181.1; NP_034682.1 (mouse) |
| TGF-beta 1 | NP_000651.3 (human) |
| | NP_035707.1 (mouse) |
| TGF-beta 2 | NP_001129071.1; NP_003229.1 (human) |
| | NP_033393.2 (mouse) |
| TGF-beta 3 | NP_003230.1 (human) |

Fragments and variants of the aforementioned T-cell homeostatic agents are known in the art. For example, the UNIPROT database entry of each of the aforementioned homeostatic agents lists "natural variants," including structural relationship between the variant and the wild-type biomarker. Purely as representation, the human IL-1β protein (UNIPROT: P01584) includes a natural variant (VAR_073951) having E→N amino acid substitution at amino acid residue 141 of the putative human IL-1β protein sequence. Fragments, if known, are similarly listed under this section.

Preferably, the T-cell homeostatic agent is interleukin-2 (IL-2) or an agonist thereof, a mimetic thereof, a variant thereof, a functional fragment thereof, or a combination thereof with one or more T-cell homeostatic agents listed in Table 1. Examples of IL-2 agonists include, for example, BAY 50-4798 (Margolin et al., *Clin Cancer Res*. 2007 Jun. 1; 13(11):3312-9). Examples of IL-2 mimetics include, for example, peptide 1-30 (P1-30), which acts in synergy with IL-2 (Eckenberg et al., *J Immunol* 2000; 165:4312-4318). Examples of IL-2 fragments include, for example, a ballast portion containing the first 100 amino acids of IL-2 (see, U.S. Pat. No. 5,496,924). Examples of IL-2 variants include, for example, natural variant VAR_003967 and natural variant VAR_003968. Also included are fusion proteins containing IL-2, e.g., F16-IL2, which is an scFv against the extra-domain A1 of tenascin-C that is fused, via a short 5-amino acid linker, to a recombinant form of the human IL-2. The monoclonal antibody portion of the F16-IL2 fusion protein binds to tumor cells expressing the tumor associated antigen (TAA) tenascin-C. In turn, the IL-2 moiety of the fusion protein stimulates natural killer (NK) cells, macrophages and neutrophils and induces T-cell anti-tumor cellular immune responses. Other IL-2 mimetics that may be employed in accordance with the invention include, for example, an IL-2 superkine peptide (Levin et al., *Nature* 484, 529-533, 2012), and an IL-2 partial agonist peptide (Zurawski et al., *EMBO Journal*, 9(12): 3899-3905, 1990 and U.S. Pat. No. 6,955,807), or a combination thereof.

Embodiments of the instant invention further include MSR-SLB scaffolds, including, APC-MS scaffolds made from such scaffolds, which further comprise a plurality of the aforementioned T-cell homeostatic agents. Thus, in one embodiment, the invention provides for MSR-SLB scaffolds containing a first T-cell homeostatic agent which is IL-2 and a second T-cell homeostatic agent which is IL-7, IL-21, IL-15, or IL-15 superagonist. In this context, IL-15 superagonist (IL-15 SA) is a combination of IL-15 with soluble IL-15 receptor-α, which possesses greater biological activity than IL-15 alone. IL-15 SA is considered an attractive antitumor and antiviral agent because of its ability to selectively expand NK and memory CD8+ T (mCD8+ T) lymphocytes. See, Guo et al., *J Immunol.* 2015 Sep. 1; 195(5): 2353-64.

Embodiments of the instant invention further relate to an scaffolds which comprise a plurality of T-cell stimulatory molecules, T-cell co-stimulatory molecules and T-cell homeostatic agents. A typical scaffold may comprise at least 2, at least 3, at least 4, at least 5, at least 6, at least 7, at least 8, at least 9, at least 10, at least 11, or more of each of the aforementioned T-cell stimulatory molecules, T-cell co-stimulatory molecules and T-cell homeostatic agents.

In the scaffolds of the invention, any functional molecule, for example, antigens, antibodies, proteins, enzymes, including fragments thereof, may be directly or indirectly immobilized onto the MSR base layer and/or the SLB using routine techniques. In certain embodiments, the functional molecules may be provided in an organelle (e.g., golgi membrane or plasma membrane), a cell, a cell cluster, a tissue, a microorganism, an animal, a plant, or an extract thereof, which in turn is immobilized onto the MSR layer or the SLB layer. A functional molecule may also be synthesized by genetic engineering or chemical reactions at the desired situs, e.g., outer face of the SLB layer.

The scaffolds described herein comprise and release signaling molecules, e.g., T-cell homeostatic agents, to elicit functional T-cell responses. In one embodiment, the released T-cell homeostatic agents are polypeptides that are isolated from endogenous sources or synthesized in vivo or in vitro. For instance, endogenous IL-2 polypeptides may isolated from healthy human tissue. Alternately, synthetic functional molecules may be synthesized via transfection or transformation of template DNA into a host organism or cell, e.g., a cultured human cell line or a mammal (e.g., humanized mouse or rabbit). Alternatively, synthetic functional molecules in protein form may be synthesized in vitro by polymerase chain reaction (PCR) or other art-recognized methods Sambrook, J., Fritsch, E. F., and Maniatis, T., Molecular Cloning: A Laboratory Manual. Cold Spring Harbor Laboratory Press, NY, Vol. 1, 2, 3 (1989), incorporated by reference herein).

The functional molecules may be modified to increase protein stability in vivo. Alternatively, the functional molecules are engineered to be more or less immunogenic. For instance, insofar as the structures of the various functional molecules are known, the sequences may be modified at one or more of amino acid residues, e.g., glycosylation sites, to generate immunogenic variants.

In one embodiment, the functional molecules are recombinant. Alternatively, the functional molecules are humanized derivatives of mammalian counterparts. Exemplary mammalian species from which the functional molecules are derived include, but are not limited to, mouse, rat, hamster, guinea pig, ferret, cat, dog, monkey, or primate. In a preferred embodiment, the functional molecules are human or humanized version of the aforementioned functional molecules.

Each of the aforementioned functional molecules, e.g., T-cell stimulatory molecules, T-cell co-stimulatory molecules and T-cell homeostatic agents, may, independently from one another, be adsorbed or integrated into the MSR base layer or the SLB base layer. Therefore, in one embodiment, there is provided an APC-MS, wherein the T-cell stimulatory molecules are adsorbed or integrated into the MSR base layer. Preferably, there is provided an APC-MS, wherein the T-cell stimulatory molecules are adsorbed or integrated into the SLB layer. In another embodiment, there is provided an APC-MS, wherein the T-cell stimulatory molecules are adsorbed or integrated into both the MSR base layer as well as the SLB layer. In another embodiment, there is provided an APC-MS, wherein the T-cell co-stimulatory molecules are adsorbed or integrated into the MSR base layer. Preferably, there is provided an APC-MS, wherein the T-cell co-stimulatory molecules are adsorbed or integrated into the SLB layer. Yet in another embodiment, there is provided an APC-MS, wherein the T-cell co-stimulatory molecules are adsorbed or integrated into both the MSR base layer as well as the SLB layer. In another embodiment, there is provided an APC-MS, wherein the T-cell homeostatic agents are adsorbed or integrated into the MSR base layer. In another embodiment, there is provided an APC-MS, wherein the T-cell homeostatic agents are adsorbed or integrated into the SLB layer. Yet in another embodiment, there is provided an APC-MS, wherein the T-cell homeostatic agents are adsorbed or integrated into both the MSR base layer as well as the SLB layer.

In general, the functional molecules and the MSR base layer and/or the SLB layer, may be linked together through the use of reactive groups, which are typically transformed by the linking process into a new organic functional group or unreactive species. The reactive functional group(s), may be located in any of the aforementioned components. Reactive groups and classes of reactions useful in practicing the present invention are generally those that are well known in the art of bioconjugate chemistry. Currently favored classes of reactions available with reactive chelates are those that proceed under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, *Advanced Organic Chemistry,* 3rd Ed., John Wiley & Sons, New York, 1985; Hermanson, Bioconjugate Techniques, Academic Press, San Diego, 1996; and Feeney et al., *Modification of Proteins*; vol. 198, American Chemical Society, Washington, D.C., 1982.

Useful reactive pendant functional groups include, for example:

(a) carboxyl groups and various derivatives thereof including, but not limited to, N-hydroxysuccinimide esters, N-hydroxybenztriazole esters, acid halides (e.g., I, Br, Cl), acyl imidazoles, thioesters, p-nitrophenyl esters, alkyl, alkenyl, alkynyl and aromatic esters;

(b) hydroxyl groups, which can be converted to, e.g., esters, ethers, aldehydes, etc.

(c) haloalkyl groups, wherein the halide can be later displaced with a nucleophilic group such as, for example, an amine, a carboxylate anion, thiol anion, carbanion, or an alkoxide ion, thereby resulting in the covalent attachment of a new group at the functional group of the halogen atom;

(d) dienophile groups, which are capable of participating in Diels-Alder reactions such as, for example, maleimido groups;

(e) aldehyde or ketone groups, such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be, for example, converted to disulfides or reacted with acyl halides;

(h) amine or sulfhydryl groups, which can be, for example, acylated, alkylated or oxidized;

(i) alkenes, which can undergo, for example, cycloadditions, acylation, Michael addition, etc;

(j) epoxides, which can react with, for example, amines and hydroxyl compounds; and (k) phosphoramidites and other standard functional groups useful in nucleic acid synthesis.

The reactive functional groups can be chosen such that they do not participate in, or interfere with, the reactions necessary to assemble the reactive chelates. Alternatively, a reactive functional group can be protected from participating in the reaction by the presence of a protecting group. Those of skill in the art understand how to protect a particular functional group such that it does not interfere with a chosen set of reaction conditions. See, for example, Greene et al., *Protective Groups in Organic Synthesis*, John Wiley & Sons, New York, 1991.

In one embodiment, the functional molecules are loaded/adsorbed onto the MSR base layer or the SLB or both the MSR layer and the SLB via affinity pairing or chemical coupling.

The term "affinity pair" as used herein includes antigen-antibody, receptor-hormone, receptor-ligand, agonist-antagonist, lectin-carbohydrate, nucleic acid (RNA or DNA) hybridizing sequences, Fc receptor or mouse IgG-protein A, avidin-biotin, streptavidin-biotin, biotin/biotin binding agent, Ni2+ or Cu2+/HisTag (6× histidine) and virus-receptor interactions. Various other specific binding pairs are contemplated for use in practicing the methods of this invention.

As used herein, "biotin binding agent" encompasses avidin, streptavidin and other avidin analogs such as streptavidin or avidin conjugates, highly purified and fractionated species of avidin or streptavidin, and non or partial amino acid variants, recombinant or chemically synthesized avidin analogs with amino acid or chemical substitutions which still accommodate biotin binding. Preferably, each biotin binding agent molecule binds at least two biotin moieties and more preferably at least four biotin moieties. As used herein, "biotin" encompasses biotin in addition to biocytin and other biotin analogs such as biotin amido caproate N-hydroxysuccinimide ester, biotin 4-amidobenzoic acid, biotinamide caproyl hydrazide and other biotin derivatives and conjugates. Other derivatives include biotin-dextran, biotin-disulfide-N-hydroxysuccinimide ester, biotin-6 amido quinoline, biotin hydrazide, d-biotin-N hydroxysuccinimide ester, biotin maleimide, d-biotin p-nitrophenyl ester, biotinylated nucleotides and biotinylated amino acids such as Nε-biotinyl-1-lysine. The ligands that may be functionalized via affinity pairing include, but are not limited to, receptors, monoclonal or polyclonal antibodies, viruses, chemotherapeutic agents, receptor agonists and antagonists, antibody fragments, lectin, albumin, peptides, proteins, hormones, amino sugars, lipids, fatty acids, nucleic acids and cells prepared or isolated from natural or synthetic sources. In short, any site-specific ligand for any molecular epitope or receptor to be detected through the practice of the invention may be utilized. Preferably, the ligand is a membrane-anchored protein. The ligand may also be a derivative of a membrane-anchored protein, such as a soluble extracellular domain A ligand can be a receptor involved in receptor-receptor cellular interactions such as TCR binding to the MHC receptor.

The ligands of the instant invention can be expressed and purified by any method known in the art. In a certain embodiment, the proteins are expressed by a baculovirus-based insect expression system or a mammalian expression system. Fifteen residues of AVITAG™ peptide may be added to the C-terminals of all of the molecules. The lysine residue in the AVITAG™ (Avidity, Colo.) can be specifically biotinylated by BirA enzyme (Avidity, Colo.). The proteins may also be designed to be secreted into the supernatant of the cell culture.

The functional molecules, as noted hereinabove, can be any protein or peptide. Preferably, the proteins are involved in ligand-receptor interactions. For example, an important event of T cell activation is a result of membrane-membrane contact between T cells and APCs, wherein a variety of ligand-receptor interactions take place between the two opposing membranes, including, MHC-peptide and TCR, LFA-1 and ICAM-1, CD2 and CD48, as well as B7 or CTLA-4 and CD28. Understanding the valency requirements of these interactions will facilitate the design of therapeutics that enhance or inhibit the immune response to certain antigens. The instant invention can also be used as a tool to study the subtle differences in T cell intracellular signaling pathways induced by agonist and antagonist antigens. The scaffolds provide a clean physiological setting to test the subtle differences without using native antigen presenting cells that often complicate biochemical analyses.

While streptavidin-biotin interactions are exemplified throughout the specification and examples, specific binding pair members as described hereinabove may be employed in place of streptavidin and biotin in the methods of the instant invention. Furthermore, more than one set of specific binding pairs can be employed, particularly when more than one ligand is attached to the membrane surface. In this context, traditional pep-MHC-streptavidin tetramer technology can also be used to screen T cells of certain pep-MHC specificity. However, T cells with the same specificity may or may not be activated by the same antigen stimulation. To study immune responses (e.g. responses to vaccination [viral or cancer vaccines], immune tolerance, autoimmunity), it is important to discriminate T cells based on their responsiveness to antigen. Using calcium flux by microscopy as an indicator for T cell activation, the instant invention also provides a screening assay to quantify primary T cells responsive to a specific antigen. Alternately, biotinylated pep-MHC and co-stimulatory molecules may be coupled onto a streptavidin coated chips, and the chips are paired with the scaffolds of the invention.

In another embodiment, the functional molecules are chemically coupled to the MSR base layer and/or the SLB layer. In certain embodiments, the chemical coupling includes, click-chemistry reagents, for example, azide-alkyne chemical (AAC) reaction, dibenzo-cyclooctyne ligation (DCL), or tetrazine-alkene ligation (TAL). For instance, in the context of AAC, either the MSR or the SLB contains a plurality of single click chemistry functionalities, and frequently contains two, three or more of such functionalities. One or two such functionalities per molecule are preferred. In one embodiment, a clickable reagent such as 3-azidopropylamine or 10-undecynoic acid may be amide-bonded to the carboxy- or amino-terminus, respectively, of a peptide or protein via a click reaction with a corresponding alkyne or azido compound and appropriate catalyst to form the 1,2,3-triazole ring linking groups. See, e.g., U.S. Publication No. 2007/0060658. To further extend arsenal of bioorthogonal copper-free click reagents, aza-dibenzocyclooctyne (ADIBO)-containing compounds for azide-coupling reactions may be used for the site-specific covalent anchoring of protein functional molecules, e.g., antibodies, interluekins and cytokines. The same metal-free click reaction is employed for the PEGylation of unfunctionalized areas of the surface. Such treatment allows for a dramatic reduction or complete elimination of non-specific binding. The copper-free click immobilization methods can be applied to the preparation of various types of arrays, as well as to the derivatization of microbeads and nanoparticles. See, e.g., U.S. Pat. No. 8,912,322. In some embodiments, the functional molecules are coupled to the MSR base layer and/or the SLB layer using a click reagent selected from the group consisting of azide, dibenzocyclooctyne (DBCO), transcyclooctene, tetrazine and norbornene and variants thereof. In some embodiments, the functional molecule comprises azide and a lipid of the lipid bilayer of the MSR-SLB comprises DBCO.

The term "click chemistry" refers to a chemical philosophy introduced by K. Barry Sharpless of The Scripps Research Institute, describing chemistry tailored to generate covalent bonds quickly and reliably by joining small units comprising reactive groups together. Click chemistry does not refer to a specific reaction, but to a concept including reactions that mimic reactions found in nature. In some embodiments, click chemistry reactions are modular, wide in scope, give high chemical yields, generate inoffensive byproducts, are stereospecific, exhibit a large thermodynamic driving force >84 kJ/mol to favor a reaction with a single reaction product, and/or can be carried out under physiological conditions. A distinct exothermic reaction makes a reactant "spring loaded". In some embodiments, a click chemistry reaction exhibits high atom economy, can be carried out under simple reaction conditions, use readily available starting materials and reagents, uses no toxic solvents or use a solvent that is benign or easily removed (preferably water), and/or provides simple product isolation by non-chromatographic methods (crystallization or distillation).

The term "click chemistry handle," as used herein, refers to a reactant, or a reactive group, that can partake in a click chemistry reaction. For example, a strained alkyne, e.g., a cyclooctyne, is a click chemistry handle, since it can partake in a strain-promoted cycloaddition. In general, click chemistry reactions require at least two molecules comprising click chemistry handles that can react with each other. Such click chemistry handle pairs that are reactive with each other are sometimes referred to herein as partner click chemistry handles. For example, an azide is a partner click chemistry handle to a cyclooctyne or any other alkyne. Exemplary click chemistry handles suitable for use according to some aspects of this invention are described herein, for example, US 2014/0249296. Other suitable click chemistry handles are known to those of skill in the art.

In one embodiment, the instant invention provides APC-MS comprising a plurality of T-cell activating molecules and T-cell co-stimulatory molecules optionally together with T-cell homeostatic agents, which are adsorbed into the scaffold via metal-chelating lipid headgroups. See, Maloney et al., Chem Biol., 3(3):185-92, 1996. Several approaches using chelated metal ions have been reported that allow histidine-tagged proteins to be immobilized at several types of interfaces, such as lipid interfaces and lipid monolayers with metal-chelating lipids, gold surfaces with self-assembling monolayers formed with metal-chelating alkanethiols, and oxide surfaces with metal-chelating silanes. For example, Peterson et al. (U.S. Pat. No. 5,674,677) describes a method for joining two amino acid sequences by coupling an organic chelator to a protein, e.g., an enzyme, and charging the chelator with a metal ion. This complex is then mixed with any protein containing a histidine tag to couple the complex with the histidine tagged protein. See also, U.S. Pat. No. 6,087,452, which is incorporated by reference herein in its entirety.

The functional molecules of the invention are preferably proteins. The terms "protein," "peptide" and "polypeptide" are used interchangeably, and refer to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins. One or more of the amino acids in a protein, peptide, or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein, peptide, or polypeptide may also be a single molecule or may be a multi-molecular complex. A protein, peptide, or polypeptide may be just a fragment of a naturally occurring protein or peptide. A protein, peptide, or polypeptide may be naturally occurring, recombinant, or synthetic, or any combination thereof.

The term "conjugated" or "conjugation" refers to an association of two molecules, for example, two proteins, with one another in a way that they are linked by a direct or indirect covalent or non-covalent interaction. In the context of conjugation via click chemistry, the conjugation is via a covalent bond formed by the reaction of the click chemistry handles. In certain embodiments, the association is covalent, and the entities are said to be "conjugated" to one another. In some embodiments, a protein is post-translationally conjugated to another molecule, for example, a second protein, by forming a covalent bond between the protein and the other molecule after the protein has been translated, and, in some embodiments, after the protein has been isolated. In some embodiments, the post-translational conjugation of the protein and the second molecule, for example, the second protein, is effected via installing a click chemistry handle on the protein, and a second click chemistry handle, which can react to the first click chemistry handle, on the second molecule, and carrying out a click chemistry reaction in which the click chemistry handles react and form a covalent bond between the protein and the second molecule, thus generating a chimeric protein. In some embodiments, two proteins are conjugated at their respective C-termini, generating a C-C conjugated chimeric protein. In some embodiments, two proteins are conjugated at their respective N-termini, generating an N-N conjugated chimeric protein.

In certain embodiments, a plurality of detectable labels may be used to analyze and/or study the conjugation process. As used herein, a "detectable label" refers to a moiety that has at least one element, isotope, or functional group incorporated into the moiety which enables detection of the molecule, e.g., a protein or polypeptide, or other entity, to which the label is attached. Labels can be directly attached (i.e., via a bond) or can be attached by a tether (such as, for example, an optionally substituted alkylene; an optionally substituted alkenylene; an optionally substituted alkynylene; an optionally substituted heteroalkylene; an optionally substituted heteroalkenylene; an optionally substituted heteroalkynylene; an optionally substituted arylene; an optionally substituted heteroarylene; or an optionally substituted acylene, or any combination thereof, which can make up a tether). It will be appreciated that the label may be attached to or incorporated into a molecule, for example, a protein, polypeptide, or other entity, at any position.

In general, a label can fall into any one (or more) of five classes: a) a label which contains isotopic moieties, which may be radioactive or heavy isotopes, including, but not limited to, $^2$H, $^3$H, $^{13}$C, $^{14}$C, $^{15}$N, $^{18}$F, $^{31}$P, $^{32}$P, $^{35}$S, $^{67}$Ga, $^{99m}$Tc (Tc-99 m), $^{111}$In, $^{125}$I, $^{131}$I, $^{153}$Gd, $^{169}$Yb, and $^{186}$Re; b) a label which contains an immune moiety, which may be antibodies or antigens, which may be bound to enzymes (e.g., such as horseradish peroxidase); c) a label which is a colored, luminescent, phosphorescent, or fluorescent moieties (e.g., such as the fluorescent label fluorescein isothiocyanate (FITC) or carboxyfluorescein); d) a label which has one or more photo affinity moieties; and e) a label which is a ligand for one or more known binding partners (e.g., biotin-streptavidin, FK506-FKBP). In certain embodiments, a label comprises a radioactive isotope, preferably an isotope which emits detectable particles. In certain embodiments, the label comprises a fluorescent moiety. In certain embodiments, the label is the fluorescent label fluorescein isothiocyanate (FITC). In certain embodiments, the label comprises a ligand moiety with one or more known binding partners. In certain embodiments, the label comprises biotin. In some embodiments, a label is a fluorescent polypeptide (e.g., GFP or a derivative thereof such as enhanced GFP (EGFP)) or a luciferase (e.g., a firefly, Renilla, or Gaussia luciferase). It will be appreciated that, in certain embodiments, a label may react with a suitable substrate (e.g., a luciferin) to generate a detectable signal. Non-limiting examples of fluorescent proteins include GFP and derivatives thereof, proteins comprising chromophores that emit light of different colors such as red, yellow, and cyan fluorescent proteins, etc. Exemplary fluorescent proteins include, e.g., Sirius, Azurite, EBFP2, TagBFP, mTurquoise, ECFP, Cerulean, TagCFP, mTFP1, mUkG1, mAG1, AcGFP1, TagGFP2, EGFP, mWasabi, EmGFP, TagYPF, EYFP, Topaz, SYFP2, Venus, Citrine, mKO, mKO2, mOrange, mOrange2, TagRFP, TagRFP-T, mStrawberry, mRuby, mCherry, mRaspberry, mKate2, mPlum, mNeptune, T-Sapphire, mAmetrine, mKeima. See, e.g., Chalfie, M. and Kain, S R (eds.) Green fluorescent protein: properties, applications, and protocols (*Methods of Biochemical Analysis*, v. 47). Wiley-Interscience, Hoboken, N.J., 2006, and/or Chudakov et al., *Physiol Rev.* 90(3):1103-63, 2010 for discussion of GFP and numerous other fluorescent or luminescent proteins. In some embodiments, a label comprises a dark quencher, e.g., a substance that absorbs excitation energy from a fluorophore and dissipates the energy as heat.

In another embodiment, the functional molecules may be loaded onto mesoporous silica and/or the lipid bilayer using art known, covalent or non-covalent loading techniques. In one embodiment, the functional molecules are loaded non-covalently. For instance, Lei et al. (U.S. Publication No. 2011-0256184) describe mesoporous silicates that provide enhanced, spontaneous loading of antibodies such as IgG via non-covalent bonding within the native or functionalized structure. Accordingly, the scaffolds of the invention may be formulated with such silicates.

In another embodiment, the functional molecules are chemically coupled onto the MSR. In such embodiments, the coupling may be conducted by utilizing one or more of the following molecules and the reactive groups contained therein: cysteine (thiol group), serine or threonine (hydroxyl group), lysine (amino group), aspartate or glutamate (carboxyl group). Alternatively, the functional molecules may be conjugated to the MSR via utilization of polyhistidine-tag (His-tag), a peptide containing polyhistidine-tag or an antibody containing polyhistidine-tag. Herein, the polyhistidine-tag consists of at least four, five, six or seven histidine (His) residues.

In one embodiment, an anchor is used to connect the functional molecule to a pore wall. However, the anchor is not an essential component. In certain embodiments, each pore of the mesoporous silica accommodates at least one functional molecule. Thus, the pores must have a size appropriate to immobilize a biological substance. The pore size depends on the size of the functional molecule to be immobilized. When a functional molecule is immobilized in a pore, the functional molecule can be adsorbed on an inner surface of the pore by electrostatic bonding. A functional molecule may also be held in a pore by a noncovalent bonding, such as van der Waals forces, hydrogen bonding, or ionic bonding.

In the aforementioned embodiment where the MSR comprises anchoring moieties, the anchor may have an effect of reducing a large structural change of the functional molecule to hold it stably. Preferably, the anchor is composed of substantially the same component as the mesoporous material. The anchor may comprise one or more functional groups to permit binding to a desired functional molecule: a hydroxyl group, an amide group, an amino group, a pyridine group, a urea group, a urethane group, a carboxyl group, a phenol group, an azo group, a hydroxyl group, a maleimide group, a silane derivative, or an aminoalkylene group.

Embodiments of the invention further relate to MSR-SLB scaffolds of the invention, including, scaffolds containing such scaffolds, comprising, a plurality of the aforementioned functional molecules which are adsorbed in the lipid matrix.

In one embodiment, the functional molecules are adsorbed into the supported lipid bilayer via physical insertion. Techniques for inserting proteins into the bilayer of amphipathic molecules are known in the art. In one embodiment, proteins in the environment of the bilayer, for example in the hydrophobic medium and/or in the hydrophilic body and/or in the hydrated support, may insert spontaneously into the bilayer. Alternatively, proteins may be driven into the bilayer by the application of a voltage and/or by fusion of protein loaded vesicles with the bilayer. The vesicles may be contained within or introduced to the hydrophilic body. In one instance, proteins may be introduced into the membrane by using the probe method disclosed in PCT Publication No. WO 2009/024775. The inserted protein may be a known membrane-associated protein, e.g., one or more of the aforementioned T-cell activating molecules and/or T-cell co-stimulatory molecules.

In another embodiment, the functional molecule may be an antigen that is used in expansion of T-cells. Representative examples of such antigens usable in T-cell expansion include, full-length CD19 or a fragment thereof or a variant thereof. CD19 is a prototypical antigen used in the expansion of chimeric antigen receptor (CAR) T-cells. See, Turtle et al., *Blood*, 126:184, 2015; Turtle et al., *J Clin Invest.*, 126, 2123-38, 2016. In another embodiment, the antigen is full-length CD22 or a fragment thereof or a variant thereof, which are also useful in the expansion of CAR T-cells. See, Haso et al., *Blood*, 121(7): 1165-1174, 2013; Qin et al., *Blood*, 122:1431, 2013.

In an alternate embodiment, the functional molecule may be a membrane-associated protein which is anchored directly or indirectly to the bilayer. Other functional molecules, e.g., selective or non-selective membrane transport proteins, ion channels, pore forming proteins or membrane-resident receptors, etc. may also be inserted into the SLB via this method.

In another embodiment, the functional molecules may be conjugated to membrane-associated proteins which associate with and/or insert into the SLB, e.g. gramicidin; α-helix bundles, e.g. bacteriorhodopsin or K+ channels; and β-barrels, e.g., α-hemolysin, leukocidin or E. coli porins; or combinations thereof.

In certain embodiments, the fabricated SLB (containing one or more functional molecules) may be stabilized by compounds such as ionic or non-ionic surfactants. Suitable surfactants include, but are not limited to, the following examples: synthetic phospholipids, their hydrogenated derivatives and mixtures thereof, sphingolipids and glycosphingolipids, saturated or unsaturated fatty acids, fatty alcohols, polyoxyethylene-polyoxypropylene copolymers, ethoxylated fatty acids as well as esters or ethers thereof, dimyristoyl phosphatidyl choline, dimyristoyl phosphatidyl glycerol or a combination of two or more of the above mentioned. A preferred surfactant according to the invention is the dimyristoyl phosphatidyl glycerol.

The fabricated SLBs may be optionally stabilized by at least one co-surfactant selected in the group comprising or consisting of butanol, butyric acid, hexanoic acid, sodium cholate, sodium taurocholate and sodium glycocholate, more particularly sodium cholate.

The fabricated SLBs may also include other excipients, such as polymers having bioadhesive or absorption enhancing properties and selected from the group comprising or consisting of acrylic polymers (CARBOPOL®, Polycarbophil, NOVEON®), medium chain fatty acids and polyethylene glycols. Preferred excipients are the above-mentioned acrylic polymers.

The SLB may be modified with reagents for detecting membrane-associated proteins. Preferably the membrane-associated proteins are ion channel proteins and/or pore forming proteins. Preferably the membrane-associated proteins diffuse into and/or associate with the bilayer causing a detectable change in the properties at the bilayer. The properties changed may be physical, optical, electrical or biochemical.

In some embodiments, the MSR-SLB scaffolds and/or the antigen-presenting cell mimetic scaffolds comprises a small molecule drug. In some embodiments, the MSR-SLB scaffolds and/or the antigen-presenting cell mimetic scaffolds comprises a thalomid analog. In some embodiments, the MSR-SLB scaffolds and/or the antigen-presenting cell mimetic scaffolds comprises a IDO/MEK inhibitor. In some embodiments, the MSR-SLB scaffolds and/or the antigen-presenting cell mimetic scaffolds comprises a small molecule drug that has immunomodulatory effects. Small molecule drugs with immunomodulatory effects are known the art (see, e.g., Murphy et al. *Hum. Vaccin. Immunother.* 11(10): 2463-8 (2015), the entire contents of which are expressly incorporated herein by reference).

In certain embodiments, the MSR-SLB scaffolds containing the functional molecules may be used to detect cells which are capable of interaction with amphipathic molecules in the bilayer and/or with the functional molecule in the bilayer. The interaction may be specific or non-specific in nature. Alternatively the cells may interact with the functional molecule or with the lipid bilayer to cause physical, optical, electrical, or biochemical changes. Such interaction may be detected in many different ways, including, but limited to, by visual changes, via activation of fluorescently labelled lipids or proteins in the SLB, or changes in capacitance of the SLB.

Biodegradable Scaffolds

Embodiments of the invention further relate to biodegradable scaffolds. In one embodiment, the scaffold structure may substantially degrade when exposed to a biological milieu. In one embodiment, the biological milieu is a tissue culture condition, e.g., tissue culture media that has been optionally adapted to culture lymphocytes such as T-cells. In another embodiment, the biological milieu is a biological fluid, e.g., blood, lymph, CSF, peritoneal fluid, or the like. In yet another embodiment, the biological milieu is the tissue environment at the site of implant, e.g., blood vessels, lymphatic system, adipose tissue, or the like.

In certain embodiments, the biodegradable scaffolds are substantially degraded following contact with a biological milieu in vivo over 1 day, 2 days, 3 days, 4 days, 5 days, 6 days, 7, days, 8 days, 9 days, 10 days, 11 days, 12 days, 13 days, 14 days, 15 days, 20 days, 30 days, 45 days, 60 days, 90 days, or more. In certain embodiments, the biodegradable scaffolds are substantially degraded following contact with a biological milieu in vivo in less than 1 week. In certain embodiments, the biodegradable scaffolds are substantially degraded following contact with a biological milieu in vitro over 1 day, 2 days, 3 days, 4 days, 5 days, 6 days, 7, days, 8 days, 9 days, 10 days, 11 days, 12 days, 13 days, 14 days, 15 days, 20 days, 30 days, 45 days, 60 days, 90 days, or more. In certain embodiments, the biodegradable scaffolds are substantially degraded following contact with a biological milieu in vitro in less than 1 week. By substantial degradation, it is meant that at least 30%, at least 50%, at least 60%, at least 70%, at least 90%, at least 95%, or more of the scaffold composition is degraded when the scaffold composition is contacted with the biological milieu.

In certain embodiments, it may be advantageous to use biodegradable scaffolds. For instance, by fabricating the scaffold composition such that it substantially degrades during the incubation period (e.g., when the T-cells are allowed to expand), it may be possible to use the expanded T-cells without subjecting them to additional purification and/or formulation steps. Avoiding downstream purification and/or formulation steps would ensure that the T-cells are fit and possess the desired functionality for the desired application.

Accordingly, in certain embodiments, it may be advantageous to tailor the degradation kinetics of the scaffold compositions by modifying the properties of mesoporous silica rods, such as size, geometry, porosity. Alternately, the degradation kinetics of the scaffold compositions may be modified by changing the culture conditions (e.g., by adjusting the pH of the media).

In accordance with the aforementioned objectives, embodiments of the invention relate to MSR-SLB scaffolds comprising a plurality of functional molecules which are optionally biodegradable. In one embodiment, the scaffolds of the instant invention may be encapsulated into other biodegradable scaffolds. Reagents and techniques that are useful in making such composite biodegradable scaffold compositions are known in the art. See, Liao et al., *J. Biomed. Mater. Res. B. Appl. Biomater.*, 102(2):293-302, 2014. In one embodiment, the scaffolds are made up of physiologically-compatible and optionally biodegradable polymers. Examples of polymers that are employable in the scaffolds are known in the art. See, for example, U.S. Publication No. 2011/0020216, the entire contents of which are incorporated herein by reference. Representative examples of such polymers include, but are not limited to, poly(lactide)s, poly(glycolide)s, poly(lactic acid)s, poly(glycolic acid)s, polyanhydrides, polyorthoesters, polyetheresters, polycaprolactones, polyesteramides, polycarbonates, polycyanoacrylates, polyurethanes, polyacrylates, and blends or copolymers thereof. Biodegradable scaffolds may comprise biodegradable materials, e.g., collagen, alginates, polysaccharides, polyethylene glycol (PEG), poly(glycolide) (PGA), poly(L-lactide) (PLA), or poly(lactide-co-glycolide) (PLGA) or silk. Methods for fabricating the scaffold compositions are known in the art. See, for example, Martinsen et al. (*Biotech. & Bioeng.*, 33 (1989) 79-89), (Matthew et al. (*Biomaterials*, 16 (1995) 265-274), Atala et al. (*J Urology*, 152 (1994) 641-643), and Smidsrod (*TIBTECH* 8 (1990) 71-78), the disclosures in which are incorporated by reference herein.

Exemplary scaffolds utilize glycolides or alginates of a relatively low molecular weight, preferably of size which, after dissolution, is at the renal threshold for clearance by humans, e.g., the alginate or polysaccharide is reduced to a molecular weight of 1000 to 80,000 daltons. Preferably, the molecular mass is 1000 to 60,000 daltons, particularly preferably 1000 to 50,000 daltons. It is also useful to use an alginate material of high guluronate content since the guluronate units, as opposed to the mannuronate units, provide sites for ionic cross-linking through divalent cations to gel the polymer. For example, U.S. Pat. No. 6,642,363, which incorporated herein by reference, discloses methods for making and using polymers containing polysaccharides such as alginates.

The scaffolds of the invention may be porous such that the scaffolds can sustain antigen presentation and attract and manipulate immune cells. In one embodiment, the scaffolds contain porous matrices, wherein the pores have a diameter between 10 nm to 500 μm, particularly between 100 nm and 100 μm. In these embodiments, the invention utilizes scaffolds comprising mesoporous scaffolds. Methods of making polymer matrices having the desired pore sizes and pore alignments are described in the art, e.g., US pub. No. 2011/0020216 and U.S. Pat. No. 6,511,650, which are incorporated herein by reference.

The mesoporous silica rods can be modified into multi-functional delivery platforms for delivering drugs such as chemotherapeutic agents and DNA/siRNA, antibody and protein biologics, cells, etc. (Lee et al., *Adv. Funct. Mater.*, 215-222, 2009; Liong et al., *ACS Nano*, 889-896, 2008; Meng et al., *ACS Nano*, 4539-4550, 2010; Meng et al., *J. Am. Chem. Soc.*, 12690-12697, 2010; Xia et al., *ACS Nano*, 3273-3286, 2009; Radu et al., *J. Am. Chem. Soc.*, 13216-13217, 2004; Slowing et al., *J. Am. Chem. Soc.*, 8845-8849, 2007). This delivery platform allows effective and protective packaging of hydrophobic and charged anticancer drugs for controlled and on demand delivery, with the additional capability to also image the delivery site (Liong et al., *ACS Nano*, vol. 2, pp. 889-896, 2008). The key challenge now is to optimize the design features for efficient and safe in vivo drug delivery (He et al., *Small*, vol. 7, pp. 271-280, 2011; Lee et al., *Angew. Chem. Int. Ed.*, vol. 49, pp. 8214-8219, 2010; Liu et al., *Biomaterials*, vol. 32, pp. 1657-1668, 2011; Al Shamsi et al., *Chem. Res. Toxicol.*, vol. 23, pp. 1796-1805, 2010), which can be assessed through the use of human xenograft tumors in nude mice (Lu et al., *Small*, vol. 6, pp. 1794-1805, 2010).

Embodiments described herein further relate to MSR-SLB scaffolds, including, scaffolds containing such scaffolds, wherein the dry weight ratio of the mesoporous silica micro-rods (MSR) to the T-cell activating/co-stimulatory molecules is between about 1:1 to about 100:1, preferably between about 10:1 to about 50:1, particularly between about 20:1 to about 50:1. In some embodiments, the dry weight ratio of the mesoporous silica micro-rods (MSR) to the T-cell activating/co-stimulatory molecules of the MSR-SLB scaffolds is between about 10,000:1 to about 1:1. In some embodiments, the dry weight ratio of the mesoporous silica micro-rods (MSR) to the T-cell activating/co-stimulatory molecules of the MSR-SLB scaffolds is between about 5,000:1 to about 1:1, between about 1,000:1 to about 1:1, between about 500:1 to about 1:1, between about 100:1 to about 1:1. In some embodiments, the dry weight ratio of the mesoporous silica micro-rods (MSR) to the T-cell activating/co-stimulatory molecules of the MSR-SLB scaffolds is about 10,000:1, about 5,000:1, about 2,500:1, about 1,000:1, about 750:1, about 500:1, about 250:1, about 100:1, about 75:1, about 50:1, about 40:1, about 30:1, about 25:1, about 20:1, about 10:1, or about 1:1.

Embodiments described herein further relate to compositions and devices containing aforementioned scaffolds containing the MSR-SLB scaffolds together with the functional molecules, e.g., T-cell activating molecule, T-cell co-stimulatory molecule, and T-cell homeostatic agent, optionally together with one or more additional agents (listed below). In one embodiment, the invention provides for compositions comprising the scaffold and T-cells clustered therein. In one embodiment, the T-cells are selected from the group consisting of natural killer (NK) cells, a CD3+ T-cells, CD4+ T-cells, CD8+ T-cells, and regulatory T-cells (Tregs), or a combination thereof. In other embodiments, the composition may be a pharmaceutical composition, which may be produced using methods that are well-known in the art. For instance, pharmaceutical compositions may be produced by those of skill, employing accepted principles of medicinal chemistry. The compositions, scaffolds, and devices may be provided with one or more reagents for selecting, culturing, expanding, sustaining, and/or transplanting the cells of interest. Representative examples of cell selection kits, culture kits, expansion kits, transplantation kits for T-cells, B-cells and antigen presenting cells are known in the art. For example, where the target cell of interest are T-cells, such may be initially sorted using DYNABEADS, MACS-beads (Miltenyi Biosciences), maintained in STEMXVIVO Human T cell base media (R&D Systems) and expanded with OPTIMIZER culture media (Thermo Fisher Scientific). The cells may be enriched in the sample by using centrifugation techniques known to those in the art including, e.g., FICOLL® gradients. Cells may also be enriched in the sample by using positive selection, negative selection, or a combination thereof, based on the expression of certain markers.

Further embodiments of the invention relate to T-cell manipulating devices. The devices contain the scaffolds of the invention together with a plurality of molecules which attract/bind to target T cells. In one embodiment, the invention relates to devices containing scaffolds that are stacked to selectively permit infiltration of T-cells into the mesoporous silica micro-rods (MSR). By selective infiltration, it is meant that owing to selective permissibility/permeability, specificity of binding, selective elimination (of undesired cells) and/or expansion (of desired cells), the scaffold contains at least 10% more, 20% more, 30% more, 40% more, 50% more, 60% more, 70% more, 80% more, 90% more, 100% more, 150% more, 200% more, 300% more, 400% more, 500% more, 600% more, 800% more, 1000% more, or greater number of target T-cells after a period of incubation compared to that which is present in whole blood. In certain embodiments, the period of incubation is between 1-30 days, preferably between 4-15 days, particularly between 7-12 days. In other embodiments, selective infiltration relates to retention and/or expansion of T-cells compared to other blood cells, e.g., B-cells, dendritic cells, macrophages, red blood cells or platelets that are present in whole blood.

In other embodiments, the scaffolds of the invention permit selective infiltration of a specific sub-population of T-cells, e.g., natural killer (NK) cells, a CD3+ T-cells, CD4+ T-cells, CD8+ T-cells, or regulatory T-cells (Tregs). Herein, the scaffold contains at least 10% more, 20% more, 30% more, 40% more, 50% more, 60% more, 70% more, 80% more, 90% more, 100% more, 150% more, 200% more, 300% more, 400% more, 500% more, 600% more, 800% more, 1000% more, or greater number of target T-cells after 4-14 days incubation compared to that which is present in whole blood. The percentages and the ranges of various types of lymphocytes in human whole blood are as follows: NK cells 7% (range: 2-13%); helper T cells 46% (range: 28-59%); cytotoxic T cells 19% (range: 13-32%); γδ T cells 5% (range: 2%-8%); B cells 23% (range: 18-47%) (Berrington et al., *Clin Exp Immunol* 140 (2): 289-292, 2005).

Additional Agents

The scaffolds of the invention include one or more agents, which may be naturally-occurring, synthetically produced, or recombinant compounds, e.g., peptides, polypeptides, proteins, nucleic acids, small molecules, haptens, carbohydrates, or other agents, including fragments thereof or combinations thereof. In one embodiment, the agents are antigens. In one embodiment, the antigens are peptides or proteins or immunologically active fragments thereof. In one embodiment, the antigens described herein are purified. Purified compounds contain at least 60% by weight (dry weight) of the compound of interest. Particularly, the antigens are at least 75% pure, preferably at least 90% pure, and more preferably at least 99% pure. Purity is measured by any appropriate standard method, for example, by column chromatography, gel electrophoresis, or HPLC analysis. The antigens may be self-antigens or non-self antigens.

Representative examples of non-self antigens include, for example, antigens derived from a pathogen selected from the group consisting of a virus, a bacterium, a protozoan, a parasite, and a fungus. The antigens may be optionally loaded onto MHC molecules, e.g., HLA-A, HLA-B, HLA-C, DP, DQ and DR, which are then incorporated into the scaffolds.

Alternately, the scaffolds contain a plurality of self-antigens, which are optionally linked to or associated with a disease or disorder. Preferably, the self-antigens are specifically associated with a human disease or a disorder. In one embodiment, the self-antigen is associated with an autoimmune disorder selected from the group consisting of rheumatoid arthritis, lupus, celiac disease, inflammatory bowel disease or Crohn's disease, sjogren's syndrome polymyalgia rheumatic, multiple sclerosis, ankylosing spondylitis, Type 1 diabetes, alopecia areata, vasculitis, temporal arteritis, etc. Specific types of antigens, including fragments thereof, which are associated with type 1 diabetes, multiple sclerosis, Crohn's disease, and rheumatoid arthritis and the like have been characterized in literature. For example, rheumatoid arthritis-related antigen is a 47kDa protein (RA-A47). See Hattori et al, *J Bone Miner Metab.*, 18(6):328-34 (2000). In Crohn's disease, the antigen may be bacterial flagellin. See, Lodes et al., *J Clin Invest.* 113(9):1296-306 (2004). Likewise, major myelin proteins such as myelin basic protein (MBP) and proteolipid protein (PLP), are likely to be of importance in the course of multiple sclerosis (MS). See, deRosbo et al., *J Clin Invest.* 92(6): 2602-260 (1993). In the context of type 1 diabetes, a plurality of autoantigens may be involved, such as, preproinsulin (PPI), islet-specific glucose-6-phosphatase (IGRP), glutamate decarboxylase (GAD65), insulinoma antigen-2 (IA-2), chromogranin A and heat shock protein 60. See Roep et al., *Cold Spring Harb Perspect Med.*2(4), 2012 (PMID: 22474615).

In another embodiment, the self-antigens are associated with a cancer. Representative types of cancer antigens include, for example, MAGE-1, MAGE-2, MAGE-3, CEA, Tyrosinase, midkin, BAGE, CASP-8, β-catenin, β-catenin, γ-catenin, CA-125, CDK-1, CDK4, ESO-1, gp75, gp100, MART-1, MUC-1, MUM-1, p53, PAP, PSA, PSMA, ras, trp-1, HER-2, TRP-1, TRP-2, IL13Ralpha, IL13Ralpha2, AIM-2, AIM-3, NY-ESO-1, C9orf 112, SART1, SART2, SART3, BRAP, RTN4, GLEA2, TNKS2, KIAA0376, ING4, HSPH1, C13orf24, RBPSUH, C6orf153, NKTR, NSEP1, U2AF1L, CYNL2, TPR, SOX2, GOLGA, BMI1, COX-2, EGFRvIII, EZH2, LICAM, Livin, Livinβ, MRP-3, Nestin, OLIG2, ART1, ART4, B-cyclin, Gli1, Cav-1, cathepsin B, CD74, E-cadherin, EphA2/Eck, Fra-1/Fosl 1, GAGE-1, Ganglioside/GD2, GnT-V, β1,6-N, Ki67, Ku70/80, PROX1, PSCA, SOX10, SOX11, Survivin, UPAR, WT-1, Dipeptidyl peptidase IV (DPPIV), adenosine deaminase-binding protein (AD Abp), cyclophilin b, Colorectal associated antigen (CRC)-C017-1A/GA733, T-cell receptor/CD3-zeta chain, GAGE-family of tumor antigens, RAGE, LAGE-I, NAG, GnT-V, RCAS1, α-fetoprotein, p120ctn, Pmel117, PRAME, brain glycogen phosphorylase, SSX-I, SSX-2 (HOM-MEL-40), SSX-I, SSX-4, SSX-5, SCP-I, CT-7, cdc27, adenomatous polyposis coli protein (APC), fodrin, P1A, Connexin 37, Ig-idiotype, p15, GM2, GD2 gangliosides, Smad family of tumor antigens, lmp-1, EBV-encoded nuclear antigen (EBNA)-I, UL16-binding protein-like transcript 1 (Multi), RAE-1 proteins, H60, MICA, MICB, and c-erbB-2, or an immunogenic peptide thereof, and combinations thereof.

In another embodiment, the antigen is a target of modified T-cells, e.g., CAR T-cells described above. In such embodiments, the antigen is CD19 or a fragment thereof or a variant thereof. In another embodiment, the antigen is CD22 or a fragment thereof or a variant thereof.

The aforementioned antigens may be combined with the scaffold compositions using any known methods, including covalent and non-covalent interactions. Some of these methods have been outlined above in sections relating to fabricating the MSR-SLB scaffolds with the functional molecules of the invention. Examples of non-covalent interactions include, for example, electrostatic interactions, van der Waals' interactions, π-effects, hydrophobic interactions, physical insertion etc. For example, full length transmembrane protein antigens can be incorporated into the lipid bilayer via physical insertion using routine methods. See, Cymer et al., *Journal of Molecular Biology*, 427.5: 999-1022, 2015 and U.S. Pat. No. 7,569,850, which are incorporated by reference herein.

The antigens may also be attached or tethered to scaffold compositions via covalent interactions. Methods for attaching antigens to scaffolds/surfaces are known in the art, e.g., surface absorption, physical immobilization, e.g., using a phase change to entrap the substance in the scaffold material. Alternatively, covalent coupling via alkylating or acylating agents may be used to provide a stable, long-term presentation of an antigen on the scaffold in a defined conformation. Exemplary reagents and methods for covalently coupling peptides/proteins to polymers are known in the art. See, for example, U.S. Pat. No. 6,001,395, which is incorporated herein by reference. In other embodiments, the antigens are encapsulated into the scaffolds. Methods for encapsulating antigens into suitable scaffolds, e.g., PLGA microspheres, are known in the art. See, for example, U.S. Pat. No. 6,913,767 and International Publication No. WO 1995/011010, the disclosures of each of which are incorporated herein by reference.

The antigens may be formulated to interact with the immune cell via direct binding or indirect binding. Types of direct binding include, for example, engagement or coupling of the antigen with the cognate receptor, e.g., T-cell receptor. Indirect binding may occur through the intermediacy of one or more secondary agents or cell-types. For example, the antigen may first bind to a B-cell or an antigen-presenting cell (APC), get processed (e.g., degraded) and presented on cell-surface major-histocompatibility complexes (MHC), to which the target cell population, e.g., T-cell, binds. Alternately, the antigen may recruit other intermediary cells that secrete various cytokines, growth factors, chemokines, etc., which in turn attract the target immune cell population. Whatever the mechanism may be, the recited components act in concert to manipulate or modify the immune cells.

The antigen may be derived from a cell lysate, a fractionated cell lysate, freshly harvested cells, biological fluids (including blood, serum, ascites), tissue extracts, etc. In one embodiment, the antigens are derived from lysates of target cells to which the desired immune cells, e.g., T cells, bind. In these embodiments, the antigens are first fractionated in the cell lysate prior to loading the scaffolds. The lysates may be derived from a desired target tissue, e.g., an autoimmune disease-specific cells obtained from primary tissues. Alternately, the lysates may be derived from cancer cells, e.g., individual cells obtained from tumor samples or tissue cultures or tumor cells obtained from biopsies histologies.

The scaffolds of the invention may also contain one or more recruiting agents. The recruiting agent may be an agent selected from the group consisting of a T-cell recruiting agent, a B-cell recruiting agent, a dendritic cell recruiting agent, and a macrophage recruiting agent.

In one embodiment, the scaffolds contain T-cell recruiting agents. Non-limiting examples of T-cell recruiting agents include, e.g., granulocyte macrophage-colony stimulating factor (GM-CSF), chemokine (C-C motif) ligand 21 (CCL-21), chemokine (C-C motif) ligand 19 (CCL-19), or a FMS-like tyrosine kinase 3 (Flt-3) ligand, granulocyte-colony stimulating factor (G-CSF), IFNγ, a C-X-C Motif chemokine ligand (CXCL) selected from the group consisting of CXCL12 and CXCR4, or a fragment thereof, a variant thereof, or a combination thereof. Other types of T-cell recruiting agents include, ligands for CCR5 and CXCR3 receptors for recruiting T helper type 1 (Th1) subset. The CCR5 ligands, CCL5 and macrophage inflammatory proteins (MIP-1α), are known. Alternately, ligands for CCR3, CCR4, CCR8 and CXCR4 may be employed for specific recruitment of the Th2 subset. A combination of the ligands may also be employed.

Various homologs of the aforementioned T-cell recruiting agents, including functional fragments thereof, or variants thereof, are known in the art. Representative examples of homologs include related proteins from fly, mouse, rat, pig, cow, monkey, humans or the like. The homologs preferably include human or mouse homologs of the aforementioned recruiting agents.

The scaffolds of the instant invention are adapted for the preferential recruitment of a single type or single sub-type of cell, for example, preferential recruitment of T-cells and particularly a subset of Treg cells or NK cells. Preferential recruitment is characterized by an accumulation of at least 10%, at least 20%, at least 30%, at least 50%, at least 75%, at least 100%, at least 2-fold, at least 5-fold, at least 8-fold, at least 10-fold, or greater increase in one or more of a particular type of immune cells (e.g., T cells, B-cells, DC/macrophages) in the device compared to other types of immune cells in the device (or in control scaffolds that are devoid of recruitment agents). In scaffolds that are adapted to recruit a combination of immune cells, e.g., a combination of T-cells and DC/macrophages, preferential recruitment is characterized where the total percentage of recruited cells is at least 10%, at least 20%, at least 30%, at least 50%, at least 75%, at least 100%, at least 2-fold (i.e., 200%), at least 5-fold, at least 8-fold, at least 10-fold, or greater than other types of immune cells in the device (or in control scaffolds). Particularly, preferential recruitment is characterized by 1-10 fold increase in the number of the cells of interest compared to other immune cells.

In one embodiment, the instant invention relates to MSR-SLB scaffolds further comprising a recruitment agent which is GM-CSF, an agonist thereof, a mimetic thereof, a fragment thereof, a variant thereof, or a combination thereof. Preferably, the recruitment agent is GM-CSF in combination with at least one of CCL-21, CCL-19, Flt-3 or GCSF. Representative examples of such recruitment agents include, e.g., human GM-CSF (NCBI Accession #NP_000749.2) and mouse GM-CSF (NCBI Accession #NP_034099.2). In another embodiment, the instant invention relates to MSR-SLB scaffolds containing fragments of GM-CSF, e.g., a polypeptide containing amino acids 18-144 of the hGM-CSF sequence. In yet another embodiment, the invention relates to scaffolds containing GM-CSF variants including, for example, VAR_013089 and VAR_001975, the sequences of which have been accessioned in UNIPROT (Accession No. P04141). In another embodiment, the invention relates to MSR-SLB scaffolds containing GM-CSF mimetics including, for example, antibodies binding to GM-CSF receptor, e.g., those described by Monfardini et al., *Curr Pharm Des.*, 8(24): 2185-99, 2002.

Embodiments of the invention further provide for scaffolds for manipulating immune cells which comprise a plurality of additional agents. In such embodiments, the additional agent may comprise a growth factor, a cytokine, a chemokine, an interleukin, an adhesion signaling molecule, an integrin signaling molecule or a fragment thereof or a combination thereof.

Representative examples of growth factors/cytokines include, but are not limited to, adrenomedullin (AM), angiopoietin (Ang), autocrine motility factor, bone morphogenetic proteins (BMPs), brain-derived neurotrophic factor (BDNF), epidermal growth factor (EGF), erythropoietin (EPO), fibroblast growth factor (FGF), foetal Bovine Somatotrophin (FBS) glial cell line-derived neurotrophic factor (GDNF), granulocyte colony-stimulating factor (G-CSF), granulocyte macrophage colony-stimulating factor (GM-CSF), growth differentiation factor-9 (GDF9), hepatocyte growth factor (HGF), hepatoma-derived growth factor (HDGF), insulin-like growth factor (IGF), keratinocyte growth factor (KGF), migration-stimulating factor (MSF), myostatin (GDF-8), nerve growth factor (NGF), neurotrophins, platelet-derived growth factor (PDGF), thrombopoietin (TPO), T-cell growth factor (TCGF), transforming growth factor (TGF-α or TGF-β), tumor necrosis factor-alpha (TNF-α), vascular endothelial growth factor (VEGF), Wnt, placental growth factor (PGF), or functional fragment thereof, or a combination thereof.

Representative types of interleukins include, but are not limited to, IL-1 (activates T cells, B-cells, NK cells, and macrophages), IL-2 (activates B-cells and NK cells), IL-3 (stimulates non-lymphoid cells), IL-4 (growth factor for activated B cells, resting T cells, and mast cells), IL-5 (for differentiation of activated B cells), IL-6 (growth factor for plasma cells and T-cells), IL-7 (growth factor for pre B-cells/pre T-cells and NK cells), IL-10 (activates macrophages, B-cells, mast cells, Th1/Th2 cells), IL-12 (activates T cells and NK cells), IL-17 (activates Th cells). Functional fragments of interleukins, which are characterized by their ability to modulate the activity of target cells, may also be employed.

Optionally, the scaffolds may contain adhesion molecules, which may also serve as signaling agents. Representative examples of adhesion signaling molecules include, but are not limited to, fibronectin, laminin, collagen, thrombospondin 1, vitronectin, elastin, tenascin, aggrecan, agrin, bone sialoprotein, cartilage matrix protein, fibronogen, fibrin, fibulin, mucins, entactin, osteopontin, plasminogen, restrictin, serglycin, SPARC/osteonectin, versican, von Willebrand Factor, polysaccharide heparin sulfate, connexins, collagen, RGD (Arg-Gly-Asp) and YIGSR (Tyr-Ile-Gly-Ser-Arg) peptides and cyclic peptides, glycosaminoglycans (GAGs), hyaluronic acid (HA), condroitin-6-sulfate, integrin ligands, selectins, cadherins and members of the immunoglobulin superfamily. Other examples include neural cell adhesion molecules (NCAMs), intercellular adhesion molecules (ICAMs), vascular cell adhesion molecule (VCAM-1), platelet-endothelial cell adhesion molecule (PECAM-1), L1, and CHL1. Functional fragments of the adhesion molecules, which are characterized by their ability to modulate the binding of target cells to the scaffolds of the invention, may also be employed. Particularly, adhesion molecules comprise peptides or cyclic peptides containing the amino acid sequence arginine-glycine-aspartic acid (RGD), which is known as a cell attachment ligand and found in various natural extracellular matrix molecules. In another embodiment, the adhesion peptide is a collagen mimic. Representative examples include, the peptide having the structure GGYGGGPC(GPP)5GFOGER(GPP)5GPC, wherein O is hydroxyproline. Such peptides may be collectively referred to as GFOGER peptides. GFOGER peptides have been previously shown to be particularly good for T cell adhesion. See, Stephan et al, *Nature Biotechnology* 33, 2015.

A polymer matrix with such a modification provides cell adhesion properties to the scaffold of the invention, and sustains long-term survival of mammalian cell systems, as well as supporting cell growth and differentiation. The adhesion molecules may be coupled to the polymer matrix is accomplished using synthetic methods which are in general known to one of ordinary skill in the art and are described in the examples. See, e.g., Hirano et al., *Advanced Materials*, 17-25, 2004; Hermanson et al., *Bioconjugate Techniques*, p. 152-185, 1996; Massia and Hubbell, *J. Cell Biol.* 114:1089-1100, 1991; Mooney et al., *J. Cell Phys.* 151:497-505, 1992; and Hansen et al., *Mol. Biol. Cell* 5:967-975, 1994, the disclosures in which are incorporated by reference.

Depending on the target cell type, it may be preferable to employ adhesion signaling molecules that are specific for the target cells. Thus, in one embodiment, the scaffolds contain adhesion receptors that are useful in the binding/sequestration of T-cells. In these embodiments, the scaffolds may contain T-cell specific adhesion molecules, for example, a receptor selected from the group consisting of MHC class II (for CD4+ cells), MHC class I (for CD8+ cells), LFA-3 (CD2 ligand), ICAM1 (ligand for LFA-1) or a variant thereof, a fragment thereof or a combination thereof.

Depending on need, the scaffolds may be specifically formulated to contain a subset of recruitment agents and adhesion molecules so as to manipulate a particular subset of immune cells, e.g., a particular sub-population of T-cells. In these embodiments, the scaffolds may be formulated/fabricated using agents that specifically bind to cell-surface markers that are expressed in the target cells. For example, in the context of T-cells, the scaffolds may be adapted for the preferential recruitment of helper T-cells ($T_H$ cells; which differentially express CD4+), cytotoxic T-cells (T. cells; which differentially express CD8+), memory T-cells ($T_m$ cells; which differentially express CD45RO), suppressor T-cells ($T_s$ which cells), regulatory T-cells (Tregs; further characterized as FOXP3+ Treg cells and FOXP3− Treg), natural killer T-cells (NK cells; differentially express CD1d+), mucosal associated invariant (MAITs; differentially express MR1), gamma delta T cells, (γδ T cells; comprise TCRs containing one γ-chain and one δ-chain). Such agents which bind to cell-surface markers may include, for example, haptens, peptides, ligands, antibodies, or the like. Other routine techniques for enriching the isolates with one or more cell subtype may be optionally used in situ or ex situ.

The scaffolds may also be adapted for recruiting immune cells that are specific for a disease. For example, a plurality of T cells that are specific for a particular type of autoimmune disease may be recruited. Thus in one embodiment, scaffolds that are useful in the diagnosis of autoimmune disorders may be formulated to contain recruitment agents that are specific to the immune cells implicated in the disorder. Such recruitment agents may, for example, be specific to regulatory T cells (Tregs), suppressor T cells (Ts) or a combination thereof. In a related embodiment, scaffolds that are useful in the diagnosis of cancers may be formulated to contain recruitment agents for preferentially recruiting cancer-specific T-cell types, e.g., cytotoxic T cells (Tc), natural killer cells (NK) or a combination thereof.

In certain embodiments, the scaffold is useful to pan for disease-specific cells. Such may include, for example, cells that directly promote disease progression. In the context of many autoimmune diseases, the disease may mediate and promote via targeted killing of specific population of cells, e.g., beta cells of pancreas in T1D and neuronal cells in multiple sclerosis. In other autoimmune diseases, the disease may be precipitated by targeted attack of specific epitopes such as, for example, rheumatoid factors (RF) and citrullinated peptides (ACPA) in the context of rheumatoid arthritis and antigens present in the gut flora in the context of Crohn's disease. The targeted destruction of the cells generally involves specific type or subset of immune cells. Thus, based on the nature and properties of the cellular targets, immune cells that are specific thereto may be preferentially manipulated using the scaffolds of the instant invention.

In the aforementioned embodiments, the scaffolds are provided with antigens to which disease-specific immune cells, e.g., T cells, bind. These autoimmune cells can be manipulated and optionally re-programmed to a non-autoimmune phenotype. Methods of reprogramming T-cells to pluripotency are known in the art. See, Nishimura et al., *Stem Cell* 12, 114-126 (2013); Themeli et al., *Nature Biotechnology* 31, 928-933 (2013). In certain instances, particularly in the context of cancer-specific T-cells, the reprogrammed cells may be rejuvenated to target the cancer. Alternately, in the context of T-cells that are specific to autoimmune diseases, the cells may be eliminated.

In certain embodiments, the scaffold of the invention are fabricated as porous structures that have been engineered to sustain antigen presentation. Methods for fabricating porous scaffolds have been described in the art. See, for example, U.S. Publication Nos. 2011/0020216, 2013/0202707, 2011/0020216 and U.S. Pat. No. 8,067,237, the disclosures in which are incorporated by reference herein.

Embodiments of the invention further provide for scaffolds containing MSR-SLB scaffolds that possess the desired stability for various ex vivo and in vivo applications. For example, the scaffolds are stable in tissue culture applications, cell growth experiments, or as transplant material to be administered into tissues (harvested or engineered) and also into subjects. In one embodiment, the invention relates to mesoporous silica microrod-lipid bilayer (MSR-SLB) scaffolds which retain a continuous, fluid architecture for at least 0.5 days, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 25 days, 30 days, 35 days, 40 days, 45 days, 50 days, or more. The stability and/or fluid architecture of the scaffolds may be monitored using routine techniques, e.g., the microscopic visualization techniques illustrated in the Examples below.

II. Methods of Making the Scaffolds of the Invention

Figure 24:
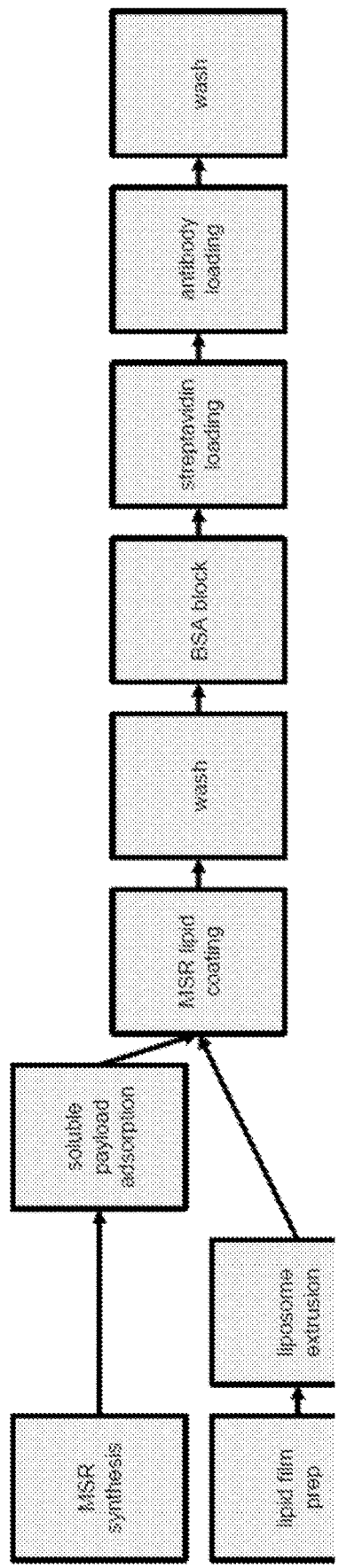
FIG. 24 outlines a representative scheme for making the scaffolds of the instant invention.

Embodiments of the invention further relate to methods for making the antigen-presenting cell mimetic scaffolds (APC-MS) of the invention. The method comprises providing a base layer comprising high surface area mesoporous silica micro-rods (MSR); optionally loading the T-cell homeostatic agents on the MSR; layering a continuous, fluid supported lipid bilayer (SLB) on the base layer comprising the MSRs, thereby generating an MSR-SLB scaffold; loading the T-cell homeostatic agents on the MSR-SLB scaffold if step (b) is not carried out; optionally blocking one or more non-specific integration sites in the MSR-SLB scaffold with a blocker; and loading the T-cell activating molecules and the T-cell co-stimulatory molecules onto the MSR-SLB scaffold, thereby making the APC-MS. In these embodiments, the method(s) may include further loading at least one additional agent which is a growth factor, a cytokine, an interleukin, an adhesion signaling molecule, an integrin signaling molecule, or a fragment thereof or a combination thereof in the scaffold. Methods for loading the additional ingredients have been described previously in the device fabrication section. A representative method for making the scaffolds of the invention is provided in FIG. 24.

In one embodiment, a mixture of functional molecules containing a 1:1 mixture of the T-cell activating molecules and the T-cell co-stimulatory molecules (e.g., anti-CD3 antibody and anti-CD28 antibody) is combined with the MSR-SLB scaffold such that the weight ratio of the functional molecules: MSR-SLB scaffold is between about 1:2 and about 1:20, preferably between about 1:4 and about 1:15, a particularly between about 1:5 to about 1:10. The weight ratio of the T-cell activating molecule and the T-cell co-stimulatory molecule may be adjusted, e.g., between about 5:1 to about 1:5, while retaining the same dry weight ratio between the functional molecules and the MSR-SLB scaffold.

Furthermore, embodiments of the invention further relate to methods of making the APC-MS by assembling a plurality of scaffolds to generate stacks with sufficient porosity to permit infiltration of T cells, more specifically, distinct sub-populations of helper T-cells or cytotoxic T-cells.

III. Methods for Using the Scaffolds of the Invention

The scaffolds of the invention may be used for various applications, including, but not limited to, manipulation of target effector cells, e.g., T-cells, isolation of a specific population of effector cells, e.g., a sub-population of CD8+ T-cells, diagnosis and therapy of diseases, and the production of compositions and kits for the diagnosis and therapy of diseases.

Methods for the Manipulation of Target Cells

In one embodiment, the instant invention provides a method for manipulating target effector cells or a sub-population thereof (e.g., helper T-cells or cytotoxic T-cells). In this context, the term "manipulation" includes, for example, activation, division, differentiation, growth, expansion, reprogramming, anergy, quiescence, senescence, apoptosis or death of the target effector cells.

In one embodiment, the target effector cells, e.g., T-cells, are manipulated (e.g., activated) in situ by providing scaffolds of the invention such that the target effector cells come into contact with the scaffolds. In order to facilitate the contact, the scaffolds may be implanted at a suitable site in a subject, e.g., subcutaneously or intravenously. In other embodiments, the target cells are manipulated ex vivo by culturing a sample containing target effector cells with the scaffolds of the invention.

A variety of target effector cells may be manipulated, including, fresh samples employed from subjects, primary cultured cells, immortalized cells, cell-lines, hybridomas, etc. The manipulated cells may be used for various immunotherapeutic applications as well as for research.

The site of manipulation of target effector cells may be in situ or ex situ. Thus, in one embodiment, the cells are manipulated in situ (e.g., within the scaffold). In this context, the cells need not be physically removed from the scaffold to be manipulated. In another embodiment, the cells are manipulated ex situ (e.g., by first removing the cells from the scaffold and manipulating the removed cells). When the scaffolds are implanted into a subject, the cells may be manipulated at or near the implant site. In other embodiments, the implanted scaffolds may be first removed from the implant site and the effector cells may be manipulated in situ or ex situ, as described previously.

In certain embodiments, the scaffolds used in manipulating effector cells may be provided with antigen presenting cells (APC) and/or various antigens derived from such APCs. These secondary agents (e.g., APCs or antigens derived from APCs) may be provided in the scaffold structure or provided extrinsically, e.g., in culture media. In certain embodiments, the scaffolds may be provided with various antigens that attract and/or recruit APCs. Representative examples of such attracting and/or recruiting molecules have been provided in the previous sections.

In certain embodiments, the antigen-containing scaffolds may be used to manipulate target effector cells in vivo. For such applications, the scaffolds may be implanted inside a blood vessel, in the lymphatic tissue, at the tumor site, at a disease site (e.g., areas surrounding tissues affected by rheumatoid arthritis) or subcutaneously, such that the target effector cells come into contact with the scaffolds. Alternately, the scaffolds may be injected in a minimally invasive manner, for example, via needle, catheter or the like. The implanted scaffolds may be allowed to remain at the implant site for about 0.5 day, 1 day, 2 days, 3 days, 4 days, 5 days, 6 days, 1 week, 2 weeks, 3 weeks, 4 weeks, 1 month, 2 months, 3, months, 6 months, 7 months, 8 months, 9 months. 1 year, 2 years, or more. Periodically, the scaffolds may be explanted to study, analyze, or even further manipulate the effector cells.

In a related embodiment, the instant invention relates to manipulation of antigen-specific effector cells in situ. In this context, the scaffolds of the present invention may contain antigens of interest which are adsorbed onto the scaffold using the same strategies for adsorbing the functional molecules. Alternately, the scaffolds of the invention may be incubated with a sample containing the antigen-specific effector T-cells in culture media together with APCs that display the antigen of interest. The target effector cells are then allowed to come into contact with the scaffolds and the functional molecules contained in the scaffolds act together to promote the manipulation of effector cells. Purely as a representative embodiment, as described in the Examples section, a sample containing T cells is incubated with the scaffolds of the present invention, which activates, co-stimulates and homeostatically maintains the target effector cells. The sample may be incubated with the scaffold for about 1 day to 30 days, for about 1 to 15 days or for about 4 to 13 days, e.g., for about 7-8 days, resulting in the selective manipulation of the effector cell population. The antigen-specific effector cells may be additionally manipulated by selecting cells based on the expression of certain gene products, e.g., T-cell receptors (TCR) that recognize the antigen or the antigen-presenting cells of interest.

Embodiments described herein further relate to methods for manipulating antigen-specific effector cells ex situ, wherein the scaffolds are provided with the APC expressing the antigen of interest or the antigen itself. The manipulation step may be carried out ex situ or in situ.

In another embodiment, the effector target cells which are specific to the antigen or APCs may be selectively manipulated over other effector cells (e.g., favoring CD8+ T-cells over CD4+ T-cells). For example, a sample containing CD8+ T-cells (along with CD4+ T-cells) may be incubated with the scaffolds of the present invention which are mechanically or chemically fabricated to permit infiltration and/or sequestration of CD8+ T-cells. The infiltrated and/or sequestered CD8+ T-cells may be further expanded, activated, proliferated, or grown using techniques known in the art. Representative methods have been described previously.

In another embodiment, the effector target cells which are specific to the antigen or APCs may be undesired (e.g., regulatory/suppressor T-cells) and they are induced to undergo apoptosis, anergy or death following contact with the scaffolds of the instant invention. For example, a sample containing regulatory T cells (along with other T-cells) may be incubated with the scaffolds of the present invention which are mechanically or chemically fabricated to permit infiltration and/or sequestration of regulatory/suppressor T-cells. The infiltrated and/or sequestered T-cells may be eliminated using techniques known in the art.

In this context, the identity of the cells that have infiltrated and/or are sequestered in the scaffolds of the invention may be further determined using art-known techniques. Thus, in one embodiment, the gene product for identifying or selecting for activated T cells may be a cell surface marker or cytokine, or a combination thereof. Cell surface markers for identifying activated T cells include, but are not limited to, CD69, CD4, CD8, CD25, HLA-DR, CD28, and CD134. CD69 is an early activation marker found on B and T lymphocytes, NK cells and granulocytes. CD25 is an IL-2 receptor and is a marker for activated T cells and B cells. CD4 is a TCR coreceptor and is marker for thymoctes, TH1- and TH2-type T cells, monocytes, and macrophages. CD8 is also a TCR coreceptor and is marker for cytotoxic T cells. CD134 is expressed only in activated CD4+ T cells.

Cell surface markers for selecting for activated T cells include, but are not limited to, CD36, CD40, and CD44. CD28 acts as a stimulatory T-cell activation pathway independent of the T-cell receptor pathway and is expressed on CD4+ and CD8+ cells. CD36 is a membrane glycoprotein and is a marker for platelets, monocytes and endothelial cells. CD40 is a marker for B cells, macrophages and dendritic cells. CD44 is a marker for macrophages and other phagocytic cells. Subsets of T cells may be isolated by using positive selection, negative selection, or a combination thereof for expression of cell surface gene products of helper T cells or cytotoxic T cells (e.g., CD4 vs. CD8). Cytokines for identifying activated T cells of the present invention include, but are not limited to cytokines produced by TH1-type T cells (cell-mediated response) and TH2-type T cells (antibody response). Cytokines for identifying activated TH1-type T cells include, but are not limited to, IL-2, gamma interferon (IFN-γ) and tissue necrosis factor alpha (TNFα). Cytokines for identifying activated TH2-type T cells include, but not limited to, IL-4, IL-5, IL-10 and IL-13. Subsets of T cells may also be isolated by using positive selection, negative selection, or a combination thereof for expression of cytokine gene products of helper T cells or cytotoxic T cells (e.g., IFN-γvs. IL4).

An activated TH1-type T cell specific for an antigen of interest may be isolated by identifying cells that express CD69, CD4, CD25, IL-2, IFNγ, TNFα, or a combination thereof. An activated TH1-type T cell specific for an antigen of interest may also be isolated by identifying cells that express CD69 and CD4 together with IFNγ or TNFα. An activated TH2-type T cell specific for an antigen of interest may be isolated by identifying cells that express CD69, CD4, IL-4, IL-5, IL-10, IL-13, or a combination thereof. A combination of an activated TH1-type T cell and a TH2-type T cell specific for an antigen of interest may be isolated by identifying cells that express CD69, CD4, CD25, IL-2, IFNγ, TNFα, or a combination thereof and cells that express CD69, CD4, IL-4, IL-5, IL-10, IL-13, or a combination thereof.

The gene products used for positive or negative selection of the activated T cells of the present invention may be identified by immunoselection techniques known to those in the art which utilize antibodies including, but not limited to, fluorescence activated cell sorting (FACS), magnetic cell sorting, panning, and chromatography. Immunoselection of two or more markers on activated T cells may be performed in one or more steps, wherein each step positively or negatively selects for one or more markers. When immunoselection of two or more markers is performed in one step using FACS, the two or more different antibodies may be labeled with different fluorophores. Alternately, as described above, cells may be sorted using microbeads. For cell-surface expressed gene products, the antibody may directly bind to the gene product and may be used for cell selection. For cell-surface gene products expressed at low concentrations, magnetofluorescent liposomes may be used for cell selection. At low levels of expression, conventional fluorescently labeled antibodies may not be sensitive enough to detect the presence of the cell surface expressed gene product. Fluorophore-containing liposomes may be conjugated to antibodies with the specificity of interest, thereby allowing detection of the cell surface markers.

For intracellular gene products, such as cytokines, the antibody may be used after permeabilizing the cells. Alternatively, to avoid killing the cells by permeabilization, the intracellular gene product if it is ultimately secreted from the cell may be detected as it is secreted through the cell membrane using a "catch" antibody on the cell surface. The catch antibody may be a double antibody that is specific for two different antigens: (i) the secreted gene product of interest and (ii) a cell surface protein. The cell surface protein may be any surface marker present on T cells, in particular, or lymphocytes, in general, (e.g., CD45). The catch antibody may first bind to the cell surface protein and then bind to the intracellular gene product of interest as it is secreted through the membrane, thereby retaining the gene product on the cell surface. A labeled antibody specific for the captured gene product may then be used to bind to the captured gene product, which allows the selection of the activated T cell. Certain forms of cytokines are also found expressed at low concentration on the cell surface. For example, IFN-γ is displayed at a low concentration on the cell surface with kinetics similar to those of intracellular IFN-γ expression (Assenmacher, et al. *Eur J. Immunol*, 1996, 26:263-267). For forms of cytokines expressed on the cell surface, conventional fluorescently labeled antibodies or fluorophore containing liposomes may be used for detecting the cytokine of interest. One of ordinary skill in the art will recognize other techniques for detecting and selecting extracellular and intracellular gene products specific for activated T cells.

The T cells isolated by the methods of the present invention may be enriched by at least 40%-90% from whole blood. The T cells may also be enriched by at least 95% from whole blood. The T cells may also be enriched by at least 98% from whole blood. The T cells may also be enriched at least 99.5% from whole blood. Similar methods may be used in the in situ or ex situ manipulation of B-cells. In certain embodiments, cryopreserved cells are thawed and washed as described herein and allowed to rest for one hour at room temperature prior to activation.

Depending upon application, the dry weight ratios of scaffolds to cell sample may be adjusted. For example, the scaffold: cell dry weight ratio may range from 1:500 to 500:1 and any integer values in between may be used to manipulate effector cells. As those of ordinary skill in the art can readily appreciate, the ratio of scaffold to cells may dependent on the scaffold size relative to the target cell.

Expansion of T Cell Population

In a related embodiment, the present invention further relates to methods for expanding T-cells from a population of immune cells, e.g., expanding T-cells contained in sample containing B-cells, dendritic cells, macrophages, plasma cells, and the like. In another embodiment, the present invention also relates to methods for expanding a specific population of T-cells, e.g., expanding cytotoxic T-cells from a sample containing helper T-cells, natural killer T-cells, regulatory/suppressor T-cells, and the like. The specific sub-population of T-cells may be used downstream in various immunotherapeutic applications. Without wishing to be bound by any particular theory, it is believed that the APC-MS of the instant invention are particularly effective for the expansion of T-cells because the relatively large size and high aspect ratio of the mesoporous silica rods allow for the formation of large clusters of T-cells interacting with each rod which may promote the effective expansion of T-cells by allowing T-cell/T-cell interactions and/or paracrine signaling.

In one embodiment, the target effector cells, e.g., T-cells, are expanded (e.g., grown or differentiated) in situ by providing scaffolds of the invention such that the target effector cells come into contact with the scaffolds. In order to facilitate the contact, the scaffolds may be implanted at a suitable site in a subject, e.g., subcutaneously or intravenously. In other embodiments, the target cells are expanded ex vivo by culturing a sample containing target effector cells with the scaffolds of the invention. In one embodiment, ex vivo T cell expansion can be performed by first isolating T-cells from a sample and subsequently stimulating T-cells by contacting with the scaffolds of the invention, such that, the effector T-cells are activated, co-stimulated and homeostatically maintained.

In one embodiment of the invention, the T cells are primary T-cells obtained from a subject. The term "subject" is intended to include living organisms in which an immune response can be elicited (e.g., mammals) Examples of subjects include humans, dogs, cats, mice, rats, and transgenic species thereof. T-cells can be obtained from a number of sources, including peripheral blood mononuclear cells, bone marrow, lymph node tissue, cord blood, thymus tissue, tissue from a site of infection, spleen tissue, and tumors. In certain embodiments of the present invention, any number of primary T-cells and/or T-cell lines available in the art, may be used.

Studies on whole blood counts reveal that the number of T-cells in whole blood is very low. For example, according to the product catalog published by Stem Cell Technologies, Vancouver, BC, CANADA (Document #23629, VERSION 2.1.0), the leukocyte population in whole blood is about 0.1-0.2% (due to predominance of erythrocytes), of which T-cells make up about 7-24% of the overall leukocyte population. Among T-cells, CD4+ T-cells make up about 4-20% of the overall leukocyte population (translating to less than 0.04% of the overall cell population in whole blood) and CD8+ T-cells make up about 2-11% of the overall leukocyte population (translating to less than 0.022% of the overall cell population in whole blood). Thus, in certain embodiments of the present invention, methods of the invention may be coupled with other art-known techniques for enrichment of target cells. The enrichment step may be carried out prior to contacting the sample with the scaffolds of the instant invention. In another embodiment, the enrichment step may be carried out after the sample has been contacted with the scaffolds of the present invention.

In one embodiment, the effector cell population may be enriched using FICOLL separation. In one embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. The cells collected by apheresis may be washed to remove the plasma fraction and to place the cells in an appropriate buffer or media for subsequent processing steps. The cells are then washed with phosphate buffered saline (PBS). Alternately, the wash solution lacks calcium and may lack magnesium or may lack many if not all divalent cations. A semi-automated "flow-through" centrifuge may also be used according to the manufacturer's instructions. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, peripheral or whole blood T cells may be enriched by lysing the red blood cells and depleting the monocytes, for example, by centrifugation through a PERCOLL™ gradient. A specific subpopulation of T cells, such as CD28+, CD4+, CD8+, CD45RA+, and CD45RO+ T cells, can be further isolated by positive or negative selection techniques.

In accordance with the present invention, various sorting techniques may be optionally employed. For example, the expanded or manipulated T cell population may be further sorted using a combination of antibodies directed to surface markers unique to the cells. A preferred method is cell sorting and/or selection via magnetic immunoadherence or flow cytometry that uses a cocktail of monoclonal antibodies directed to cell surface markers present on the cells selected. For example, to enrich for CD4+ cells by negative selection, a monoclonal antibody cocktail typically includes antibodies to CD14, CD20, CD11b, CD16, HLA-DR, and CD8. In certain embodiments, it may be desirable to enrich or negatively select regulatory T cells which typically express CD4+, CD25+, CD62Lhi, GITR+, and FoxP3+.

For isolation of a desired population of cells, the concentration of cells and scaffold surface can be varied. In certain embodiments, it may be desirable to significantly decrease the volume in which the scaffolds and cells are mixed together (i.e., increase the concentration of cells), to ensure maximum contact of cells and scaffolds. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28− negative T cells, or from samples where there are many tumor cells present (i.e., leukemic blood, tumor tissue, etc.). Such populations of cells may have therapeutic value and would be desirable to obtain. For example, using high concentration of cells allows more efficient selection of CD8+ T cells that normally have weaker CD28 expression.

In a related embodiment, it may be desirable to use lower concentrations of cells. This can be achieved by lowering the scaffold:cell ratio, such that interactions between the scaffolds and cells are minimized. This method selects for cells that express high amounts of desired antigens to be bound to the scaffolds. For example, CD4+ T cells express higher levels of CD28 and are more efficiently captured than CD8+ T cells in dilute concentrations. In one embodiment, the concentration of cells used is $5 \times 10^6$/ml. In other embodiments, the concentration used can be from about $1 \times 10^5$/ml to $1 \times 10^9$/ml, and any integer value in between, e.g., $1 \times 10^5$/ml to $1 \times 10^8$/ml, $1 \times 10^6$/ml to $1 \times 10^7$/ml, $1 \times 10^7$/ml to $1 \times 10^9$/ml.

In one embodiment, the instant invention may include art-known procedures for sample preparation. For example, T cells may be frozen after the washing step and thawed prior to use. Freezing and subsequent thawing provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or other suitable cell freezing media containing for example, HESPAN and PLASMALYTE A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

Also contemplated in the context of the invention is the collection of blood samples or leukapheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment a blood sample or a leukapheresis is taken from a generally healthy subject. In certain embodiments, a blood sample or a leukapheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isolated from a blood sample or a leukapheresis from a subject prior to any number of relevant treatment modalities, including but not limited to treatment with agents such as antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxin, fludaribine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin). (Liu et al., *Cell* 66:807-815, 1991; Henderson et al., *Immun.* 73:316-321, 1991; Bierer et al., *Curr. Opin. Immun.* 5:763-773, 1993; Isoniemi (supra)). In a further embodiment, the cells are isolated for a patient and frozen for later use in conjunction with (e.g. before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g. Rituxan.

In a further embodiment of the present invention, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Scaffolds containing any ratio of T-cell activating molecules: T-cell co-stimulatory molecules may be used in accordance with the present methods. In one embodiment, wherein the T-cell activating molecule and the T-cell co-stimulatory molecules are both antibodies, a 1:1 ratio of each antibody may be used. In one embodiment, the ratio of CD3:CD28 antibody bound to the scaffolds ranges from 100:1 to 1:100 and all integer values there between. In one aspect of the present invention, more anti-CD28 antibody is bound to the scaffolds than anti-CD3 antibody, i.e. the ratio of CD3:CD28 is less than one. In certain embodiments of the invention, the ratio of anti CD28 antibody to anti CD3 antibody bound to the scaffolds is greater than 2:1. In one particular embodiment, a 1:100 CD3:CD28 ratio of antibody bound to scaffolds is used. In another embodiment, a 1:75 CD3:CD28 ratio of antibody bound to scaffolds is used. In a further embodiment, a 1:50 CD3:CD28 ratio of antibody bound to scaffolds is used. In another embodiment, a 1:30 CD3:CD28 ratio of antibody bound to scaffolds is used. In one preferred embodiment, a 1:10 CD3:CD28 ratio of antibody bound to scaffolds is used. In another embodiment, a 1:3 CD3:CD28 ratio of antibody bound to the scaffolds is used. In yet another embodiment, a 3:1 CD3:CD28 ratio of antibody bound to the scaffolds is used.

One aspect of the present invention stems from the surprising finding that wherein the method confers increased expansion of the population of T-cells after about 1 week of contact with the scaffold compared to a control scaffold containing the base layer containing high surface area mesoporous silica micro-rods (MSR) and the continuous, fluid supported lipid bilayer (SLB) but not containing the T-cell activating molecules and the T-cell co-stimulatory molecules. In one embodiment, in accordance with the methods of the invention, about a 10-fold to 1000-fold, preferably about a 50-fold to 500-fold, or greater, increase in the expansion of the population of T-cells was observed after about 1 week of contact with the scaffold compared to a control scaffold containing the base layer containing high surface area mesoporous silica micro-rods (MSR) and the continuous, fluid supported lipid bilayer (SLB) but not containing the T-cell activating molecules and the T-cell co-stimulatory molecules.

Another aspect of the present invention stems from the surprising finding that wherein the method confers increased expansion of the population of T-cells after about 1 week of contact with the scaffold as compared to a superparamagnetic spherical polymer particle (DYNABEAD) containing the T-cell activating molecules and the T-cell co-stimulatory molecules. In one embodiment, in accordance with the methods of the invention, about a 2-fold to 100-fold, preferably about a 5-fold to 20-fold, or greater, increase in the expansion of the population of T-cells was observed after about 1 week of contact with the scaffold compared to a superparamagnetic spherical polymer particle (DYNABEAD) containing the T-cell activating molecules and the T-cell co-stimulatory molecules.

Yet another aspect of the present invention stems from the surprising finding that manipulating the T-cells in accordance with the aforementioned methods improves the metabolic activity of T-cells. In particular, improved metabolic activity of T-cells was observed after 1 week of contact with the scaffold compared to a control scaffold containing the base layer containing high surface area mesoporous silica micro-rods (MSR) and the continuous, fluid supported lipid bilayer (SLB) but not containing the T-cell activating molecules and the T-cell co-stimulatory molecules. In one embodiment, in accordance with the methods of the invention, about a 2-fold to 100-fold, preferably about a 5-fold to 20-fold, or larger, improvement in the metabolic activity of the population of T-cells was observed after about 1 week of contact with the scaffold compared to a control scaffold comprising the base layer comprising high surface area mesoporous silica micro-rods (MSR) and the continuous, fluid supported lipid bilayer (SLB) but not containing the T-cell activating molecules and the T-cell co-stimulatory molecules.

Another aspect of the present invention stems from the surprising finding that the method confers better metabolic activity of the population of T-cells after about 1 week of contact with the scaffold compared to a superparamagnetic spherical polymer particle (DYNABEAD) containing the T-cell activating molecules and the T-cell co-stimulatory molecules. In one embodiment, in accordance with the methods of the invention, about a 1-fold (e.g., a 100% increase) to 20-fold, preferably a 2-fold to 10-fold increase, or a larger increase, was observed in the expansion of the population of T-cells was observed after about 1 week of contact with the scaffold compared to a superparamagnetic spherical polymer particle (DYNABEAD) containing the T-cell activating molecules and the T-cell co-stimulatory molecules.

Additionally, in accordance with the methods of the invention, it was found that the expanded T-cells are metabolically active for at least about 7 days post-contact with the scaffold. T-cell metabolic activity was measured via routine techniques, e.g., analyzing levels of cytokine production or monitoring cell doublings. Furthermore, in accordance with the methods of the invention, the expanded T-cells formed larger and more stable aggregates (e.g., lasting longer) than control scaffolds. For instance, in one experiment, the expanded T-cells formed stable aggregates for at least about 7 days post-contact with the scaffold whereas the aggregates had considerably disintegrated in samples incubated with the control scaffold containing only the MSR base layer and the SLB layer.

Further embodiments of the invention relate to methods for obtaining a polyclonal population of CD8+ cells, comprising, contacting the scaffolds of the invention with a subject's biological sample, thereby activating, co-stimulating, homeostatically maintaining and optionally expanding a population of T-cells present within the sample; contacting the T-cells in the sample with a reagent for detection of CD8+ cells; and isolating a sub-population of detected CD8+ T-cells from the sample.

In a related embodiment, the instant invention relates to methods for obtaining a polyclonal population of CD4+ cells, comprising, contacting the scaffolds of the invention with a subject's biological sample, thereby activating, co-stimulating, homeostatically maintaining and optionally expanding a population of T-cells present within the sample; contacting the T-cells in the sample with a reagent for detection of CD4+ cells; and isolating a sub-population of detected CD4+ T-cells from the sample.

In a related embodiment, the instant invention relates to methods for obtaining a polyclonal population of CD4+/FOXP3+ or CD4+/FOXP3− cells. The method comprises contacting the scaffolds of the invention with a subject's biological sample, thereby activating, co-stimulating, homeostatically maintaining and optionally expanding a population of T-cells present within the sample; contacting the T-cells in the sample with a reagent for detection of CD4+ cells; further contacting the T-cells with a reagent for detection of FOXP3+ cells; and isolating a sub-population of detected CD4+/FOXP3+ or CD4+/FOXP3− T-cells from the sample. In these embodiments, the reagent for the detection and/or isolation of CD4+ and/or FOXP3+ T-cells is preferably an antibody or antigen-binding fragment thereof which specifically binds to CD4+ and FOXP3 markers. In this context, insofar as FOXP3 is recognized as a master regulator of the regulatory pathway in the development and function of regulatory T cells (which turn the immune response down), it may be desirable to isolate FOXP3+ cells for certain applications and FOXP3− cells for other applications. For instance, in cancer therapy applications, it may be desirable to eliminate or reduce regulatory T cell activity in the T-cell pharmaceutical compositions. Accordingly, the methods may be adapted to screen for FOXP3− cells. Alternately, in the context of treatment of autoimmune disease, it may be desirable to increase regulatory T cell activity in the T-cell pharmaceutical compositions (as attenuated regulatory T cell activity may be contributing to the body's autoimmune condition). Accordingly, in such instances, the formulation methods may be modified to positively screen for and include FOXP3+ cells. In yet another embodiment, the instant invention relates to a method for obtaining a polyclonal population of effector memory and/or effector T-cells. The method comprises contacting the scaffolds of the invention with a subject's biological sample, thereby activating, co-stimulating, homeostatically maintaining and optionally expanding a population of T-cells present within the sample; contacting the T-cells in the sample with a reagent for detection of CD44+ cells; further contacting the T-cells with a reagent for detection of CD62L; and isolating a sub-population of detected CD4+//CD62L+ or CD4+//CD62L− T-cells from the sample. In these embodiments, the effector memory and/or effector T-cells are preferably CD4+//CD62L−.

In yet another embodiment, the instant invention relates to a method for obtaining a polyclonal population of activated CD8+ T-cells. The method comprises contacting the scaffolds of the invention with a subject's biological sample, thereby activating, co-stimulating, homeostatically maintaining and optionally expanding a population of T-cells present within the sample; contacting the T-cells in the sample with a reagent for detection of CD8+ cells; further contacting the T-cells with a reagent for detection of CD69+; and isolating a sub-population of detected CD8+//CD69+ or CD8+//CD69− T-cells from the sample. In these embodiments, the activated T-cells are preferably CD8+/CD69+.

In yet another embodiment, the instant invention relates to a method for obtaining a polyclonal population of cytotoxin-secreting T-cells. The method comprises contacting the scaffolds of the invention with a subject's biological sample, thereby activating, co-stimulating, homeostatically maintaining and optionally expanding a population of T-cells present within the sample; contacting the T-cells in the sample with a reagent for detection of CD8+ cells; further contacting the T-cells with a reagent for detection of granzyme B; and isolating a sub-population of detected CD8+//granzyme B+ or CD8+//Granzyme B− T-cells from the sample. In these embodiments, the cytotoxin-secreting T-cells are preferably CD8+/Granzyme B+.

In yet another embodiment, the instant invention relates to a method for obtaining a polyclonal population of activator cytokine-secreting T-cells. The method comprises contacting the scaffolds of the invention with a subject's biological sample, thereby activating, co-stimulating, homeostatically maintaining and optionally expanding a population of T-cells present within the sample; contacting the T-cells in the sample with a reagent for detection of IFNγ+; and isolating a sub-population of detected IFNγ+ T-cells from the sample. In these embodiments, the T-cells are preferably IFNγ-secreting cells.

In yet another embodiment, the instant invention relates to a method for obtaining a polyclonal population of memory T-cells. The method comprises contacting the scaffolds of the invention with a subject's biological sample, thereby activating, co-stimulating, homeostatically maintaining and optionally expanding a population of T-cells present within the sample; contacting the T-cells in the sample with a reagent for detection of CD62L+CCR7+ T-cells; and isolating a sub-population of detected CD62L+CCR7+ T-cells from the sample. In these embodiments, the T-cells are preferably CD62L+CCR7+ CD4+ central memory T-cells. See, Okada et al., *Int Immunol.*, 20(9):1189-99, 2008. In another embodiment, the instant invention relates to a method for obtaining a polyclonal population of memory T-cells comprising contacting the scaffolds of the invention with a subject's biological sample, thereby activating, co-stimulating, homeostatically maintaining and optionally expanding a population of T-cells present within the sample; contacting the T-cells in the sample with a reagent for detection of CD62L+CCR7+ T-cells; and isolating a sub-population of detected CD62L−CCR7− T-cells from the sample. In these embodiments, the CD62L−CCR7− T-cells are effector memory T-cells. See, Sallusto et al., *Nature* 401: 708-712, 1999.

In yet another embodiment, the instant invention relates to a method for detecting and/or removing a polyclonal population of exhausted T-cells from a sample. The method comprises contacting the scaffolds of the invention with a subject's biological sample, thereby activating, co-stimulating, homeostatically maintaining and optionally expanding a population of T-cells present in the sample; contacting the T-cells in the sample with a reagent for detection of CD8+ T cells; further contacting the T-cells with a reagent for detection of PD-1+ T-cells; and isolating a sub-population of detected CD8+/PD-1+ T-cells from the sample. The CD8+/PD-1+ T-cells, which indicate exhausted cells, may be optionally eliminated from the sample.

In another embodiment for detecting and/or removing T-cells from a sample, the instant invention provides a method comprising contacting the scaffolds of the invention with a subject's biological sample, thereby activating, co-stimulating, homeostatically maintaining and optionally expanding a population of T-cells present within the sample; contacting the T-cells in the sample with a reagent for detection of a co-inhibitory receptor on T-cells; and isolating a sub-population of T-cells expressing the co-inhibitory receptor from the sample. The expression of co-inhibitory receptor generally indicates exhausted cells, which may be optionally eliminated from the sample. In these embodiments, the co-inhibitory receptor is a receptor selected from the group consisting of CTLA-4, TIM3, LAG3, 2B4, BTLA, CD160, and KLRG1. See, Legat et al., *Front Immunol.*, 2013 Dec. 19; 4:455

In the aforementioned embodiments, the reagents for the detection and/or isolation of cells are preferably an antibodies or antigen-binding fragments thereof, e.g., antibodies which specifically bind to the aforementioned markers, e.g., CD8, CD4, FOXP3, CD62L, PD-1, granzyme B, etc. The detection of these cell-surface markers is preferably carried out using FACS analysis.

The invention further relates to isolating polyclonal T-cell populations using one or more of the aforementioned methods and further detecting the production of a cytokine selected from the group consisting of interferon gamma (IFNγ), tissue necrosis factor alpha (TNFα), IL-2, IL-1, IL-4, IL-5, IL-10, and IL-13, or a combination thereof. The cytokines may permit validation of the isolation methods. For instance, wherein the manipulated T-cells are T-helper 1 (Th1) cells, the methods may comprise detecting the production of a cytokine selected from the group consisting of IL-2, interferon gamma (IFNγ) and tissue necrosis factor alpha (TNFα), or a combination thereof. Likewise, wherein the manipulated T-cells are T-helper 2 (Th2) cells and the method comprises detecting the production of a cytokine selected from the group consisting of IL-4, IL-5, IL-10 and IL-13, or a combination thereof. Furthermore, wherein the manipulated T-cells are cytotoxic T (Tc) cells, the methods may further comprise detecting the production of a cytokine selected from the group consisting of interferon gamma (IFNγ) and lymphotoxin alpha (LTα/TNFβ), or a combination thereof optionally together with the detection of a secreted cytotoxin selected from the group consisting of a granzyme or a perforin, or a combination thereof.

Using certain methodologies it may be advantageous to maintain long-term stimulation of a population of T cells following the initial activation and stimulation, by separating the T cells from the stimulus after a period of about 12 to about 14 days. The rate of T cell proliferation is monitored periodically (e.g., daily) by, for example, examining the size or measuring the volume of the T cells, such as with a Coulter Counter. In this regard, a resting T cell has a mean diameter of about 6.8 microns, and upon initial activation and stimulation, in the presence of the stimulating ligand, the T cell mean diameter will increase to over 12 microns by day 4 and begin to decrease by about day 6. When the mean T cell diameter decreases to approximately 8 microns, the T cells may be reactivated and re-stimulated to induce further proliferation of the T cells. Alternatively, the rate of T cell proliferation and time for T cell re-stimulation can be monitored by assaying for the presence of cell surface molecules, such as, a cell surface marker selected from the group consisting of CD69, CD4, CD8, CD25, CD62L, FOXP3, HLA-DR, CD28, and CD134, or a combination thereof. Additionally, the methods may be complemented by assaying for the presence of non T-cell surface molecules, such as, CD36, CD40, and CD44, or a combination thereof. In certain instances, the methods may be complemented by assaying for the presence of non T-cell surface molecules, such as, CD154, CD54, CD25, CD137, CD134, which are induced on activated T cells.

Diagnosis and Therapy of Diseases

Embodiments described herein further relate to methods for treating a disease or a disorder in a subject. In one embodiment, the disease is cancer. In another embodiment, the disease is an autoimmune disorder. In a third embodiment, the disease is a disease caused by a pathogen.

In these embodiments, a subject with a disease may be treated by contacting the subject's sample comprising a T-cell population with the antigen presenting cell-mimetic scaffold (APC-MS) of the invention, thereby activating, co-stimulating and homeostatically maintaining the population of T-cells; optionally expanding the population of T-cells; and administering the activated, co-stimulated, maintained and optionally expanded T-cells into the subject, thereby treating the disease in the subject. In one embodiment, the T-cell population is contacted with the scaffold for a period, e.g., 0.5 day, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 25 days, 30 days, 35 days, 38 days, 45 days, 50 days, 60 days, or more, and the cells contained therein are manipulated using one or more of the aforementioned techniques. Examples of manipulation include, for example, activation, division, differentiation, growth, expansion, reprogramming, anergy, quiescence, senescence, apoptosis, death, etc. The cells need not be physically removed from the scaffold to be manipulated. Thus in one embodiment, the scaffolds are contacted with the subject's sample in situ (e.g., by implanting the scaffold into the subject). In other embodiments, the cells are manipulated ex situ (e.g., incubating the scaffold and the subject's withdrawn blood sample).

In the therapeutic embodiments of the invention, the T cells administered to the mammal are about 4 to about 35 days old, whereupon the regression of the disease in the mammal is promoted. In some embodiments, the administered T cells are less than about 14 days old, e.g., about 7 to about 21 days old. The inventive methods provide numerous advantages. For example, T cells that are about 4 to about 14 days old are believed to provide improved in vivo proliferation, survival, and activity as compared to T cells that are about 60 days old or older. The period of time required to generate T cells for adoptive cell therapy (ACT) may be shortened from an average of about 44 days to a range of about 4 to about 15 days (or less than about 35 days, e.g., about 7 to about 15 days). Accordingly, more patients may be treated before their disease burden progresses to a stage in which administration of ACT may no longer be safe or possible. Furthermore, because preferred embodiments of the inventive methods do not require in vitro testing of specific antigen reactivity prior to administration, the inventive methods reduce the time, expense, and labor associated with the treatment of patients. Additionally, the inventive methods may advantageously administer T cells that are pooled from bulk cultures instead of those derived from microcultures. The development of a simpler and faster method to generate clinically effective T cells is believed to aid in the more widespread use of adoptive cell therapy. The inventive methods also advantageously utilize T cell cultures that could be falsely predicted to be unreactive in vivo by in vitro testing of specific antigen reactivity. Because T cell cultures generated from a single tumor specimen have diverse specific reactivities, the lack of in vitro antigen reactivity testing advantageously avoids having to choose only a few T cell cultures to expand, and therefore provides a more diverse repertoire of tumor reactivities to be administered to the patient. T cells that are about 4 to about 30 days old also contain a greater diversity of cells and a higher frequency of active/healthy cells than T cells. In addition, one or more aspects (e.g., but not limited to, culturing and/or expanding) of the inventive methods may be automatable.

An embodiment of the method comprises culturing autologous T cells. Tumor samples are obtained from patients and a single cell suspension is obtained. The single cell suspension can be obtained in any suitable manner, e.g., mechanically (disaggregating the tumor using, e.g., a GENTLEMACS™ Dissociator, Miltenyi Biotec, Auburn, Calif.) or enzymatically (e.g., collagenase or DNase). Single-cell suspensions of tumor enzymatic digests are cultured in scaffolds or scaffolds of the invention. The cells are cultured until confluence (e.g., about $2\times10^6$ lymphocytes), e.g., from about 2 to about 21 days, preferably from about 4 to about 14 days. For example, the cells may be cultured from 5 days, 5.5 days, or 5.8 days, 6.0 days, 6.5 days, 7.0 days to 21 days, 21.5 days, or 21.8 days, preferably from 10 days, 10.5 days, or 10.8 days to 14 days, 14.5 days, or 14.8 days.

An embodiment of the method comprises expanding cultured T cells. The cultured T cells are pooled and rapidly expanded. Rapid expansion provides an increase in the number of antigen-specific T-cells of at least about 10-fold (e.g., 10-, 20-, 40-, 50-, 60-, 70-, 80-, 90-, or 100-fold, or greater) over a period of about 7 to about 14 days, preferably about 14 days. More preferably, rapid expansion provides an increase of at least about 200-fold (e.g., 200-, 300-, 400-, 500-, 600-, 700-, 800-, 900-, or greater) over a period of about 7 to about 14 days, preferably about 14 days. Most preferably, rapid expansion provides an increase of at least about 400-fold or greater over a period of about 10 to about 14 days, preferably about 14 days. Optionally, the cells may undergo initial expansion in the scaffolds, upon which they are subject to rapid expansion. Under this two-step expansion protocol, an increase of about 1000-fold over a period of about 7 to 14 days may be achieved.

Expansion can be accomplished by any of a number of methods as are known in the art. For example, T cells can be rapidly expanded using non-specific T-cell receptor stimulation in the presence of feeder lymphocytes and either interleukin-2 (IL-2) or interleukin-15 (IL-15), with IL-2 being preferred. The non-specific T-cell receptor stimulus can include around 30 ng/ml of OKT3, a mouse monoclonal anti-CD3 antibody (available from Ortho-McNeil®, Raritan, N.J.). Alternatively, T cells can be rapidly expanded by stimulation of peripheral blood mononuclear cells (PBMC) in vitro with one or more antigens (including antigenic portions thereof, such as epitope(s), or a cell) of the cancer, which can be optionally expressed from a vector, such as an human leukocyte antigen A2 (HLA-A2) binding peptide, e.g., 0.3 µM MART-1:26-35 (27 L) or gp100:209-217 (210M), in the presence of a T-cell growth factor, such as 300 IU/ml IL-2 or IL-15, with IL-2 being preferred. The in vitro-induced T-cells are rapidly expanded by re-stimulation with the same antigen(s) of the cancer pulsed onto HLA-A2-expressing antigen-presenting cells. Alternatively, the T-cells can be re-stimulated with irradiated, autologous lymphocytes or with irradiated HLA-A2+ allogeneic lymphocytes and IL-2, for example.

An embodiment of the method comprises administering to the subject, the expanded T cells, wherein the T cells administered to the mammal are about 4 to about 35 days old. For example, the administered cells may be 6, 7, or 8 to 14, 15, or 16 days old. In some embodiments, the T cells administered to the mammal are about 4 to about 29 or about 7 to about 15 days old, or about 10 days old. In this regard, the T cells that are administered to the mammal according to an embodiment of the invention are "young" T cells, i.e., minimally cultured T cells.

Young T cell cultures that are administered to the mammal in accordance with an embodiment of the invention advantageously have features associated with in vivo persistence, proliferation, and antitumor activity. For example, young T cell cultures have a higher expression of CD27 and/or CD28 than T cells that are about 44 days old. Without being bound to a particular theory, it is believed that CD27 and CD28 are associated with proliferation, in vivo persistence, and a less differentiated state of T cells (the increased differentiation of T cells is believed to negatively affect the capacity of T cells to function in vivo). T cells expressing higher levels of CD27 are believed to have better antitumor activity than CD27-low cells. Moreover, young T cell cultures have a higher frequency of CD4+ cells than T cells that are about 44 days old.

In addition, young T cell cultures have a mean telomere length that is longer than that of T cells that are about 44 days old. Without being bound to a particular theory, it is believed that T cells lose an estimated telomere length of 0.8 kb per week in culture, and that young T cell cultures have telomeres that are about 1.4 kb longer than T cells that are about 44 days old. Without being bound to a particular theory, it is believed that longer telomere lengths are associated with positive objective clinical responses in patients, and persistence of the cells in vivo.

The T-cells can be administered by any suitable route as known in the art. Preferably, the T-cells are administered as an intra-arterial or intravenous infusion, which preferably lasts about 30 to about 60 minutes. Other examples of routes of administration include subcutaneous, intraperitoneal, intrathecal and intralymphatic.

Additionally, embodiments of the instant invention provide for various modes of administering the therapeutic compositions comprising the expanded cells. In one embodiment, the expanded cells are first purified and then administered into a subject. Alternately, the expanded cells may be mixed with the scaffolds of the invention prior to administration into the subject. Under this alternate approach, the scaffolds (APC-MS) may continue to stimulate cells in vivo and may also function to selectively manipulate target whole blood cells in the in vivo setting.

The therapeutic methods of the invention may involve re-stimulating the population of T-cells prior to the administration step. The re-stimulation step may be carried out using art-known techniques. In one embodiment, the re-stimulation step is carried out by re-incubating the cells with the scaffold composition. In another embodiment, re-stimulation is carried out by addition of phorbol 12-myristate 13-acetate (PMA, 10 ng/ml, Sigma-Aldrich, Inc.), ionomycin (0.5 µg/ml, Sigma-Aldrich, Inc.) and Brefeldin A (eBiosciences, Inc.). In yet another embodiment, the re-stimulation step is carried out by including an antigen (e.g., a pathogenic antigen or a cancer antigen) in the scaffold or extrinsically in the culture.

In one embodiment, the therapeutic methods are conducted by manipulating T-cells that are obtained from a blood sample, a bone marrow sample, a lymphatic sample or a splenic sample of a subject.

Accordingly, embodiments of the instant invention provide for methods for treating cancer in a subject. The method comprises contacting the subject's sample comprising a T-cell population with the antigen presenting cell-mimetic scaffold (APC-MS) of the invention, thereby activating, co-stimulating and homeostatically maintaining the population of T-cells; optionally expanding the population of T-cells; and administering the activated, co-stimulated, maintained and optionally expanded T-cells into the subject, thereby treating the cancer in the subject. In certain embodiments, the scaffolds may be provided with a cancer antigen. In one embodiment, the cancer antigen is presented, e.g., for recognition by T-cells, in an MHC molecule or a fragment thereof. In certain instances, whole cell products may be provided.

Representative examples of cancer antigens include, but are not limited to, MAGE-1, MAGE-2, MAGE-3, CEA, Tyrosinase, midkin, BAGE, CASP-8, β-catenin, β-catenin, γ-catenin, CA-125, CDK-1, CDK4, ESO-1, gp75, gp100, MART-1, MUC-1, MUM-1, p53, PAP, PSA, PSMA, ras, trp-1, HER-2, TRP-1, TRP-2, IL13Ralpha, IL13Ralpha2, AIM-2, AIM-3, NY-ESO-1, C9orf112, SART1, SART2, SART3, BRAP, RTN4, GLEA2, TNKS2, KIAA0376, ING4, HSPH1, C13orf24, RBPSUH, C6orf153, NKTR, NSEP1, U2AF1L, CYNL2, TPR, SOX2, GOLGA, BMI1, COX-2, EGFRvIII, EZH2, LICAM, Livin, Livinβ, MRP-3, Nestin, OLIG2, ART1, ART4, B-cyclin, Gli1, Cav-1, cathepsin B, CD74, E-cadherin, EphA2/Eck, Fra-1/Fosl 1, GAGE-1, Ganglioside/GD2, GnT-V, β1,6-N, Ki67, Ku70/80, PROX1, PSCA, SOX10, SOX11, Survivin, UPAR, WT-1, Dipeptidyl peptidase IV (DPPIV), adenosine deaminase-binding protein (AD Abp), cyclophilin b, Colorectal associated antigen (CRC)-C017-1A/GA733, T-cell receptor/CD3-zeta chain, GAGE-family of tumor antigens, RAGE, LAGE-I, NAG, GnT-V, RCAS1, α-fetoprotein, p120ctn, Pmel117, PRAME, brain glycogen phosphorylase, SSX-I, SSX-2 (HOM-MEL-40), SSX-I, SSX-4, SSX-5, SCP-I, CT-7, cdc27, adenomatous polyposis coli protein (APC), fodrin, HA, Connexin 37, Ig-idiotype, p15, GM2, GD2 gangliosides, Smad family of tumor antigens, imp-1, EBV-encoded nuclear antigen (EBNA)-I, UL16-binding protein-like transcript 1 (Multi), RAE-1 proteins, H60, MICA, MICB, and c-erbB-2, or an immunogenic peptide thereof, and combinations thereof.

In another embodiment, the cancer antigen is a neoantigen identified in a patient. A neoantigenic determinant is an epitope on a neoantigen, which is a newly formed antigen that has not been previously recognized by the immune system. Neoantigens are often associated with tumor antigens and are found in oncogenic cells. Neoantigens and, by extension, neoantigenic determinants can be formed when a protein undergoes further modification within a biochemical pathway such as glycosylation, phosphorylation or proteolysis, leading to the generation of new epitopes. These epitopes can be recognized by separate, specific antibodies. See, Schumacher et al., *Science* 348 (6230): 69-74, 2015. In one embodiment, the neoantigen may be detected in a patient-specific manner. Methods for detecting neoantigens from a patient sample, e.g., blood sample, are described in U.S. Pat. No. 9,115,402, which is incorporated by reference herein. In one embodiment, the neoantigen is a peptide derived from SF3B1, MYD88, TP53, ATM, Ab1, A FBXW7, a DDX3X, MAPK1, GNB1, CDK4, MUM1, CTNNB1, CDC27, TRAPPC1, TPI, ASCC3, HHAT, FN1, OS-9, PTPRK, CDKN2A, HLA-A11, GAS7, GAPDH, SIRT2, GPNMB, SNRP116, RBAF600, SNRPD1, Prdx5, CLPP, PPP1R3B, EF2, ACTN4, ME1, NF-YC, HLA-A2, HSP70-2, KIAA1440, CASP8, or a combination thereof. See, Lu et al., *Seminars in Immunology*, 28(1), 22-27, 2016.

In practicing the cancer therapeutic embodiments outlined above, it may be advantageous to provide scaffolds that have been fabricated with cytotoxic T-cell-specific activating molecules and cytotoxic T-cell-specific co-stimulatory molecules, optionally together with one or more additional agents that confer activation, division, differentiation, growth, expansion, or reprogramming of cytotoxic T cells. Representative examples of such molecules and agents have been provided above.

In certain embodiments, the sequestered and/or isolated cells may be genetically modified. In one embodiment, the effector cells are genetically modified to express a chimeric antigen receptor (CAR) specific for CD19 (CD19 CAR-T cells). This particular type of T-cells has produced a high rate of complete remission (CR) in adult and pediatric patients with relapsed and refractory B cell acute lymphoblastic leukemia (B-ALL) in small phase I clinical trials. See, Turtle et al. (*J Clin Invest.*, 126, 2123-38, 2016) and the references cited therein. Favorable results have also been seen in clinical trials of CD19 CAR-T cell therapy in non-Hodgkin's lymphoma (NHL) and chronic lymphocytic leukemia (CLL). These studies suggest that robust proliferation of transferred CAR-T cells in the recipient correlates with clinical response and that prolonged in vivo persistence of functional CAR-T cells may prevent disease relapse.

Accordingly, in one embodiment, the invention relates to methods for further formulating T-cell compositions for cancer therapy, comprising, further genetically modifying the T-cells obtained from the scaffolds. The genetic modification may be mediated ex situ or in situ. Any technique may be used to genetically modify T-cells, including, but not relating to, using viral vectors, plasmids, transposon/transposase systems, shRNA, siRNA, antisense RNA, and the like. In some embodiments, the T-cell has been genetically-modified using a gene editing system (e.g., a CRISPR/Cas9 system). In some embodiments, the isolated T-cells are genetically modified using a viral delivery system. In some embodiments, the isolated T-cells are genetically modified using a lentiviral system. In some embodiments, the isolated T-cells are genetically modified using a retroviral system. In some embodiments, the isolated T-cells are genetically modified using an adenoviral system. In some embodiments, the isolated T-cells are contacted with an agent that promotes interaction with the viral delivery system or viral sequestration (e.g., an agent that promotes receptor-mediated interactions with the viral delivery system or agents that promote electrostatic interactions with the viral delivery system).

In some embodiments, the isolated T-cells are genetically modified using a viral delivery system in situ. In embodiments where the isolated T-cells are genetically modified in situ the scaffold may comprise an agent that promotes viral sequestration. The agent(s) that promote viral sequestration may be present on the surface of the lipid bilayer of the MSR-SLB either through adsorption or by attachment to a lipid headgroup. In some embodiments, the agent that promotes viral sequestration is a fibronectin peptide, such as RetroNectin®. In some embodiments, the agent that promotes viral sequestration is an amphipathic peptide, such as Vectofusin-1®. In some embodiments, the scaffold may further comprise a T-cell activating molecule, a T-cell co-stimulatory molecule and/or a T-cell homeostatic agent. Without wishing to be bound by any particular theory, it is believed that when a T-cell is contacted with a scaffold comprising an agent that promotes sequestration in combination with a T-cell activating molecule, a T-cell co-stimulatory molecule and/or a T-cell homeostatic agent, the scaffold may facilitate the activation and expansion of T-cells which may lead to cell clustering and allow for a viral delivery system to be in close proximity with the T-cells thereby promoting more efficient transduction of the cells. The T-cell activating molecule, a T-cell co-stimulatory molecule and/or a T-cell homeostatic agent present on the scaffold may be selected to result in the deired T-cell phenotype which may enhance the therapeutic efficacy of the resulting T-cell (see, e.g., Sommermeyer et al, *Leukemia* 30(2): 492-500 (2016)).

In some embodiments, the isolated T-cells are genetically modified to express a chimeric antigen receptor (CAR). In one embodiment, CD4+ and CD8+ T cells are lentivirally transduced to express the CD19 CAR and a truncated human epidermal growth factor receptor (EGFRt) that enables identification of transduced cells by flow cytometry using the anti-EGFR monoclonal antibody cetuximab. Transduced EGFRt+ CD4+ and CD8+ T cells are enriched during culture by a single stimulation with irradiated CD19+ lymphoblastoid cell line (LCL). The median frequency of EGFRt+ CAR-T cells within the CD3+CD4+ and CD3+CD8+ subsets in the products at release for infusion, which confers good therapeutic outcome, is about 80% (range 50.0%-95.9%) and about 85% (range 13.0%-95.6%), respectively. See, Turtle et al. (*J Clin Invest.*, 126, 2123-38, 2016). The genetically modified T-cells may be further expanded by incubating the T-cell product with the scaffolds of the invention. In one embodiment, scaffolds containing CAR T-cell-specific antigens, e.g., CD19, CD22 or a fragment thereof or a variant thereof, may be employed to selectively expand the desired CAR T-cells.

In certain embodiments, the scaffolds are provided with products that are useful in practicing the cancer therapy methods. Representative examples include, for example, hybridomas of B-cells, stable lineages of T-cells, antibodies derived from B-cells or hybridomas thereof, receptors which bind to the cancer antigens (receptors which bind to MHC molecules presenting the antigens), including fragments thereof, nucleic acids encoding the receptors or antigen-binding domains thereof, nucleic acids encoding antibodies, including whole cells.

Embodiments of the instant invention provide for methods for treating an immunodeficiency disorder in a subject comprising contacting the subject's sample comprising a T-cell population with the antigen presenting cell-mimetic scaffold (APC-MS) of the invention, thereby activating, co-stimulating and homeostatically maintaining the population of T-cells; optionally expanding the population of T-cells; and administering the activated, co-stimulated, maintained and optionally expanded T-cells into the subject, thereby treating the immunodeficiency disorder in the subject.

In one embodiment, there is provided a method for treating an immunodeficiency disorder selected from the group consisting of primary immunodeficiency disorder and acquired immunodeficiency disorder, comprising contacting the subject's sample comprising a T-cell population with the APC-MS of the invention, thereby activating, co-stimulating and homeostatically maintaining the population of T-cells; optionally expanding the population of T-cells; and administering the activated, co-stimulated, maintained and optionally expanded T-cells into the subject, thereby treating the immunodeficiency disorder in the subject. In one embodiment, the immunodeficiency disorder may be an acquired immunodeficiency disorder, e.g., acquired immunodeficiency syndrome (AIDS) or a hereditary disorder, e.g., DiGeorge syndrome (DGS), chromosomal breakage syndrome (CBS), ataxia telangiectasia (AT) and Wiskott-Aldrich syndrome (WAS), or a combination thereof.

In practicing the therapy of immunodeficiency disorders, as outlined above, it may be advantageous to provide scaffolds that have been fabricated with helper T-cell-specific activating molecules and helper T-cell-specific co-stimulatory molecules, optionally together with one or more additional agents that confer activation, division, differentiation, growth, expansion, or reprogramming of helper T cells. Representative examples of such molecules and agents have been provided above.

Embodiments of the instant invention provide for methods for treating a pathogenic disease in a subject comprising contacting the subject's sample comprising a T-cell population with the antigen presenting cell-mimetic scaffold (APC-MS) of the invention, thereby activating, co-stimulating and homeostatically maintaining the population of T-cells; optionally expanding the population of T-cells; and administering the activated, co-stimulated, maintained and optionally expanded T-cells into the subject, thereby treating the pathogenic disease in the subject. In some instances, the immune cells or compositions derived from the manipulation step may be administered prophylactically, e.g., before the onset of the disease symptoms in the subject. Pathogenic diseases that may be treated in accordance with the aforementioned embodiment include, bacterial diseases, viral diseases, fungal diseases, or a combination thereof.

Embodiments of the instant invention provide for methods for treating an autoimmune disease in a subject. The method comprises contacting the subject's sample comprising a T-cell population with the antigen presenting cell-mimetic scaffold (APC-MS) of the invention, thereby activating, co-stimulating and homeostatically maintaining the population of T-cells; optionally expanding the population of T-cells; and administering the activated, co-stimulated, maintained and optionally expanded T-cells into the subject, thereby treating the autoimmune disease in the subject.

In the context of treating autoimmune diseases, it may be preferable not to administer active immune cells (as these are autoreactive) but rather quiescent, senescent or inactivated immune cells. Preferably, the immune cells are T-cells. Alternately, regulators of immune cells e.g., regulatory T cells or suppressor T cells, may be administered. The scaffolds/devices may be fabricated for the manipulation of Ts/Treg cell sub-populations, which, are then administered into subjects.

Accordingly, in some embodiments, the invention provides for a method for treating an autoimmune disease by administering to subject in need thereof, the scaffold of the invention, wherein the plurality of antigens in the scaffold are specific for the autoimmune disease, collecting a plurality of regulatory or suppressor T-cells in the scaffold/device, wherein the plurality of regulatory or suppressor T-cells are specific to the autoimmune antigens, and administering the plurality of regulatory T-cells or suppressor T-cells or products derived therefrom into the subject, thereby treating the autoimmune disease.

Cell products that are useful in practicing the therapy of autoimmune diseases include, for example, antibodies and receptors which bind to autoreactive cells, regulatory proteins located in suppressor or regulatory T-cells, including nucleic acid sequences which encode such molecules.

In the therapeutic embodiments described above, cells may be formulated at total cell concentrations including from about $5 \times 10^2$ cells/ml to about $1 \times 10^9$ cells/ml. Preferred doses of T cells range from about $2 \times 10^6$ cells to about $9 \times 10^7$ cells.

Embodiments of the instant invention further relate to therapy of diseases by administering one or more of the aforementioned compositions. The composition may be a pharmaceutical composition, which is administered by any means that achieve their intended purpose. For example, administration may be by parenteral, subcutaneous, intravenous, intraarterial, intradermal, intramuscular, intraperitoneal, transdermal, transmucosal, intracerebral, intrathecal, or intraventricular routes. Alternatively, or concurrently, administration may be by the oral route. The pharmaceutical compositions may be administered parenterally by bolus injection or by gradual perfusion over time.

The dosage administered may be dependent upon the age, sex, health, and weight of the recipient, kind of concurrent treatment, if any, frequency of treatment, and the nature of the effect desired. The dose ranges for the administration of the pharmaceutical compositions may be large enough to produce the desired effect, whereby, for example, autoreactive T cells are depleted and/or the autoimmune disease is significantly prevented, suppressed, or treated. The doses may not be so large as to cause adverse side effects, such as unwanted cross reactions, generalized immunosuppression, anaphylactic reactions and the like.

Embodiments described herein further relate to methods for detecting or diagnosing a disease or a disorder in a subject. Any disease or disorder may be detected or diagnosed using the aforementioned methods. Particularly preferably, the disease is an autoimmune disease selected from the group consisting of rheumatoid arthritis, lupus, celiac disease, inflammatory bowel disease or Crohn's disease, sjögren's syndrome polymyalgia rheumatic, multiple sclerosis, ankylosing spondylitis, Type 1 diabetes, alopecia areata, vasculitis, temporal arteritis, etc. In other embodiments, the disease is a cancer which is selected from the group consisting of head and neck cancer, breast cancer, pancreatic cancer, prostate cancer, renal cancer, esophageal cancer, bone cancer, testicular cancer, cervical cancer, gastrointestinal cancer, glioblastoma, leukemia, lymphoma, mantle cell lymphoma, pre-neoplastic lesions in the lung, colon cancer, melanoma, and bladder cancer. Pathogenic diseases that may be diagnosed in accordance with the aforementioned embodiment include, bacterial diseases, viral diseases, fungal diseases, or a combination thereof.

In these embodiments, a subject with a disease may be diagnosed by first contacting a subject's sample containing the immune cell of interest with a scaffold of the invention, wherein the antigens in the scaffold are specific to the disease. In one embodiment, the sample contains T-cells and the scaffold/device is contacted with the sample for a period, e.g., 0.5 days, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 25 days, 30 days, 35 days, 40 days, 45 days, 50 days, 60 days, or more, and the cells in the scaffold are analyzed using one or more of the aforementioned techniques. For example, in the context of diagnosing autoimmune diseases, the cells that are analyzed may include activated T-cells. In the context of cancer diagnosis, the cells that are analyzed my include tumor-antigen specific T-cells. In the context of pathogenic diseases, the cells that are analyzed may include T-cells which specifically eliminate the pathogens (e.g., by analyzing Th1 cells in case of intracellular pathogens and Th2 cells in case of extracellular pathogens).

The subject is an animal, preferably a mammal or a bird. Particularly preferably, the subject is selected from the group consisting of humans, dogs, cats, pigs, cows, buffalo and horses. Most preferably, the subject is a human. Any immune cell may be used in the diagnosis of the disease or disorder. Preferably, diagnosis is performed with a lymphocyte, e.g., T-cells.

The analytical step may be carried out using any routine methods. Accordingly, in one embodiment, the analytical step may involve determining the number of immune cells that are specific to the autoimmune disease. Any routine technique may be used to determine antigen-binding specificity of immune cells, e.g., loading cell samples onto antigen-coated surfaces, washing away non-specifically bound cells, and quantitating the number of antigen-specific cells (either in free form by releasing the bound cells or in bound form) using a detection agent (e.g., an antibody that binds to a cell-surface epitope located on the antigen-specific cells). In another embodiment, the analytical step may involve determining the physical or biological characteristics of the antigen-specific immune cells. Examples of physical characteristics include, for example, size, shape, reflectivity, morphology, density. Examples of biological characteristics include, for example, expression of particular cell surface markers, secretion of cytokines, reactivity to particular antigens or agents, patterns of gene expression.

The analytical step may be tied to a correlation step, wherein, the results of the analytical step are correlated to the parameter of interest. Representative types of parameters include, presence (or absence of disease), type of disease (e.g., aggressive vs. non-aggressive autoimmune disorder; druggable vs. non-druggable disease, e.g., antibiotic susceptible vs. antibiotic resistant bacterial infection, immunotherapy-resistant vs immunotherapy-sensitive cancer), stage of disease, progression/regression of disease (over time), etc. In one embodiment, the parameter relates to presence or absence of disease (which can be expressed in binary terms). In another embodiment, the parameter relates to staging of disease (which can be expressed in a nominal scale, e.g., stage I-IV, with stage IV being the highest). Yet in another embodiment, the parameter relates to odds or likelihood of occurrence of the disease, e.g., at least 20%, 30%, 40%, 50%, 60%, 70%, 80%, 2-fold, 3-fold, 5-fold, 10-fold, 20-fold or more.

In the aforementioned diagnostic methods the parameters may be compared to a baseline value. The baseline value may be a value that is pre-determined, e.g., in a population of healthy subjects. For example, where the antigen of interest is rheumatoid arthritis (RA) antigen, a baseline level of RA-specific antibodies (or T-cells) in healthy subjects may be used in the correlation step. Alternately, the baseline value may be experimentally identified using suitable controls. The skilled worker can use routine techniques to correlate and/or draw inferences between various subject groups.

Accordingly, embodiments of the invention relate to detecting or diagnosing autoimmune disease, cancer, or a pathogenic disease in a subject by contacting a subject's sample with the scaffolds of the invention containing antigens which are specific to the autoimmune disease, cancer disease, or pathogenic disease, and analyzing the immune cells contained therein. The contacting step may be performed in vivo (e.g., by implanting the scaffold in a subject) or ex vivo (e.g., by culturing a blood sample withdrawn from a subject with the scaffold). In certain embodiments, the analytical step may be performed by first removing the immune cells from the scaffolds using routine techniques, i.e., via ex situ analysis. For instance, mild detergents and enzymes may be used to dislodge the cells from the scaffolds. Alternately, the detection/analytical steps may be carried out without removing the cells from the scaffolds, i.e., via in situ analysis.

Related embodiments are directed to methods of monitoring the progression of a disease in a subject. The method comprises contacting a subject's sample with the scaffolds of the invention containing antigens that are specific to the disease and analyzing the immune cells contained therein. The number/types of immune cells contained in the device may offer valuable cues as to the progression of the disease. Alternately, wherein the subject has undergone therapeutic intervention, analogous methods may be used to monitor the therapy of disease and/or disease management.

The aforementioned methods may be used to monitor the progression/therapy of autoimmune disorders, cancers, pathogenic diseases, and the like. Preferably, the immune cells that are used in the diagnostic methods are T-cells.

In the context of autoimmune disorders, the progression of the disease may be monitored by analyzing the number and/or type of autoreactive T cells. Depending on the result of the analysis, methods of intervention and/or therapy may be designed to minimize the severity of the symptoms. In other instances, preventive methods may be undertaken, including providing recommendations to subjects on dietary, nutritional and/or other lifestyle changes.

Embodiments described herein further relate to methods for devising and producing novel compositions for treating a disease. The method comprises administering the scaffolds of the invention containing disease specific antigens to a subject, which then manipulate immune cells that are specific to the disease, optionally isolating, enriching, and expanding the immune cells manipulated in the device, and then administering the immune cells back to the subject. Alternately, products derived from such immune cells may be administered to the subjects. Examples of products derived from the immune cells include, nucleic acids (including vectors and cells containing such nucleic acids), peptides, proteins, antibodies, cytokines, etc.

Preferably, the disease is an autoimmune disease. In one embodiment, autoreactive T cells which have been isolated (and optionally expanded in culture as described herein) by the aforementioned methods may be inactivated in situ or ex situ. Methods of inactivating T cells are known in the art. Examples include, but not limited to, chemical inactivation or irradiation. The autoreactive T cells may be preserved either before or after inactivation using a number of techniques known to those skilled in the art including, but not limited to, cryopreservation. As described below, the composition may be used as a vaccine to deplete autoreactive T cells in autoimmune patients.

Embodiments described herein further relate to compositions and vaccines produced by the aforementioned methods. The composition may be a pharmaceutical composition, which may be produced using methods well known in the art. Pharmaceutical compositions used as preclinical and clinical therapeutics in the treatment of disease or disorders may be produced by those of skill, employing accepted principles of diagnosis and treatment.

In one embodiment, the vaccine may comprise autoreactive T cells comprising homogeneous ("monoclonal") or heterogeneous ("polyclonal") patterns of Vβ-Dβ-Jβ gene usage. Clinical studies indicate that autoimmune patients receiving autologous monoclonal T cell vaccination may show a gradual decline in the immunity against autoreactive T cells. In some cases, the reappearing autoreactive T cells may originate from different clonal populations, suggesting that the T cells may undergo clonal shift or epitope spreading potentially associated with the ongoing disease process. Clonal shift or epitope spreading may be a problem in autoimmune diseases mediated by autoreactive T cells. A vaccine comprising polyclonal autoreactive T cells capable of depleting multiple populations of autoreactive T cells may avoid problems with clonal shift or epitope spreading. The compositions/vaccines of the invention containing desired T-cells may be provided with a pharmaceutically acceptable carrier. Lyophilized preparations of T-cells may be provided as well.

IV. Kits/Devices

In certain embodiments, the present invention provides kits comprising, in one or separate compartments, the scaffolds of the instant invention. The kits may further comprise additional ingredients. The kits may optionally comprise instructions for formulating the scaffolds for diagnostic or therapeutic applications. The kits may also comprise instructions for using the kit components, either individually or together, in the therapy or diagnosis of various disorders and/or diseases.

In a related embodiment, the present invention provides kits comprising the scaffolds of the invention along with reagents for selecting, culturing, expanding, sustaining, and/or transplanting the manipulated cells of interest. Representative examples of cell selection kits, culture kits, expansion kits, transplantation kits for T-cells, B-cells and antigen presenting cells are known in the art.

This invention is further illustrated by the following examples which should not be construed as limiting. The entire contents of all references, patents and published patent applications cited throughout this application, as well as the Figures are hereby incorporated herein by reference.

EXAMPLES

Example 1: Construction of Scaffolds and Microscopic Analysis of the Assembled Structures Antigen-presenting cells-mimetic scaffolds (APC-MS) were assembled using the methodology described below. Briefly, a base layer containing high surface area mesoporous silica micro-rods (MSR) was first provided, onto which various T-cell homeostatic agents, e.g., interleukins such as IL2 and/or cytokines such as TGF-beta, are optionally loaded. In certain embodiments, it may be preferable to load the homeostatic agents on to the MSR layer. Then, a continuous, fluid supported lipid bilayer (SLB) was layered on the base layer, thereby generating an MSR-SLB scaffold. If the homeostatic agents are not directly loaded on the MSR layer, then they can be loaded after SLB payload has been applied on top of the MSR layer. Then, a blocking agent such as BSA may be applied to block non-specific integration sites in the MSR-SLB scaffold, after which, one or more T-cell activating molecule(s) and T-cell co-stimulatory molecules are loaded onto the MSR-SLB scaffold. The structures of lipids in association with mesoporous silica microrods (MSRs) with phase contrast microscopy, wherein a digital camera mounted on the microscope was used to obtain images of the structures are shown in FIG. 1. The top panel shows merged pictures of the lipids (green) and mesoporous silica microrods (grey) at a lipid:MSR ratio of 1:20 (Scale=200 μm). The middle panel shows merged pictures of the lipids (green) and mesoporous silica microrods (grey) at a lipid:MSR ratio of 1:4 (Scale=200 μm). The bottom panel shows a merged phase-contrast microscope image of lipids in association with MSRs at a higher magnification (Scale=20 μm).

Figure 2A:
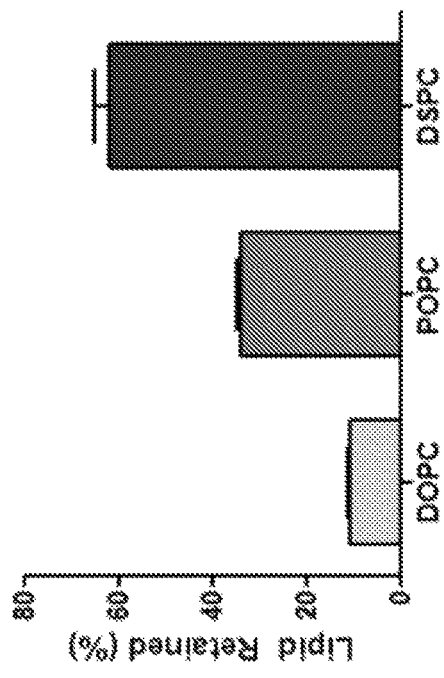
FIGS. 2A, 2B, 2C, and 2D show that the assembly and the characteristics of the antigen-presenting cell-mimetic scaffolds (APC-MS) is dependent on the type of lipid and the content of the lipid.
Figure 2B:
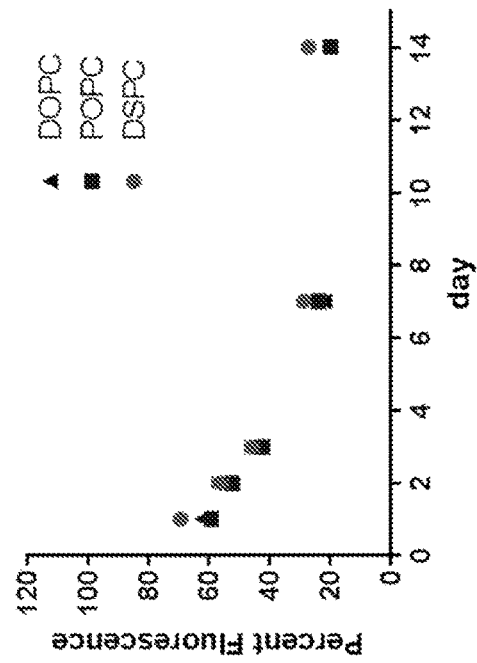
Figure 2C:
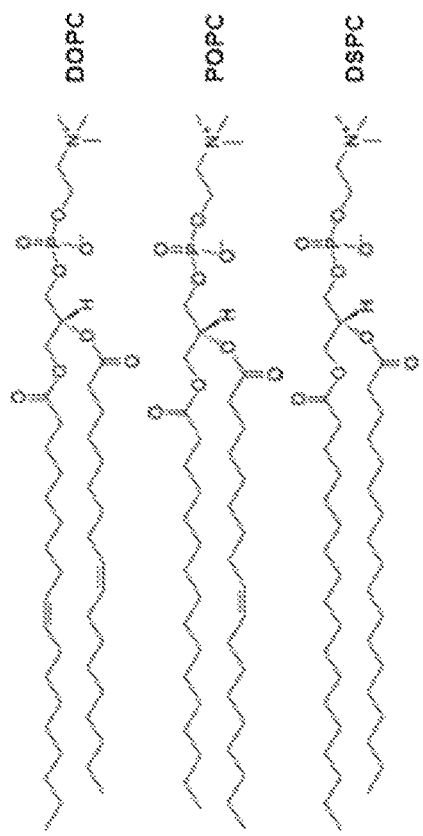
Figure 2D:
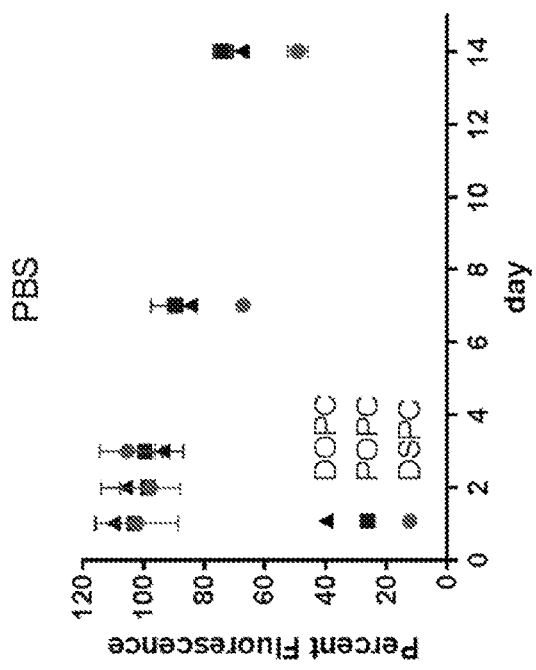

The characteristics of the antigen-presenting cell-mimetic scaffolds (APC-MS) were found to be dependent on the type of lipid and the content of the lipid. FIG. 2A provides a list of lipids that may be used to achieve the desired architecture and/or properties of the scaffold, e.g., dioleoyl-phosphatidylcholine (DOPC); palmitoyl-oleoylphosphatidylcholine (POPC); or distearoyl-phosphatidylcholine (DSPC). Furthermore, it was found that the retention of lipids layered on the MSR-SLB compositions depends on the type and/or content of the lipid (see FIG. 2B). Next, the organization of the lipid bilayers in the scaffolds of the invention was studied using fluorescence analysis. FIG. 2C shows changes in relative florescence of various MSR-SLB compositions containing DOPC, POPC or DSPC in phosphate-buffered saline (PBS) over a two-week (14-day) period. FIG. 2D shows changes in relative florescence of various MSR-SLB compositions containing DOPC, POPC or DSPC in complete Roswell Park Memorial Institute medium (cRPMI) over a two-week (14-day) period at 37° C.

Figure 3:
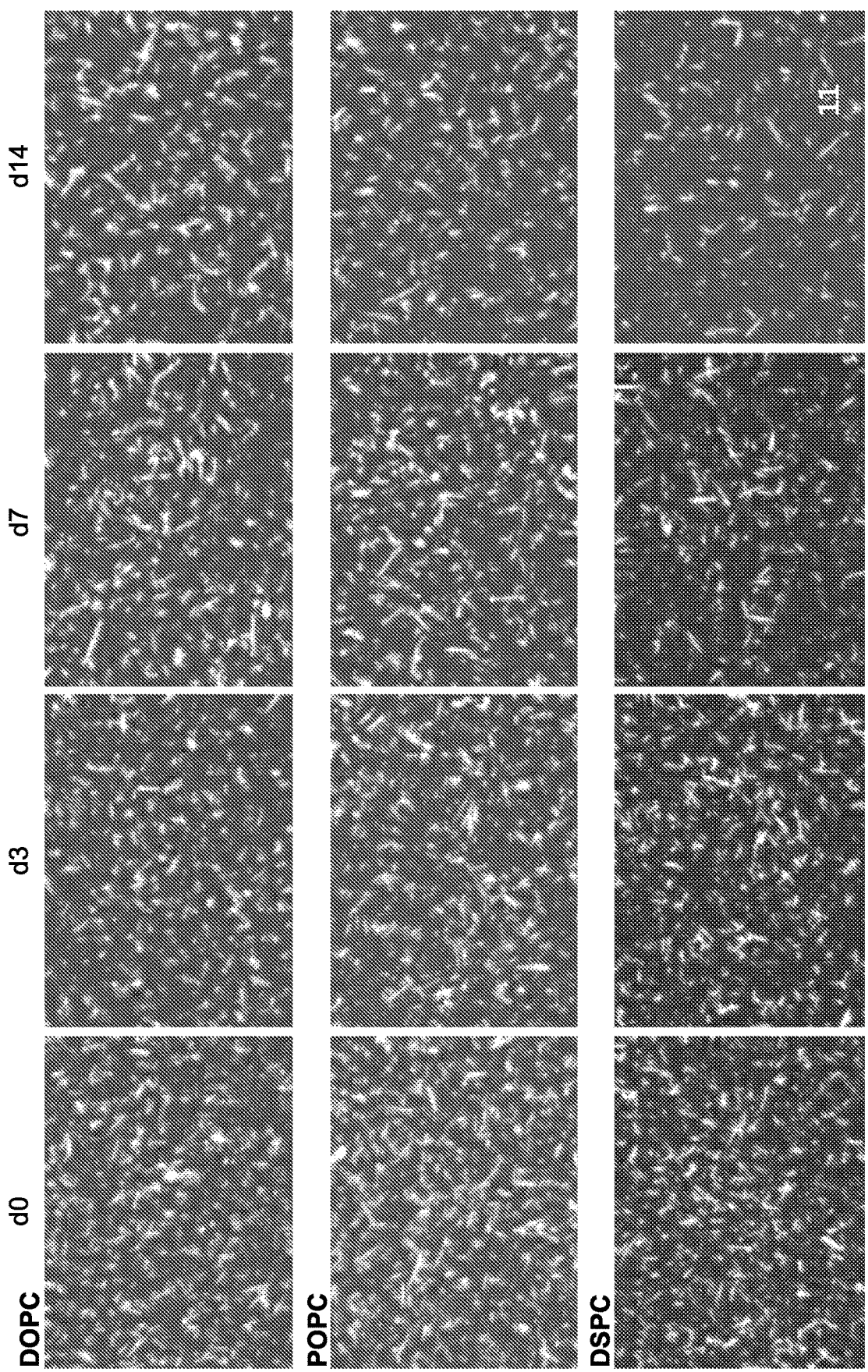
FIG. 3 shows stability of various MSR-SLB compositions in PBS at day 0, day 3, day 7, and day 14, as analyzed with phase-contrast and fluorescence microscopy (lipid coating). The top panel shows the stability of DOPC in the MSR-SLB composition; the middle panel shows the stability of POPC in the MSR-SLB composition; and the bottom panel shows the stability of DSPC in the MSR-SLB composition.

Additionally, the stability of various MSR-SLB compositions at various time-points was investigated by suspending the scaffolds in PBS for 3 days, 7 days, and 14 days. The scaffold architecture and/or structure was then analyzed with phase-contrast fluorescence microscopy. Results are shown in FIG. 3. The top panel shows the stability of DOPC in the MSR-SLB composition; the middle panel shows the stability of POPC in the MSR-SLB composition; and the bottom panel shows the stability of DSPC in the MSR-SLB composition.

Figure 4A:
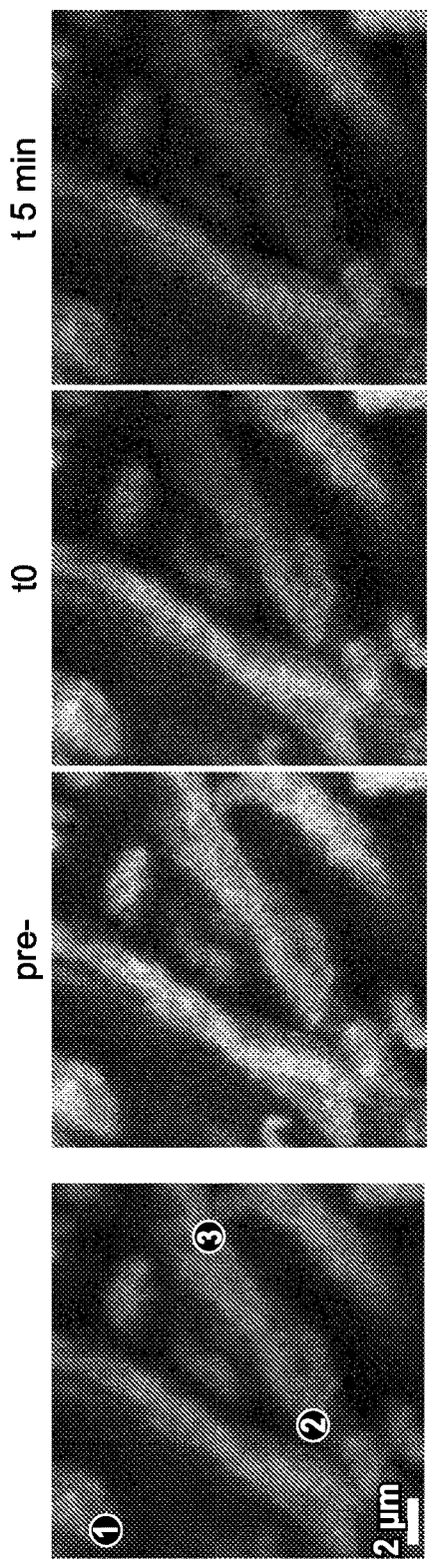
Figure 4C:
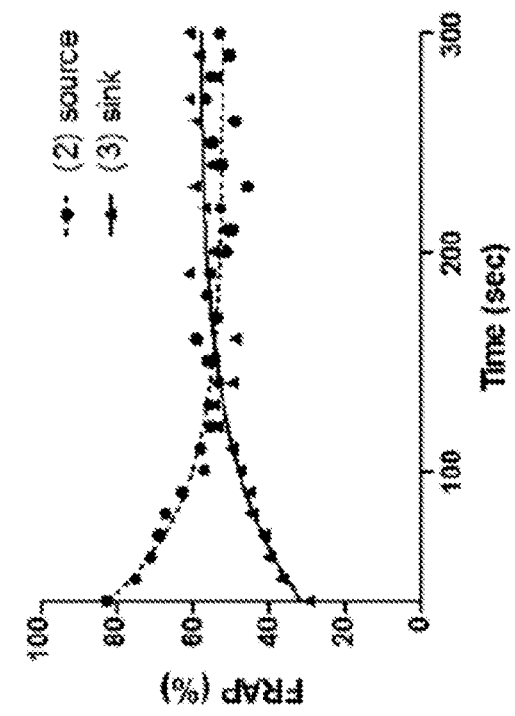
Figure 4B:
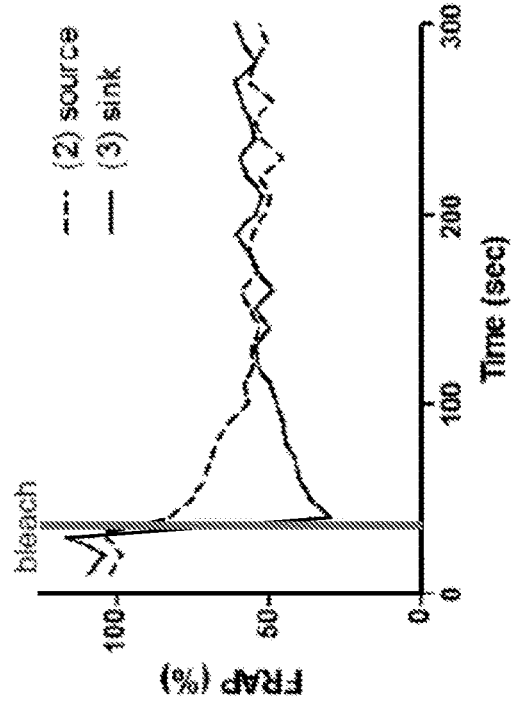

Subsequently, the assembly and the characteristics of MSR-SLB fluid structures were studied over time with phase contrast microscopy. Results are shown in FIGS. 4A-4E. FIG. 4A shows phase-contrast confocal fluorescence microscope images of lipids in association with mesoporous silica microrods (MSRs) taken at high magnification (scale=2 μM) prior to bleaching the lipid composition ("pre"), at the time of bleaching the lipid composition (t=0) and 5 minutes post-bleaching the lipid composition (t=5 min). FIG. 4B shows changes in fluorescence recovery after photo-bleaching (FRAP) with time. The sources are depicted in region (2), the sinks are depicted in region (3), and the normalization point is indicated as region (1). The differential distribution was best seen at early time points after bleaching and achieved an equilibrium at around 2 mins (120 s). The figure on the right shows smooth-fitting curves depicting average changes in FRAP, as derived from normalized images, over time. FIG. 4C and FIG. 4D show two sets of high resolution images of MSR-SLB fluid structures prior to bleaching (pre), at bleaching (t=0) and after 3 minutes post-bleaching (t=3 min) with the lipid composition.

Figure 5B:
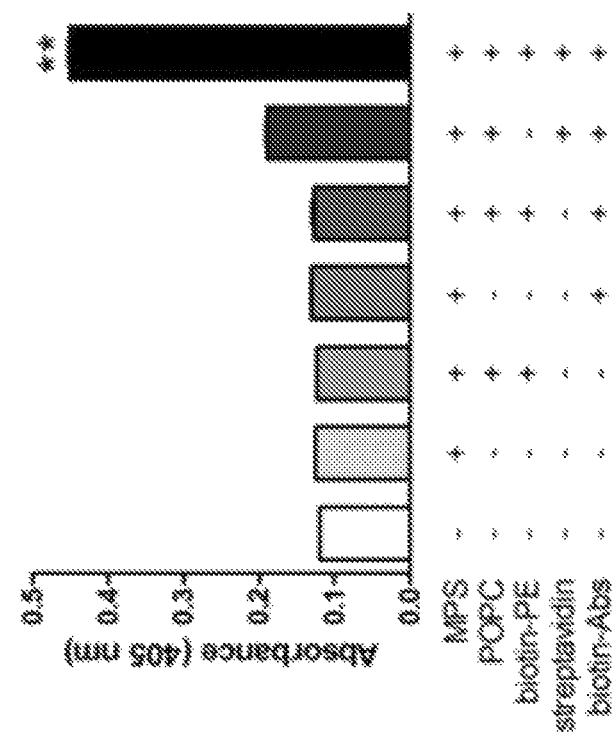
FIGS. 5A and 5B show structural and functional properties of MSR-SLB compositions containing various moieties. Based on experiments using the B3Z reporter T-cell line, maximum functionality of the APC-MS scaffold was observed when all the individual components are present in the scaffold.
Figure 5A:
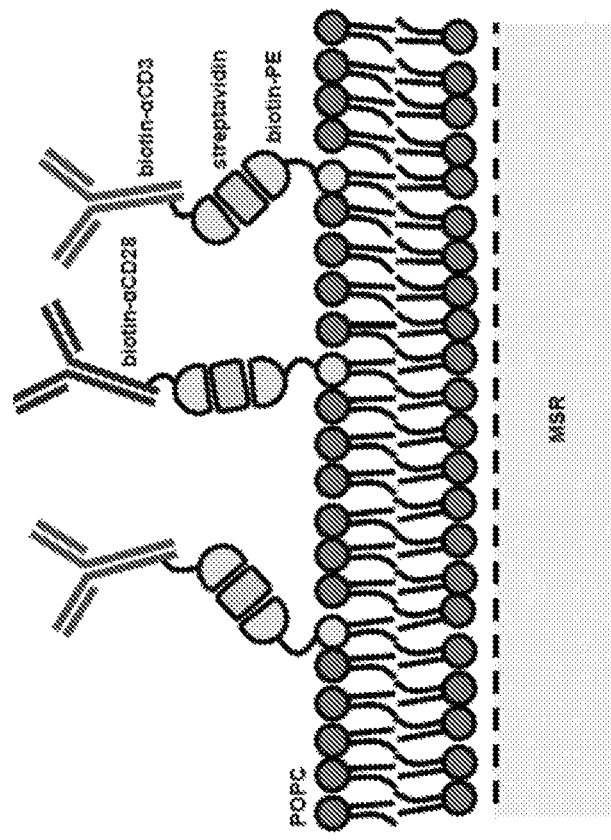

Furthermore, the structural and functional properties of MSR-SLB compositions containing various lipid moieties was studied using spectrophotometric analysis. Results are shown in FIGS. 5A and 5B. FIG. 5A shows a schematic representation of MSR-SLB compositions containing a lipid bilayer of POPC containing phosphoethanolamine biotin (biotin PE), which is conjugated to a streptavidin molecule (e.g., a streptavidin dimer), which in turn is conjugated to a biotinylated antibody (e.g., a biotinylated anti-CD3 antibody or a biotinylated anti-CD28 antibody or another specific or non-specific antibody). FIG. 5B shows spectrophotometric analysis of MPS (silica), POPC (lipid), MPS-POPC composite, biotinylated MPS-POPC composite (in the presence or absence of streptavidin) and the MPS-POPC composite together with the biotinylated antibody in the presence or absence of phycoerythrin biotin (biotin PE) and/or streptavidin. Significant increase in absorbance is observed in MSR-SLB compositions containing phosphoethanolamine biotin (biotin PE) conjugated to a biotinylated antibody via a streptavidin linker (dark bars; ** indicates statistical significance). An increase in the activity of B3Z hybridoma cells, which produce β-galactosidase in response to activation, was observed with all components present, indicating that APC-MS primarily adopts the structure depicted in (A).

Example 2: Analysis of the Functional Properties of the APC-MS Release of Homeostatic Factors Such as IL-2

Figure 6B:
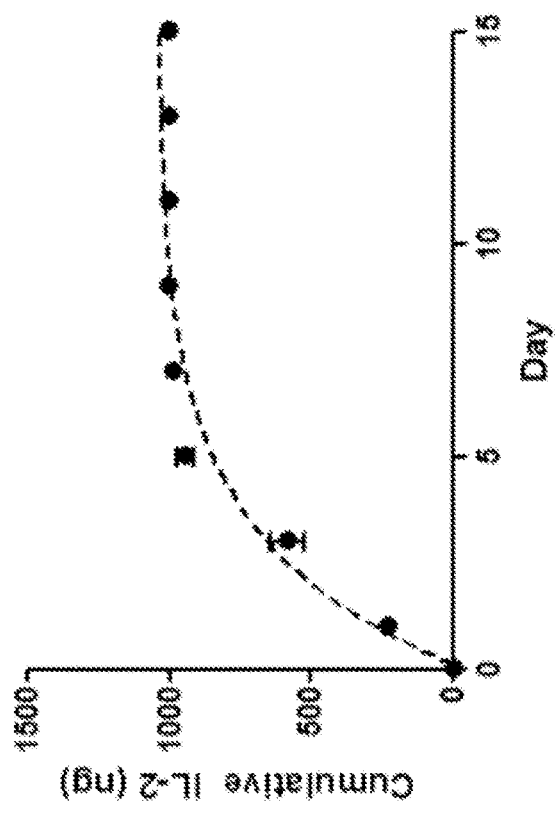
FIGS. 6A and 6B show controlled release of IL-2 from MSR-SLB compositions containing IL-2.
Figure 6A:
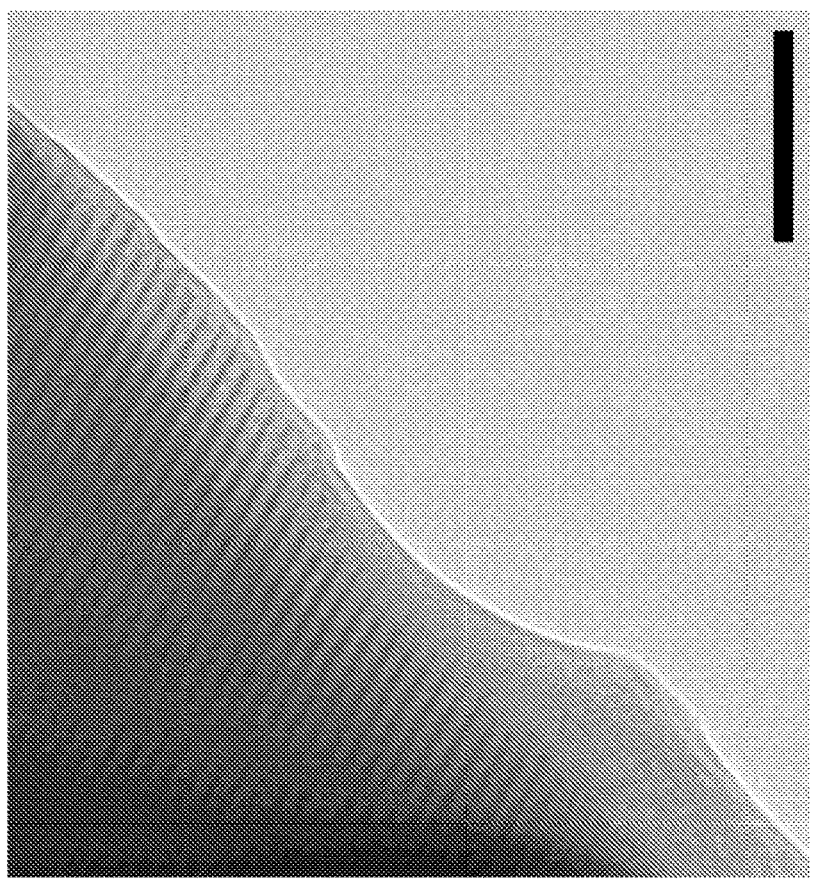

APC-MS containing mesoporous silica rods (MSR) and supported lipid bilayer (SLB), which further contain IL-2 were manufactured using the methods described in Example 1. The release of IL-2 from these MSR-SLB compositions was analyzed using staining techniques and/or binding assays. The results are presented in FIGS. 6A and 6B. As illustrated in the electron micrograph of FIG. 6A, high surface area pores of MSRs are available for potential adsorption of IL2 or other soluble payloads (scale bar=100 nm). The plot showing cumulative IL-2 release over a 15-day period (FIG. 6B) shows that the APC-MS of the invention are capable of releasing homeostatic agents such as IL-2 in a controlled and sustained manner during the entire course of the two-week study period.

Association with T-Cells

Figure 7B:
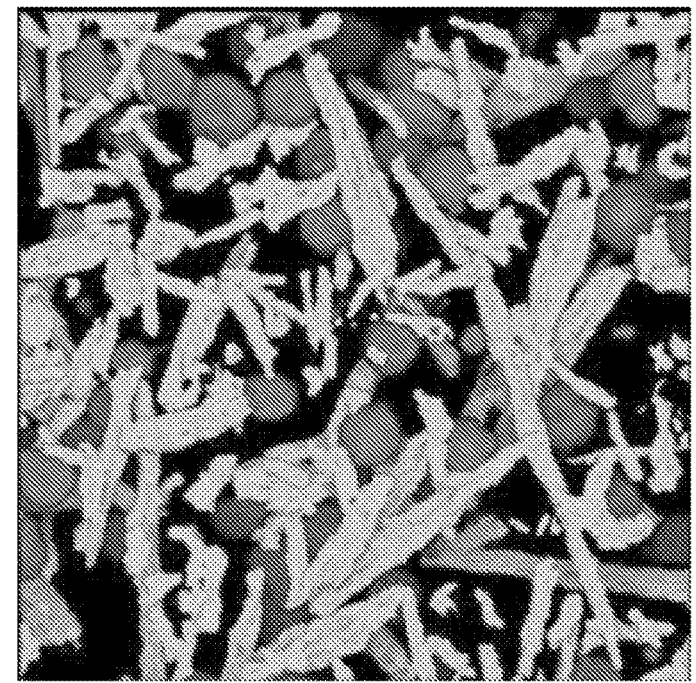
FIGS. 7A and 7B show confocal microscopy images showing infiltration of T-cells (spheres) into the antigen presenting cell-mimetic scaffolds containing MSR-SLB composites.
Figure 7A:
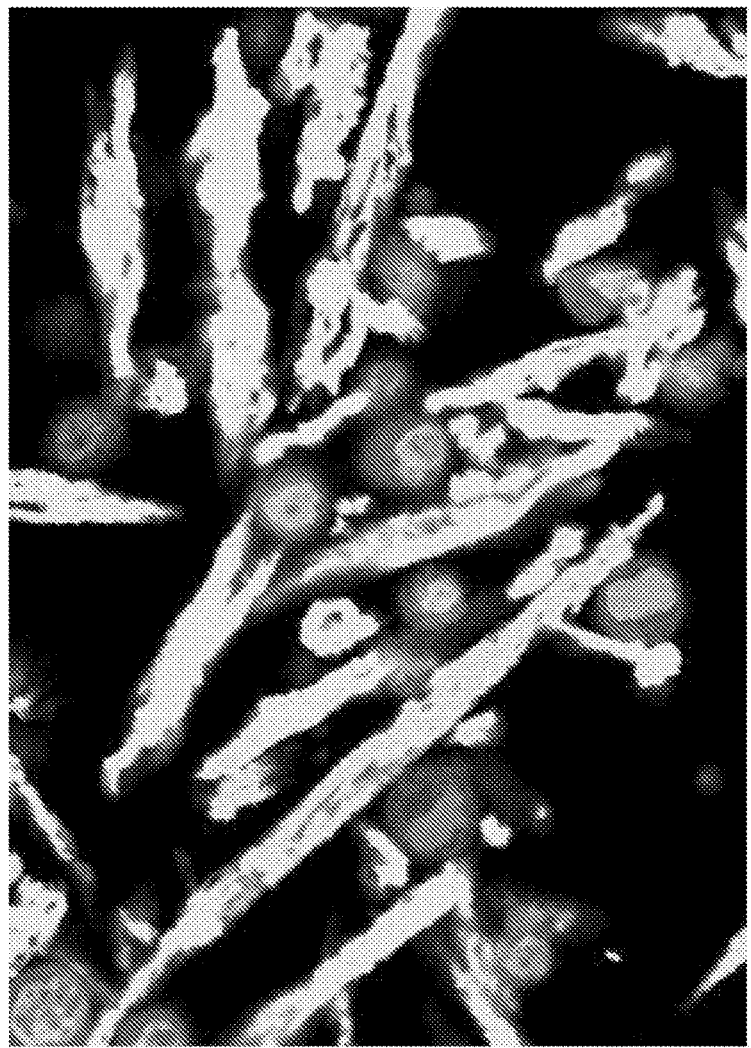

Antigen presenting cell-mimetic scaffolds containing MSR-SLB scaffolds (APC-MS) were incubated with media containing functional T-cells and the infiltration of T-cells into the scaffolds was analyzed with phase contrast microscopy. The results are presented in FIGS. 7A and 7B. FIG. 7A shows whole cells stained with a live-cell dye and a nuclear dye. The image depicts live T-cells that have infiltrated into the interparticle space of stacked high-aspect ratio lipid-coated MSR-SLB scaffolds. FIG. 5B shows cells that have been stained with a single dye.

Example 3: Antibody Loading

Figure 8:
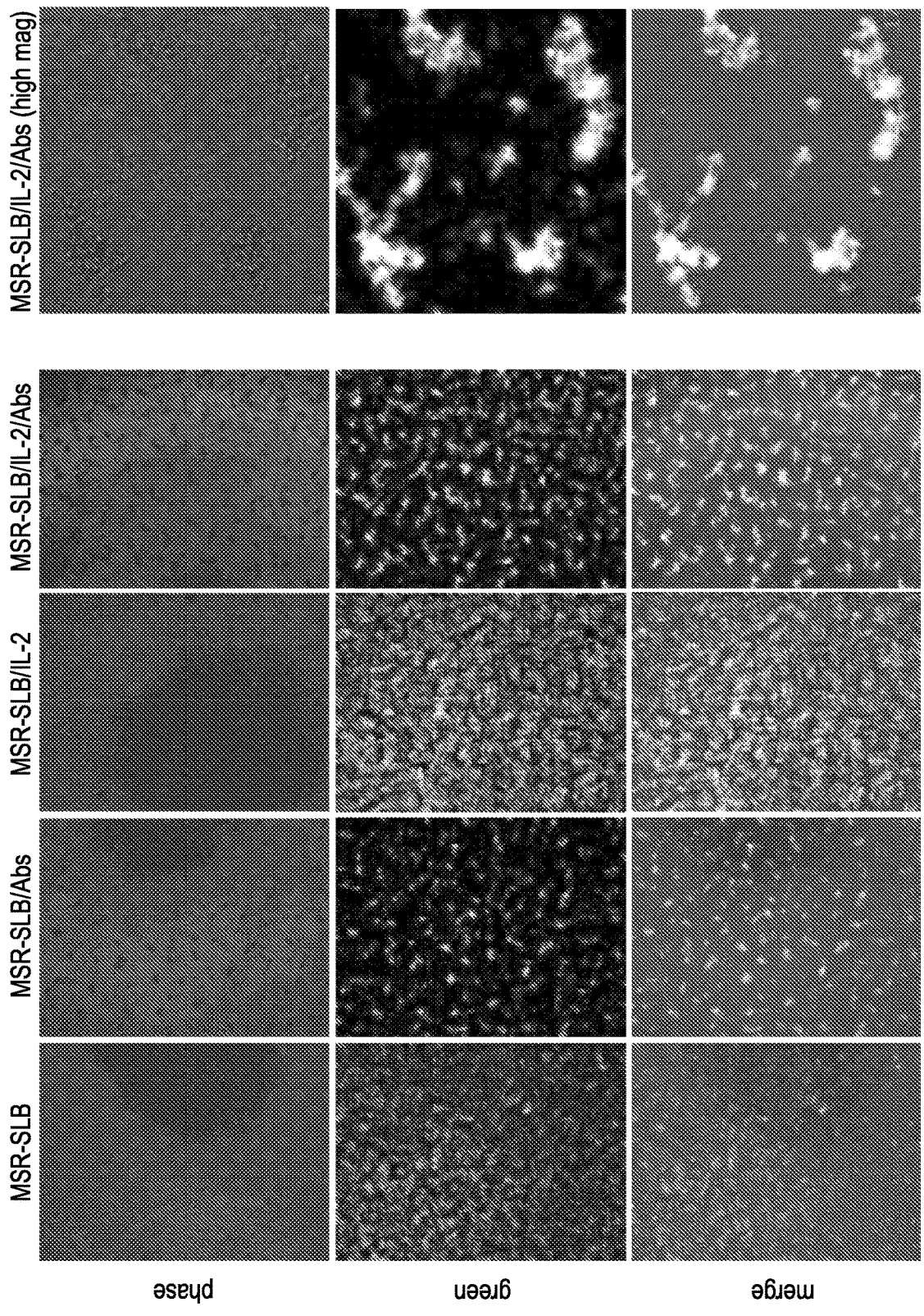
FIG. 8 shows phase-contrast microscope and fluorescence images of lipids in association with mesoporous silica microrods (MSRs) co-cultured with primary T cells. It was observed that primary T cells tend to form cell/material clusters when T cell activating cues are attached to the surface of the material. The bottom panel shows merged pictures of the lipids and mesoporous silica microrods in MSR-SLB composites containing conjugated antibodies, IL-2 or a combination of conjugated antibodies and IL-2. The images on the right show MSR-SLB composites containing both conjugated antibodies and IL-2 (Scale=20 µm) at high magnification.

The APC-MS containing MSR-SLB were then loaded with various stimulatory molecules, co-stimulatory molecules and/or T-cell homeostatic agents and the resulting structures were analyzed with fluorescence microscopy. Four different types of MSR-SLB scaffolds were analyzed— (1) nude MSR-SLB scaffold (control); (2) MSR-SLB containing conjugated antibodies; (3) MSR-SLB containing IL-2; and (4) MSR-SLB containing conjugated antibodies and IL-2. The photomicrographs are shown in FIG. 8 (low resolution images are on the left and high resolution images are on the right). The top panel (greyscale images) contains phase-contrast microscope images of each of the aforementioned MSR-SLB scaffolds. The bottom panel merges images capturing lipid fluorescence with the greyscale images of mesoporous silica microrods (MSR). The images on the right show MSR-SLB scaffolds at high magnification (scale bar=20 μm).

Example 4: Properties of Antibody-Loaded APC-MS

Figure 9A:
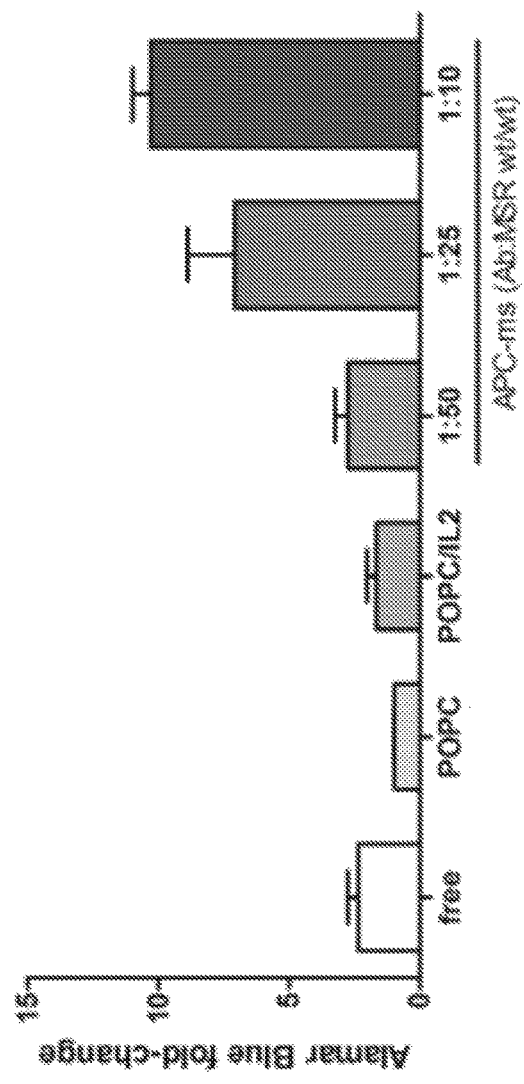
FIGS. 9A and 9B shows dose-response charts of antibody-induced changes in mouse splenic T cells.
Figure 9B:
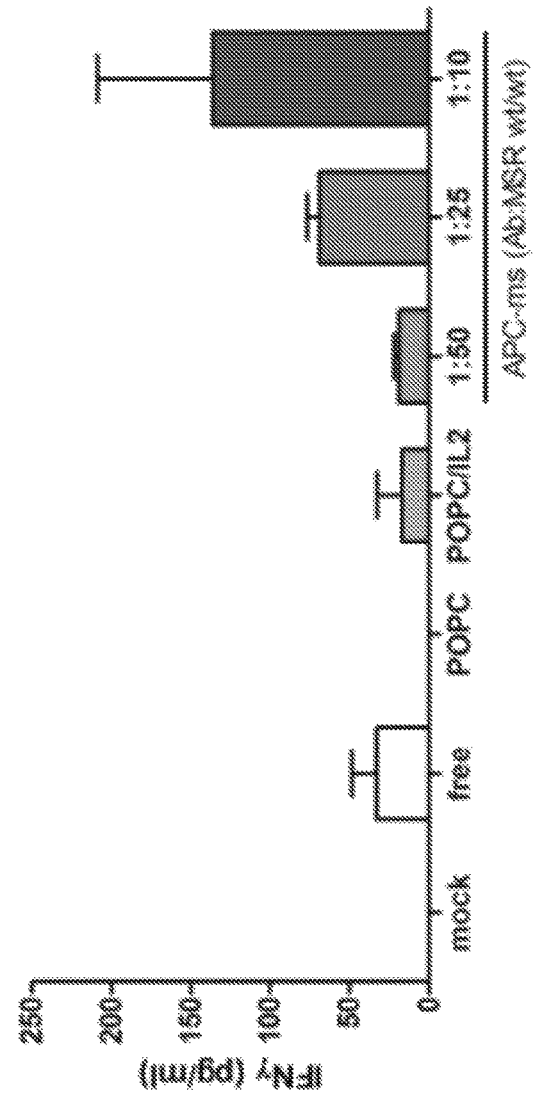

The effect of antibody-loaded APC-MS on T-cell expansion was investigated using routine cytological assays. To this end, T-cells were contacted with various control and experimental scaffolds and the effect of each on T-cell populations was measured by Alamar blue dye (indicates metabolic activity) and IFNγ production was measured by ELISA. The control scaffolds include shams ("mock"), SLB-free scaffolds ("free"), scaffolds containing POPC lipid only ("POPC") and scaffolds containing a combination of POPC and IL-2. The experimental scaffolds contain a combination of POPC and IL-2, along with antibody. Three different doses of the antibody (MSR: antibody ratio of 1:50, 1:25 and 1:10) were investigated. The results are presented in FIGS. 9A and 9B. As is shown in FIG. 9A, a 3-day stimulation of T-cells with the experimental scaffold significantly increased T-cell expansion. Moreover, the effect of the antibody on the expansion of T-cells was found to be dose-dependent. Next, an identical setup was used to analyze IFNγ production by T-cells. Results are presented in FIG. 9B. It was found that incubation of T-cells in experimental scaffolds (containing POPC and IL-2 and the antibody) greatly improves IFNγ secretion compared to T-cells that were incubated in control scaffolds. Moreover, the effect of the antibody on the T-cell dependent secretion of IFNγ was found to be dose-dependent.

Figure 10:
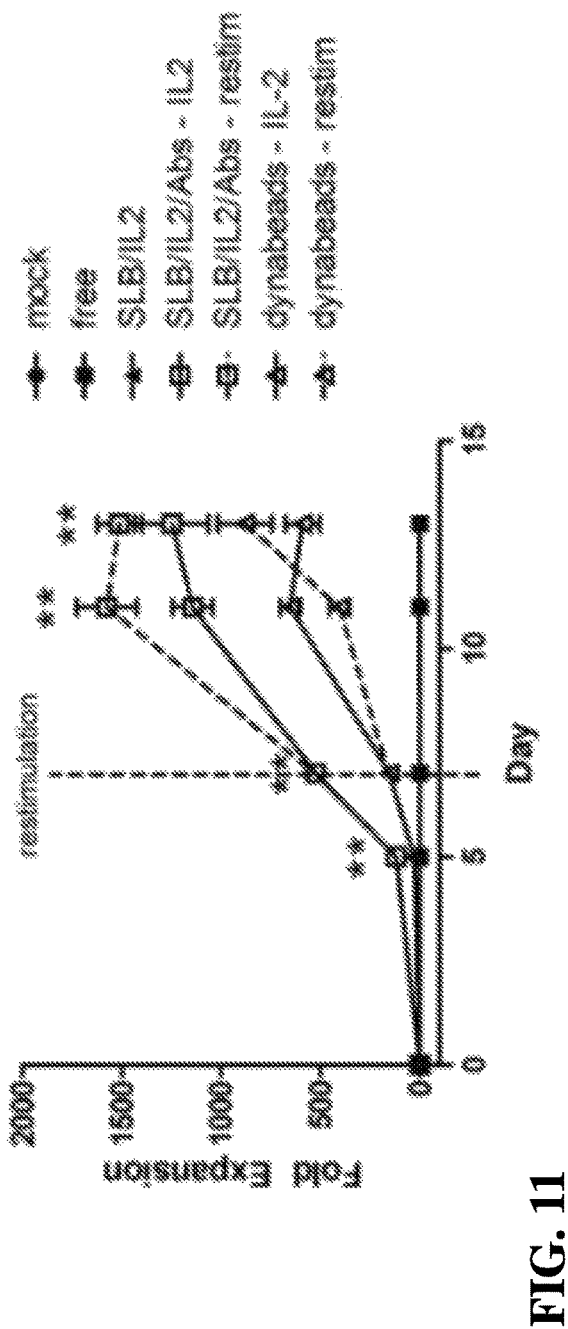
FIGS. 10 and 11 show antigen-presenting cell-mimetic scaffolds (APC-MS) of the present invention promote rapid expansion of metabolically-active T cells.
Figure 11:
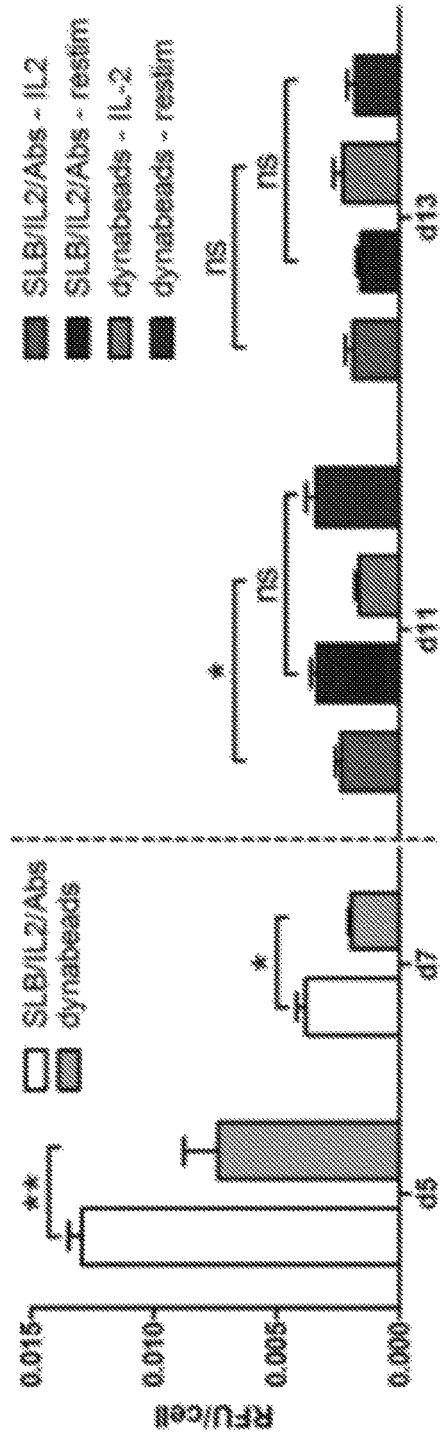

The effect of the antigen-presenting cell-mimetic scaffolds (APC-MS) of the present invention on the expansion of metabolically-active T cells was analyzed using routine cytometry studies. Results are presented in FIGS. 10 and 11. In general, the scaffolds of the invention were found to promote rapid expansion of T-cells in vitro. In this regard, FIG. 10 shows fold-expansion of primary T-cells upon incubation with control or experimental scaffolds. It was found that incubation of primary T-cells with the compositions of the instant invention significantly induced T-cell expansion (with or without re-stimulation) compared to mock compositions or compositions free of SLB. More importantly, compared to a composition of DYNABEADS and IL-2, incubation of primary T-cells with the scaffolds of the invention resulted in a measurably stronger proliferation upon re-stimulation at day 7. FIG. 11 shows a bar-chart of metabolic activity of T-cells (as measured by relative Alamar Blue (RFU) per cell) that were incubated with the scaffolds of the instant invention loaded with IL-2 (SLB/IL2/ABS) or DYNABEADS loaded with IL-2 (DYNABEADS-IL2). A significantly higher metabolic activity was observed in samples incubated with the scaffolds of the instant invention (left-hand columns) at day 5 and day 7 (prior to re-stimulation), and also at day 11 (in the non-re-stimulated samples, as indicated by green and orange bars). Re-stimulation at day 7 increased metabolic activity of both groups of T-cells i.e., those incubated with the SLB/IL2/ABS composition or the DYNABEADS-IL2 composition compared to non-re-stimulated cells, achieving levels that were previously observed at day 7. Re-stimulation failed to elevate mitotic activity at day 13, indicating T-cell exhaustion at this point.

Figure 12B:
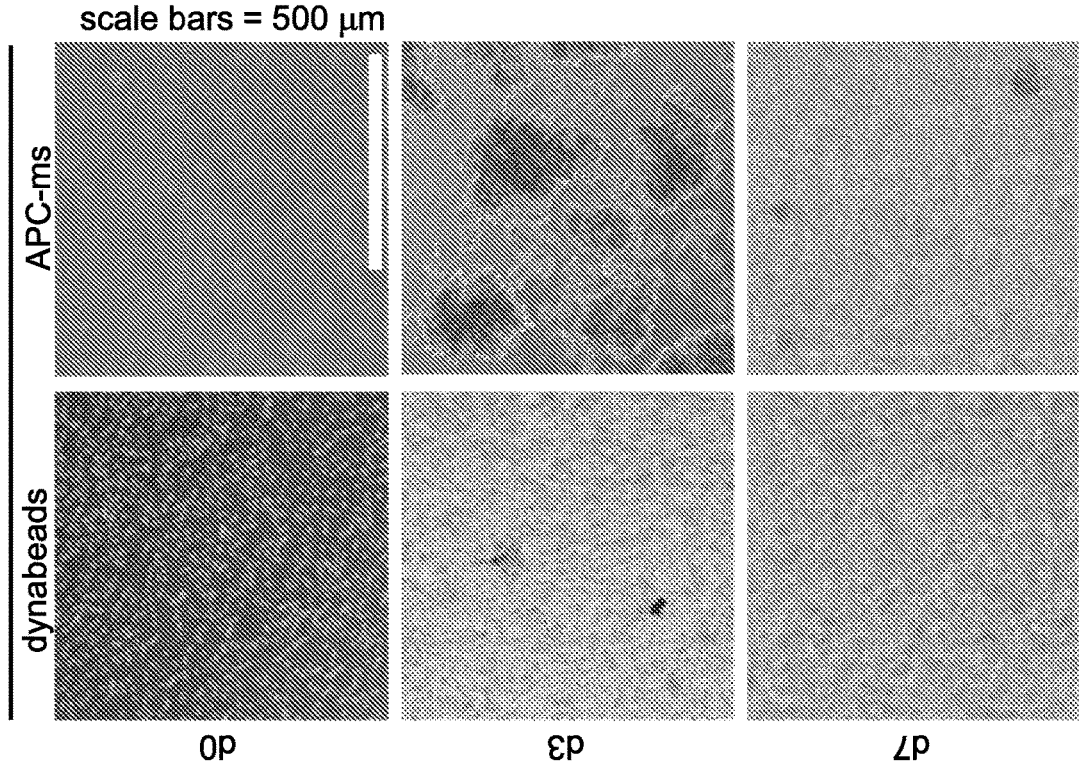
FIGS. 12A and 12B show that the scaffolds of the invention (APC-MS) confer polyclonal expansion of splenic T cells (mouse) and facilitate formation of T cell aggregates.
Figure 12A:
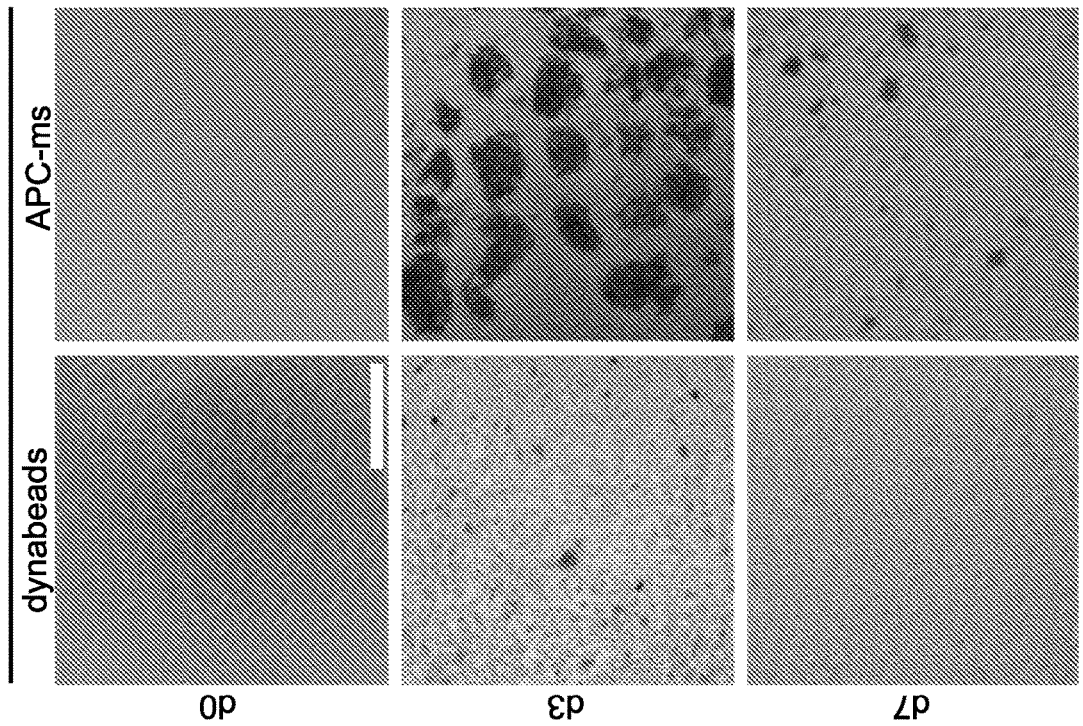

The effect of the scaffolds of the instant invention on the formation of T-cell aggregates was also studied using microscopic analysis. Results are presented in FIG. 12. The images on the left-hand panel show photomicrographs (at 4× magnification) of aggregates of splenic T cells upon incubation with DYNABEADS or APC-MS at day 0, day 3, and day 7. The images on the right-hand panel show photomicrographs (at 10× magnification) of aggregates of splenic T cells upon incubation with DYNABEADS or APC-MS at day 0, day 3, and day 7. (White scale bars=100 μM). It was found that the scaffolds of the invention (APC-MS) confer greater polyclonal expansion of splenic T cells (mouse) and facilitate formation of T cell aggregates than DYNABEADS.

Example 5: Use of Scaffolds to Stimulate and Expand Distinct T-Cell Sub-Populations The utility of the APC-MS compositions of the invention in stimulating and expanding specific T-cell sub-populations was performed using cell sorting techniques. Splenic T-cells were incubated with APC-MS or DYNABEADS and changes in cellular phenotype (based on expression of cell-surface markers) were analyzed by FACS at various time-points post-incubation (t=0 days, 5 days, 7 days, 11 days and 13 days). In the first experiment, changes in the relative frequencies of CD4+ and CD8+ T-cell sub-populations were analyzed using FACS, wherein the values on the X-axis depict intensity of CD8+ staining and the values on the Y-axis depict intensity of CD4+ staining. In a second experiment, polyclonal expansion of a subset of FoxP3+ mouse splenic T cells upon incubation with APC-MS or DYNABEADS was analyzed. In a third experiment, polyclonal expansion of a subset of CD62L+ mouse splenic T cells upon incubation with the scaffolds of the invention (APC-MS) or DYNABEADS. In a fourth experiment, polyclonal expansion of a subset of CD8+/CD69+ mouse splenic T cells upon incubation with APC-MS or DYNABEADS. In a fifth experiment, polyclonal expansion of a subset of CD8+/Granzyme B+ mouse splenic T cells upon incubation with APC-MS or DYNABEADS. In each of the aforementioned experiments, after 7 days, a first T-cell sub-population was subject to IL-2 treatment while a second T-cell sub-population was re-stimulated and the cell suspensions were cultured for 6 additional days. Additionally, both the APC-MS and DYNABEADS used in the experiments were ensured to contain an identical repertoire of stimulatory and co-stimulatory molecules.

Figure 13A:
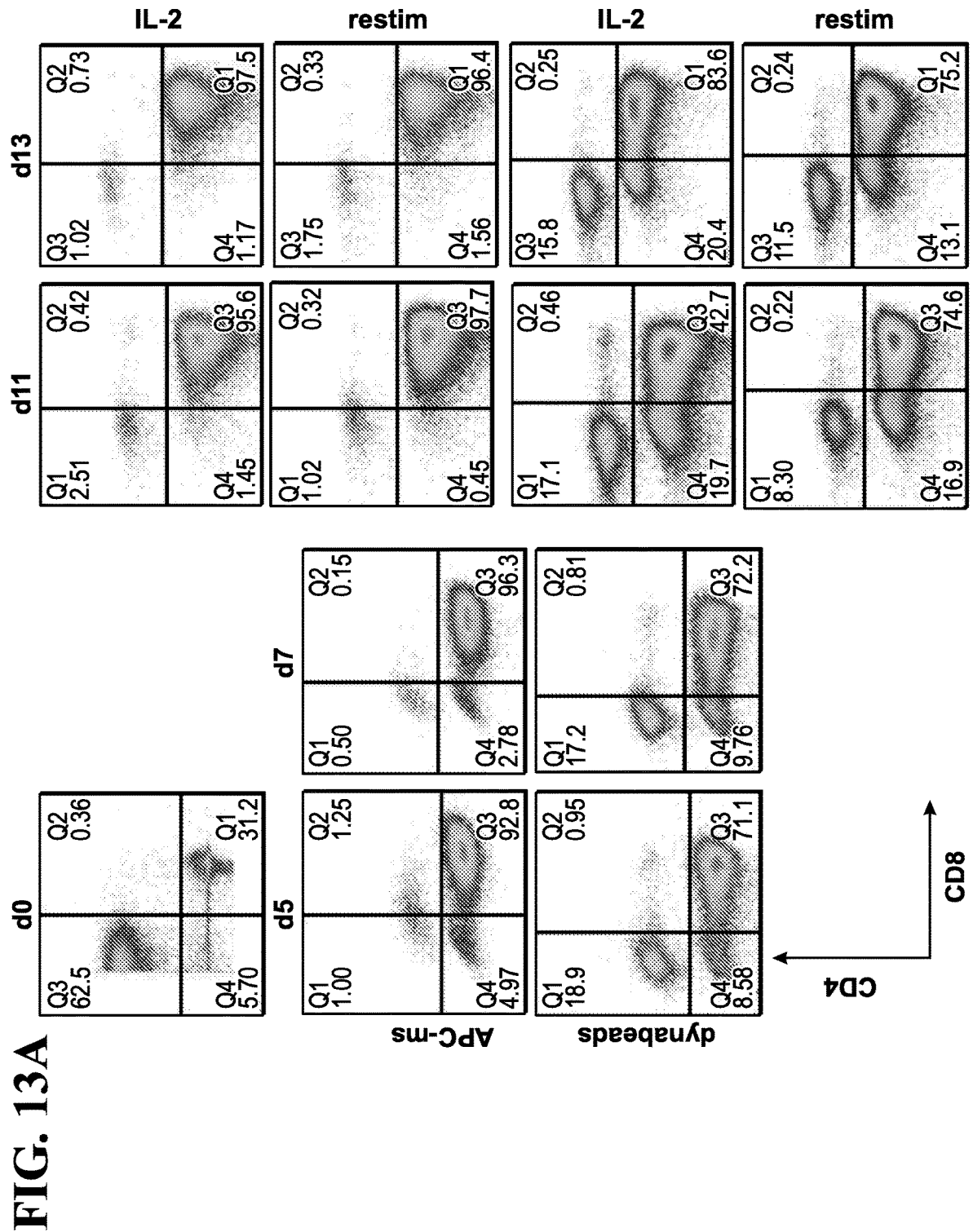
FIGS. 13A and 13B show polyclonal expansion of mouse splenic T cells upon incubation with APC-MS or DYNABEADS.
Figure 13B:
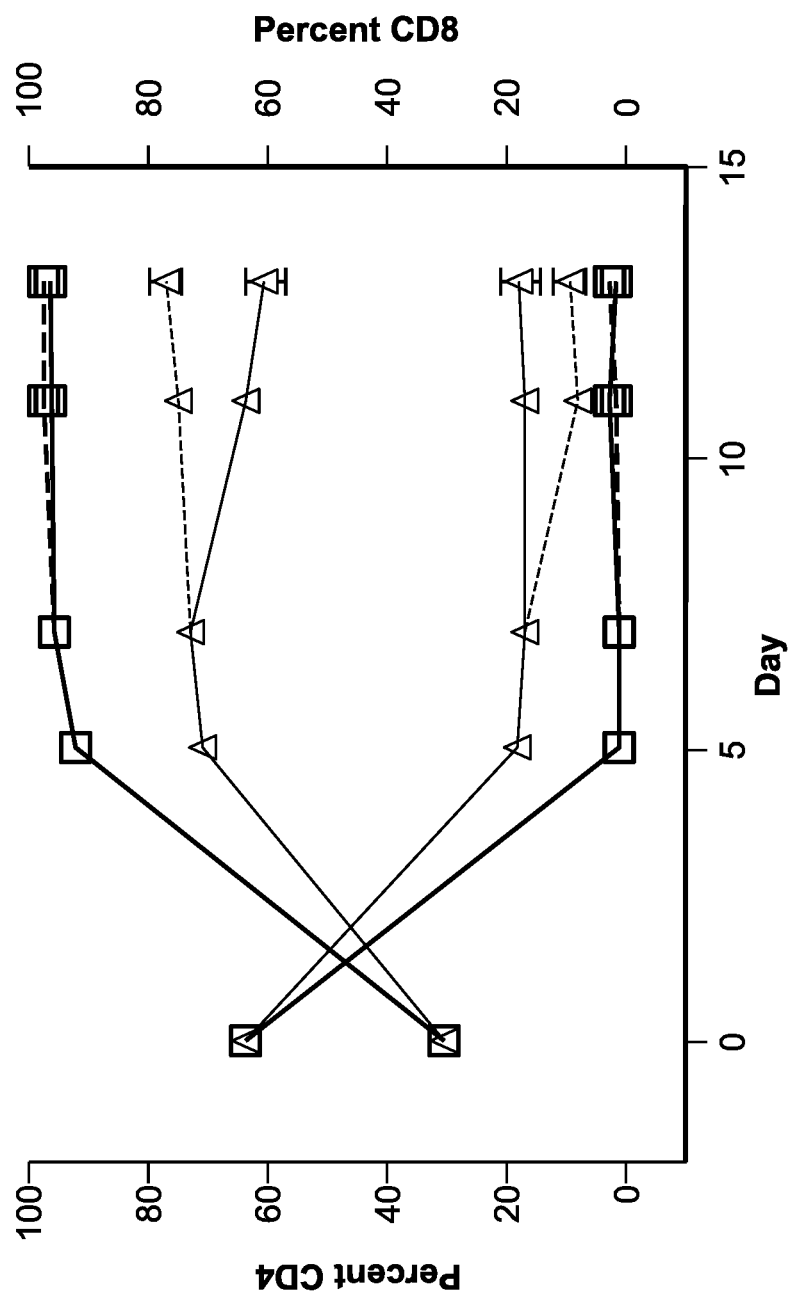

The results of the first experiment are presented in FIGS. 13A and 13B. The results show that compared to incubation with DYNABEADS, incubation with the scaffolds of the invention (APC-MS) achieved greater expansion of polyclonal CD8+ mouse splenic T cells at the end of the 14-day incubation period. Also, while IL-2 treatment inhibited expansion of cells stimulated with DYNABEADS (about 20% reduction), no such effect was observed with cells incubated with APC-MS.

Figure 14:
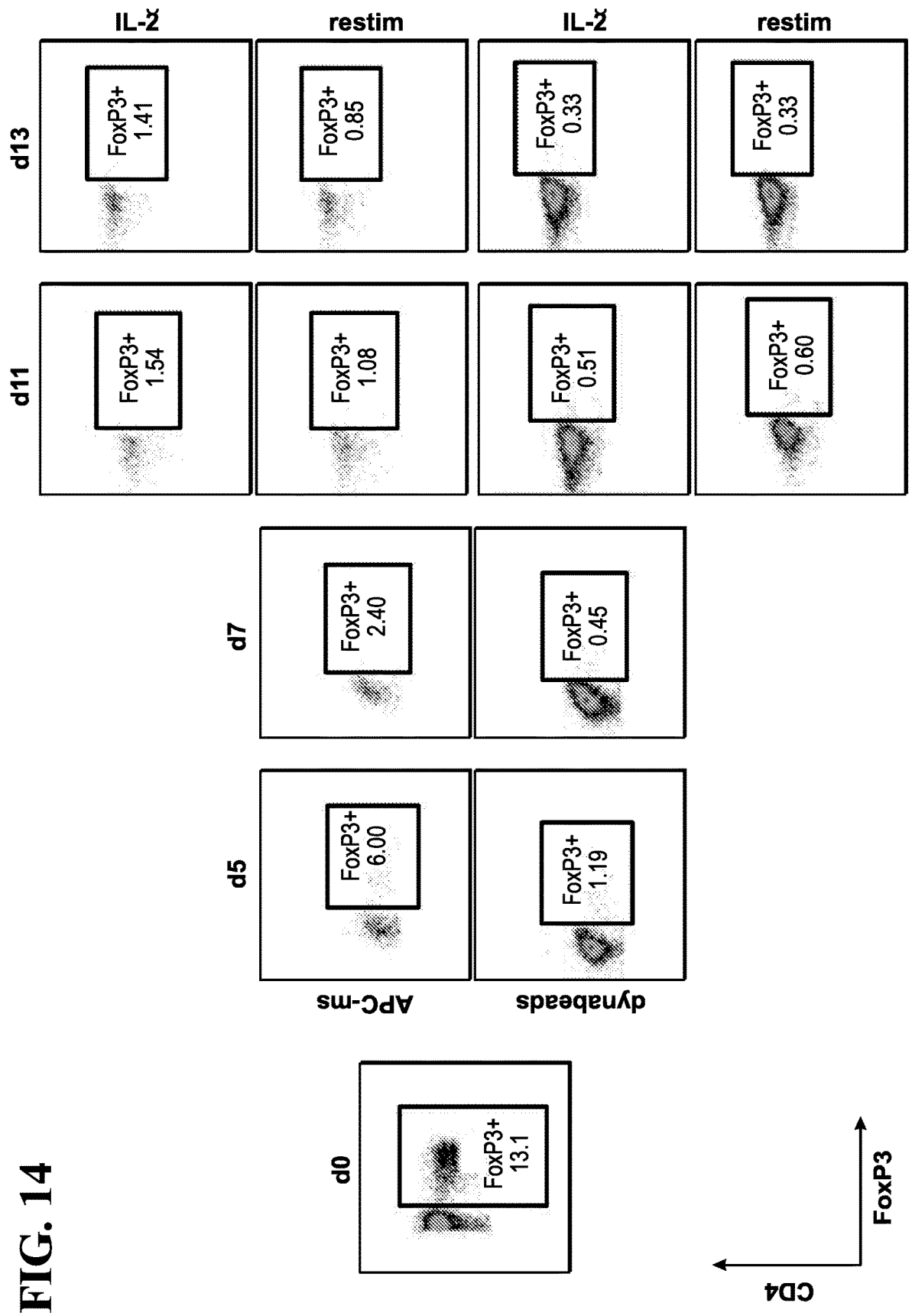
FIG. 14 shows measurement of polyclonal expansion of a subset of FoxP3+ mouse splenic T cells upon incubation with APC-MS or DYNABEADS. The results are depicted in the form of flow cytometric (FACS) scatter plots of T-cell population(s) at various time-points (t=0 days, 5 days, 7 days, 11 days and 13 days) following incubation with APC-MS or DYNABEADS (with re-stimulation or IL-2 treatment after 7 days of incubation), wherein the values on the X-axis depict intensity of FoxP3+ staining and the values on the Y-axis depict intensity of CD4+ staining. A rectangular gate was applied to count the number and/or proportion of FoxP3+ cells in the various fractions. As shown, there was limited or no expansion of FoxP3+ mouse splenic T cells with the particular formulation.

In the second experiment, a rectangular gate was applied to count the number and/or proportion of FoxP3+ cells in the various fractions. The results are presented in FIG. 14.

Figure 15:
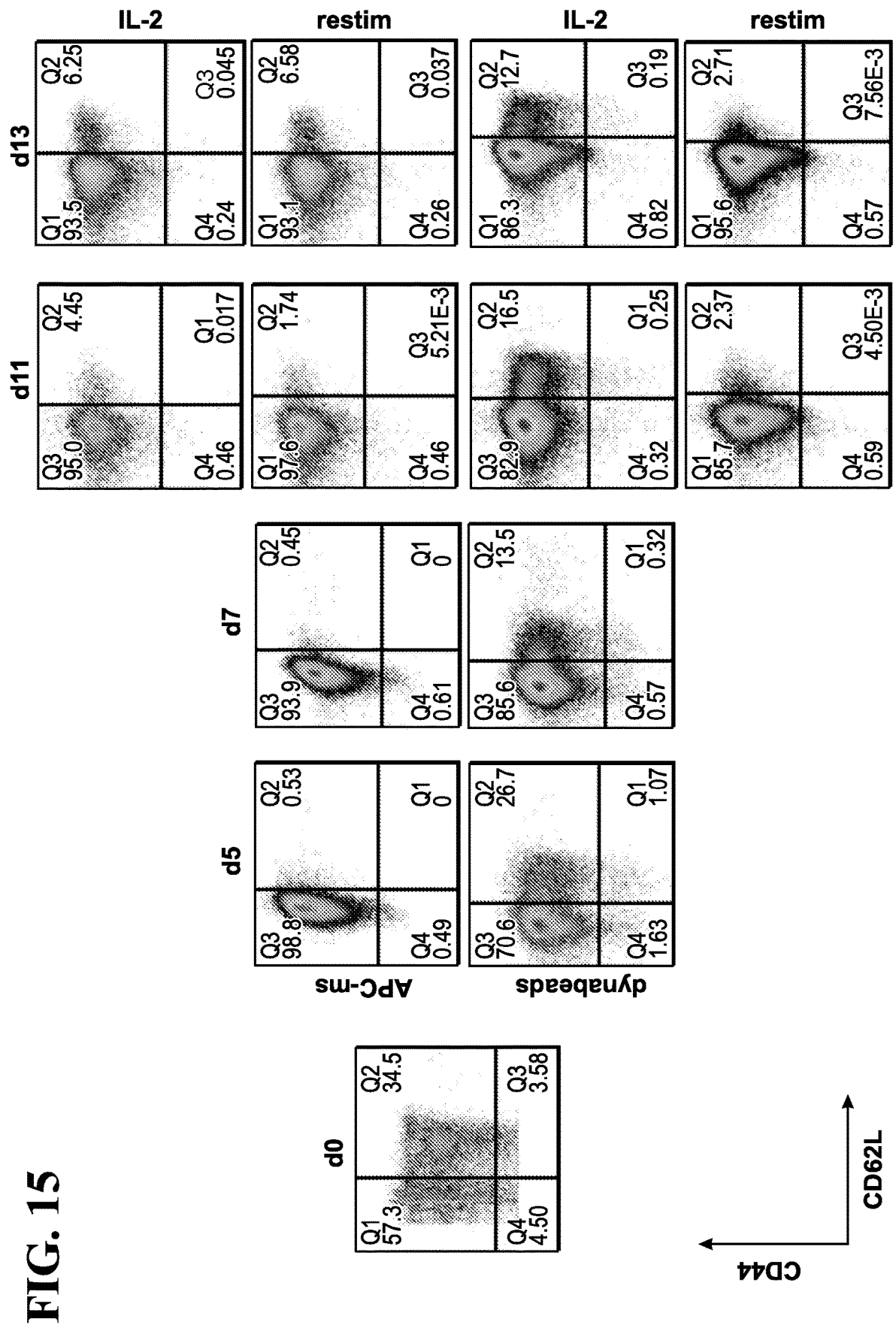
FIG. 15 shows polyclonal expansion of a subset of CD62L+ mouse splenic T cells upon incubation with APC-MS or DYNABEADS. The results are depicted in the form of flow cytometric (FACS) scatter plots of T-cell population(s) at various time-points (t=0 days, 5 days, 7 days, 11 days and 13 days) following incubation with APC-MS or DYNABEADS (with re-stimulation or IL-2 treatment after 7 days of incubation), wherein the values on the X-axis depict intensity of CD62L+ staining and the values on the Y-axis depict intensity of CD44+ staining. The CD62L+ cells appear in the right hand (top and bottom right quadrants) of the scatter plots.

In the third experiment, the results of which are shown in FIG. 15, it was found that the APC-MS compositions of the invention confer polyclonal expansion of a subset of CD62L+ mouse splenic T cells in a manner that is similar and comparable to those achieved with DYNABEADS. The results are depicted in the form of flow cytometric (FACS) scatter plots of T-cell population(s) at various time-points (t=0 days, 5 days, 7 days, 11 days and 13 days) following incubation with APC-MS or DYNABEADS (with re-stimulation or IL-2 treatment after 7 days of incubation). The CD62L+ cells appear in the right hand (top and bottom) quadrants of the scatter plots. The results demonstrate that the APC-MS compositions of the invention are equally effective at selectively expanding the target T cell sub-populations, which may then be manipulated or formulated using known cytological techniques.

Figure 16:
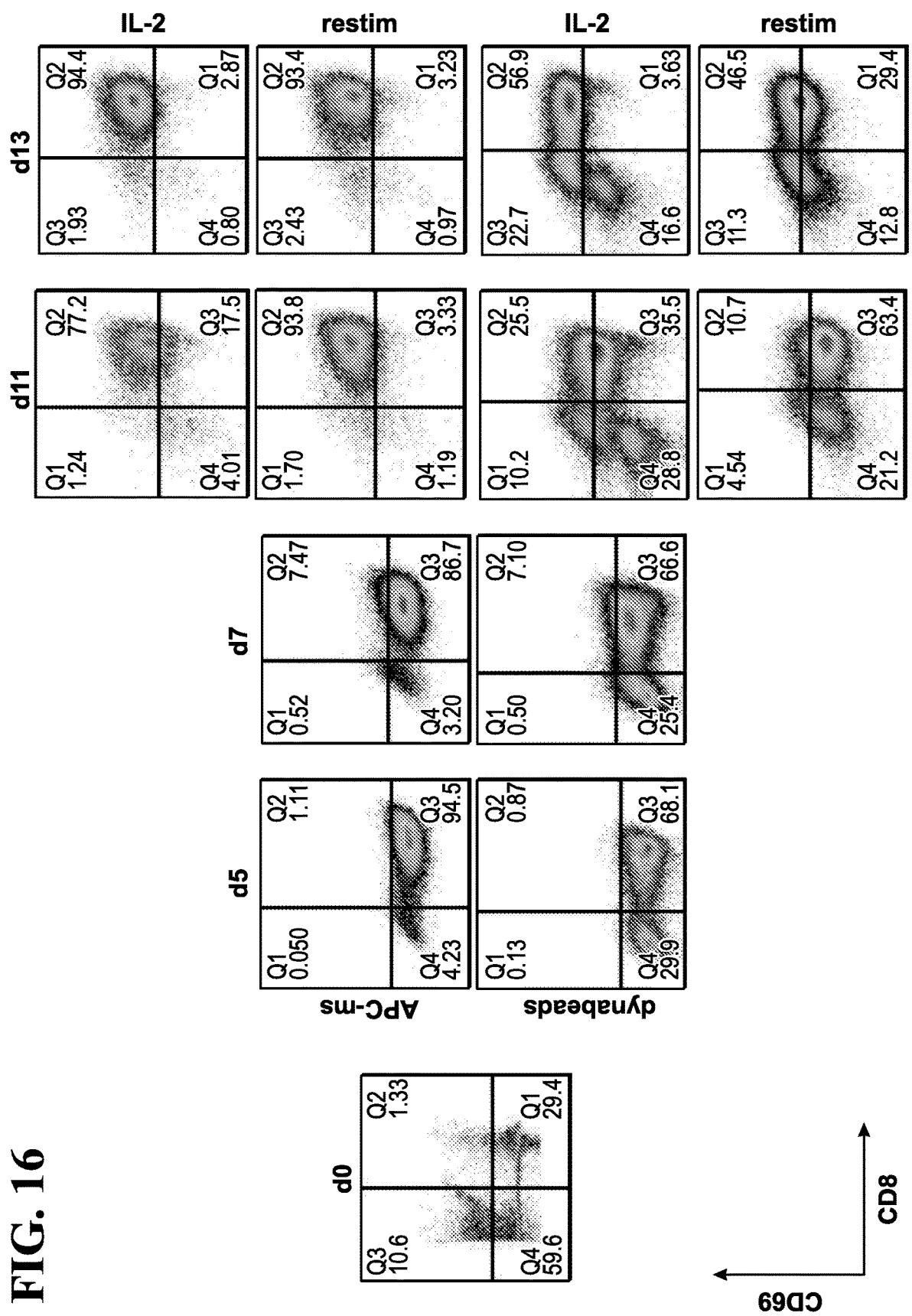
FIG. 16 shows polyclonal expansion of a subset of CD8+/CD69+ mouse splenic T cells upon incubation with APC-MS or DYNABEADS. The results are depicted in the form of flow cytometric (FACS) scatter plots of T-cell population(s) at various time-points (t=0 days, 5 days, 7 days, 11 days and 13 days) following incubation with APC-MS or DYNABEADS (with re-stimulation or IL-2 treatment after 7 days of incubation), wherein the values on the X-axis depict intensity of CD8+ staining and the values on the Y-axis depict intensity of CD69+ staining. The CD8+/CD69+ cells appear in the top right hand quadrant of the scatter plots.

In the fourth experiment, the results of which are shown in FIG. 16, it was found that the APC-MS compositions of the invention confer polyclonal expansion of a subset of CD8+/CD69+ mouse splenic T cells in a manner that is similar and comparable to those achieved with DYNABEADS. The results are depicted in the form of flow cytometric (FACS) scatter plots of T-cell population(s) at various time-points (t=0 days, 5 days, 7 days, 11 days and 13 days) following incubation with APC-MS or DYNABEADS (with re-stimulation or IL-2 treatment after 7 days of incubation). The CD8+/CD69+ cells appear in the top right hand quadrant of the scatter plots. The results demonstrate that compared to incubation with DYNABEADS, incubation with APC-MS achieved greater expansion of polyclonal CD8+/CD69+ T cells at the end of the 14-day incubation period (relative proportion of about 90% CD8+/CD69+ T cells in samples incubated with APC-MS versus about 50% CD8+/CD69+ T cells in samples incubated with DYNABEADS).

Figure 17:
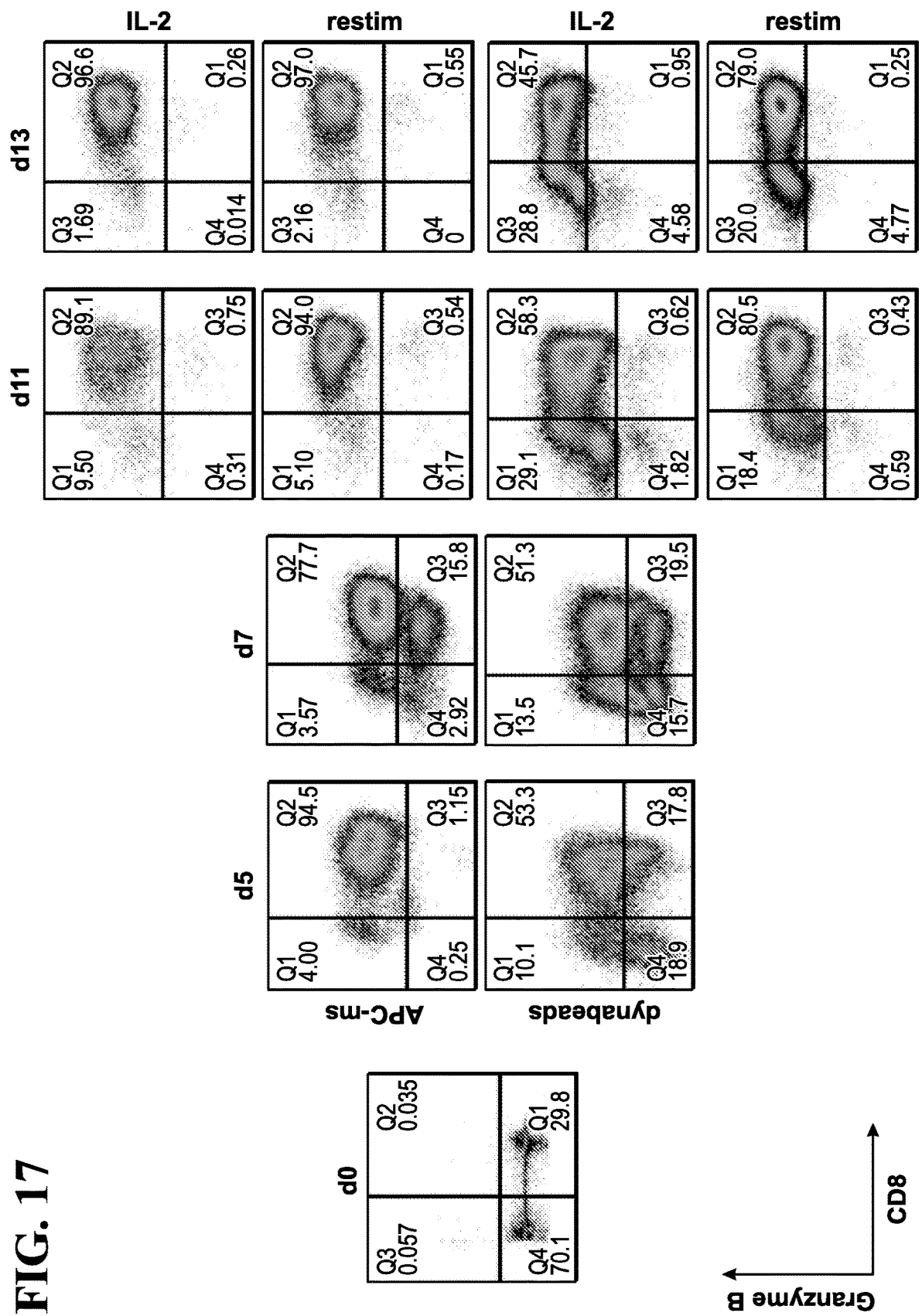
FIG. 17 shows polyclonal expansion of a subset of CD8+/Granzyme B+ mouse splenic T cells upon incubation with APC-MS or DYNABEADS. The results are depicted in the form of flow cytometric (FACS) scatter plots of T-cell population(s) at various time-points (t=0 days, 5 days, 7 days, 11 days and 13 days) following incubation with APC-MS or DYNABEADS (with re-stimulation or IL-2 treatment after 7 days of incubation), wherein the values on the X-axis depict intensity of CD8+ staining and the values on the Y-axis depict intensity of Granzyme B+staining. The CD8+/Granzyme B+ cells appear in the top right hand quadrant of the scatter plots.

In the fifth experiment, the results of which are shown in FIG. 17, it was found that the APC-MS compositions of the invention confer polyclonal expansion of a subset of CD8+/Granzyme B+ mouse splenic T cells in a manner that is similar and comparable to those achieved with DYNABEADS. The results are depicted in the form of flow cytometric (FACS) scatter plots of T-cell population(s) at various time-points (t=0 days, 5 days, 7 days, 11 days and 13 days) following incubation with APC-MS or DYNABEADS (with re-stimulation or IL-2 treatment after 7 days of incubation). The CD8+/Granzyme B+ cells appear in the top right hand quadrant of the scatter plots. The results demonstrate that compared to incubation with DYNABEADS, incubation with APC-MS achieved greater expansion of polyclonal CD8+/Granzyme B+ T cells at the end of the 14-day incubation period (relative proportion of about 95% CD8+/Granzyme B+ T cells in samples incubated with APC-MS versus about 80% CD8+/Granzyme B+ T cells in samples incubated with DYNABEADS).

Example 6: Use of Scaffolds to Stimulate and Expand Cytokine-Secreting Cells

Figure 18:
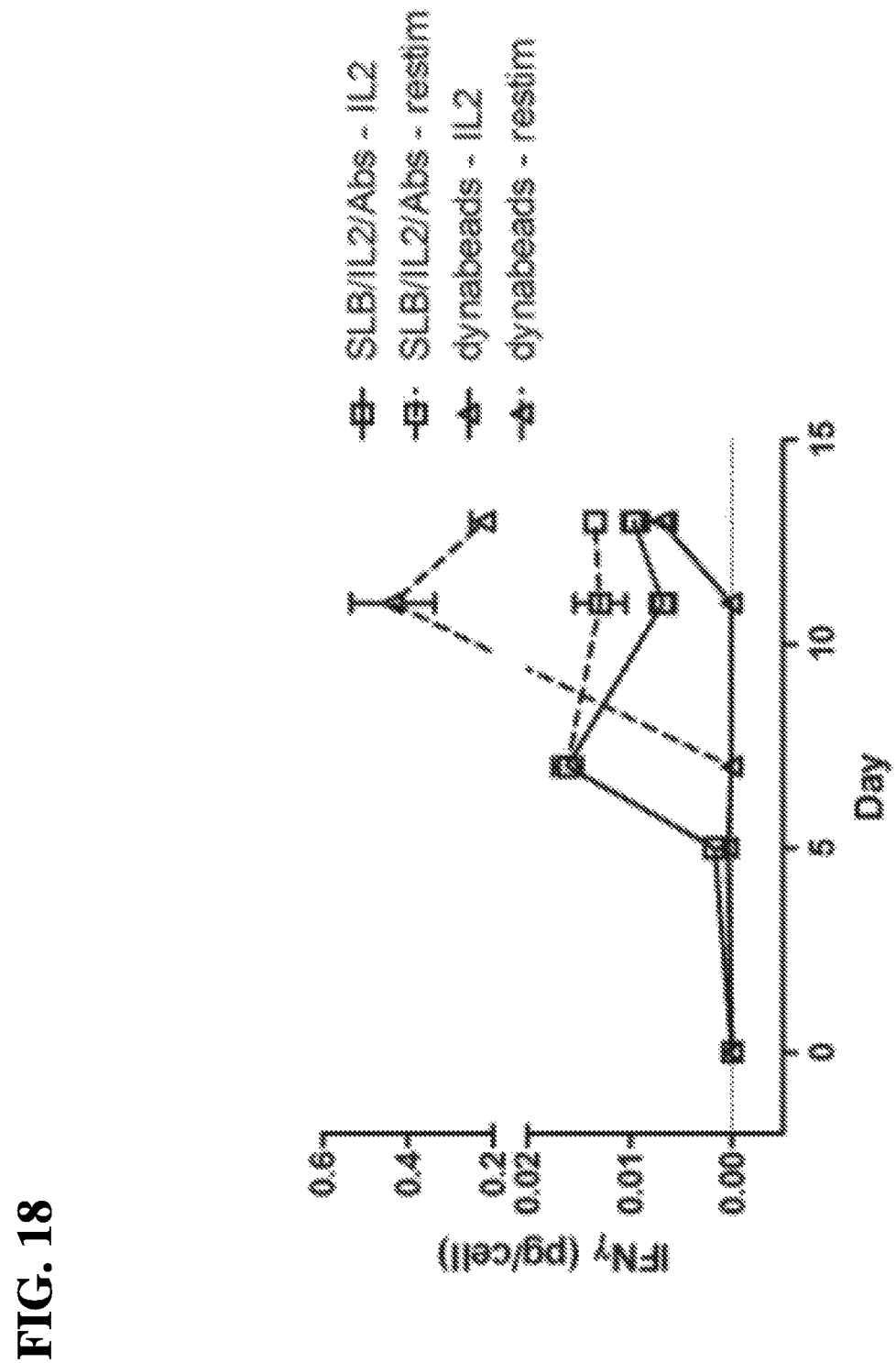
FIG. 18 shows T-cell secretion of IFNγ (pg/cell) at various time-points (t=0 days, 5 days, 7 days, 11 days and 13 days) following incubation with APC-MS (squares) or DYNABEADS (triangles). After 7-days of incubation, the cells were divided into two sub-populations, wherein the first sub-population was re-stimulated (dashed line) and the second sub-population was treated with IL-2 (solid line). Herein, APC-MS was used in the re-stimulation of both APC-MS-incubated and DYNABEAD-incubated cell populations.

Mouse splenic T-cells were incubated for various durations (t=0 days, 5 days, 7 days, 11 days and 13 days) with the APC-MS or DYNABEADS. After 7-days of incubation, a first sub-population of T-cells was re-stimulated with APC-MS or DYNABEADS, respectively, and a second sub-population was treated with IL-2. Cytokine (IFNγ) secretion was measured using standard assays for measuring IFNγ concentrations in biological samples, e.g., ELISA assays. The results, which are presented in FIG. 18, demonstrate that compared to incubation with DYNABEADS, incubation with APC-MS achieved greater expansion of polyclonal CD8 mouse splenic T cells after 5-days of incubation. This effect was sustained throughout the 13-day experimental period. Incubation of splenic T-cells with the scaffolds increased IFNγ secretion. Furthermore, it was found that re-stimulation was particularly effective in enhancing IFNγ secretion in the sub-population of cells that were incubated with DYNABEADS.

Example 7: Use of Scaffolds to Remove Anergeic, Quiescent or Spent T-Cells

Figure 19:
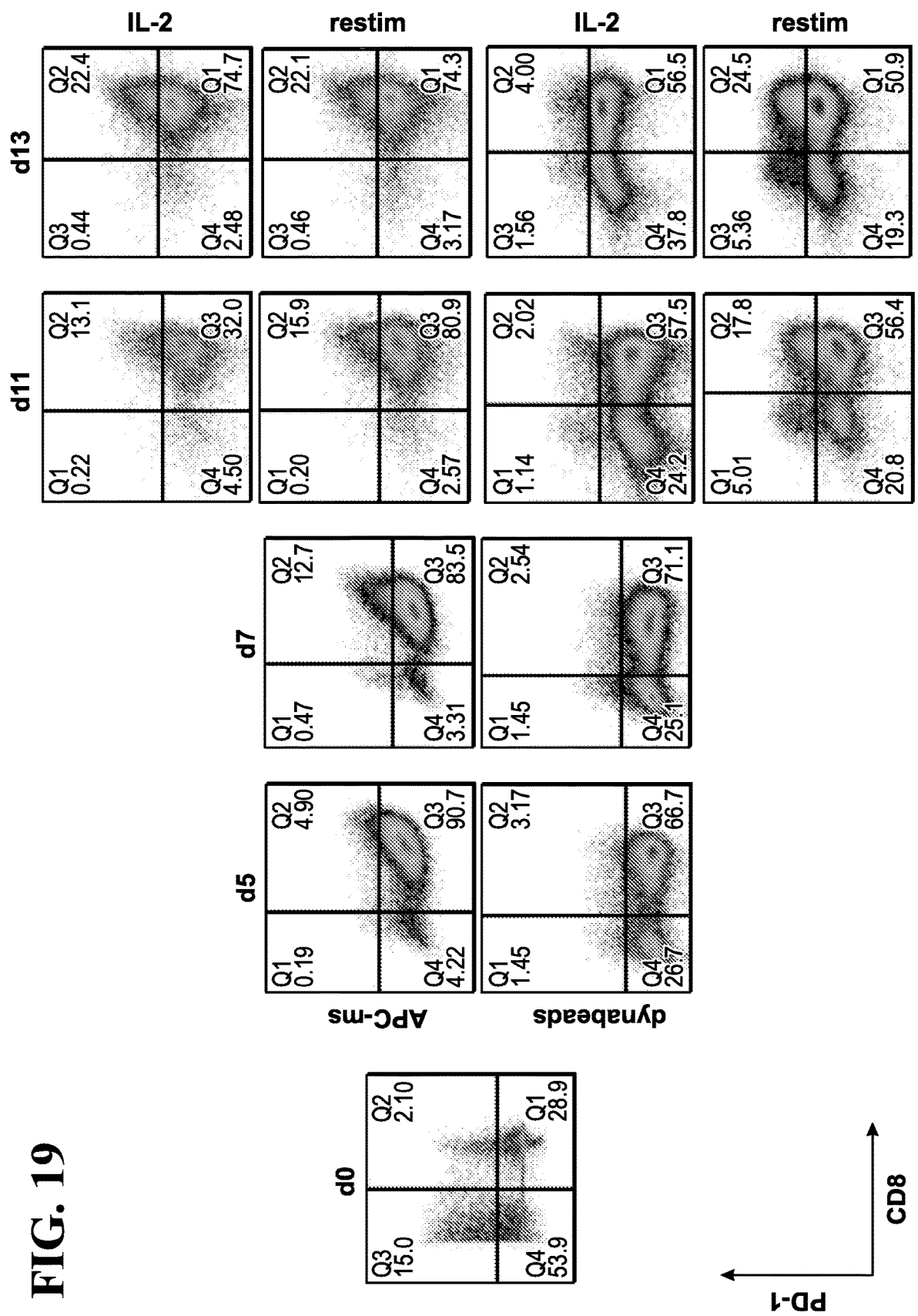
FIG. 19 shows levels of PD-1+ mouse splenic T cells upon incubation with APC-MS or DYNABEADS. The results are depicted in the form of flow cytometric (FACS) scatter plots of T-cell population(s) at various time-points (t=0 days, 5 days, 7 days, 11 days and 13 days) following incubation with APC-MS or DYNABEADS (with re-stimulation or IL-2 treatment after 7 days of incubation), wherein the values on the X-axis depict intensity of CD8+ staining and the values on the Y-axis depict intensity of PD-1+ staining (a potential marker of exhaustion).

Several new co-stimulatory molecules have been discovered based on their homology with the B7 and CD28 families. Programmed cell death protein 1 (PD-1; UNIPROT Accession No. Q15116) is expressed on activated T cells and has two B7 like ligands, PD-L1 and PD-L2 (Freeman et al., *J. Exp. Med.* 192:1027-1034 (2000); Latchman et al., *Nat. Immunol.* 2:261-268 (2001); Dong et al., *Nat. Med.* 5:1365-1369 (1999); Tseng et al., *J. Exp. Med.* 193:839-846 (2001)). It is thought that that PD-1 is a marker of anergy (Chikuma et al., *J Immunol.,* 182(11):6682-9, 2009). Thus, the effect of the scaffolds of the instant invention on inducing T-cell anergy was investigated using flow cytometry. Mouse splenic T-cells were incubated for various durations (t=0 days, 5 days, 7 days, 11 days and 13 days) with the scaffolds of the invention (APC-MS) or DYNABEADS. After 7-days of incubation, a first sub-population of T-cells was re-stimulated and a second sub-population was treated with IL-2. Each T-cell sub-population was analyzed for expression of cell-surface markers using FACS scatter plots, wherein the values on the X-axis depict intensity of CD8+ staining and the values on the Y-axis depict intensity of PD-1+ staining. The results, which are presented in FIG. 19, show increased PD-1 expression (i.e., increased anergy) of mouse splenic T cells with time. T-cell exhaustion was achieved in both sub-populations. The results indicate that the majority of cells throughout culture period is PD-1 negative (lower quadrants), although some cells do upregulate expression of PD-1. Restimulation with APC-MS tends to increase PD-1 expression. Note: exposure to IL-2 was provided in all setups.

Figure 20A:
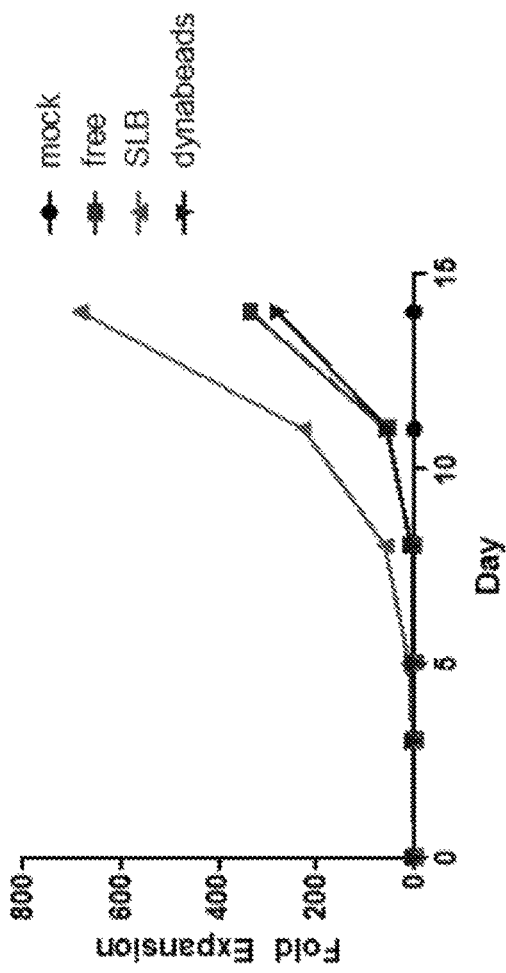
FIGS. 20A and 20B show the effect of incubating human peripheral blood T-cells with various compositions.

Example 8: Use of Scaffolds to Increase T-Cell Expansion and Improve Cell Activity The effect of the APC-MS compositions of the invention in improving T-cell expansion and/or metabolic activity was performed using cytometry. Human peripheral blood T-cells were incubated with control scaffolds or experimental scaffolds and the number and/or metabolic activity of T-cells was measured at various time-points (t=0 days, 5 days, 7 days, 11 days and 13 days) using standard assays, e.g., manual cell counts of live cells using Trypan Blue exclusion/hemocytometer, metabolic activity analyzed using Alamar Blue assay. Results are presented in FIGS. 20A and 20B. In the case of T-cell expansion studies, control scaffolds include sham compositions (labeled: "mock"; depicted with a black line) and compositions containing soluble, free form of stimulants anti-CD3, anti-CD28, IL-2 ("free"; depicted with a red line), while the experimental scaffolds include (1) DYNABEADS (blue line) and (2) lipid bilayers (SLB) of the present invention (green line). Results are shown in FIG. 20A. It can be seen that at the end of the 13-day experimental period, incubation with SLB resulted in almost a two-fold greater expansion of T-cells compared to incubation with DYNABEADS. More surprisingly, even the "free" scaffolds elicited a stimulatory effect on T-cells which was comparable to the effect of DYNABEADS.

Figure 20B:
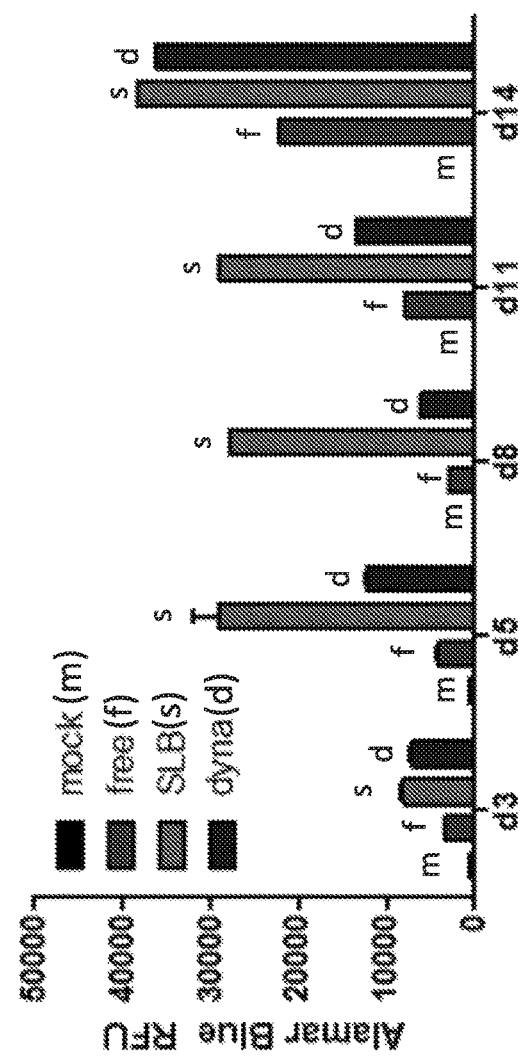

Results on the effect of the scaffolds of the instant invention on the metabolic activity of primary T-cells are presented in FIG. 20B. Splenic T-cells were incubated with control scaffolds or experimental scaffolds and the metabolic activity of T-cells was measured at various time-points (t=0 days, 5 days, 7 days, 11 days and 13 days) was measured using Alamar Blue staining. The control scaffolds include sham compositions ("mock"; "m") and compositions that are free of SLB ("free"; "f"), while the experimental scaffolds include (1) DYNABEADS ("d") and (2) lipid bilayers (SLB) ("s"). It can be seen that at the end of the 14-day experimental period, cells incubated with "mock" scaffolds all perish, while cells incubated with the experimental scaffolds (SLB or DYNABEADS) experience sustained growth and expansion over time. More importantly, the SLB scaffolds of the invention promoted better growth and metabolic activity of T-cells at the end of the 14-day experimental period compared to the effects conferred by DYNABEADS.

Example 9: Use of Scaffolds to Promote Expansion of Human T-Cells

Figure 21A:
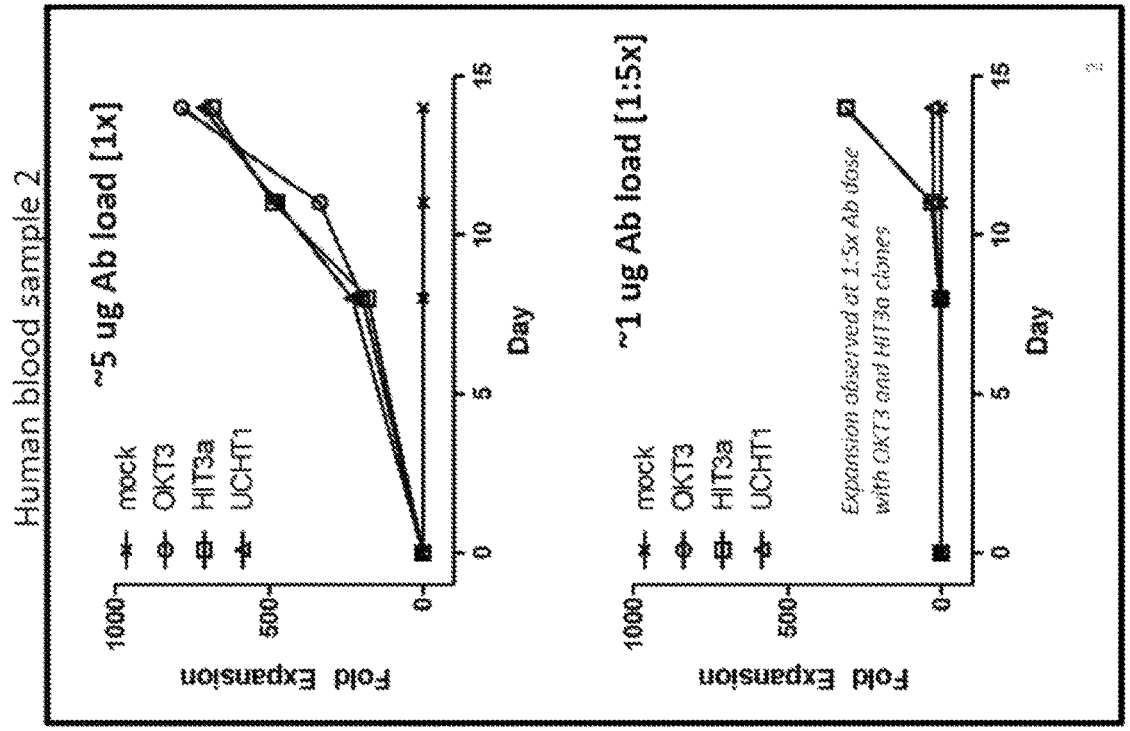
FIGS. 21A and 21B show the effect of incubating human peripheral blood T-cells with various anti-CD3 antibodies. Human blood samples obtained from subject 1 (FIG. 21A) and subject 2 (FIG. 21B) were incubated with control scaffolds ("mock") or experimental scaffolds containing the listed anti-CD3 antibodies—muromonab (OKT3), an antibody recognizing 17-19 kD ε-chain of CD3 within the CD3 antigen/T cell antigen receptor (TCR) complex (HIT3a) and a monoclonal antibody recognizing a 20 kDa subunit of the TCR complex within CD3ε (UCHT1). Three different dosages were investigated—5 µg (top slides), 1 µg (bottom slide for subject 2) and 0.5 µg (bottom slide for subject 1). In each case, co-stimulation was provided with anti-CD28 antibodies, wherein the ratio of anti-CD3 antibody:anti-CD28 antibody was maintained at 1:1. Fold expansion of T cells was measured at various time-points (t=0 days, 7 days, 11 days and 13 days).
Figure 21B:
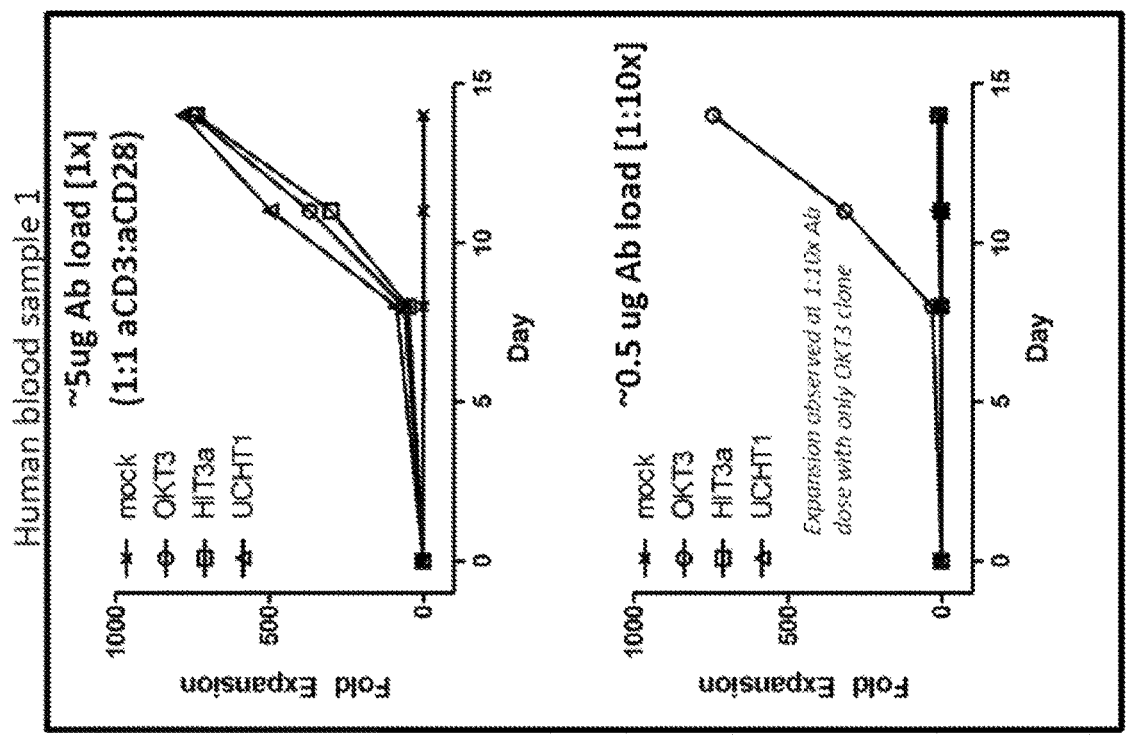

Human blood samples obtained from subject 1 (FIG. 21A) and subject 2 (FIG. 21B) were incubated with control scaffolds ("mock") or experimental scaffolds containing the listed anti-CD3 antibodies—muromonab (OKT3), an antibody recognizing 17-19 kD ε-chain of CD3 within the CD3 antigen/T cell antigen receptor (TCR) complex (HIT3a) and a monoclonal antibody recognizing a 20 kDa subunit of the TCR complex within CD3e (UCHT1). Three different dosages were investigated—5 μg (top slides), 1 μg (bottom slide for subject 2) and 0.5 μg (bottom slide for subject 1). In each case, co-stimulation was provided with anti-CD28 antibodies, wherein the ratio of anti-CD3 antibody:anti-CD28 antibody was maintained at 1:1. Fold expansion of T cells was measured at various time-points (t=0 days, 7 days, 11 days and 13 days). The results, which are presented in FIGS. 21A and 21B, show that at higher antibody dosages (5 μg), all three anti-CD3 antibodies were capable of stimulating expansion of human T-cells. In all cases, the expansion of T-cell population was initially slow until day 7, after which, it increased exponentially. At the highest dose, a 600-800 fold increase in the number of T-cells was achieved at the end of the experimental period (day 13). With intermediate dosage (1 μg), only OKT3 and HIT3a (but not UCHT1) were capable of stimulating T-cell expansion, wherein, a 300-400- fold increase in the number of T-cells was achieved at the end of the experimental period (day 13). At the lowest dosage (0.5 µg), only OKT3 (but not UCHT1 and/or HIT3a) was capable of stimulating T-cell expansion, wherein, a 600-700 fold increase in the number of T-cells was achieved at the end of the experimental period (day 13). The results show an effect of both the anti-CD3 antibody clone as well as dose of the antibody on the expansion rate.

Figure 22:
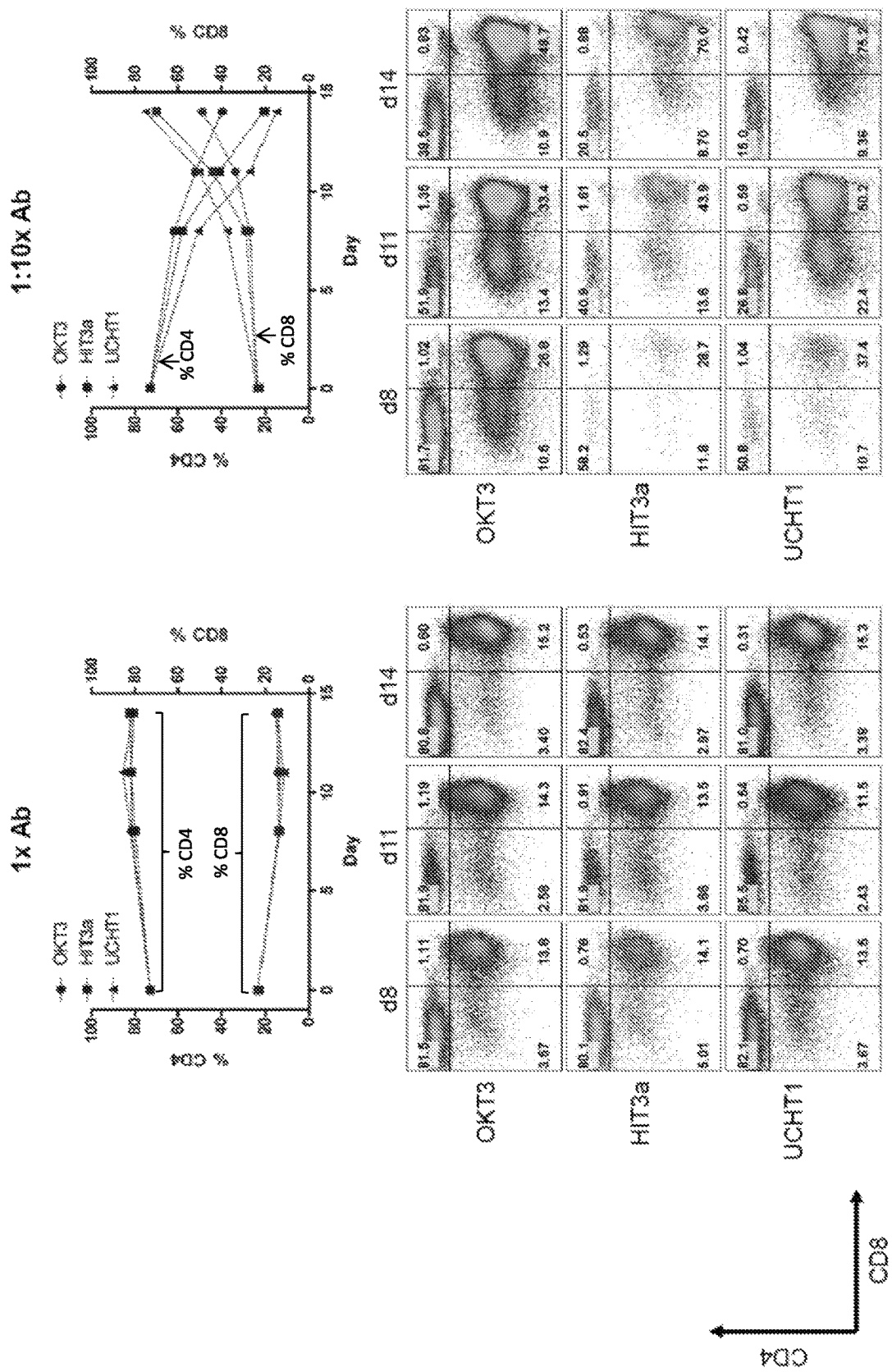
FIG. 22 shows polyclonal expansion of a human T cells upon incubation with control scaffolds ("mock") or experimental scaffolds containing the listed anti-CD3 antibodies—OKT3, HIT3a, and UCHT1. The bottom panels show flow cytometric (FACS) scatter plots of T-cell population(s) at various time-points (t=8 days, 11 days and 14 days) following incubation with APC-MS containing each of the anti-CD3 antibodies as a stimulatory molecule and an anti-CD28 antibody as the co-stimulatory molecule. The values on the X-axis of the scatter plots depict intensity of CD8+ staining and the values on the Y-axis depict intensity of CD4+ staining. The plots are summarized in the line-graphs of the top panel, which show changes in percentage of CD4+ versus CD8+ T-cell sub-populations after incubation with APC-MS containing the aforementioned anti-CD3 antibodies—OKT3 (circles), HIT3a (squares) and UCHT1 (triangles). Two different antibody dosages were investigated—5 µg (1× dilution) and 0.5 µg (1:10× dilution).

Next, the polyclonal expansion of a human T cells upon incubation with control scaffolds ("mock") or experimental scaffolds containing the listed anti-CD3 antibodies—OKT3, HIT3a, and UCHT1, was analyzed via flow cytometry. Results are presented in FIG. 22, wherein the bottom panels show flow cytometric (FACS) scatter plots of T-cell population(s) at various time-points (t=8 days, 11 days and 14 days) following incubation with APC-MS containing each of the anti-CD3 antibodies as a stimulatory molecule and an anti-CD28 antibody as the T-cell co-stimulatory molecule. The values on the X-axis of the scatter plots depict intensity of CD8+ staining and the values on the Y-axis depict intensity of CD4+ staining. The scatter plots are summarized in the line-graphs of the top panel, which show changes in percentage of CD4+ versus CD8+ T-cell sub-populations after incubation with APC-MS containing the aforementioned anti-CD3 antibodies—OKT3 (circles), HIT3a (squares) and UCHT1 (triangles). Two different antibody dosages were studied—a first dose of 5 µg (1× dilution) and a second dose of 0.5 µg (1:10× dilution). The results show that at low antibody dosages (1:10× dilution; 0.5 µg), all three anti-CD3 antibodies were capable of enriching CD8+-specific T-cells using a low antibody concentration versus a high antibody concentration. A 3-4 fold increase in the number of CD8+-specific T-cells was achieved at the end of the experimental period (day 14). For instance, the relative frequency of CD8+ T-cells was 20% at the start of the experiment, which had increased to about 60%-80% at day 14. Moreover, it was found that anti-CD3 antibodies UHCT1 and OKT1 were equally effective and superior to the anti-CD3 antibody HIT3a in promoting the expansion of CD8+ T-cells. At high (5 µg) antibody doses, the ratio of CD8+: CD4+ in the global T-cell population was unchanged (or even attenuated) at day 14. The results show an effect of both the anti-CD3 antibody clone as well as dose of the antibody on the expansion of CD8+-specific T cells.

Figure 23:
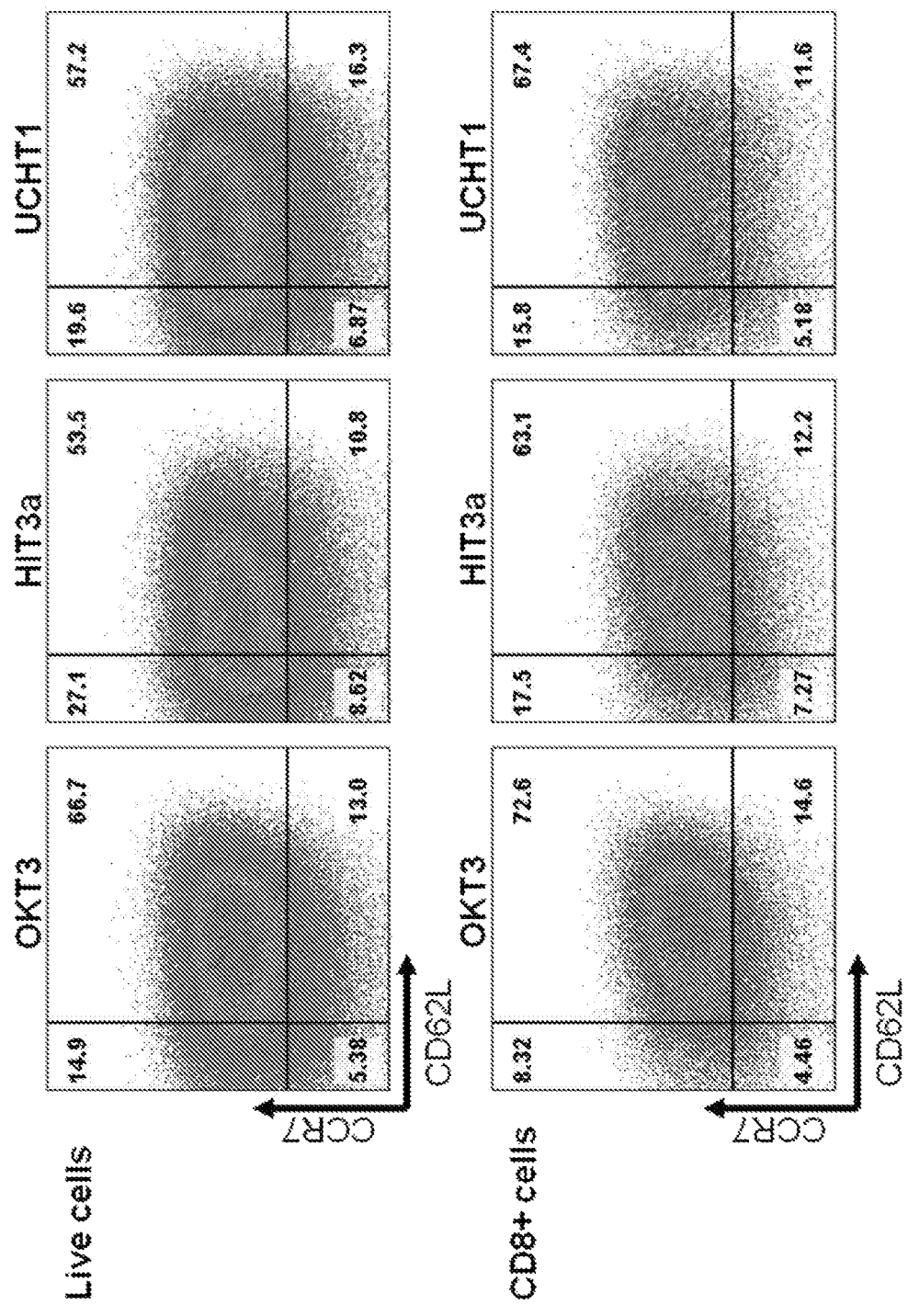

Example 10: Use of Scaffolds to Promote Expansion of a Specific Human T-Cell Sub-Population Human blood samples were incubated with experimental scaffolds containing the listed anti-CD3 antibodies—muromonab (OKT3), HIT3a and UCHT1 at 1× dosage (5 µg). In each case, co-stimulation was provided with anti-CD28 antibodies. Fold expansion of T cells was measured after 14 days. The expression of CD62L and CCR7 in total live cells is shown in the top panels and the expression of these markers in gated CD8+ cells is shown in the bottom panels. The results, which are presented in FIG. 23, show that all three anti-CD3 antibodies were capable of stimulating the expansion of a distinct sub-population of human T-cells. Surprisingly, a majority of cells expanded with the various antigen-presenting cell-mimetic scaffolds (APC-MS) of the instant invention remain CD62L+CCR7+ even after 14 days post-incubation. The results point to the retained in vivo functionality of expanded T-cells after ex vivo expansion. Accordingly, it is possible to selectively expand and sustain a distinct sub-population of CD62L+ CCR7+ T-cells (e.g., memory cells) using the antigen-presenting cell-mimetic scaffolds.

Additionally, APC-MS scaffolds containing OKT3 were particularly effective in expanding and/or retaining CD62L+ CCR7+ T-cells compared to scaffolds containing UCHT1 and/or HIT3a.

Example 11: Expansion of T-Cells Ex Vivo Using Antigen-Presenting Cell-Mimetic Scaffolds (APC-MS)

Adoptive cell transfer (ACT) of T cells is a promising treatment for cancer and infectious disease. However, current approaches for ex vivo T cell expansion, a key step in ACT, frequently yield suboptimal expansion rates and limited functionality of cells. Here, we developed mesoporous silica micro-rod-supported lipid bilayers that presented cues for T cell receptor stimulation and costimulation at pre-defined densities locally on a fluid lipid bilayer, and facilitated the controlled release of soluble interleukin-2, similar to how these cues are naturally presented by antigen-presenting cells (APCs). In cell culture, the material formed into an APC-mimetic scaffold (APC-MS) that promoted the activation of infiltrating mouse and human T cells. APC-MS promoted two- to ten-fold greater polyclonal T cell expansion than commercial expansion beads after two weeks, and robust antigen-specific expansion of rare subpopulations of functional cytotoxic T cells. This study demonstrates a new platform to rapidly expand functional T cells for ACT.

Adoptive cell transfer (ACT) using T cells is a promising approach for the treatment of various malignancies and infectious diseases (see e.g., Rosenberg, S. A. & Restifo, N. P. *Science* 348, 62-68 (2015); June, C. H. et al. *Science Translational Medicine* 7(280): 280ps7 (2015); and Fesnak, A. D. et al. *Nature Reviews Cancer* 16, 566-581 (2016)). However, the rapid ex vivo expansion of functional T cells, a key step in the production of T cells for ACT, remains a major challenge. T cell activation requires three signals: (1) T cell receptor (TCR) stimulation, (2) costimulation, and (3) pro-survival cytokines (Huppa, J. B. & Davis, M. M. *Nature Reviews Immunology* 3, 973-983 (2003)). In the body, these signals are provided by antigen-presenting cells (APCs), which present these cues to T cells in specific spatiotemporal patterns (Huppa and Davis (2003); Lee, K.-H. et al. *Science* 302, 1218-1222 (2003); Alarcon, B. et al. *Immunology* 133, 420-425 (2011); and Minguet, S. et al. *Immunity* 26, 43-54 (2007)). Various approaches are used to expand T cells ex vivo for ACT, and synthetic artificial APCs (aAPCs) are particularly convenient (Rosenberg and Restifo (2015); Hasan, A. et al. *Advancements in Genetic Engineering* 2015 (2015);Hollyman, D. et al. *Journal of Immunotherapy* (Hagerstown, Md.: 1997) 32, 169 (2009); Maus, M. V. et al. *Nature Biotechnology* 20, 143-148 (2002); Zappasodi, R. et al. *Haematologica* 93, 1523-1534 (2008); Perica, K. et al. *ACS Nano* 9, 6861-6871 (2015); Mandal, S. et al. *ACS Chemical Biology* 10, 485-492 (2014); Steenblock, E. R. & Fahmy, T. M. *Molecular Therapy* 16, 765-772 (2008); Fadel, T. R. et al. *Nature Nanotechnology* 9, 639-647 (2014); Sunshine, J. C. et al. *Biomaterials* 35, 269-277 (2014); Fadel, T. R. et al. *Nano letters* 8, 2070-2076 (2008); Meyer, R. A. et al. *Small* 11, 1519-1525 (2015); and Steenblock, E. R. et al. *Journal of Biological Chemistry* 286, 34883-34892 (2011)). Currently, commercial microbeads (DYNA-BEADS) functionalized with activating antibodies for CD3 (αCD3; TCR stimulus) and CD28 (αCD28; costimulatory cue) are the only FDA-approved synthetic system for expanding T cells (Hollyman et al. (2009)). These beads promote polyclonal T cell activation with exogenous interleukin-2 (IL-2) supplementation. Although these cultures provide T cells with the three critical signals, the context in which these signals are presented is not representative of how they are naturally presented by APCs. This contextual inconsistency can lead to suboptimal T cell expansion rates and T cell products with limited or dysregulated functions (Zappasodi et al. (2008); Fadel et al. (2014); Li, Y. & Kurlander, R. J. *Journal of Translational Medicine* 8, 1 (2010); and JJin, C. et al. *Molecular Therapy-Methods & Clinical Development* 1 (2014)). In addition, these beads are not amenable to the presentation of large sets of cues, which may be important for the generation of highly functional therapeutic T cells (Hasan et al. (2015); and Hendriks, J. et al. *Nature immunology* 1, 433-440 (2000)).

A composite material was developed comprised of supported lipid bilayers (SLBs) formed on high aspect ratio mesoporous silica micro-rods (MSRs) (Kim, J et al. *Nature Biotechnology* 33, 64-72 (2015); and Li, W. A. et al. *Biomaterials* 83, 249-256 (2016)). The SLBs enabled the presentation of combinations of T cell activation cues at predefined densities on a fluid lipid bilayer, while the MSRs facilitated the sustained paracrine release of soluble cues to nearby T cells. Thus, composite MSR-SLBs enabled the presentation of surface and soluble cues to T cells in a context analogous to natural APCs. In cell culture, the high aspect ratio rods settled and stacked to form a 3D scaffold structure. The scaffolds formed from MSR-SLBs that were functionalized with T cell activation cues are referred to as APC-mimetic scaffolds (APC-MS). APC-MS facilitated between two- to ten-fold greater polyclonal expansion of primary mouse and human T cells than commercial DYNABEADS after two weeks. APC-MS also facilitated robust antigen-specific expansion of functional mouse and human cytotoxic T cells. In particular, APC-MS presenting Epstein bar virus (EBV)-associated antigens expanded and enriched for rare subpopulations of human T cells in an antigen-specific manner. Overall, APC-MS represents a flexible and tunable platform technology that could enable the rapid expansion of highly functional T cells for ACT. specific spatiotemporal patterns (Huppa and Davis (2003); Lee et al. (2003); Alarcón et al. (2011); and Minguet et al. (2007)).

Assembly and Characterization of APC-MS

Figure 25A:
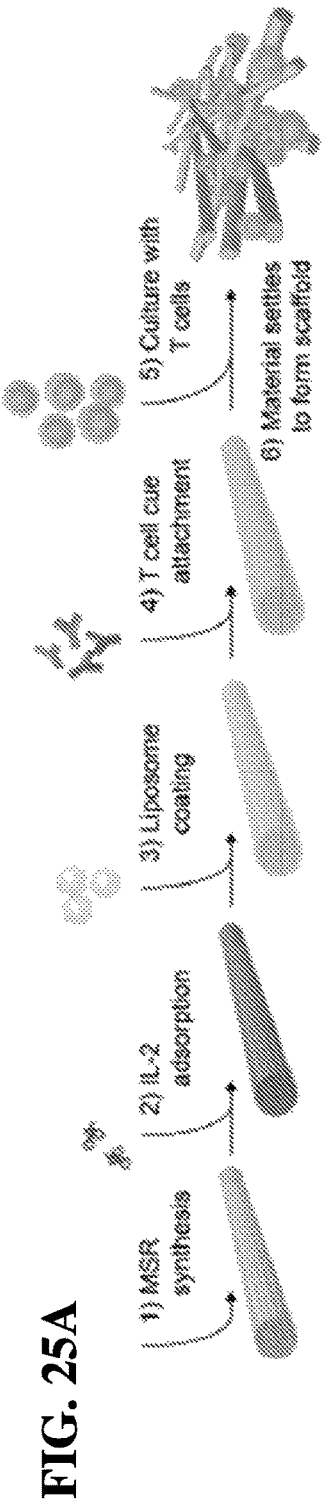
FIGS. 25A and 25B depict the design of antigen-presenting cell-mimetic scaffolds (APC-MS).
Figure 25B:
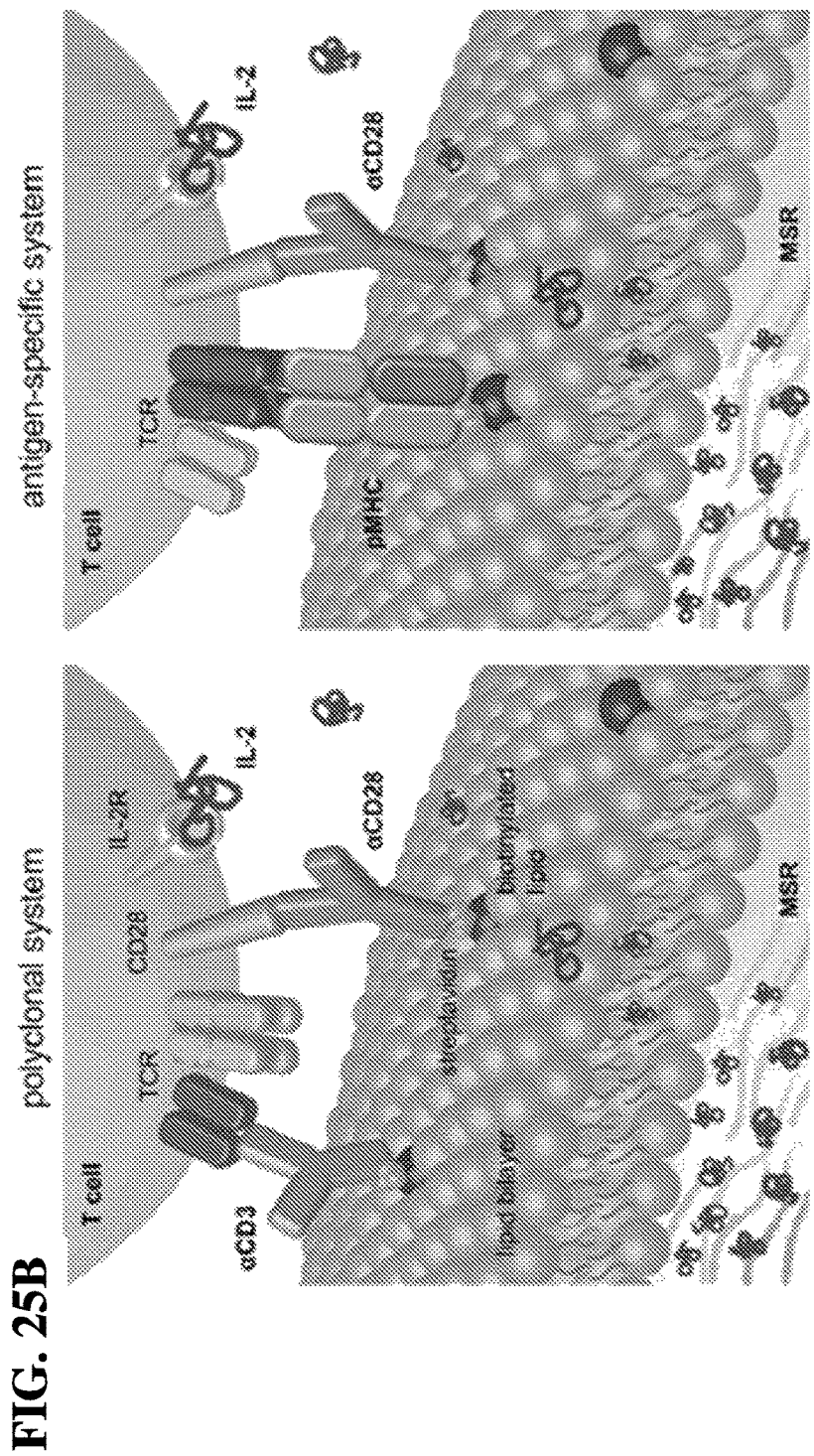

APC-MS were prepared for T cell activation (FIG. 25A), using unique cues for polyclonal and antigen-specific expansion (FIG. 25B). High aspect ratio MSRs with average dimensions of 88 µm length, 4.5 µm diameter (aspect ratio ~20), and 10.9 nm pores were synthesized as previously described (Kim et al. (2015); and Li et al. (2016)) (see FIG. 26A), and adsorbed with IL-2.

Figure 26B:
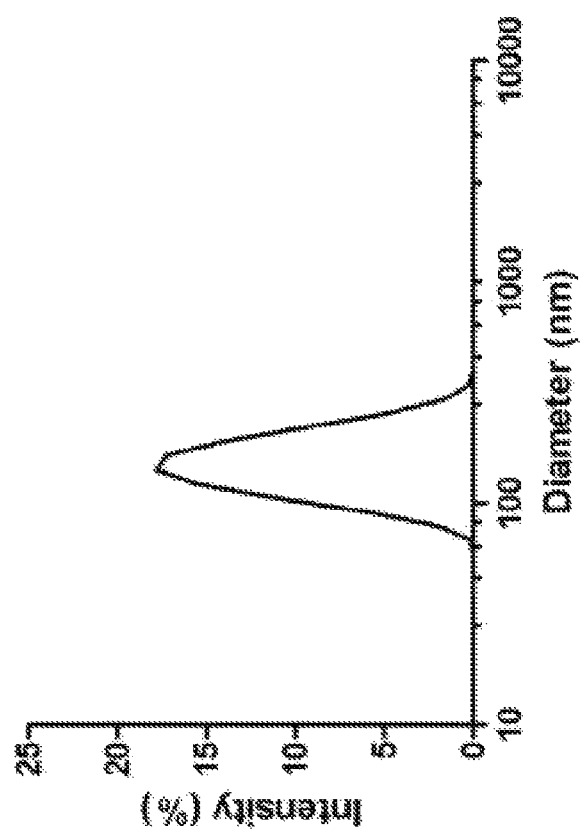
FIGS. 26A and 26B depicts the physical characterization of components used to assembly MSR-SLBs.
Figure 26A:
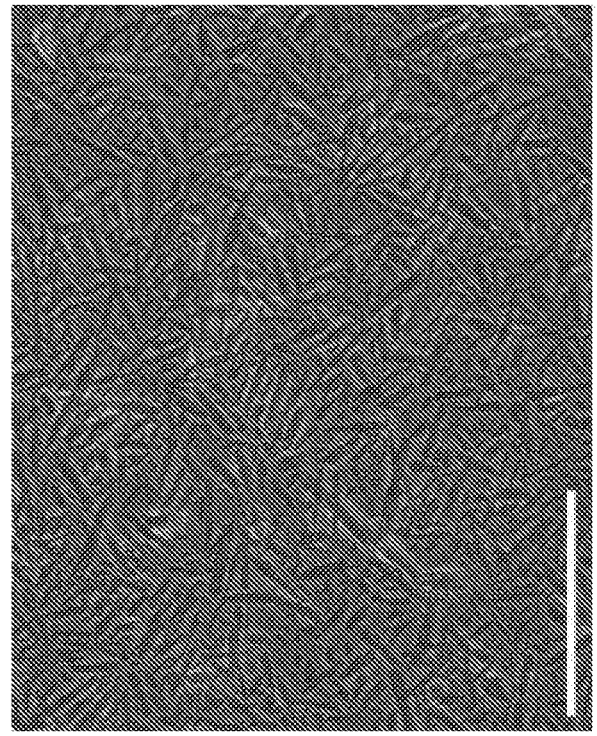

Liposomes (140 nm) containing predefined amounts of a biotinylated-lipid were prepared, and coated onto the 1L-2-laden MSRs, forming MSR-SLBs (see FIG. 26B). Next, biotinylated cues for TCR activation and costimulation were attached to the MSR-SLB surfaces via a streptavidin intermediate. In cell culture, 3D scaffolds spontaneously formed through the settling and random stacking of the rods, forming APC-MS. T cells infiltrated the interparticle space of the scaffolds. Together, scaffolds present cues for TCR-activation and costimulation on the surface of the lipid bilayer, and release soluble IL-2 over time in a paracrine fashion to infiltrating T cells, similar to how these cues are presented to T cells by natural APCs (see Huppa and Davis (2003)).

Figure 27A:
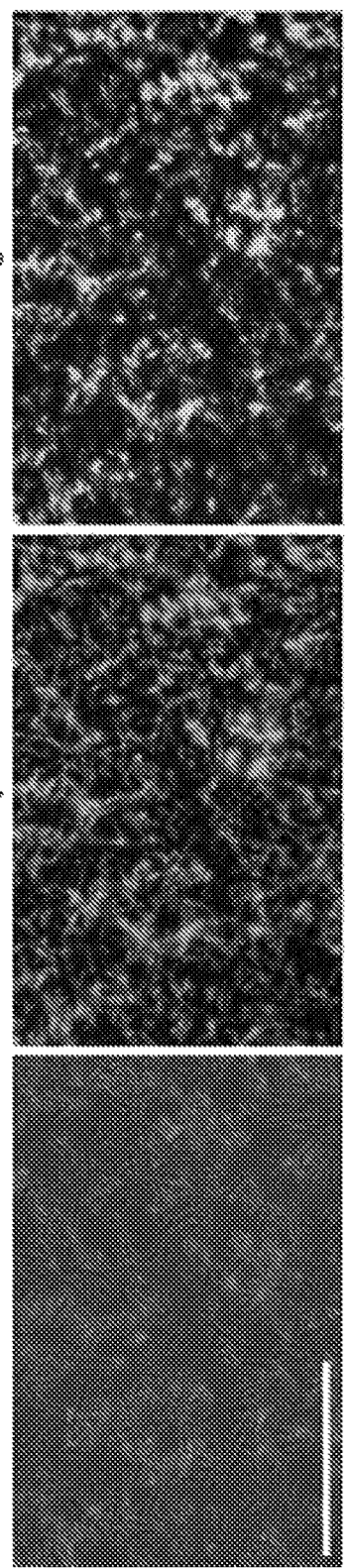
FIGS. 27A and 27B are microscopy images of lipid-coated MSRs.
Figure 27B:
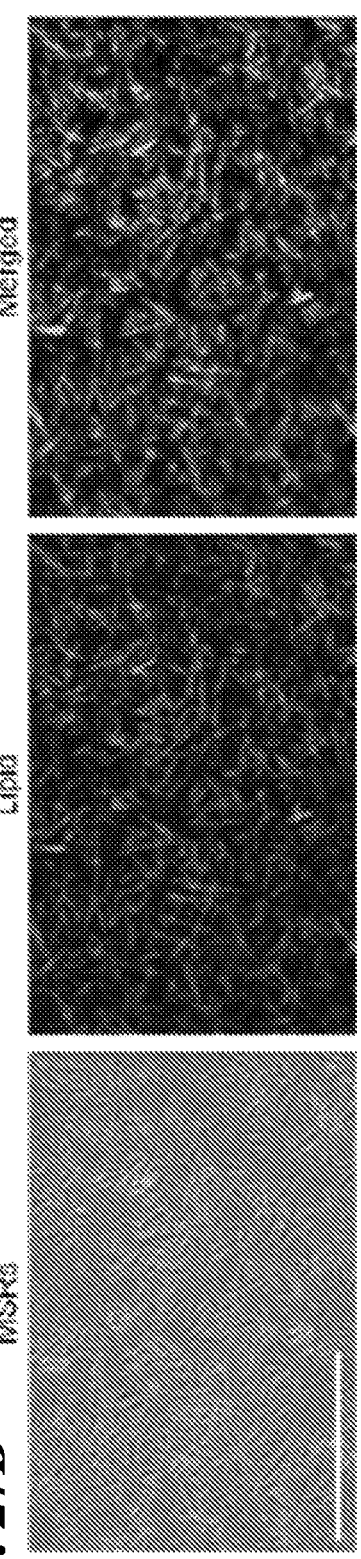
Figure 28A:
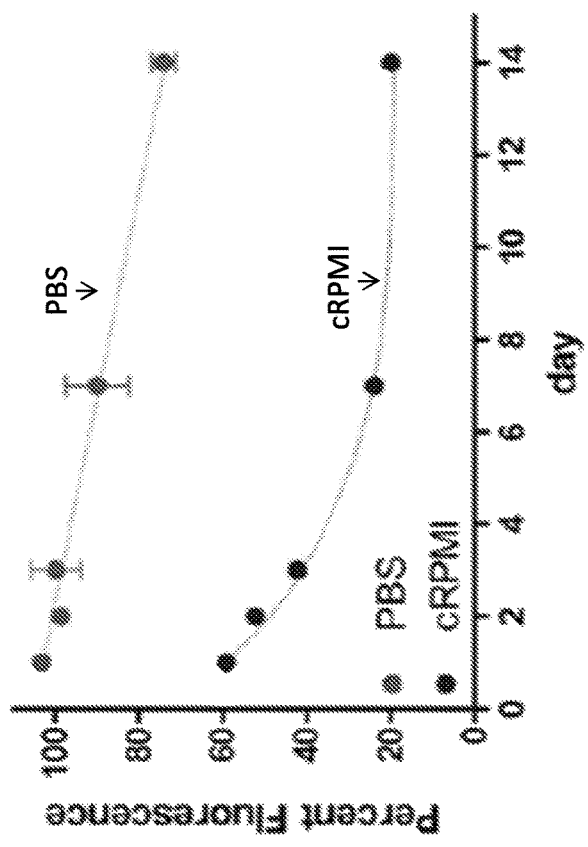
FIGS. 28A-28E depict the assembly and characterization of APC-MS.
Figure 28B:
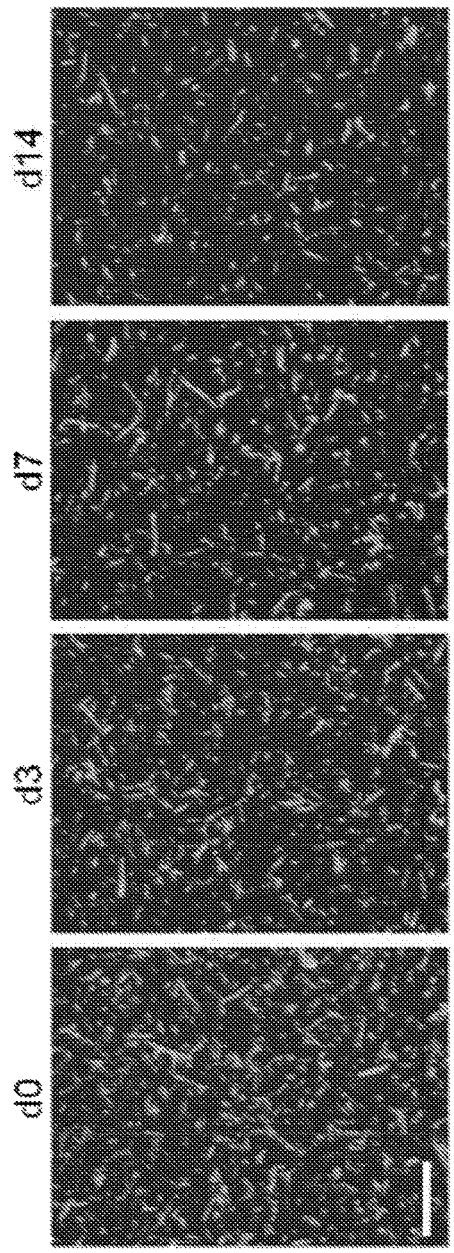
Figure 28D:
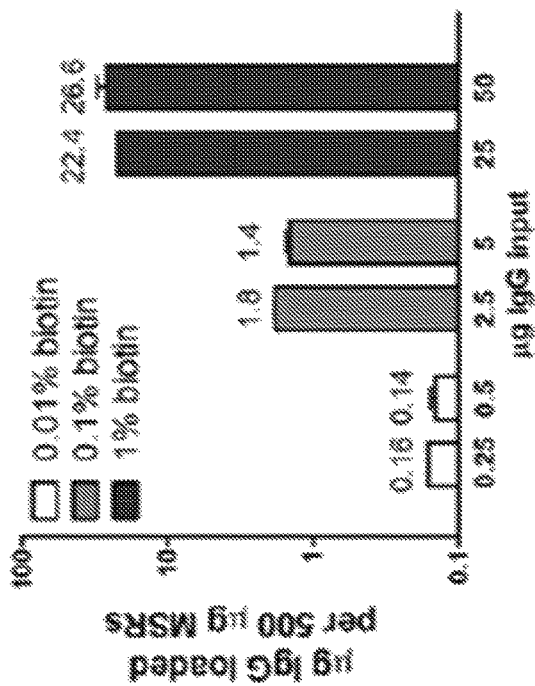
Figure 28C:
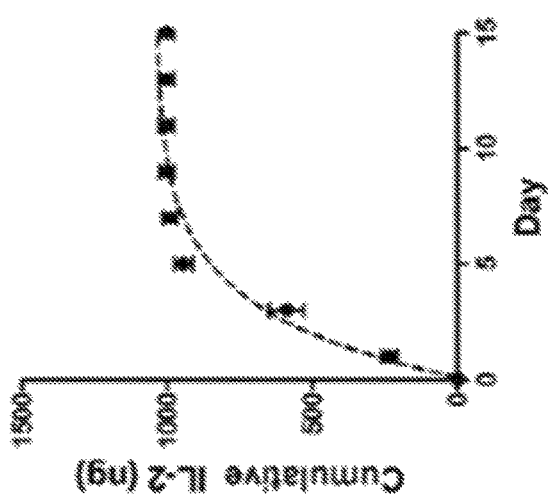
Figure 39A:
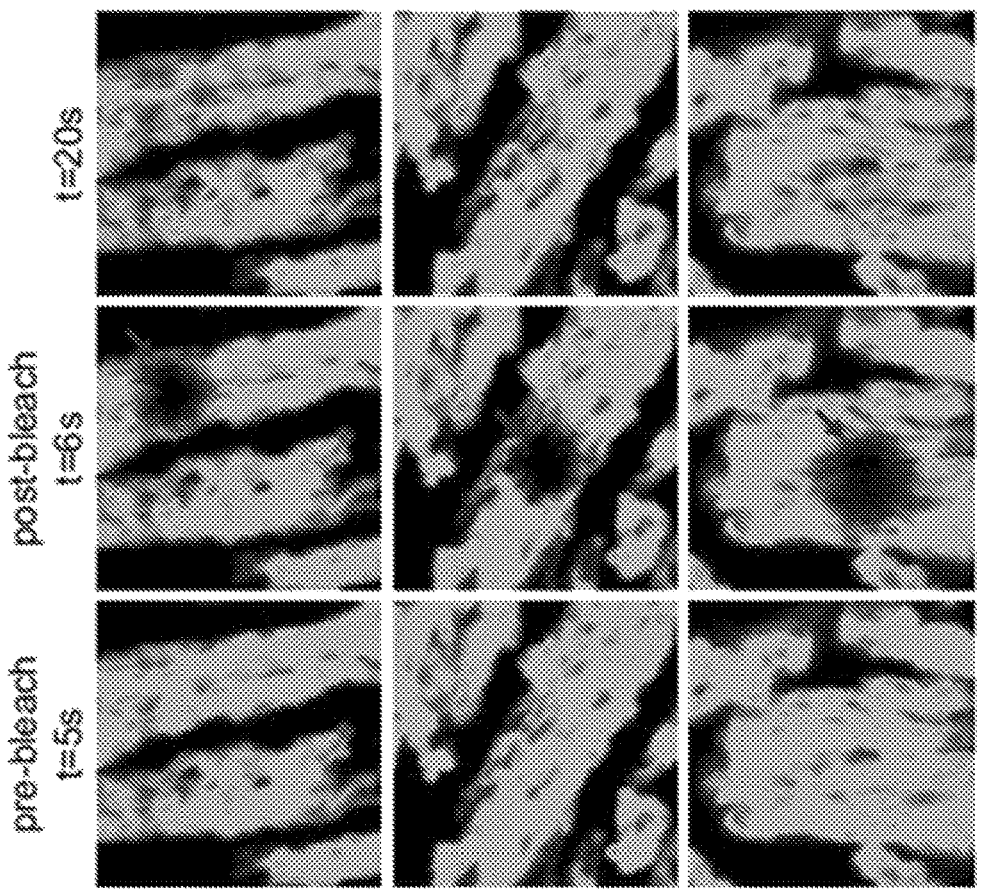
FIGS. 39A and 39B depict fluorescence recovery after photobleaching (FRAP) experiments using MSR-SLBs containing 10% carboxyfluoresceinheadgroup-tagged lipid.
Figure 39B:
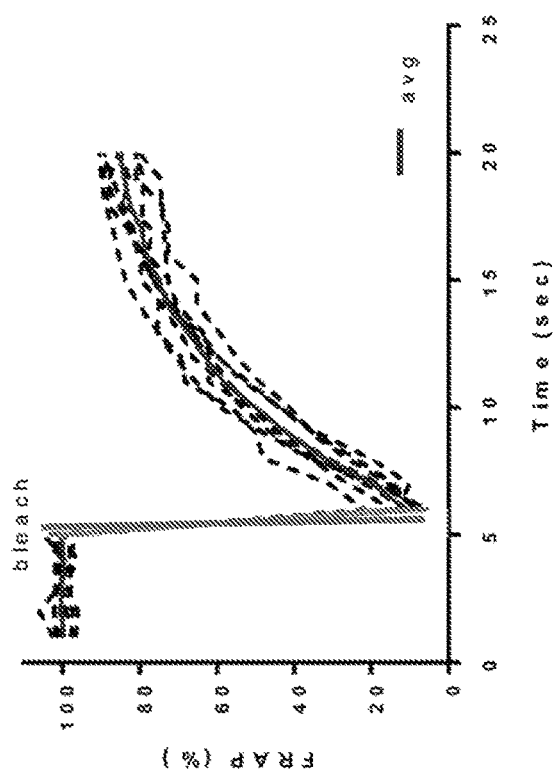

MSRs were coated with the phospholipid 1-palmitoyl-2-oleoyl-sn-glycero-3-phosphocholine (POPC), which is commonly used as a model for mammalian cell membranes (Jerabek, H. R. et al. *Journal of the American Chemical Society* 132, 7990-7 (2010); and Tones et al. *Lab on a Chip* 13, 90-99 (2013)). At low lipid:MSR ratios, lipid-mediated aggregation of MSRs was observed (FIG. 27A), while at higher lipid:MSR ratios, lipid-coated MSRs were maintained in a well dispersed, single-particle state (FIG. 27B). At this higher lipid:MSR ratio, 34.1±0.9% of the input POPC was initially associated with the MSRs, and the POPC coating was slowly lost over time in cell culture conditions (FIG. 28A) as the POPC-coated MSRs degraded (FIG. 28B). MSRs were also successfully coated with 1,2-dioleoyl-sn-glycero-3-phosphocholine (DOPC) and 1,2-distearoyl-sn-glycero-3-phosphocholine (DSPC). The amount of lipid associated with MSRs was inversely related to the saturation of the lipid, likely due to tighter packing of more highly saturated lipids in the lipid bilayers. No significant differences were observed in the stability of the various lipid coatings. To evaluate whether MSR lipid coatings were continuous, fluid SLB structures, fluorescence recovery after photobleaching (FRAP) studies were carried out using a fluorophore-tagged lipid. Recovery of fluorescence at photobleached regions of lipid-coated MSRs and coincident normalization of fluorescence across bleached rods was observed, demonstrating that the MSR lipid coatings were continuous, fluid SLBs (FIGS. 39A and 39B).

Figure 28E:
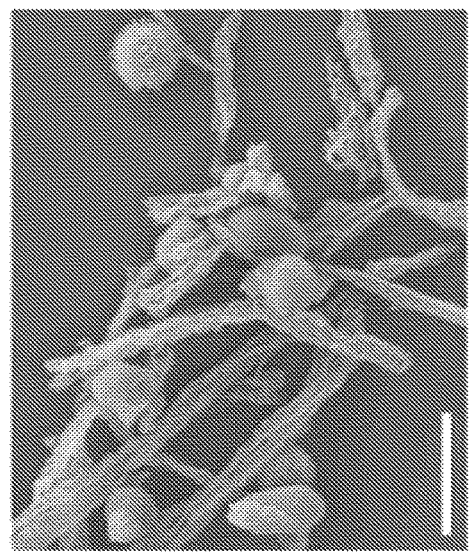

The loading and release of soluble cues, and the loading of surface cues, were also analyzed. MSRs have a very high surface area available for surface adsorption of molecular payloads (Kim et al. (2015)), and when 500 µg of MSRs were loaded with 2 µg of IL-2 (0.04 mg/ml IL-2), 50±1% of the input IL-2 was retained with the MSRs. The loaded IL-2 was subsequently released in a controlled manner over 9 days. The trend could be well approximated using a one phase exponential function ($R2=0.98$), indicating that the release of IL-2 followed first-order kinetics (FIG. 28E). The attachment of surface cues as the amount of the biotinylated lipid species incorporated into the lipid formulation was varies was also analyzed. Streptavidin was added at 30% of the molar amount of biotinylated lipid groups on the respective MSR-SLB formulations, and biotinylated IgG was added as a surface cue proxy. At saturation, the maximal amount of biotinylated IgG that could be loaded onto the various MSR-SLB formulations differed by a factor of ~10 (FIG. 28F). This difference is consistent with the relative differences in the amounts of biotinylated lipid in the various MSR-SLB formulations, indicating that the density of surface-bound IgG could be precisely controlled by defining the amount of adhesive lipid in the coating lipid formulation. In all subsequent experiments, MSR-SLBs were saturated with surface cues as described, and relative surface cue density is described by the mol % of biotinylated lipid in the formulation.

Figure 29:
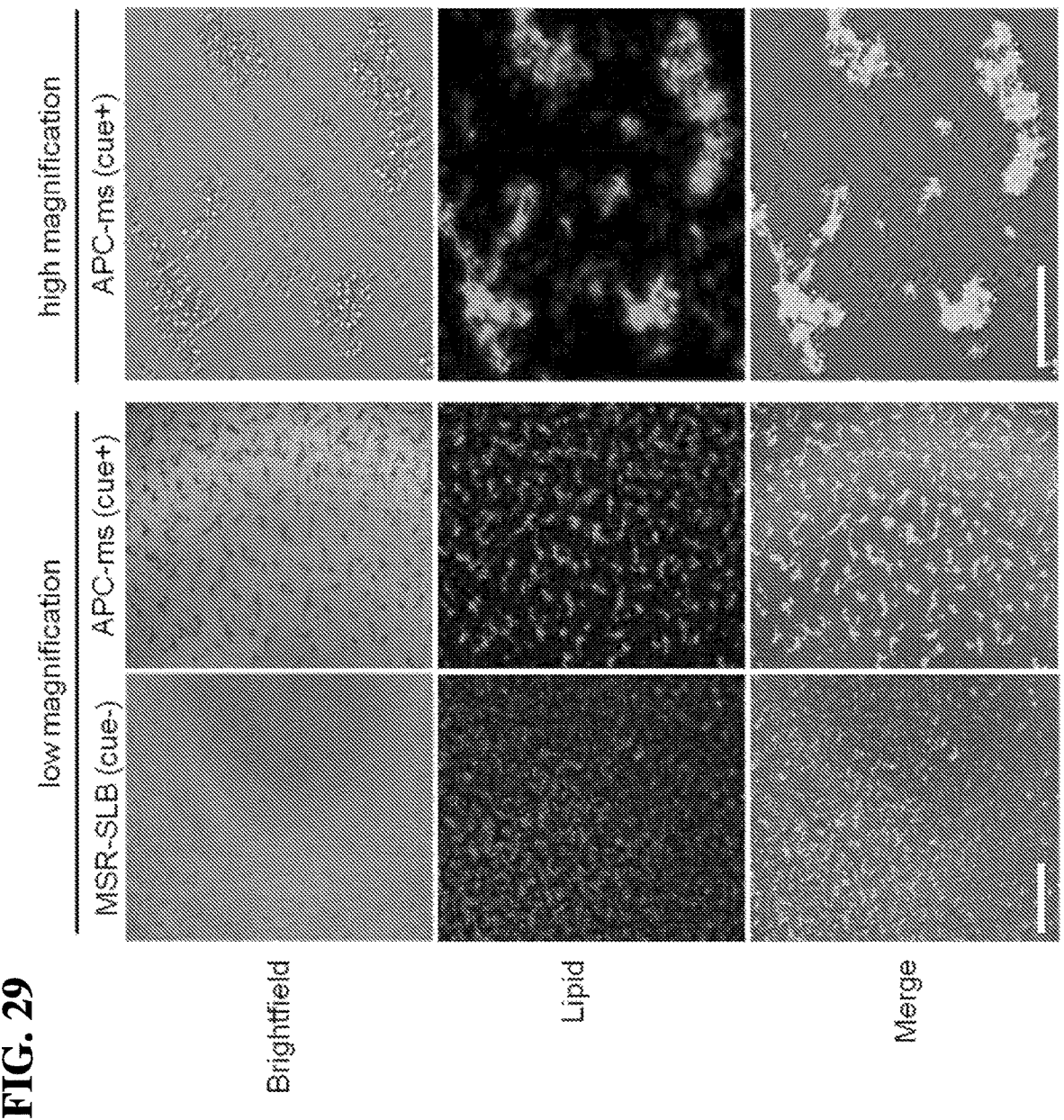
FIG. 29 shows the association of T cells with APC-MS. Representative microscopy images of MSR-SLBs either not presenting any surface cues (cue-), or surface-presenting αCD3 and αCD28 (cue+), at low (left) and high (right) magnification, cultured with primary mouse T cells for one day. Cells and material are visible in brightfield images (top) and MSR-SLB lipid coatings are visible in the green channel (1 mol % fluorophore-tagged lipid; middle). Merged images are shown on the bottom. Low magnification scale bar=500 μm, high magnification scale bar=100 μm.

To confirm that the presentation of activation cues on the scaffold surface promoted T cell interactions, primary T cells were cultured either with MSR-SLBs without surface T cell cues, or complete APC-MS. Whereas T cells largely ignored MSR-SLBs without surface T cell cues, they interacted robustly with APC-MS, reorganizing the structure of the scaffolds to form extensive, high density cell-material clusters (FIG. 28G and FIG. 29).

Polyclonal Expansion of Primary Mouse and Human T Cells

Figure 30A:
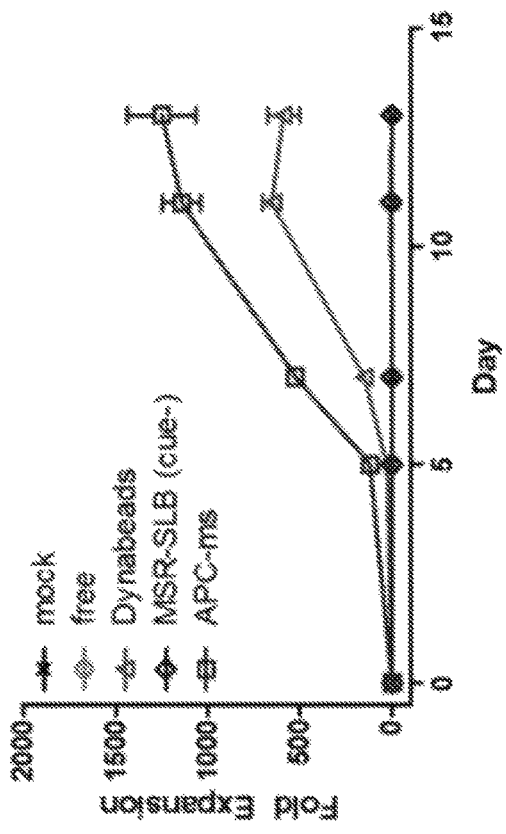
FIGS. 30A, 30B, 30C, 30D, 30E, 30F, and 30G show the polyclonal expansion of primary mouse and human T cells.
Figure 30B:
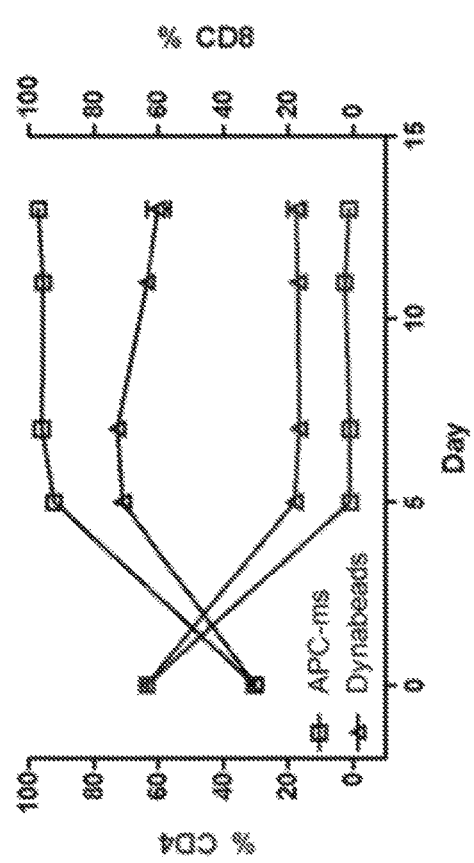
Figure 30C:
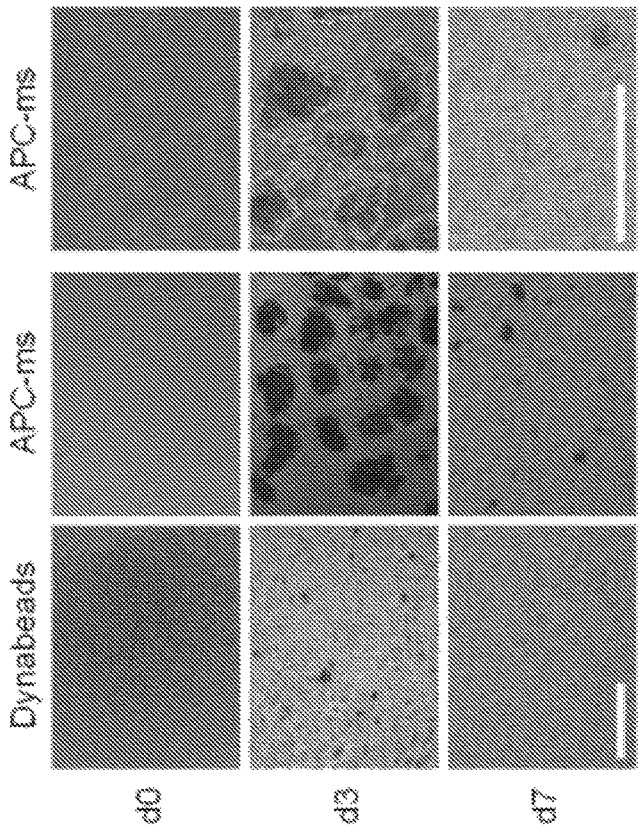
Figure 31:
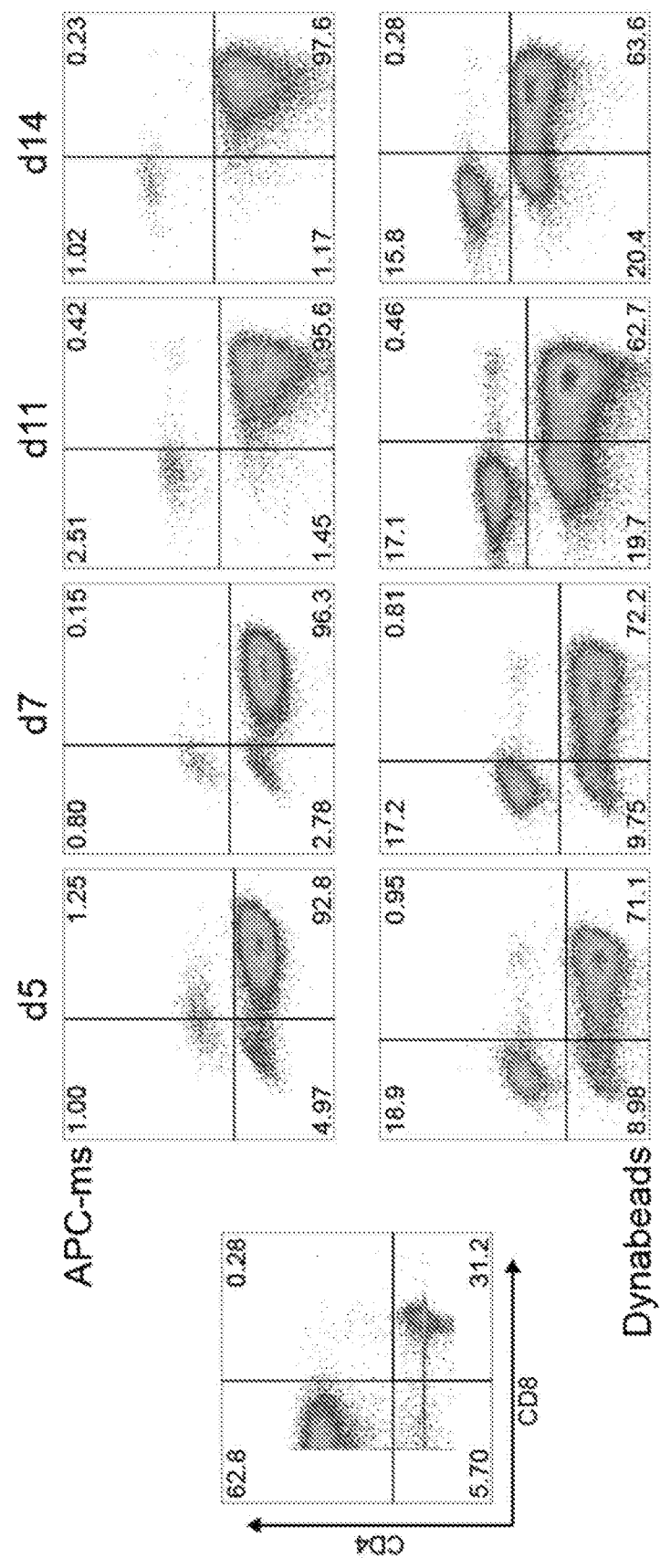
FIG. 31 depicts representative FACS plots of CD4 and CD8 expression on polyclonally expanded primary mouse T cells. Representative FACS plots showing CD4 and CD8 expression on live single cells that were polyclonally expanded with either APC-MS or DYNABEADS. Flow data were gated on Fluorescence Minus One (FMO) controls for each sample, at each timepoint. Data is representative of at least two independent experiments.
Figure 32A:
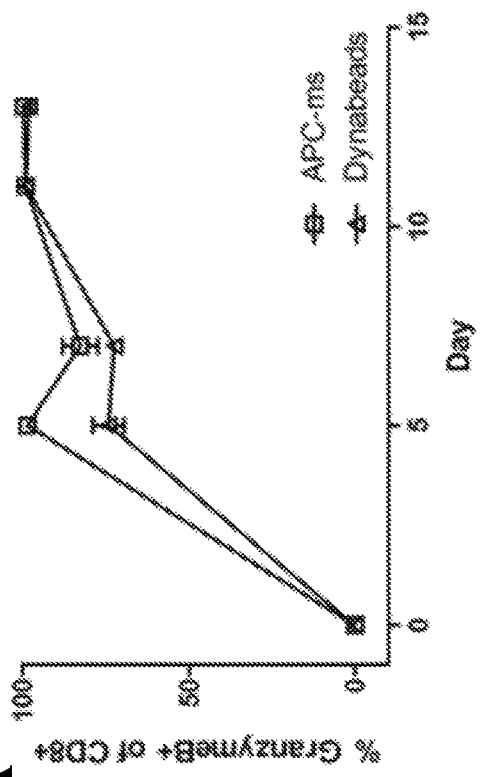
Figure 32B:
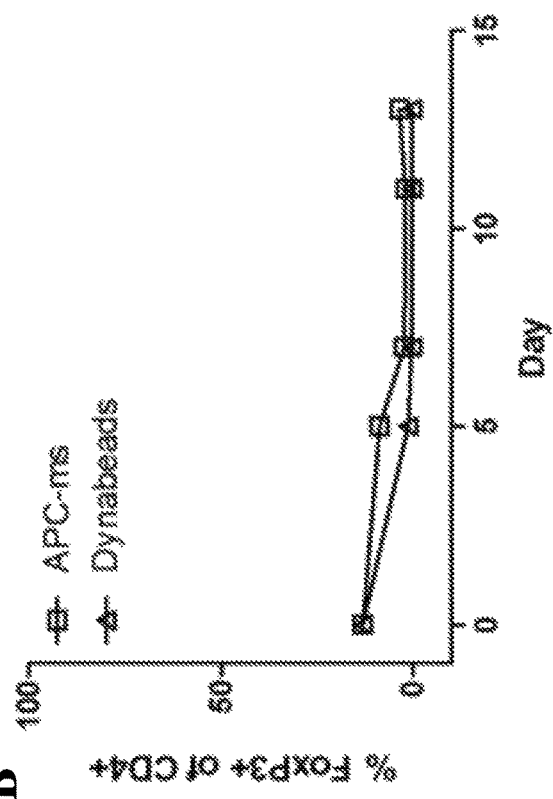

Primary mouse T cells were cultured with either DYNABEADS or with APC-MS. Culture with APC-MS led to the formation of large cell-material clusters, and the size and frequency of these clusters was greater in APC-MS cultures than in Dynabead cultures (FIG. 30A). Culture with APC-MS promoted more than two-fold greater expansion than culture with DYNABEADS (FIG. 30B). Interestingly, whereas DYNABEADS promoted moderate CD8-biased skewing of the T cell population over the culture period, APC-MS promoted greater than 95% of total T cells being CD8+ (FIG. 30C and FIG. 31). Effector CD8+ T cells expanded using APC-MS upregulated the cytotoxic mediator Granzyme B more rapidly and to a greater extent over the culture period than did CD8+ T cells expanded with DYNABEADS (FIG. 32A). In both Dynabead- and APC-MS-expanded T cell products, no expansion of CD4+ FoxP3+ cells was observed (FIG. 32B). Importantly, despite the rapid expansion rate observed, the majority of APC-MS-expanded T cells remained negative for the exhaustion marker PD-1 (FIG. 32C).

Figure 30D:
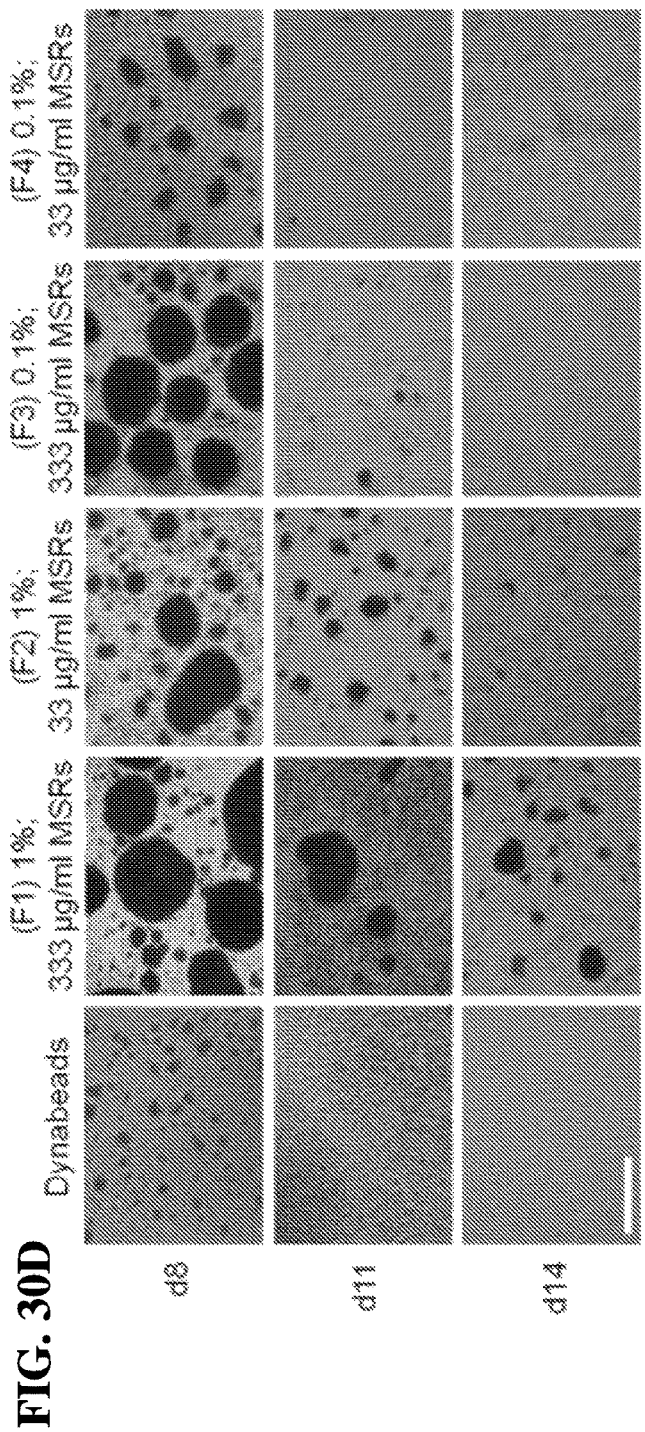
Figure 30E:
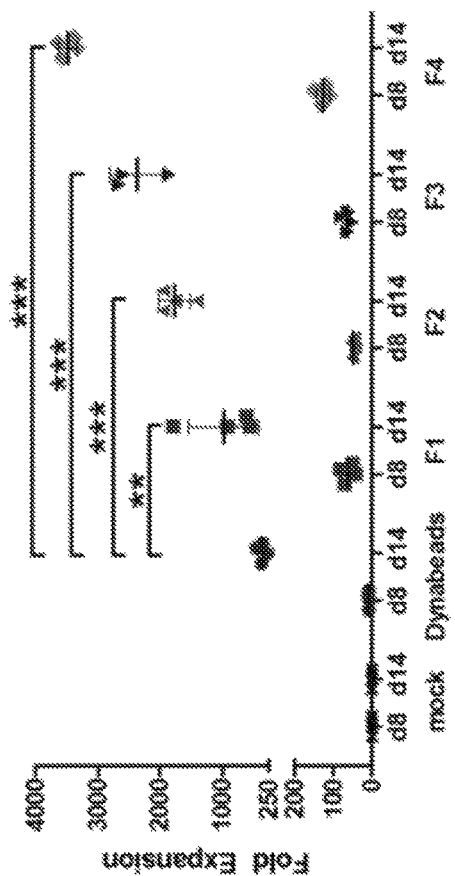
Figure 30F:
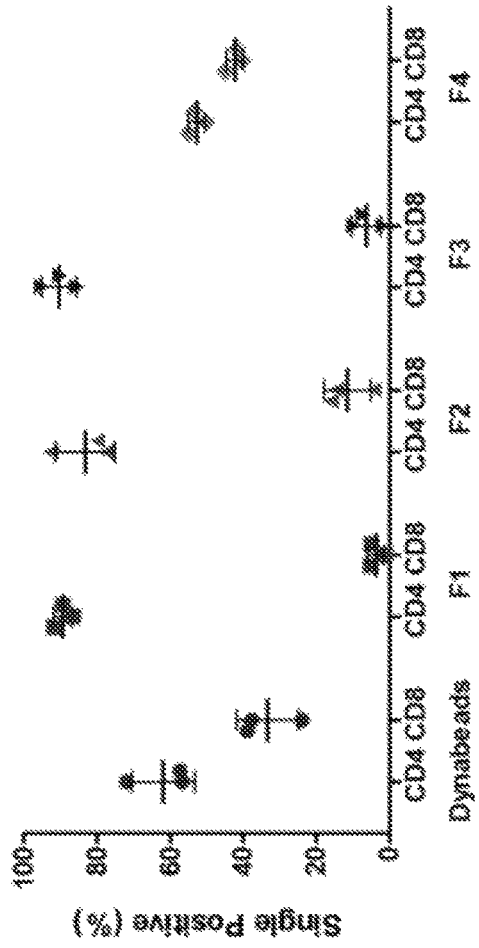
Figure 30G:
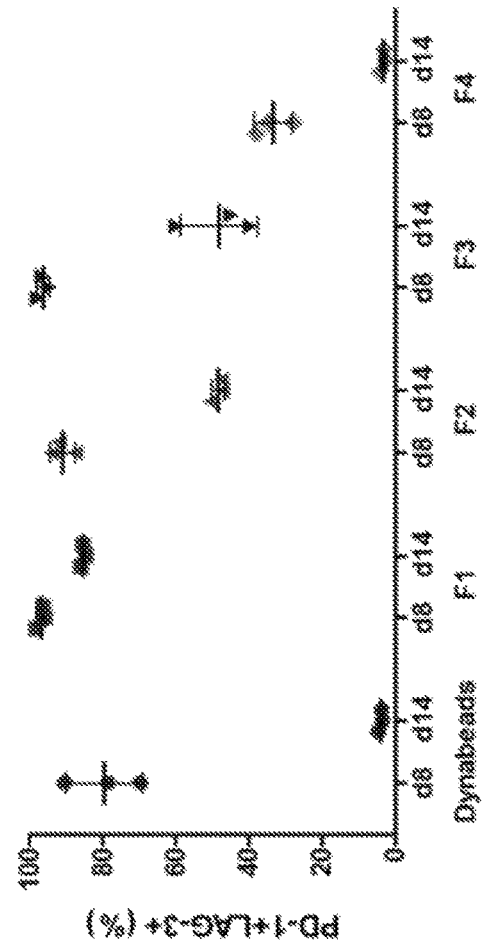
Figure 33:
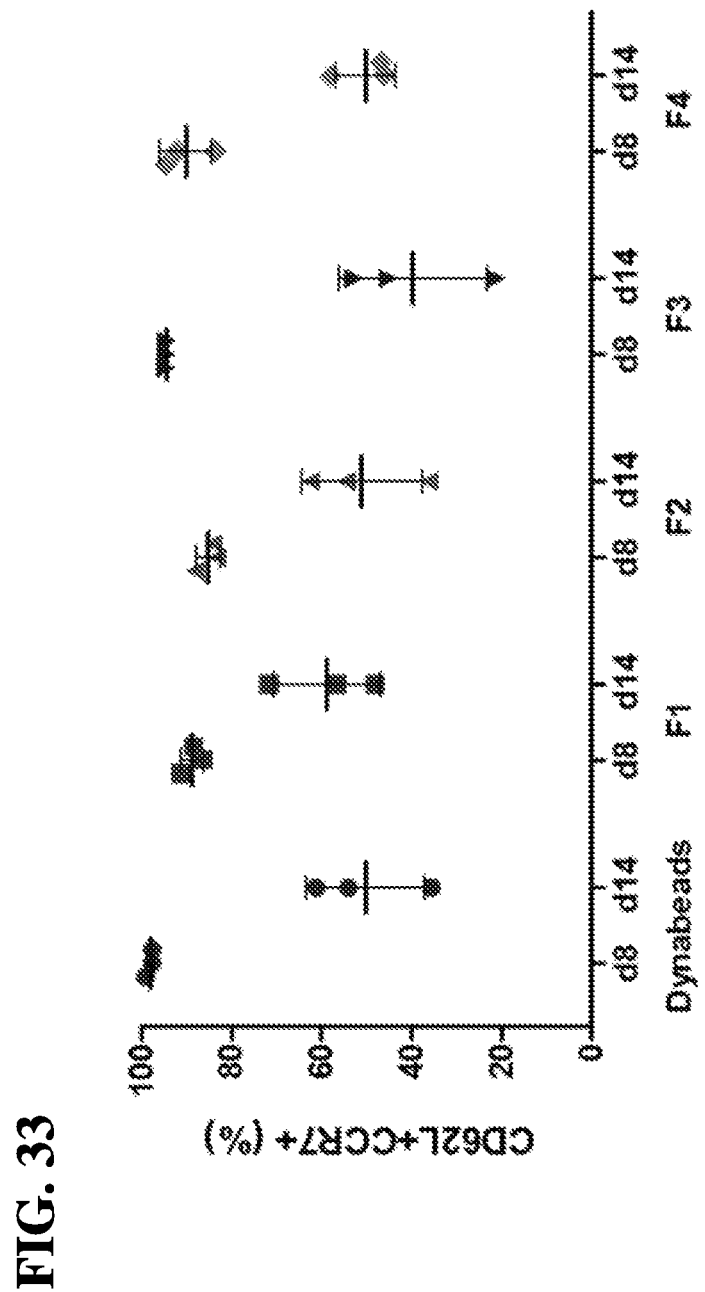
FIG. 33 shows adhesion molecule expression on polyclonally expanded primary human T cells. FACS quantification of live single cells co-expressing CD62L and CCR7, in samples expanded either with DYNABEADS or with various APC-MS formulations. (F1) APC-MS presenting αCD3 and αCD28 saturating 1 mol % biotinylated lipid, input at 333 μg/ml of MSRs to initial culture, (F2) APC-MS presenting αCD3 and αCD28 saturating 1 mol % biotinylated lipid, input at 33 μg/ml of MSRs to initial culture, (F3) APC-MS presenting αCD3 and αCD28 saturating 0.1 mol % biotinylated lipid, input at 333 μg/ml of MSRs to initial culture, and (F4) APC-MS presenting αCD3 and αCD28 saturating 0.1 mol % biotinylated lipid, input at 33 μg/ml of MSRs to initial culture. Data represents mean±s.d. of three different donor samples and is representative of at least two independent experiments.

APC-MS formulations were also evaluated for the polyclonal expansion of primary human T cells. Culture of primary human T cells with APC-MS also led to the formation of large cell-material clusters, with the size and frequency of these clusters being greater in APC-MS cultures than in Dynabead cultures. The stability and persistence of these clusters was observed to be dependent on both surface cue density and initial material input (FIG. 30D). Culture for 14 days with all of the tested APC-MS formulations led to between two- to ten-fold greater expansion than with DYNABEADS (FIG. 30E). Interestingly, APC-MS formulations containing higher amounts of T cell stimuli, either via a higher surface cue density or higher mass of initial material, promoted extreme CD4-biased skewing after 14 days of culture. In contrast, the APC-MS formulation that contained a lower overall amount of T cell stimuli relative to the other APC-MS formulations (F4), promoted a more balanced CD4+ and CD8+ expansion, comparable to the DYNABEADS (FIG. 30F). Among the APC-MS formulations tested, a positive correlation was observed between the total amount of T cell stimuli in the formulation and the frequency of cells that co-expressed the exhaustion markers PD-1 and LAG-3 at the end of the culture period. Strikingly, despite nearly a 10-fold greater expansion over a two-week culture period, low frequencies of PD-1 and LAG-3 co-expressing cells (<5%) was observed with the low T cell stimuli APC-MS formulation (F4), similar to DYNABEADS. However, a higher frequency of cells co-expressing PD-1 and LAG-3 was observed in the DYNABEADS condition at day 7 (FIG. 30G). No significant differences were observed between Dynabead- or APC-MS-expanded T cell products in the frequency of cells that co-expressed the lymphoid homing molecules CCR7 and CD62L (FIG. 33), which indicate a more naive T cell phenotype and have been shown to be important for function after in vivo transfer (Gattinoni, L. et al. *The Journal of Clinical Investigation* 115, 1616-1626 (2005)). Together, these data show that APC-MS were capable of polyclonally expanding mouse and human T cells more rapidly than DYNABEADS.

Antigen-Specific Expansion of Primary Mouse T Cells

Figure 34A:
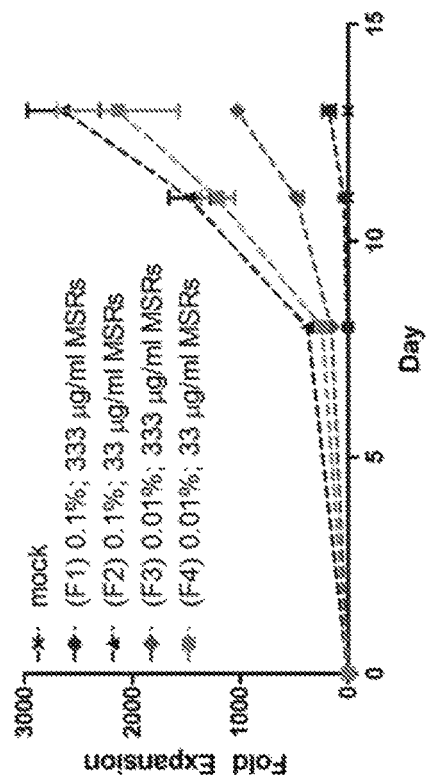
FIGS. 34A, 34B, 34C, 34D, and 34E depict antigen-specific expansion of primary mouse T cells.
Figure 34B:
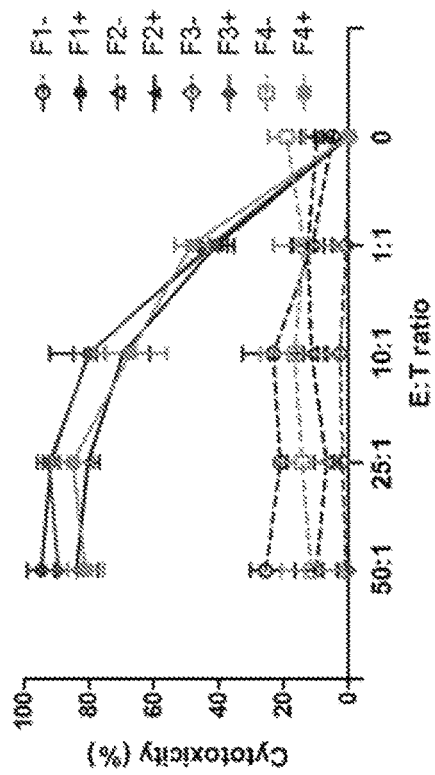
Figure 34C:
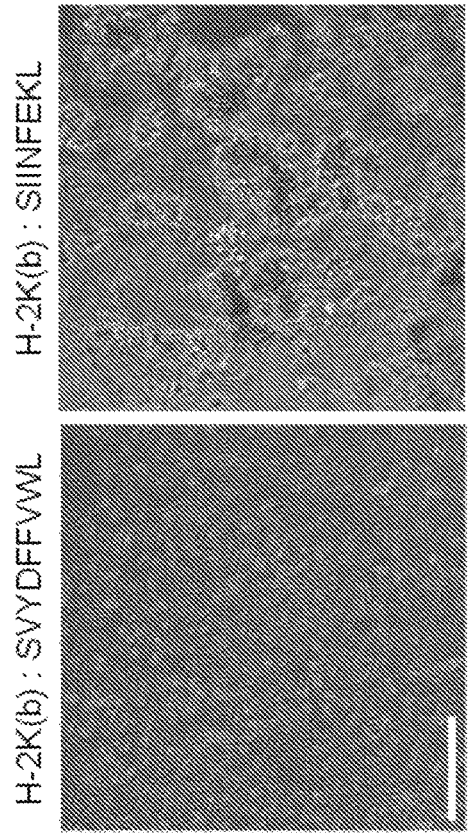
Figure 34D:
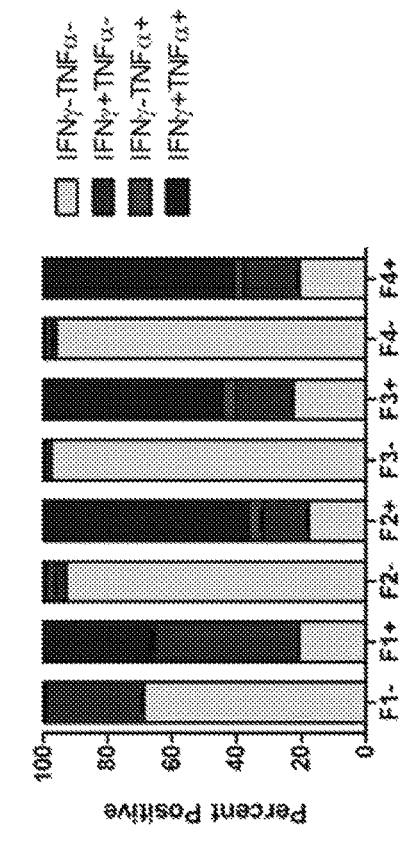
Figure 34E:
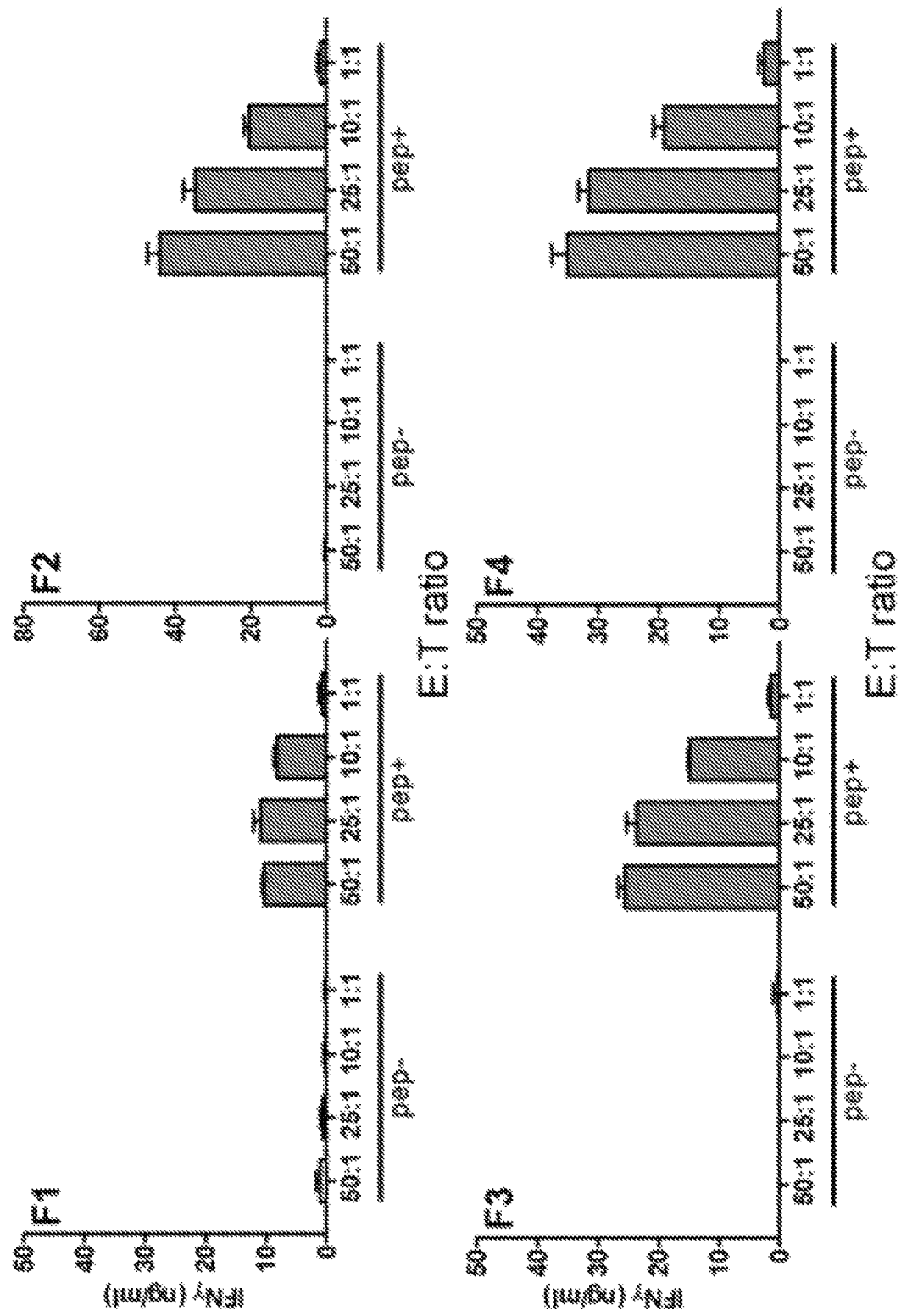

To determine whether APC-MS could be adapted for antigen-specific expansion using primary mouse CD8+ T cells isolated from OT-I mice, which express a TCR specific for the SIINFEKL (SEQ ID NO: 4) peptide from chicken ovalbumin in the context of H-2K(b) MHC class I. Minimal cell-material interactions were observed when these cells were cultured with an APC-MS formulation presenting an irrelevant peptide-loaded MHC (pMHC). However, when the cells were cultured with an APC-MS formulation presenting SIINFEKL (SEQ ID NO: 4), robust interactions resulting in the formation of extensive cell-material clusters was observed (FIG. 34A). APC-MS formulations presenting SIINFEKL (SEQ ID NO: 4) promoted robust expansion of OT-I CD8+ T cells, even with surface cues presented on as low as 0.01 mol % of the lipids (FIG. 34B). In response to SIINFEKL (SEQ ID NO: 4) presentation from B16-F10 melanoma cells, the expanded T cells secreted IFNy (FIG. 34E), upregulated the co-expression of IFN-γ and TNFα (FIG. 34C), and killed target cells in vitro (FIG. 34D).

Antigen-Specific Expansion of Primary Human T Cells

Figure 35A:
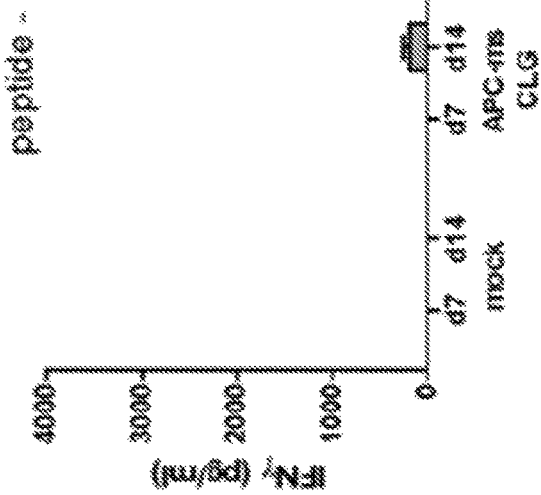
FIGS. 35A, 35B, 35C, 35D and 35E show the extended characterization of primary human T cells expanded with antigen-specific APC-MS formulations.
Figure 35B:
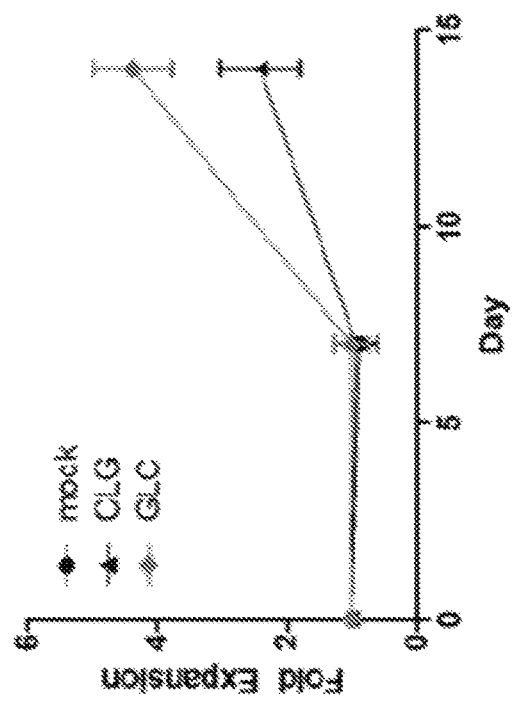
Figure 35C:
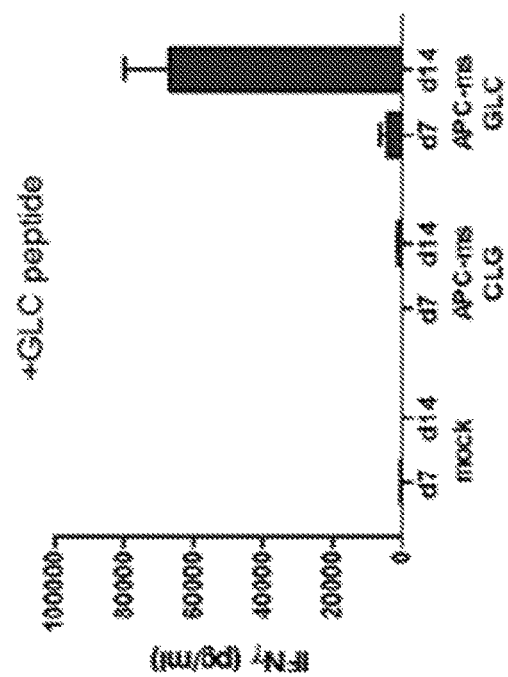
Figure 35D:
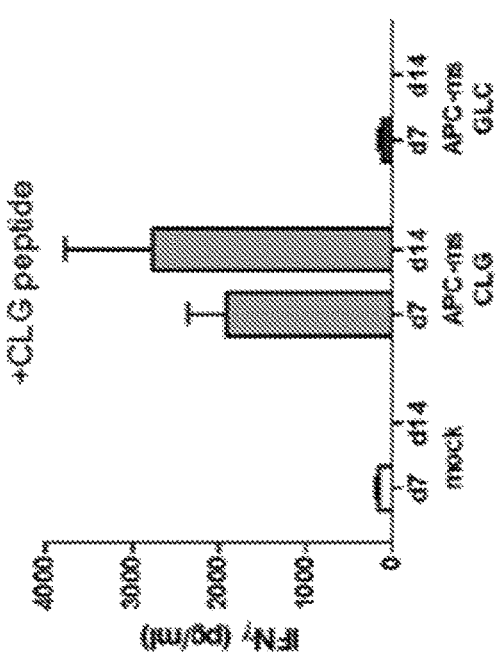
Figure 35E:
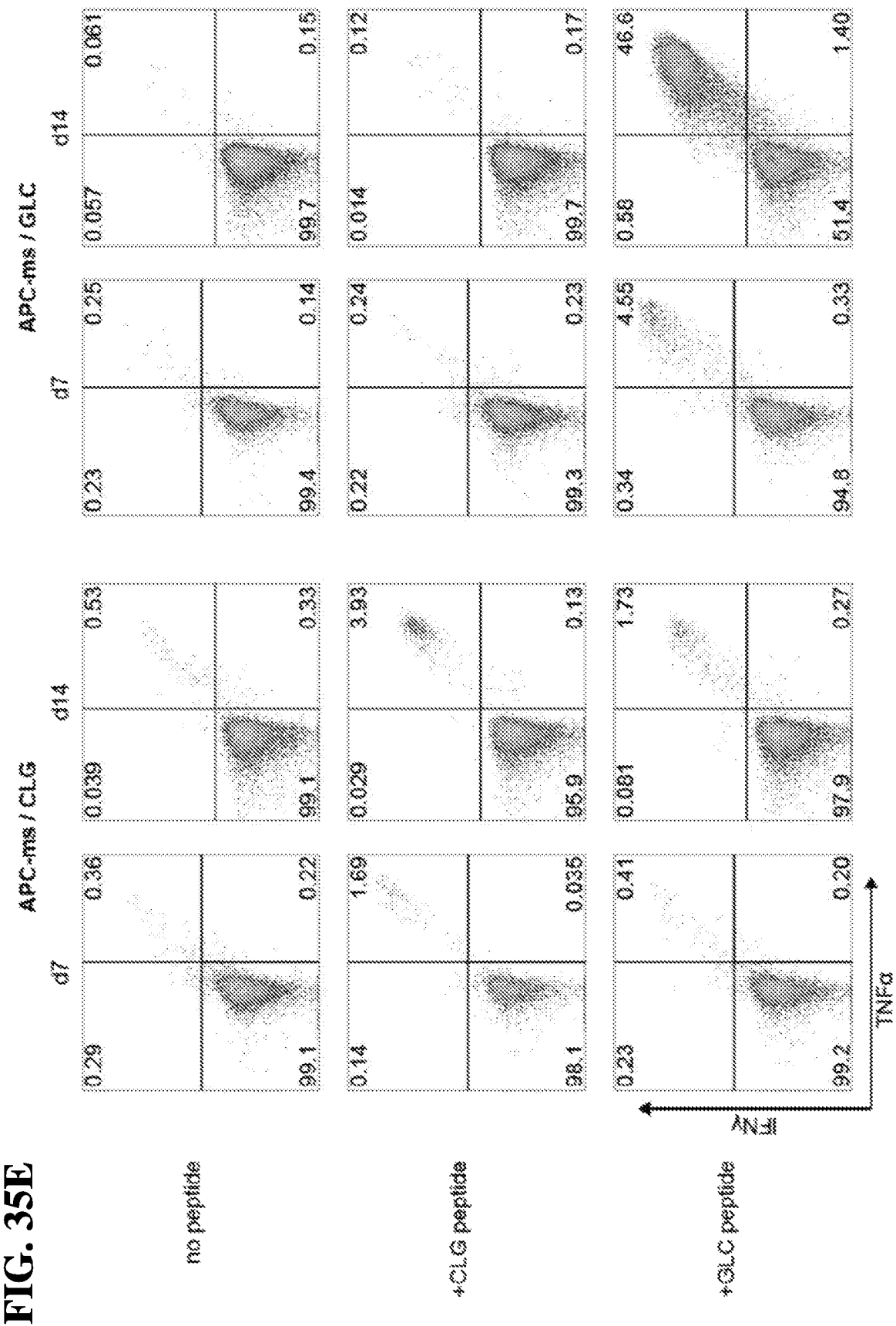
Figure 36B:
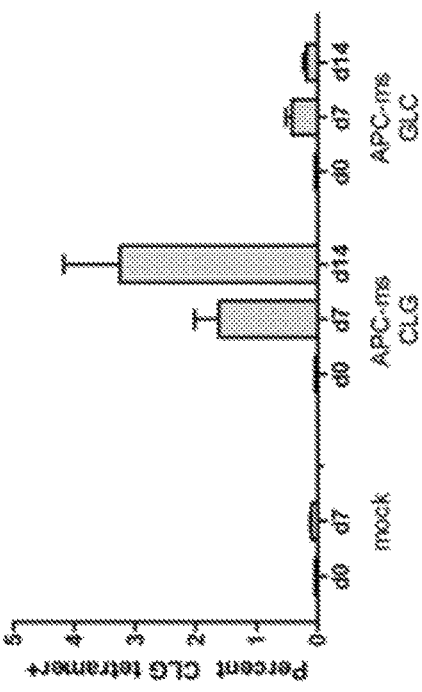
Figure 36A:
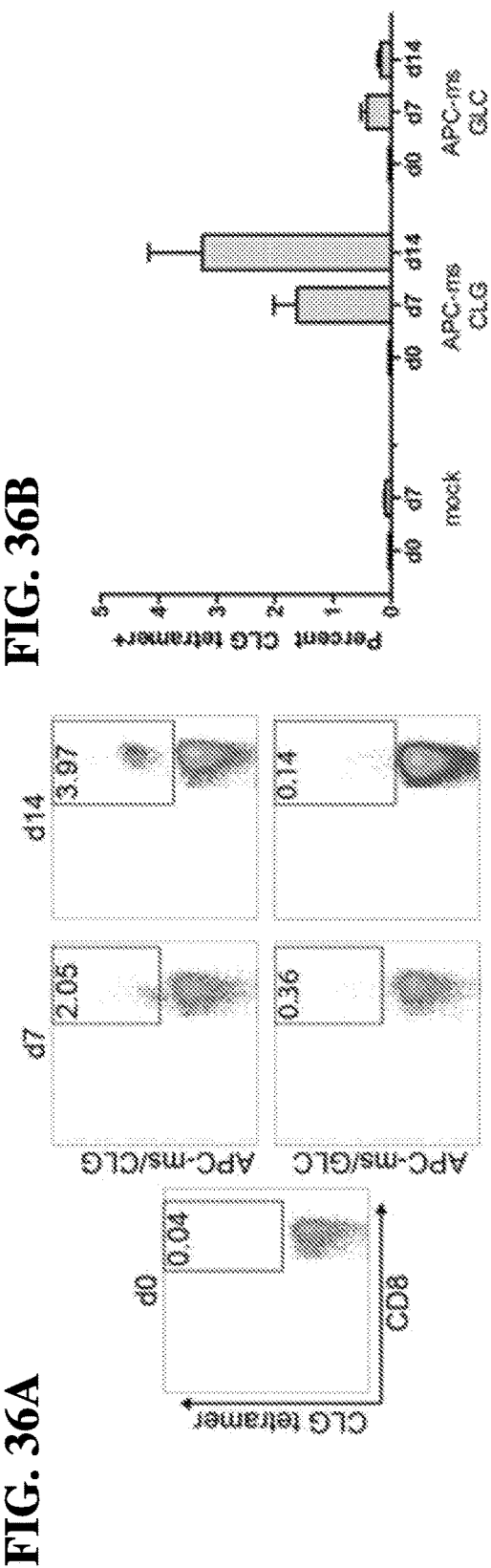
Figure 36C:
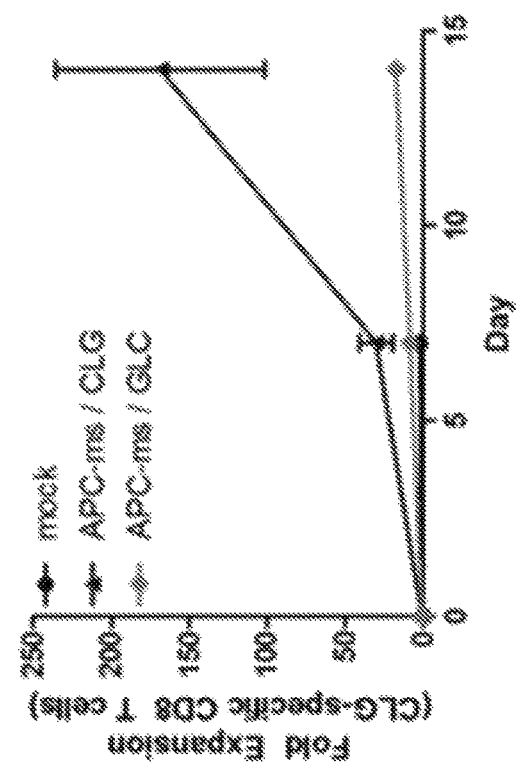
Figure 36E:
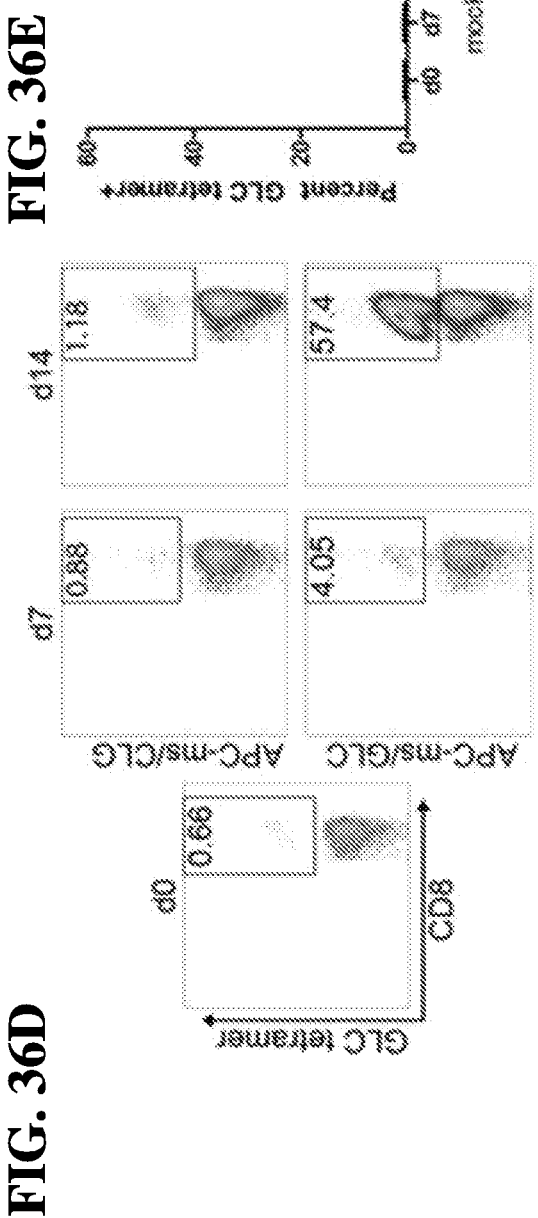
Figure 36D:
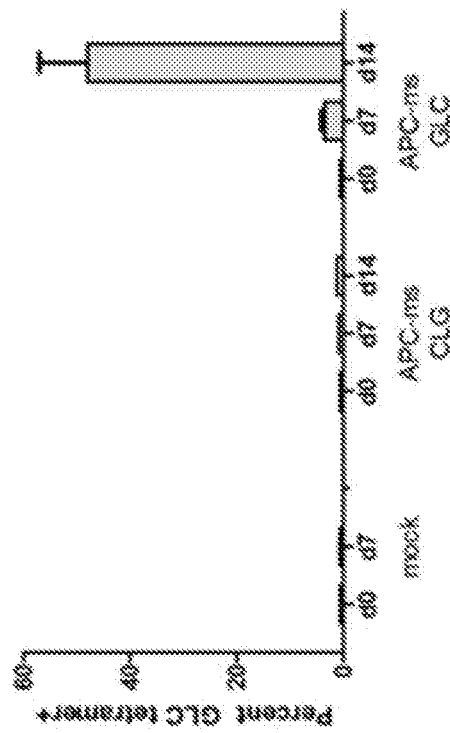
Figure 36F:
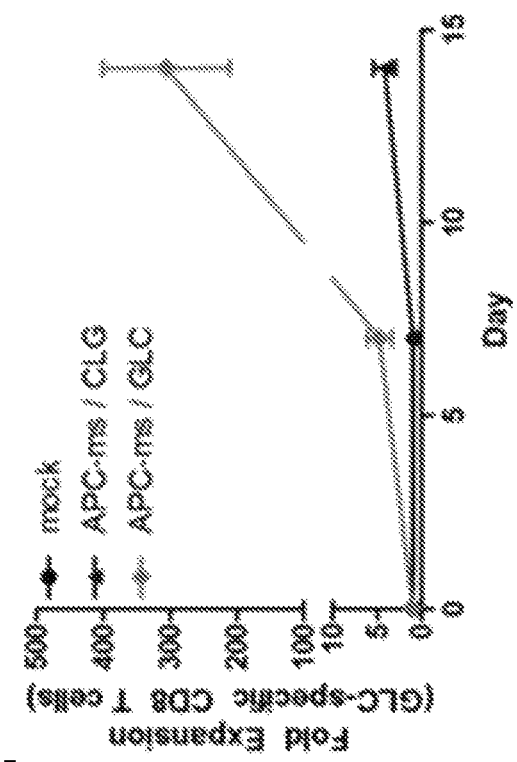

To determine whether APC-MS could be used for the antigen-specific enrichment and expansion of rare human T cell subpopulations, which could be useful for the selective expansion of rare cancer antigen-specific T cells from tumors or blood (Cohen, C. J. et al. *The Journal of Clinical Investigation* 125, 3981-3991 (2015); and Streinen, E. et al. *Science* 352, 1337-1341 (2016)). APC-MS formulations presented one of two peptides (abbreviated either CLG or GLC), from different EBV-associated proteins, in the context of the HLA-A2 allotype of MHC class I. CD8+ T cells were isolated from human blood samples from HLA-A2-matched donors with prior EBV exposure, and treated with either soluble IL-2 (30 U/ml) alone (mock), or cultured with APC-MS presenting either the CLG or GLC peptide. Robust antigen-specific enrichment and expansion of the two T cell subsets was observed, while a minimal increase in total T cells was noted (FIG. 35A). The frequency of CLG-specific CD8+ T cells increased from 0.04% of all CD8+ T cells at day 0, to 3.3±0.9% of CD8+ T cells at day 14 when cultured with CLG-presenting APC-MS (FIGS. 36A and 36B), corresponding to a 170±70-fold expansion in cell number (FIG. 36C) Similarly, the frequency of GLC-specific CD8+ T cells increased from 0.66% of all CD8+ T cells at day 0, to 48±9% at day 14 when cultured with GLC-presenting APC-MS (FIGS. 36D and 36E), corresponding to a 300±100-fold expansion in cell number (FIG. 36F). The functionalities of the various T cell products were analyzed in co-culture experiments with T2 stimulator cells by evaluating IFN-γ secretion (FIG. 35B), IFNγ and TNFα co-expression (FIG. 35C, and FIGS. 36G, 36H, and 36I), and the in vitro killing of peptide-loaded target cells (FIG. 36J). CD8+ T cell populations expanded with either CLG or GLC-presenting APC-MS responded strongly to stimulator cells that presented their cognate antigen. Notably, following co-culture with T2 cells, the frequency of CLG- and GLC-specific cells detected via tetramer staining was similar to the frequency of cells that co-expressed IFN-γ and TNFα, indicating that the majority of the expanded T cells were functional.

Figure 36K:
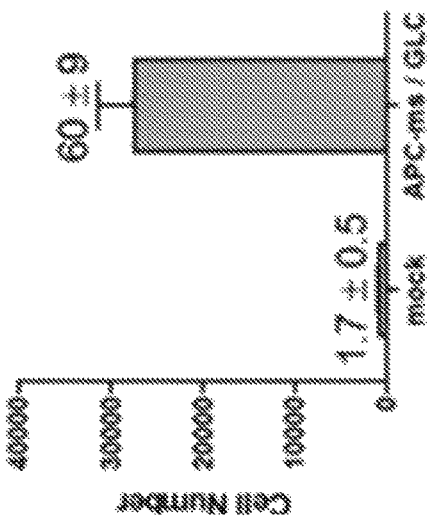
Figure 36M:
Figure 36L:
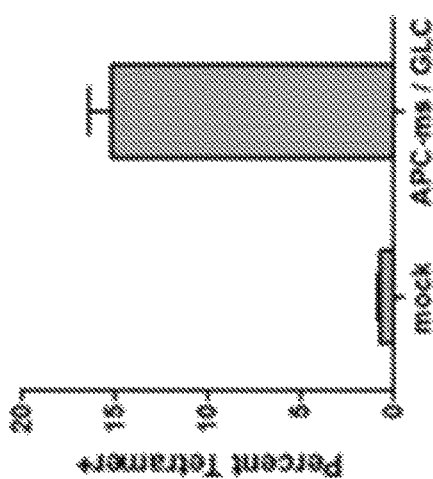
Figure 36N:
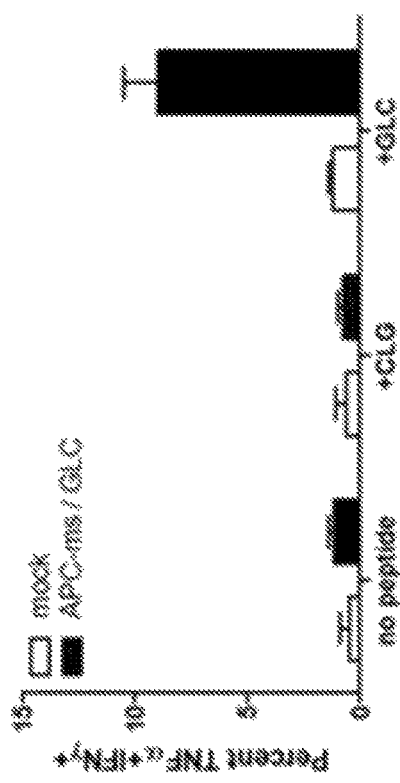

To determine whether antigen-specific T cells could be expanded directly from heterogeneous cell populations, such as PBMCs, obviating the need for T cell isolation the following experiments were performed. PBMC samples from BLA-A2-matched donors with prior EBV exposure were cultured with a GLC-presenting APC-MS formulation. Remarkably, the frequency of GLC-specific T cells increased from 0.66% of total CD8+ T cells at day 0, to 15±1% at day 7; minimal changes were found in mock-treated samples (FIG. 36K). This corresponds to a 60±9-fold expansion of GLC-specific T cells (FIG. 36L). The functionality of the expanded T cells was evaluated by co-culturing with T2 cells that were either unpulsed, or pulsed with the CLG or GLC peptide. Quantification of the frequency of cells co-expressing TNFα and IFN-γ (FIG. 36M), and 1FN1 secretion (FIG. 36N), demonstrated that CD8+ T cell populations that were expanded from PBMCs with GLC-presenting APC-MS responded robustly only to T2 cells that presented their cognate antigen. Taken together, these data demonstrate the ability of APC-MS to robustly expand both mouse and human T cells in an antigen-specific manner.

Figure 40A:
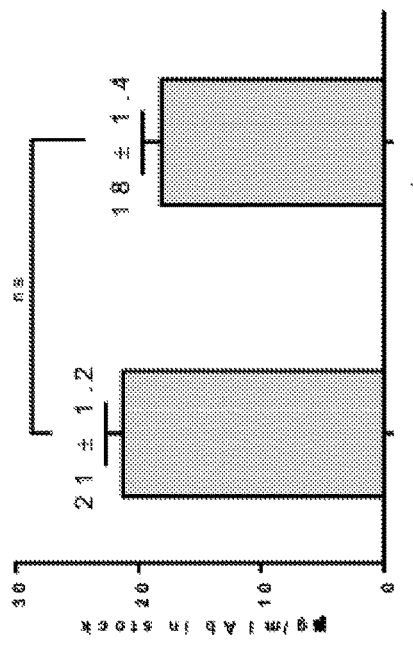
Figure 40B:
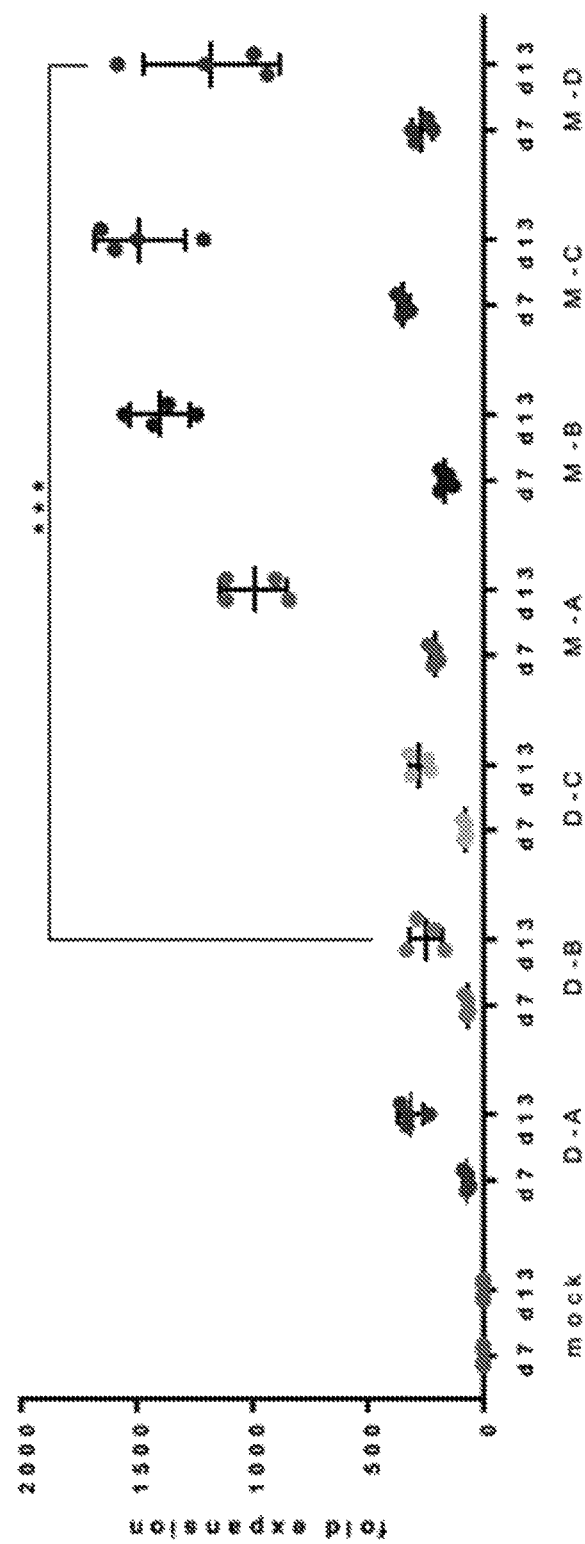

To determine whether the improvements observed using APC-MS over DYNABEADS were not solely attributable to differences in the amount of anti-CD3 antibody and anti-CD28 antibody presented, the amount of anti-CD3 and anti-CD28 antibodies in the DYNABEADS was normalized to correspond to the concentration of these antibodies in the APC-MSs. As shown in FIGS. 40B, 40C and 40D,when the amount of anti-CD3 and anti-CD28 antibodies present in the APC-MS and DYNABEADs was matched, APC-MS promoted more rapid expansion of primary mouse T cells (FIG. 40B) while maintaining comparable co-expression levels of the exhaustion markers PD-1 and LAG-3 (FIG. 40C). Also, by tuning the APC-MS formulation, the CD4:CD8 ratio can be tuned (FIG. 40D).

Figure 41A:
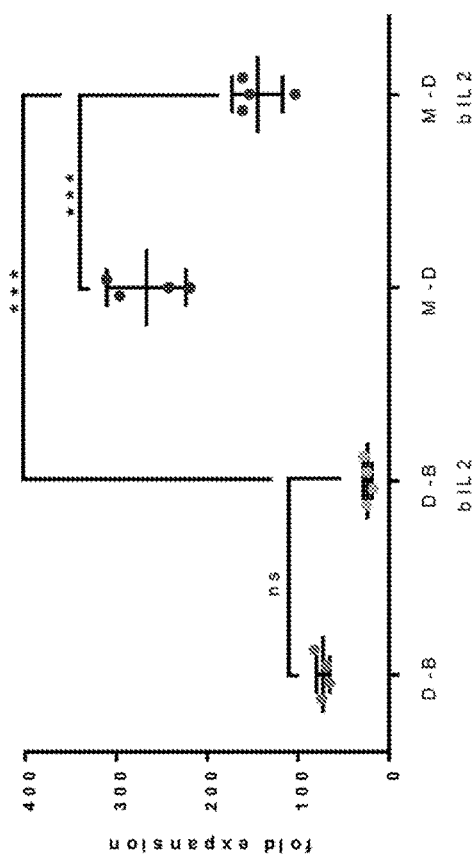
FIGS. 41A and 41B depict the results of experiments performed to evaluate the effect on primary mouse T-cell expansion of IL-2 dose and sustained release from APC-MS as compared to DYNABEADs.
Figure 41B:
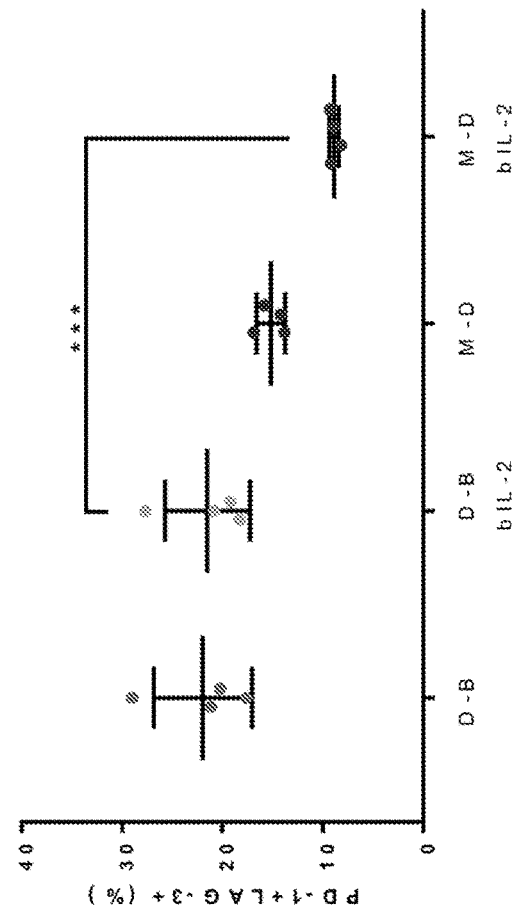

IL-2 was observed to be released from APC-MS in a sustained manner over the course of approximately one week. To evaluate the effect of IL-2 dose and sustained release from APC-MS, primary mouse T cells were cultured for 7 days with either DYNABEADs or APC-MS presenting the same amount of anti-CD3 and anti-CD28 antibodies. For APC-MS conditions, IL-2 was either loaded onto the APC-MS and allowed to release over time (M-D), or the same dose of IL-2 was added as a soluble bolus into the media on d0 (M-D/bIL-2). For DYNABEAD conditions, IL-2 was either supplemented in the media at the manufacturer recommended dose and refreshed at each media change (D-B), or added as a soluble bolus into the media on d0 at the same dose as was loaded into APC-MS (D-B/bIL-2). As shown in FIG. 41A, APC-MS promoted greater expansion of primary mouse T cells when IL-2 was loaded into the APC-MS and allowed to be released over time than when the same dose of IL-2 was added into the media as a soluble bolus, demonstrating the benefit of presenting IL-2 in this context. APC-MS promoted greater expansion of primary mouse T cells than DYNABEADs when the amounts of anti-CD3, anti-CD28 and IL-2 presented are matched (M-D/bIL-2 vs D-B/eIL-2) demonstrating the benefit of presenting these cues in the context of APC-MS. As shown in FIG. 41B, when the amounts of anti-CD3, anti-CD28 and IL-2 presented are matched, T-cells expanded with APC-MS showed lower co-expression of the exhaustion markers PD-1 and LAG-3 than those expanded with DYNABEADs (M-D/bIL-2 vs D-B/bIL-2).

The experiments above demonstrate that the APC-MS are a multifunctional material can present TCR stimuli and costimulatory cues locally on the surface of a fluid lipid bilayer, and facilitate the sustained, paracrine delivery of soluble cytokines to nearby T cells. Ternary formulations presenting aCD3 or pMHC, aCD28, and IL-2 promoted rapid polyclonal and antigen-specific expansion of primary mouse and human T cells, including significantly faster polyclonal expansion than commercial DYNABEADS. Importantly, despite the increased expansion rate observed with the APC-MS used in this example, expanded T cells could retain a functional phenotype, demonstrating that expansion rate is not fundamentally inversely coupled to function. T cells largely ignored the APC-MS unless they were formulated to present relevant TCR cues, which allowed for specific expansion of rare subpopulations of T cells even from complex cell mixtures, such as PBMCs.

The results of these studies support the importance of presenting both surface and soluble cues to T cells in a manner that is comparable to how these cues are naturally presented. Prior work on synthetic aAPCs have demonstrated that delivering cytokines such as IL-2 to T cells in a paracrine manner can potentiate the effects of the cytokine (Steenblock and Fahmy (2008); and Fadel et al. (2014)). Current systems primarily focus on enhancing T cell activation through the static high density presentation of stimuli to promote TCR clustering (Zappasodi et al. (2008); Fadel et al. (2014); and Fadel et al. (2008)). However, the clustering of TCRs is only one step in a dynamic process involving the reorganization of many cell surface molecules over time that serves not only to enhance T cell activation, but also to limit the duration of TCR signaling in order to protect against T cell overstimulation (Huppa and Davis (2003); Lee et al. (2003); Alarcon et al. (2011)). When presenting T cell cues across the surface of a fluid lipid bilayer, emulating how these cues are naturally encountered on the surface of APC plasma membranes, relatively lower surface cue densities were observed to promote more rapid expansion rates and generated T cells with a more functional and less exhausted phenotype.

Very high aspect ratio particles were used to form APC-MS, which is in contrast to most previously described synthetic aAPC materials (Steenblock and Fahmy (2008); Fadel et al. (2014); Sunshine et al. (2014); Fadel et al. (2008); Meyer et al. (2015); and Steenblock (2011)). These particles spontaneously settled and stacked to form high surface area, 3D structures, which infiltrating T cells remodeled to form dense cell-material clusters, creating a microenvironment in which T cells are in close proximity to the material. This likely allows for more efficient paracrine delivery of IL-2, and increased T cell-T cell paracrine signaling (Long, M. & Adler, A. J. The Journal of Immunology 177, 4257-4261 (2006)). The relatively large size and high aspect ratio of the rods likely contributed to the formation of the larger clusters observed in APC-MS versus Dynabead cultures, since many more T cells could interact with each rod than with the smaller spherical DYNABEADS. The persistence of these clusters in APC-MS cultures was dependent on surface cue density and the amount of material in the culture, which likely contributed to the different phenotypes observed in the various APC-MS conditions.

In polyclonal mouse T cell expansion studies, APC-MS promoted extreme CD8-biased skewing of the T cell population. This is consistent with previous observations that paracrine delivery of IL-2 enhanced the proliferation of mouse CD8+ T cells, but promoted activation-induced cell death in mouse CD4+ T cells (Steenblock et al. (2011)). However, in polyclonal human T cell expansion studies, skewing was dependent on the overall amount of T cell stimuli presented by the APC-MS, with conditions containing higher amounts of T cell stimuli promoting extreme CD4-biased skewing. This discrepancy could indicate fundamental differences in how mouse and human T cells respond to these cues. A better understanding of this behavior could enable material formulations that bias mixed T cell populations toward specific CD4:CD8 ratios, a property that has recently been shown to be important for the function of adoptively transferred T cells (Turtle, C. J. et al. The Journal of Clinical Investigation 126 (2016)).

The need to rapidly generate therapeutically relevant numbers of functional T cells ex vivo is a significant challenge in personalized T cell therapies, and the results of this study indicate that APC-MS provides a significant advancement towards meeting this need (Turtle, C. J. & Riddell, S. R. Cancer Journal (Sudbury, Mass.) 16, 374 (2010); and Eggermont, L. J. et al. Trends in Biotechnology 32, 456-465 (2014)). A single stimulation with ternary APC-MS formulations was observed to promote significantly faster T cell expansion than commercial DYNABEADS, and demonstrated that parameters of the material could be manipulated to improve the phenotype of the cell product without compromising the rapid expansion rate. As APC-MS is a modular platform technology, components of the system can be altered or changed to modify the spatial and temporal context in which cues are presented. For example, altering MSR properties may allow for tuning of the scaffold microenvironment or degradation kinetics. Changing the lipid formulation may enable tuning of SLB stability, fluidity, or surface cue partitioning, or the attachment of cues via different chemistries (Torres et al. (2013); Puu, G. & Gustafson, I. *Biochimica et Biophysica Acta (BBA)-Biomembranes* 1327, 149-161 (1997); Anderson, N. A. et al. *Journal of the American Chemical Society* 129, 2094-2100 (2007); Collins, M. D. & Keller, S. L. *Proceedings of the National Academy of Sciences* 105, 124-128 (2008); Reich, C. et al. *Biophysical Journal* 95, 657-668 (2008); Longo, G. S. et al. *Biophysical Journal* 96, 3977-3986 (2009); Kwong, B. et al. *Biomaterials* 32, 5134-5147 (2011); Koo, H. et al. *Angewandte Chemie International Edition* 51, 11836-11840 (2012); and Desai, R. M. et al. *Biomaterials* 50, 30-37 (2015)). TheAPC-MS described herein may also be altered to present larger sets of both surface and soluble cues, which may enable the generation of further optimized T cells for ACTS (Hasan et al. (2015); and Hendriks et al. (2000)).

Methods

Cells and Reagents

The B16-F10 murine melanoma cell line was obtained from ATCC, and confirmed to be negative for mycoplasma. B16-F10 cells were cultured in Dulbecco's modified Eagle's medium (DMEM) supplemented with 10% heat-inactivated fetal bovine serum (FBS) (HI-FBS) and 1% penicillin-streptomycin. The B3Z murine T cell hybridoma cells were cultured in RPMI 1640 supplemented with 10% HI-FBS, 2 mM L-glutamine, 1 mM sodium pyruvate, 50 µM beta-mercaptoethanol, and 1% penicillin-streptomycin. The T2 (174×CEM.T2) human lymphoblast cells were cultured in RPMI 1640 supplemented with 10% HI-FBS, 2 mM L-glutamine, 1 mM sodium pyruvate, 50 µM beta-mercaptoethanol, 0.1 mM non-essential amino acids, 1 mM sodium pyruvate, 10 mM HEPES, and 1% penicillin-streptomycin. Primary mouse and human T cells were cultured in RPMI 1640 supplemented with 10% HI-FBS, 2 mM L-glutamine, 1 mM sodium pyruvate, 50 µM beta-mercaptoethanol, 0.1 mM non-essential amino acids, 1 mM sodium pyruvate, 10 mM HEPES, and 1% penicillin-streptomycin, supplemented with 30 U/ml recombinant mouse- or human-IL-2, respectively.

All chemical reagents for MSR synthesis were purchased from Sigma-Aldrich. All lipids were purchased from Avanti Polar Lipids. Specific lipids used in these studies are as follows: DOPC (850375C), POPC (850457C), DPSC (850365C), PE-cap-biotin (870273C), 18:1 PE-carboxyfluorescein (810332C). FoxP3 antibodies were purchased from eBioscience. All other antibodies were purchased from Biolegend. Murine and human recombinant IL-2 were purchased from Biolegend. Biotinylated peptide-loaded MHC monomers and fluorophore-labeled tetramers were obtained from the National Institutes of Health Tetramer Core Facility. Mouse and human CD3/CD28 T cell expansion DYNA-BEADS were purchased from ThermoFisher Scientific. The ovalbumin-derived peptide SIINFEKL (SEQ ID NO: 4) was purchased from Anaspec. The EBV-derived peptides CLG-GLLTMV (SEQ ID NO: 1) and GLCTLVAML (SEQ ID NO: 2) were purchased from Proimmune.

Synthesis of Mesoporous Silica Micro-Rods (MSRs)

MSRs were synthesized as previously reported (Kim et al. (2015); and Li et al. (2016)). Briefly, 4 g of Pluronic P123 surfactant (average Mn ~5,800, Sigma-Aldrich) was dissolved in 150 g of 1.6 M HCl solution and stirred with 8.6 g of tetraethyl orthosilicate (TEOS, 98%, Sigma-Aldrich) at 40° C. for 20 h, followed by aging at 100° C. for 24 h. Subsequently, surfactant was removed from the as-prepared particles by extraction in 1% HCl/ethanol (v/v) at 70° C. for 20 hours. Particles were recovered by running the suspension through a 0.22 µm filter, washed with ethanol, and dried.

Primary Mouse T Cell Isolation

All procedures involving animals were done in compliance with National Institutes of Health and Institutional guidelines. Animals were purchased from The Jackson Laboratory. For polyclonal T cell expansion studies, C57BL/6J mice were used as cell donors. For antigen-specific T cell expansion studies, C57BL/6-Tg(TcraTcrb)1100Mjb/J (OT-I) mice were used as cell donors. All animals were female and used between 6 and 9 weeks old at the start of the experiment. To isolate T cells, splenocytes were prepared by mashing spleens through 70 µm nylon cell strainers, and red blood cells were lysed in ACK buffer. Subsequently, either CD3+ T cells were isolated for polyclonal T cell expansion studies using a pan T cell isolation MACS kit (Miltenyi Biotec), or CD8+ T cells were isolated for antigen-specific T cell expansion studies using a CD8a+ T cell isolation MACS kit (Miltenyi Biotec).

Primary Human T Cell Isolation

De-identified leukoreduction collars were obtained from the Brigham and Women's Hospital Specimen Bank. PBMCs were isolated from leukoreductions in a Ficoll gradient, followed by two washes to remove platelet contaminants. Subsequently, in some studies, either CD3+ T cells were isolated for polyclonal T cell expansion studies using a pan T cell isolation MACS kit (Miltenyi Biotec), or CD8+ T cells were isolated for antigen-specific T cell expansion studies using a CD8+ T cell isolation MACS kit (Miltenyi Biotec).

Preparation of Antigen-Presenting Cell-Mimetic Scaffolds (APC-MS)

MSRs and liposomes were prepared prior to APC-MS assembly. To prepare liposomes, lipid films composed of predefined lipid formulations were first prepared by mixing lipid-chloroform suspensions, evaporating the bulk chloroform under nitrogen, and removing residual chloroform overnight in a vacuum chamber. For all functional studies, 1-palmitoyl-2-oleoyl-sn-glycero-3-phosphocholine (POPC) was used as the primary lipid, and lipid formulations were doped with between 0.01-1 mol % of either the carboxyfluorescein-tagged lipid 1,2-dioleoyl-sn-glycero-3-phosphoethanolamine-N-(carboxyfluorescein), or the biotinylated lipid 1,2-di-(9Z-octadecenoyl)-sn-glycero-3-phosphoethanolamine-N-(cap biotinyl). For some characterization studies, the lipids 1,2-dioleoyl-sn-glycero-3-phosphocholine (DOPC) and 1,2-distearoyl-sn-glycero-3-phosphocholine (DSPC) were alternatively used as the primary lipid. Lipid films were resuspended in PBS at 2.5 mg/ml lipid, and rehydrated by vortexing every 10 minutes for an hour. Lipid suspensions were subsequently extruded through 100 nm polycarbonate filters using a Mini-Extruder (Avanti Polar Lipids) to obtain monodisperse liposome suspensions. Liposome suspensions were stored at 4° C. and used within a week. To prepare APC-MS formulations, MSRs (10 mg/ml) were incubated with recombinant IL-2 (0.04 mg/ml) in PBS for 1 hour at room temperature. To form MSR-SLBs, liposomes were added at lipid:MSR 1:4 (w/w), and incubated for 1 hour at room temperature with pipetting every 10 minutes. Next, the material was washed twice with PBS, and then blocked for 15 minutes by resuspending the material at 2.5 mg/ml (with respect to MSRs) in 0.25% bovine serum albumin (BSA) in PBS (w/v). Streptavidin, at a molar amount corresponding to 30% theoretical saturation of the amount of biotinylated lipid in the particular formulation (assuming 34% lipid retention for POPC), was subsequently added (25 μg streptavidin per 500 μg MSRs for 1% biotinylated-lipid formulations), and the suspension was mixed by pipetting every 5 minutes for 20 minutes. Next, biotinylated T cell activating cues (1:1 molar ratio TCR-activating cue:αCD28) were added at an amount corresponding to 80% molar saturation of the added streptavidin, and the suspension was mixed by pipetting every 10 minutes for 1 hour. Finally, the material was washed twice with PBS, and resuspended in cell culture media for in vitro assays. APC-MS formulations were used immediately for T cell expansion experiments, or stored at 4° C. and used within a week for characterization studies.

Characterization of MSR-Supported Lipid Bilayer (MSR-SLB) Structure and Stability Brightfield and fluorescence microscopy, used to evaluate MSR lipid coating, MSR-SLB dispersibility, and MSR-SLB degradation, were performed with an EVOS FL Cell Imaging System. Confocal microscopy was performed using a Zeiss LSM 710 confocal system. To evaluate lipid retention with MSRs, MSRs were coated with lipid formulations containing 1 mol % fluorophore-tagged lipid, and lipid retention was quantified using a plate reader. To calculate percent lipid retention over time, cultured material was recovered at specified timepoints by centrifuging at 700 rcf for 5 minutes, and fluorescence intensity was normalized to the fluorescence intensity prior to culture. To evaluate MSR-SLB fluidity, fluorescence recovery after photobleaching (FRAP) experiments were carried out on MSRs coated with lipid formulations containing 1 mol % fluorophore-tagged lipid using a Zeiss LSM 710 confocal system. Photobleaching was performed on the 488 nm laser line and images were taken every 10 seconds for at least 150 seconds. Fluorescence recovery was analyzed using ImageJ by normalizing the fluorescence intensity within the photobleached region to the fluorescence intensity in an unbleached region on a different rod, at each timepoint.

To quantify IL-2 loading and release, 500 μg of MSRs were loaded with 2 μg of IL-2, and then coated with lipid as described. After washing twice with PBS, IL-2-loaded MSR-SLBs were resuspended in 500 μl release buffer (1% BSA in PBS (w/v)) and incubated at cell culture conditions. At indicated timepoints, samples were spun down (700 rcf for 5 minutes) and the supernatants were collected. Subsequently, MSRs were resuspended in fresh release buffer and returned to culture. IL-2 in supernatant samples was quantified via ELISA (Biolegend).

To quantify surface cue loading, MSR-SLB samples were prepared using lipid formulations containing 0.01, 0.1, or 1 mol % biotinylated lipid. Streptavidin, at an amount corresponding to 30% theoretical saturation of the retained biotinylated lipid (assuming 35% lipid retention for POPC), was added, followed by the addition of biotinylated IgG at an amount equal to either 40% or 80% saturation of the added streptavidin. As controls, samples containing the same amount of biotinylated IgG but no material were also prepared. All samples were spun at 700 rcf for 5 minutes to pellet the material, and the amount of IgG in the supernatant fractions were quantified via ELISA (eBioscience). The biotinylated IgG stock that was used for preparing the samples was also used to prepare standard curves. The amount of IgG loaded onto the material was calculated by subtracting the amount of IgG detected in control sample supernatants from the amount of IgG detected in respective material sample supernatants. For scanning electron microscopy (SEM), cells were cultured with APC-MS on glass coverslips overnight, fixed in 4% paraformaldehyde, and then centrifuged at 2000 rpm for 5 minutes. Fixed samples were serially transitioned through a gradient of 0, 30, 50, 75, 90, 100% ethanol in water. Samples were submerged in hexamethyldisilazane (Electron Microscopy Sciences) and maintained in a benchtop desiccator overnight. Dried coverslips were mounted on SEM stubs using carbon tape, sputter coated with 5 nm of platinum-palladium, and imaged using secondary electron detection on a Carl Zeiss Supra 55 VP field emission scanning electron microscope.

In Vitro T Cell Expansion Studies

Polyclonal mouse and human T cell expansion experiments were carried out using primary CD3+ T cells. Antigen-specific mouse T cell expansion experiments were carried out using CD8+ T cells isolated from OT-I mice. Antigen-specific human T cell expansion experiments were carried out using either CD8+ T cells, or PBMCS, isolated from de-identified donor blood samples. Isolated primary mouse or human T cells, or human PBMCs, were mixed with activation stimuli, and cultured for up to two weeks. In all experiments, non-tissue culture-treated culture vessels were used. For human antigen-specific T cell expansion studies, prior to establishment of cultures, donor samples were assayed for HLA-A2 MEW I expression via FACS, and prior EBV exposure via anti-EBV VCA ELISA (1BL International) of serum. Only HLA-A2+ EBV-experienced samples were used for expansion studies.

Mock-treated samples in human antigen-specific T cell expansion experiments were cultured in media supplemented with 30 U/ml recombinant IL-2. Mock-treated samples in all other T cell expansion experiments were cultured in non-supplemented media. For commercial Dynabead conditions, DYNABEADS were used according to the manufacturer-optimized protocol included with the kit. Briefly, T cells were seeded at a density of $1 \times 10^6$ T cells/ml with pre-washed DYNABEADS at a bead-to-cell ratio of 1:1, in media supplemented with 30 U/ml recombinant IL-2. For Dynabead cultures, $1 \times 10^5$ cells were seeded in the starting culture. Cells were counted every third day and fresh IL-2-supplemented media was added to bring the cell suspension to a density of $0.5-1 \times 10^6$ cells/ml. In general, cells were maintained below a density of $2.5 \times 10^6$ cells/ml throughout the culture period.

For mouse polyclonal studies, APC-MS were prepared that presented surface cues (αCD3+αCD28) on between 0.2-1 mol % of the lipids at a 1:1 molar ratio, and added into the starting culture at 333 μg/ml. For human polyclonal studies, APC-MS were prepared that presented surface cues (αCD3+ αCD28) on either 0.1 mol % or 1 mol % of the lipids at a 1:1 molar ratio, and added into the starting culture at 33 μg/ml or 333 μg/ml. For mouse antigen-specific studies, APC-MS were prepared that presented surface cues (SVYDFFVWL (SEQ ID NO: 3)/H-2K(b) or SIINFEKL (SEQ ID NO: 4)/H-2K(b)+αCD28) on either 0.01 mol % or 0.1 mol % of the lipids at a 1:1 molar ratio, and added into the starting culture at 33 μg/ml or 333 μg/ml. For human antigen-specific studies, APC-MS were prepared that presented surface cues (CLGGLLTMV (SEQ ID NO: 1)/HLA-A2 or GLCTLVAML (SEQ ID NO: 2)/HLA-A2+ αCD28) on 1 mol % of the lipids at a 1:1 molar ratio, and added into the starting culture at 333 μg/ml. APC-MS presenting cues on 1 mol % of lipids, added at 333 μg/ml, corresponds to ~55 nM of TCR stimuli and αCD28 in the starting culture. For APC ms conditions, T cells were seeded with the specified amount of material at 5x104 cells/ml in media that was not supplemented with IL-2. In all APC-MS conditions, 2.5x104 cells were seeded in the starting culture. Media was added throughout the culture period to maintain cells below a density of $2.5 \times 10^6$ cells/ml. Starting on day 7, when most material-loaded IL-2 has been released, fresh media that was added was supplemented with 30 U/ml recombinant IL-2. At specified timepoints, live cells were manually enumerated with a hemocytometer using Trypan blue exclusion, to avoid possible artifacts with automated counting systems as a result of material contaminants After enumeration, cell phenotype was evaluated using flow cytometry. Gates were set for each timepoint and sample set independently based on fluorescence minus one (FMO) controls.

In Vitro T Cell Functional Studies

For co-culture experiments in which T cell expression of IFNγ and TNFα was evaluated via intracellular cytokine staining, stimulator cells (mouse, B16-F10; human, T2) were first either unpulsed or pulsed with 1 μg/ml peptide (mouse, SIINFEKL (SEQ ID NO: 4); human, CLG-GLLTMV (SEQ ID NO: 1) or GLCTLVAML (SEQ ID NO: 2)) for 30 minutes at 37° C. Subsequently, $1 \times 10^5$ expanded cells were cultured with $2 \times 10^4$ stimulator cells for one hour before adding Brefeldin A (BD Biosciences) to inhibit cytokine secretion, and then cultured for another four hours. Cells were then stained and analyzed using FACS.

In vitro killing assays were carried out by first incubating target cells (mouse, B16-F10; human, T2) in 20 μg/ml Calcein AM (Biotium) for 30 minutes at 37° C. Target cells were subsequently either unpulsed or pulsed with 1 μg/ml peptide (mouse, SIINFEKL (SEQ ID NO: 4); human, CLG-GLLTMV (SEQ ID NO: 1) or GLCTLVAML (SEQ ID NO: 2)) for 30 minutes at 37° C. $5 \times 10^3$ target cells were then cultured with expanded effector cells at effector cell:target cell (E:T) ratios of 0, 1, 10, 25, or 50 for four hours. Cells were then pelleted and the fluorescence intensity of supernatant samples was quantified using a plate reader. IFNγ concentrations in supernatant samples were also quantified via ELISA (Biolegend).

Statistical Analysis

All values were expressed as mean±s.d., unless otherwise specified. Statistical analysis was performed using Graph-Pad Prism and statistical methods are stated in the text. In all cases, $p<0.05$ was considered significant.

Example 12: Analysis of the Degradation of APC-MS In Vitro

Figure 37:
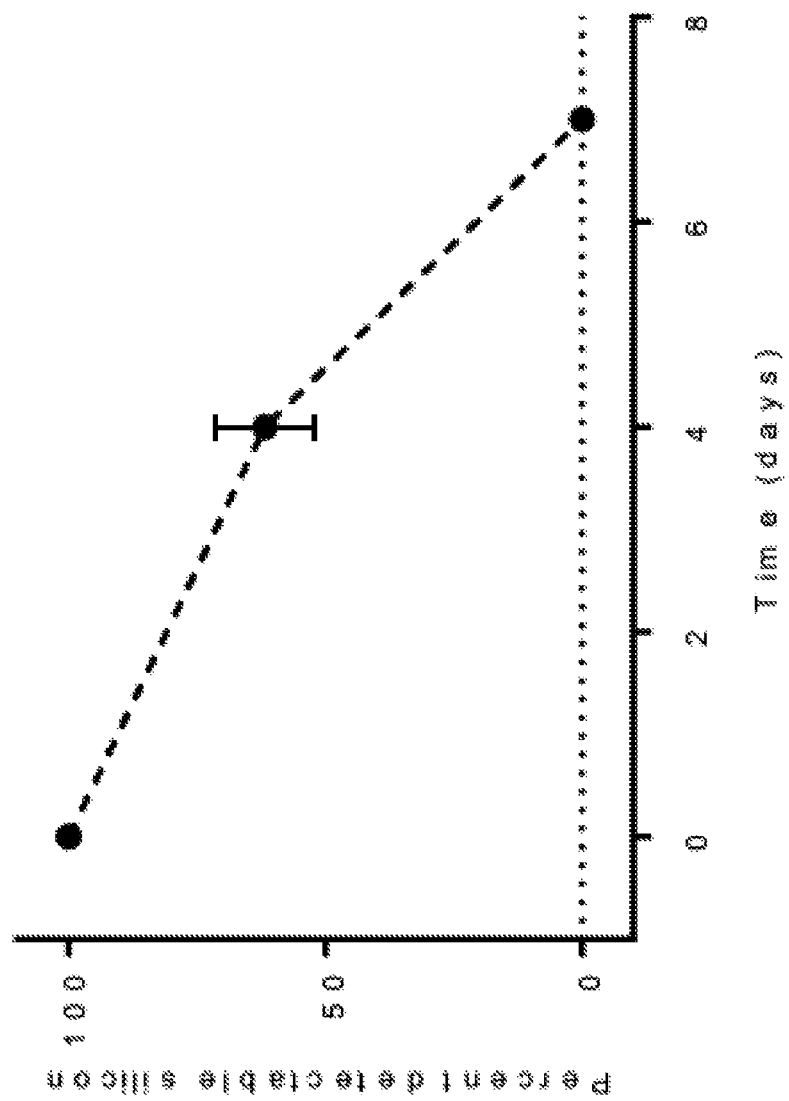
FIG. 37 depicts the degradation of APC-MS scaffold in vitro. APC-MS (167 μg) presenting αCD3/αCD28 (1% biotinylated lipid) and releasing IL-2 was cultured with primary mouse T cells ($25 \times 10^4$ T cells/167 μg APC-MS). At various timepoints, cultures were centrifuged at 700 rcf for 5 min, and Si content in pellets was quantified via inductively coupled plasma optical emission spectrometry (ICP-OES; Galbraith Laboratories). Si is undetectable in culture pellets by 1 week after starting culture.

To study the degradation of an exemplary APC-MS in vitro, the following experiment was performed. APC-ms (167 μg) comprising αCD3/αCD28 antibodies (1% biotinylated lipid) and releasing IL-2 was cultured with primary mouse T cells ($25e^4$ T cells/167 μg MSRs). At various timepoints, cultures were centrifuged at 700 rcf for 5 min, and silica (Si) content in pellets was quantified via inductively coupled plasma optical emission spectrometry (ICP-OES; Galbraith Laboratories). As shown in FIG. 37, silica was undetectable in culture pellets after about 1 week.

Figure 38:
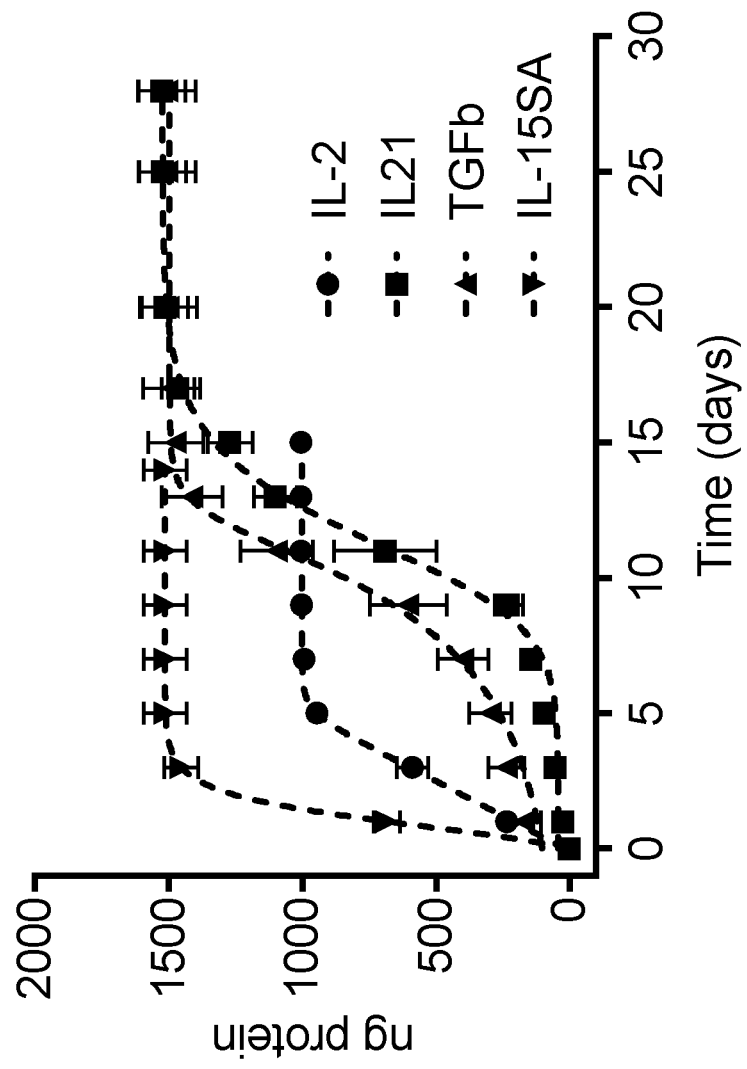
FIG. 38 shows the controlled release of diverse soluble immune-directing payloads from APC-MS. 4 APC-MS were generated, each comprising 2 μg of either IL-2, IL-21, TGFβ or IL-15SA loaded into 500 μg APC-MS prior to lipid coating. Samples were thoroughly washed to remove unloaded protein and subsequently maintained at 37° C. for up to 28 days. Payload release over time was evaluated via ELISA.

Example 13: Controlled Release of Diverse Soluble Immune-Directing Payloads from APC-MSs To study the release of a cytokine payloads from exemplary APC-MSs, the following experiment was performed. Four APC-MSs each comprising either 2 μg of IL-2, IL-21, TGFβ or IL-15SA were loaded into 500 μg mesoporous silica micro-rods (MSR) prior to lipid coating. Samples were thoroughly washed to remove any unloaded protein and subsequently maintained at 37° C. for up to 28 days. Payload release over time was evaluated using ELISA. As shown in FIG. 38, controlled release of the cytokines from the APC-MSs was observed over the course of the experiment. Release kinetics are likely dependent on physicochemical properties of the particular cytokine.

Example 14: Conjugation of Antibodies to MSR-SLBs Via Click-Chemistry Reaction

Figure 42A:
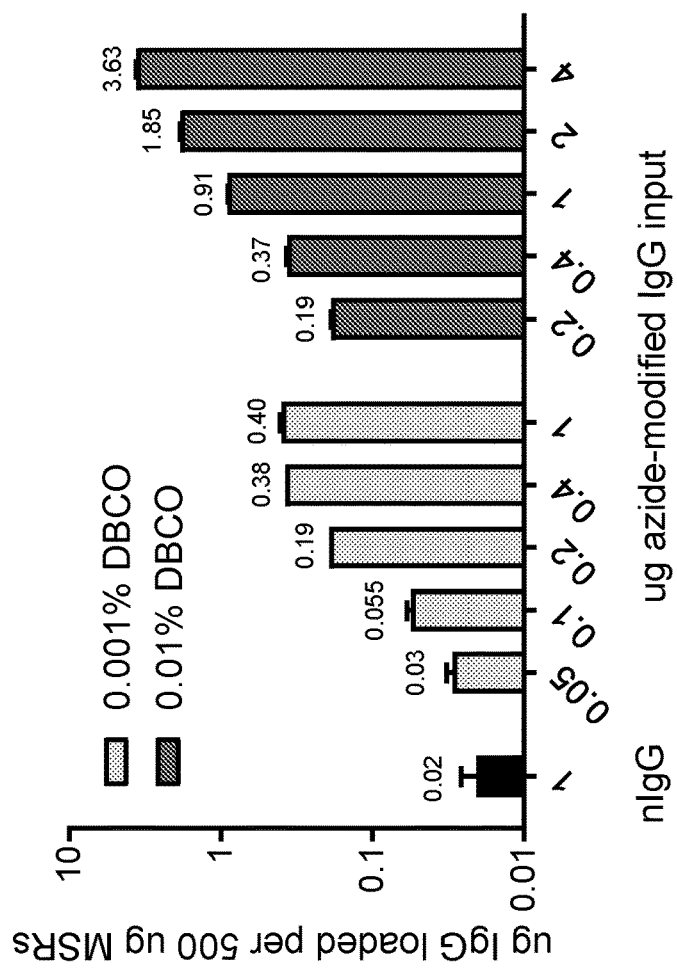
FIGS. 42A and 42B depict the attachment of azide-labeled IgG to DBCO-presenting MSR-SLBs via click-chemistry conjugation.
Figure 42B:
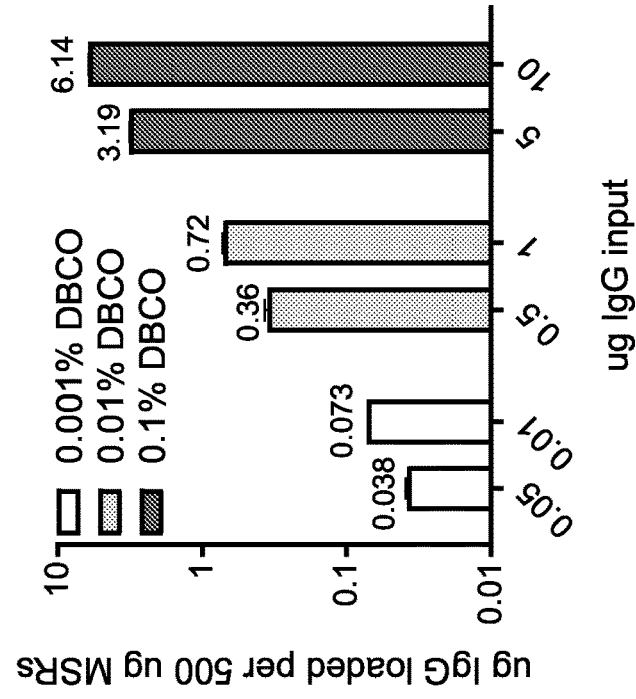

To determine whether a functional molecule could be conjugated to the MSR-SLB lipid bilayer the following experiment was performed. IgG was site-specifically labeled with azide groups using the Thermo SiteClick Antibody Labeling System. MSR-SLBs containing varying amounts (mol %) of DBCO-modified lipids (Avanti Polar Lipids) were also prepared. As shown in FIGS. 42A and 42B, azide-modified IgG was successfully conjugated onto the lipid bilayer of MSR-SLBs in a concentration-dependent manner.

Equivalents

Those skilled in the art will recognize, or be able to ascertain using no more than routine experimentation, many equivalents to the specific embodiments and methods described herein. Such equivalents are intended to be encompassed by the scope of the following claims.

We claim:

1. An antigen presenting cell-mimetic scaffold (APC-MS), comprising
high surface area mesoporous silica micro-rods (MSR);
a fluid supported lipid bilayer (SLB) layered on the MSR; and
a functional molecule selected from the group consisting of a T-cell activating molecule, a T-cell co-stimulatory molecule, and a combination thereof;
wherein the functional molecule is presented on the SLB; and
wherein the scaffold comprises spaces between the MSR which permit infiltration of T cells.

2. The scaffold of claim 1, wherein the T-cells are selected from the group consisting of natural killer T-cells, gamma delta T-cells, CD3+ T-cells, CD4+ T-cells, CD8+ T-cells, regulatory T-cells (Tregs), and a combination thereof.

3. The scaffold of claim 2, wherein the regulatory T-cells (Tregs) are selected from the group consisting of FOXP3+ Treg cells, FOXP3-Treg cells, and a combination thereof.

4. The scaffold of claim 1, further comprising a T-cell homeostatic agent.

5. The scaffold of claim 4, wherein the T-cell homeostatic agent is loaded onto the MSR.

6. The scaffold of claim 1, wherein the scaffold comprises the T-cell activating molecule and the T-cell co-stimulatory molecule, each presented on the SLB.

7. The scaffold of claim 1, wherein the T-cell activating molecule, or the T-cell co-stimulatory molecule, or both, are presented on the SLB via affinity pairing or chemical coupling.

8. The scaffold of claim 1, comprising an immunoglobulin molecule that binds specifically to an Fc-fusion protein, wherein the immunoglobulin molecule is presented on the SLB.

9. The scaffold of claim 1, wherein the scaffold further comprises a recruitment compound selected from the group consisting of granulocyte macrophage-colony stimulating factor (GM-CSF), chemokine (C-C motif) ligand 21 (CCL-21), chemokine (C-C motif) ligand 19 (CCL-19), Chemokine (C-X-C Motif) ligand 12 (CXCL12), interferon gamma (IFNγ), an FMS-like tyrosine kinase 3 (Flt-3) ligand, and a combination thereof.

10. The scaffold of claim 9, wherein the recruitment compound comprises GM-CSF.

11. The scaffold of claim 1, wherein the scaffold comprises an antigen.

12. The scaffold of claim 1, wherein the weight ratio of the SLB to the MSR is between 10:1 and 1:20.

13. The scaffold of claim 12, wherein the weight ratio of the SLB to the MSR is between 1:4 and 1:20.

14. The scaffold of claim 1, wherein the dry weight ratio of the MSR to the T-cell activating molecule, or the T-cell co-stimulatory molecule, or both, is between 500:1 to 1:1.

15. A pharmaceutical composition comprising the scaffold of claim 1 and a pharmaceutically acceptable carrier.

16. A composition comprising the scaffold of claim 1 and T-cells clustered therein.

17. The composition of claim 16, wherein the T-cells clustered therein are selected from the group consisting of natural killer T-cells, CD3+ T-cells, CD4+ T-cells, CD8+ T-cells, regulatory T-cells (Tregs), and a combination thereof.

18. The composition of claim 17, wherein the regulatory T-cells (Tregs) are selected from the group consisting of FOXP3+ Treg cells, FOXP3-Treg cells, and a combination thereof.

19. The scaffold of claim 1, wherein the dry weight ratio of the MSR to the T-cell activating molecule, or the T-cell co-stimulatory molecule, or both, is between 200:1 to 20:1.

20. The scaffold of claim 1, wherein the scaffold comprises the T-cell activating molecule and the T-cell co-stimulatory molecule, and wherein the ratio of the T-cell activating molecule to the T-cell co-stimulatory molecule ranges from 50:1 to 1:50.

21. The scaffold of claim 1, wherein the scaffold comprises at least one T-cell activating molecule presented on the SLB.

22. The scaffold of claim 1, wherein the scaffold comprises at least one T-cell co-stimulatory molecule presented on the SLB.

23. The scaffold of claim 1, wherein the spaces between the MSR permit infiltration of T cells having a mean diameter of 6.8 µm to 12 µm.

24. The scaffold of claim 1, wherein the MSR comprise a length of between 5 µm to 500 µm.

25. The scaffold of claim 1, wherein the MSR comprise a length of between 50 µm to 200 µm.

26. The scaffold of claim 1, wherein the MSR comprise a length of between 80 µm to 120 µm.

27. The scaffold of claim 1, wherein the MSR comprise an average length of 100 µm.

28. The scaffold of claim 1, wherein the MSR comprise an average length of 88 µm.

29. The scaffold of claim 28, wherein the MSR comprise an average diameter of 4.5 µm.

30. The scaffold of claim 1, wherein the MSR comprise an aspect ratio of 20.

* * * * *